US010100076B2

(12) United States Patent
Stuyver et al.

(10) Patent No.: US 10,100,076 B2
(45) Date of Patent: Oct. 16, 2018

(54) MODIFIED NUCLEOSIDES FOR THE TREATMENT OF VIRAL INFECTIONS AND ABNORMAL CELLULAR PROLIFERATION

(71) Applicant: Gilead Pharmasset LLC, Foster City, CA (US)

(72) Inventors: Lieven Stuyver, Snellville, GA (US); Kyoichi Watanabe, Stone Mountain, GA (US)

(73) Assignee: Gilead Pharmasset LLC, Foster City, CA (US)

( * ) Notice: Subject to any disclaimer, the term of this patent is extended or adjusted under 35 U.S.C. 154(b) by 376 days.

(21) Appl. No.: 13/908,098

(22) Filed: Jun. 3, 2013

(65) Prior Publication Data

US 2014/0057863 A1   Feb. 27, 2014

Related U.S. Application Data

(60) Continuation of application No. 12/805,563, filed on Aug. 5, 2010, now abandoned, which is a division of application No. 10/045,292, filed on Oct. 18, 2001, now abandoned.

(60) Provisional application No. 60/282,156, filed on Apr. 6, 2001, provisional application No. 60/241,488, filed on Oct. 18, 2000.

(51) Int. Cl.
| | |
|---|---|
| *A61K 31/7076* | (2006.01) |
| *A61K 31/7064* | (2006.01) |
| *C07H 19/16* | (2006.01) |
| *C07H 19/048* | (2006.01) |
| *C07H 19/06* | (2006.01) |
| *C07H 19/10* | (2006.01) |
| *C07H 19/20* | (2006.01) |
| *C07H 21/04* | (2006.01) |
| *C12Q 1/6809* | (2018.01) |
| *C12Q 1/689* | (2018.01) |
| *C12Q 1/6895* | (2018.01) |

(52) U.S. Cl.
CPC ......... *C07H 19/16* (2013.01); *A61K 31/7064* (2013.01); *A61K 31/7076* (2013.01); *C07H 19/048* (2013.01); *C07H 19/06* (2013.01); *C07H 19/10* (2013.01); *C07H 19/20* (2013.01); *C07H 21/04* (2013.01); *C12Q 1/6809* (2013.01); *C12Q 1/689* (2013.01); *C12Q 1/6895* (2013.01); *Y02A 50/393* (2018.01)

(58) Field of Classification Search
None
See application file for complete search history.

(56) References Cited

U.S. PATENT DOCUMENTS

| | | | |
|---|---|---|---|
| 4,211,773 A | | 7/1980 | Lopez et al. |
| 4,232,154 A | | 11/1980 | Shealy et al. |
| 4,666,892 A | | 5/1987 | Fox et al. |
| 4,835,104 A | * | 5/1989 | Yokozeki ................ C12P 19/02 |
| | | | 435/105 |
| 4,968,690 A | | 11/1990 | Marquez et al. |
| 4,975,434 A | | 12/1990 | Marquez et al. |
| 5,034,518 A | | 7/1991 | Montgomery et al. |
| 5,035,878 A | | 7/1991 | Borch et al. |
| 5,246,924 A | | 9/1993 | Fox et al. |
| 5,446,029 A | | 8/1995 | Eriksson et al. |
| 5,512,671 A | | 4/1996 | Piantadosi et al. |
| 5,565,438 A | | 10/1996 | Chu et al. |
| 5,565,688 A | | 10/1996 | Chu et al. |
| 5,587,362 A | | 12/1996 | Chu et al. |
| 5,703,058 A | | 12/1997 | Schinazi et al. |
| 5,808,040 A | | 9/1998 | Chu et al. |
| 5,886,162 A | | 3/1999 | Kalman |
| 5,905,070 A | | 5/1999 | Schinazi et al. |
| 6,080,791 A | * | 6/2000 | Bodian ................... A61K 31/05 |
| | | | 514/678 |
| 6,348,587 B1 | * | 2/2002 | Schinazi ............... C07D 405/04 |
| | | | 435/6.16 |
| 6,812,219 B2 | | 11/2004 | LaColla et al. |
| 7,307,065 B2 | | 12/2007 | Schinazi et al. |
| 7,919,247 B2 | | 4/2011 | Stuyver et al. |
| 2003/0087873 A1 | | 5/2003 | Lieven et al. |
| 2004/0110718 A1 | | 6/2004 | Devos et al. |

(Continued)

FOREIGN PATENT DOCUMENTS

| | | |
|---|---|---|
| AU | 2001-263484 | 12/2001 |
| CA | 2409613 | 11/2001 |
| EP | 0277599 | 8/1988 |

(Continued)

OTHER PUBLICATIONS

Filippini et al, Archives of Virology, 2000, 145, pp. 937-944.*

(Continued)

*Primary Examiner* — Traviss C McIntosh, III

(57) ABSTRACT

The disclosed invention is a composition for and a method of seating a Flaviviridae (including BVDV and HCV), Orthomyxoviridae (including Influenza A and B) or Paramyxoviridae (including RSV) infection, or conditions related to abnormal cellular proliferation, in a host, including animals, and especially humans, using a nucleoside of general formula (I)-(XXIII) or its pharmaceutically acceptable salt or prodrug. This invention also provides an effective process to quantify the viral load, and in particular BVDV, HCV or West Nile Virus load, in a host, using real-time polymerase chain reaction ("RT-PCR"). Additionally, the invention discloses probe molecules that can fluoresce proportionally to the amount of virus present in a sample.

5 Claims, 4 Drawing Sheets

Specification includes a Sequence Listing.

(56) References Cited

U.S. PATENT DOCUMENTS

2011/0269707 A1   11/2011   Stuyver et al.

FOREIGN PATENT DOCUMENTS

| EP | 0 292 023 | 11/1988 |
|---|---|---|
| EP | 0316 017 | 5/1989 |
| EP | 0352 248 | 1/1990 |
| EP | 0357 571 | 3/1990 |
| EP | 0409 227 | 1/1991 |
| EP | 0417999 | 3/1991 |
| EP | 0457326 | 11/1995 |
| JP | 60-008270 A | 1/1985 |
| JP | 61-087673 | 5/1986 |
| JP | 61130299 | 6/1986 |
| JP | 64-042499 | 2/1989 |
| JP | 06-065211 | 3/1994 |
| JP | 6-80688 | 3/1994 |
| WO | WO 88/08001 | 10/1988 |
| WO | WO 91/11186 | 8/1991 |
| WO | WO 91/15488 | 10/1991 |
| WO | WO 92/08727 | 5/1992 |
| WO | WO 92/14743 | 9/1992 |
| WO | WO 94/03183 | 2/1994 |
| WO | WO 94/14831 | 7/1994 |
| WO | WO 95/20595 | 8/1995 |
| WO | WO 96/22778 | 8/1996 |
| WO | WO 96/039152 | 12/1996 |
| WO | WO 96/40164 | 12/1996 |
| WO | WO 96-040166 | 12/1996 |
| WO | WO 97/032589 | 9/1997 |
| WO | WO 1998 007745 | 2/1998 |
| WO | WO 98/18324 | 5/1998 |
| WO | WO 98/024427 | 6/1998 |
| WO | WO 98/039013 | 9/1998 |
| WO | WO 99/022741 | 5/1999 |
| WO | WO 99/43691 | 9/1999 |
| WO | WO 99/058126 | 11/1999 |
| WO | WO 00/027340 | 5/2000 |
| WO | WO 01/34618 | 5/2001 |
| WO | WO 2001/060315 | 8/2001 |
| WO | WO01/91737 | * 12/2001 |
| WO | WO 2001/091737 | 12/2001 |
| WO | WO 2001/092282 | 12/2001 |
| WO | WO 2002/018404 | 3/2002 |

OTHER PUBLICATIONS

Koshida et al., Antimicrobial Agents and Chemotherapy, Dec. 1989, vol. 23(12), pp. 2083-2088.*
Richardson et al., International Journal of Cancer, 1975, vol. 15, pp. 451-456.*
Maruyama et al., Chemical & Pharmaceutical Bulletin, 1996, 44(12), pp. 2331-2334.*
Ali et al., Tetrahedron Letters, 1990, 31, 1509, Pergamon Press, Great Britain.
Antle, V. D. et al., Nucleosides and Nucleotides (1999), 18(9), 1911-1928.
Chu et al., J. Heterocycl. Chem., 1980, 17, 1435.
*Diversitech Corp. v. Century Steps, Inc.* 850 F. 2d 657, 677, 7 U.S.P.Q.2d 1315, 1317 (Fed Cir. 1988), retrieved from the Internet http://openjurist.org/850/f2d/675/diversitech-corporation-v-century-steps-inc. [retrieved on Jun. 23, 2014], 11 pages.
Dollinger, Malin R. et al: Analogs of 1-.beta.-D-arabinofuranosylcytosine. Studies on mechamisms of action in Burkitt's cell culture and mouse leukemia, and in vitro deamination studies Biochemical Pharmacology 16(4): 689-706 (1967).
Duschinsky et al., J. Med. Chem., 1967,10,47.
English abstract of JP60-008270 A, published Jan. 17, 1985.
English abstract of JP61-087673 A, published May 6, 1986.
English abstract of JP64-042499 A, published Feb. 14, 1989.
English Language Derwent Abstract for JP 6-80688.

European Search Report Inder Rule 112 EPC in corresponding European Patent Application No. 01987756.2, dated Sep. 20, 2004, 6 pages.
Extended European Search Report in corresponding European Patent Application No. 10175643.5, dated Oct. 7, 2010.
Filippini, et al., Archives of Virology 145(5))937-944 (2000).
Gu, Z. et al., "Mechanism of Action and in Vitro Activity of 1',3'-Dioxolanylpurine Nucleoside Analogues against Sensitive and Drug-Resistant Human Immunodeficiency Virus Type 1 Variants," Antimicrobial Agents and Chemotherapy, 1999, 43(1 0), 2376-2382.
Hoshino, Jiro et al., "Suppression of nuclear ADP-ribosyltransferase activity in Ehrlich ascites tumor cells by 5-azacytidine and its analogs" Biochemical and Biophysical Research Communications 142(2), 468-7 (1987).
Hronowski, L. J. J. et al., "Synthesis of cyclopentane analogs of (2'- and 3'-deoxy-erythro-pentofuranosyl and ribofuranosyl)-2-thiouracil nucleosides"Can. J. Chem. (1986), 64, 1620-1629.
Huang, G.-F. et al., J Carbohydr. Nucleosides Nucleotides, 1978, 5, 317.
Ikehara, M. et al., "Studies of Nucleosides and Nucleotides. XXXII. Purine Cyclonucleosides. 3. Synthesis of 2'-Deoxy- and 3'-Deoxyadenosine from Adenosine" Chem. Pharm. Bull., 1967, 15, 94.
In RE Robertson, 169 F.3d 743, 49 USPQ.2d 1949 (Fed. Cir. 1999), retrieved from the Internet http://www.leagle.com/decision/1999912169F3d743_1799.xml/IN%20RE%20ROBERTSON [retrieved on Jun. 23, 2014], 3 pages.
International Search Report for Appliication No. PCT/US2001/046113, dated Jul. 22, 2003, 23 pages.
Kabat et al., "Synthesis of 5-.beta.-D-ribofuranosylnicotinamide and its N-methyl derivative. The isosteric and isoelectronic analogs of nicotinamide nucleoside"J. Med. Chem., 1987, 30, 924.
Kaneko, M. et al., "Synthesis and Properties of 8, 2'-Cyclothioguanosine and Related Compounds" Chem. Pharm. Bull. 1972,20,635.
Kazimierczuk, Z. et al., "Synthesis of 2'-deoxytubercidin, 2'-deoxyadenosine, and related 2'deoxynucleosides via a novel direct stereospecific sodium salt glycosylation procedure" J. Am. Chem. Soc., 1984, 106,6379.
Kodama et al., "4'-Ethynyl Nucleoside Analogs: Potent Inhibitors of Multidrug-Resistant Human Immunodeficiency Virus Variants in Vitro," Antimicrobial Agents and Chemotherapy, 2001, 45(5), 1539-1546.
Kong et al., "Long Term Follow-Up and Late Complications of 2-Chlorodeoxyadenosine in Previously Treated Advanced, Indolent Non-Hodgkin's Lymphoma," Cancer, 82(5):957-964 (1998).
Lee, W. W. et al., J. Am. Chem. Soc., 1961, 83, 1906.
Lin, T. S. et al., "Synthesis and anticancer activity of various 3'-deoxy pyrimidine nucleoside analogs, and crystal structure of 1-(3-deoxy-.beta.-D-threo-pentofuranosyl)cytosine," Med. Chem 34(2):693-701 (1991).
Lockshin, Arnold, et al., "Selective cytotoxicity of 5-hydroxyuridine for human colon adenocarcinoma cells" Cancer Treatment Reports 69(7-8): 845-9 (1985).
Lohmann, V. et al., Virology, 108, 1998, Academic Press.
Marumoto, R. et al., Chem. Pharm. Bull. 1974, 22, 128.
Mendez, E. et al., J. Virol, 1998, 72, 4737.
Morizawa, Y. et al., Bull, Chem. Soc. Jpn. (1993), 66, 2714-2719.
Niedballa, U. et al., J. Org. Chem., 1976, 41, 2084.
Ozols, A.M. et al., Synthesis, 1980, 557.
Pankiewicz, K. W. et al., Nucleosides & Nticleotides, 1991, 10, 1333.
Pankiewicz, K. W. et al., Carbohydr. Res., 1984, 127,227.
Popescu et al., "Synthesis and Antiviral Activity of Carbocyclic 5-Substituted Uridines and Cytidines", Nucleosides & Nucleotides, 14(6): 1233-1249 (1995).
Roberts, M. et al., J. Am. Chem. Soc., 1952, 74,668.
Sagi, J. Nucleic Acids Symposium Series 18, Symp. Chem. Nucleic Acid Compon., 7th, 131-135 (1987).
Sergueeva, Z. A. et al., Nucleosides Nucleotides Nucleic Acids, 2000, 19,275.
Shealy, Y. F. et al., J. Med. Cem. (1986), 29, 1720-1725.
Shi et al., J. Med. Chem., 1999, 42, 859.

(56) References Cited

OTHER PUBLICATIONS

Smee D F et al., "Selective Inhibition of Arthropod-Borne and Arenaviruses in Vitro by 3'-Fluoro-3'-Deoxyadenosine" Antiviral Research, Elsevier Science BV., Amsterdam, NL, vol. 18, 1992, pp. 151-162.
Stavber, S. et al., J. Chern. Soc. Chern. Commun., 1983,563.
Suhadolnik, R. J. et al., Carbohydr. Res., 1978, 61, 545.
Tanaka, H. et al., Chern. Pharm. Bull., 1983,31, 787.
Tanaka, H. et al., Tetrahedron Lett., 1979, 4755.
Thurber, T. C. et al., J. Am. Chern. Soc., 1973,95, 3081.
Thurber, T.C. et al., J. Org. Chern., 1976,41, 1041.
Townsend, L. B. et al., Nucleic Acid Chern., 1978, 1, 272 and 343.
Vorbruggen, H. et al., Chern. Ber., 1981, 114, 1234.
Walton, E. et al., J. Am. Chern. Soc., 1964, 86, 2952.
Wang et al., "Asymmetric Synthesis and Antiviral Activities of L-Carbocyclic 2',3'-Didehydro-2',3'- dideoxy and 2',3'-Dideoxy Nucleosides," J. Med. Chern., 42(17): 3390-3399 (1999).
Watanabe, "The Chemistry of C-Nucleosides," Townsend, L. B., Ed., in "Chemistry of Nucleosides and Nucleotides", Plenum Publ., New York, vol. 3, 421, 1994.

* cited by examiner

Figure 1: Standard curve for BVDV

Figure 2: Growth dynamics of BVDV in MDBK cells

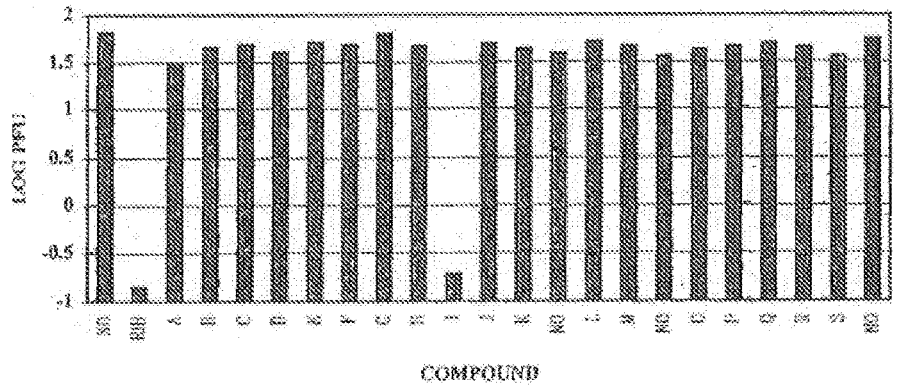

Figure 3: Anti-BVDV compound screening (40 µM) in MDBK cells

NO = no treatment;
RIB = Ribavirin;
A = 1-(2-chloro-2-deoxy-β-D-ribofuranosyl)-4-amino-1H-pyrimidin-2-one;
B = 1-(β-D-ribo-furanosyl)-5-nitro-1H,3H-pyrimidin-2,4-dione;
C = 1-(β-D-ribo-furanosyl)-4-amino-5-methyl-1H-pyrimidin-2-one;
D = 1-(α-L-manno-furanosyl)-4-benzamido-1H-pyrimidin-2-one;
E = 1-(β-D-ribo-furanosyl)-6-methyl-1H,3H-pyrimidin-2,4-dione;
F = 1-(2,3,-di-O-methyl-β-D-ribofuranosyl)4-butylamino-1H-pyrimidin-2-one;
G = S1, S2-bis [1-(β-D-ribo-furanosyl)-1H-pyrimidin-2-one]-4,4-disulfide;
H = 1-(β-D-ribo-furanosyl)-2-methoxy-1H-pyrimidin-4-one;
I = 5-hydroxyuridine (β-D-CL, R = X = OH);
J = 1-(β-D-ribo-furanosyl)-5-bromo-1H,3H-pyrimidin-2,4-dione;
K = 1-(β-D-ribo-furanosyl)-2-amino-1H-pyrimidin-2-one;
L = 1-(β-D-ribo-furanosyl)-1H,3H-pyrimidin-2,4-dithione;
M = 1-(5-deoxy-β-D-ribofuranosyl)-1H,3H-pyrimidin-2,4-dione;
N = 1-(β-D-ribo-furanosyl)-2,5-diamino-1H-pyrimidin-2-one;
O = 1-(β-D-ribo-furanosyl)-6-hydroxy-1H,3H-pyrimidin-2,4-dione;
P = 5-bromouridine;
Q = 1-(β-D-ribo-furanosyl)-5-benzyloxy-6-allyl-1H,3H-pyrimidin-2,4-dione;
R = 1-(β-D-ribo-furanosyl)-5-hydroxy-6-propyl-1H,3H-pyrimidin-2,4-dione;
S = 5-O-(1-p-nitrophenyltetrazol-5-yl)-6-propyl-uridine.

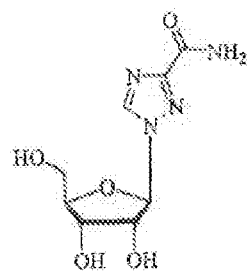
ribavirin
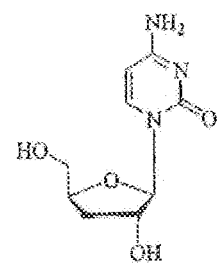
β-D-AJ
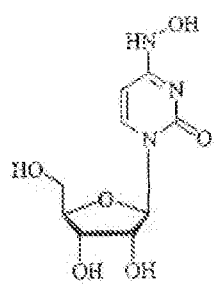
β-D-BS
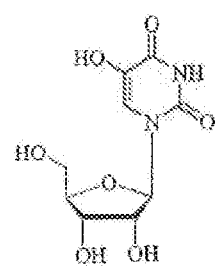
β-D-CL
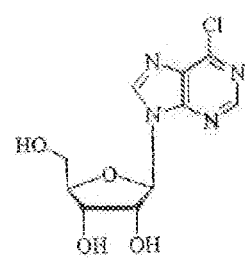
β-D-DJ
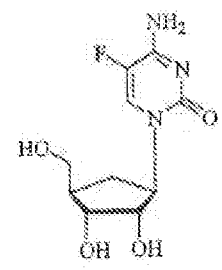
β-D-GA
Figure 5

MODIFIED NUCLEOSIDES FOR THE TREATMENT OF VIRAL INFECTIONS AND ABNORMAL CELLULAR PROLIFERATION

CROSS-REFERENCE TO RELATED APPLICATIONS

This application is a continuation of U.S. application Ser. No. 12/805,563, filed Aug. 5, 2010, which is a divisional of U.S. application Ser. No. 10/045,292, filed Oct. 18, 2001, which claims the benefit of U.S. Provisional Application Nos. 60/282,156, filed Apr. 6, 2001 and 60/241,488, filed Oct. 18, 2000. The entire contents of all of the above-mentioned applications are herein incorporated by reference.

INCORPORATION OF SEQUENCE LISTING

The Sequence Listing filed on Jul. 25, 2011, in the parent application Ser. No. 12/805,563, named USAp12805563_ST25.txt, having a size in kilobytes of 1.944 kB, is hereby incorporated by reference in its entirety.

This application claims priority to U.S. provisional application No. 60/241,488, filed Oct. 18, 2000 and U.S. provisional application No. 60/282,156, filed on Apr. 6, 2001.

FIELD OF THE INVENTION

The present invention includes compounds and methods for the treatment of Flaviviridae, Orthomyxoviridae, Paramyxoviridae infections and abnormal cellular proliferation.

BACKGROUND OF THE INVENTION

Flaviviridae

The Flaviviridae is a group of positive single-stranded RNA viruses with a genome size from 9-15 kb. They are enveloped viruses of approximately 40-50 nm. An overview of the Flaviviridae taxonomy is available from the International Committee for Taxonomy of Viruses. The Flaviviridae consists of three genera.

1. Flaviviruses. This genus includes the Dengue virus group (Dengue virus, Dengue virus type 1, Dengue virus type 2, Dengue virus type 3, Dengue virus type 4), the Japanese encephalitis virus group (Alfuy Virus, Japanese encephalitis virus, Kookaburra virus, Koutango virus, Kunjin virus, Murray Valley encephalitis virus, St. Louis encephalitis virus, Stratford virus, Usutu virus, West Nile Virus), the Modoc virus group, the Rio Bravo virus group (Apoi virus, Rio Brovo virus, Saboya virus), the Ntaya virus group, the Tick-Borne encephalitis group (tick born encephalitis virus), the Tyuleniy virus group, Uganda S virus group and the Yellow Fever virus group. Apart from these major groups, there are some additional Flaviviruses that are unclassified.
2. Hepaciviruses. This genus contains only one species, the Hepatitis C virus (HCV), which is composed of many clades, types and subtypes.
3. Pestiviruses. This genus includes Bovine Viral Diarrhea Virus-2 (BVDV-2), Pestivirus type 1 (including BVDV), Pestivirus type 2 (including Hog Cholera Virus) and Pestivirus type 3 (including Border Disease Virus).

One of the most important Flaviviridae infections in humans is caused by the hepatitis C virus (HCV). This is the second major cause of viral hepatitis, with an estimated 170 million carriers world-wide (World Health Organization; Hepatitis C: global prevalence, *Weekly Epidemiological Record*, 1997, 72, 341), 3.9 million of whom reside in the United States (Centers for Disease Control; unpublished data, http://www.cdc.gov/ncidod/diseases/hepatitis/heptab3.htm).

The genomic organization of the Flaviviridae share many common features. The hepatitis C virus (HCV) genome is often used as a model. HCV is a small, enveloped virus with a positive single-stranded RNA genome of ~9.6 kb within the nucleocapsid. The genome contains a single open reading frame (ORF) encoding a polyprotein of just over 3,000 amino acids, which is cleaved to generate the mature structural and nonstructural viral proteins. The ORF is flanked by 5' and 3' non-translated regions (NTRs) of a few hundred nucleotides in length, which are important for RNA translation and replication. The translated polyprotein contains the structural core (C) and envelope proteins (E1, E2, p7) at the N-terminus, followed by the nonstructural proteins (NS2, NS3, NS4A, NS4B, NS5A, NS5B). The mature structural proteins are generated via cleavage by the host signal peptidase (see: Hijikata, M. et al. *Proc. Nat. Acad. Sci., USA,* 1991, 88, 5547; Hussy, P. et al. *Virology,* 1996, 224, 93; Lin, C. et al. *J. Virol.,* 1994, 68, 5063; Mizushima, H. et al. *J. Virol.,* 1994, 68, 2731; Mizushima, H. et al. *J. Virol.,* 1994, 68, 6215; Santolini, E. et al. *J. Virol,* 1994, 68, 3631; Selby, M. J. et al. *Virology,* 1994, 204, 114; and Grakoui, A. et al., *Proc. Nat. Acad. Sci., USA,* 1993, 90, 10538). The junction between NS2 and NS3 is autocatalytically cleaved by the NS2/NS3 protease (see: Hijikata, M. et al. *J. Virol.,* 1993, 67, 4665 and Bartenschlager, R. et al. *J. Virol.,* 1994, 68, 5045), while the remaining four junctions are cleaved by the N-terminal serine protease domain of NS3 complexed with NS4A. (see: Failla, C. et al. *J. Virol.,* 1994, 68, 3753; Lin, C. et al. *J. Virol.,* 1994, 68, 8147; Tanji, Y. et al. *J. Virol.,* 1995, 69, 1575 and Tai, C. L. et al. *J. Virol.,* 1996, 70, 8477) The NS3 protein also contains the NTP-dependent helicase activity which unwinds duplex RNA during replication. The NS5B protein possesses RNA-dependent RNA polymerase (RDRP) activity (see: Behrens, S. E. et al. *EMBO J.,* 1996, 15, 12; Lohmann, V. et al. *J. Virol.,* 1997, 71, 8416-8428 and Lohmann, V. et al. *Virology,* 1998, 249, 108), which is essential for viral replication. (Ferrari, E. et al. *J. Virol.,* 1999, 73, 1649) It is emphasized here that, unlike HBV or HIV, no DNA is involved in the replication of HCV. Recently in vitro experiments using NS5B, substrate specificity for HCV-RDRP was studied using guanosine 5'-monophosphate (GMP), 5'-diphosphate (GDP), 5'-triphosphate (GTP) and the 5'-triphosphate of 2'-deoxy and 2',3'-dideoxy guanosine (dGTP and ddGTP, respectively). The authors claimed that HCV-RDRP has a strict specificity for ribonucleoside 5'-triphosphates and requires the 2'- and 3'-OH groups. (Lohmann; *Virology,* 108) Their experiments suggest that the presence of 2'- and 3'-substituents would be the prerequisite for nucleoside 5'-triphosphates to interact with HCV-RDRP and to act as substrates or inhibitors.

Examples of antiviral agents that have been identified as active against the hepatitis C flavivirus include:
1. Interferon and ribavirin (Battaglia, A. M. et al. *Ann. Pharmacother.* 2000, 34, 487; Berenguer, M. et al. *Antivir. Ther.* 1998, 3 (Suppl. 3), 125);
2. Substrate-based NS3 protease inhibitors (Attwood et al. PCT WO 98/22496, 1998; Attwood et al. *Antiviral Chemistry and Chemotherapy* 1999, 10, 259; Attwood et al. German Patent Publication DE 19914474; Tung et al. PCT WO 98/17679), including alphaketoamides and hydrazinoureas, and inhibitors that terminate in an electrophile such as a boronic acid or phosphonate (Llinas-Brunet et. al. PCT WO 99/07734);
3. Non-substrate-based inhibitors such as 2,4,6-trihydroxy-3-nitro-benzamide derivatives (Sudo K. et al., *Biochemical and Biophysical Research Communications*, 1997, 238, 643 and Sudo K. et al. *Antiviral Chemistry and Chemotherapy* 1998, 9, 186), including RD3-4082 and RD3-4078, the former substituted on the amide with a 14 carbon chain and the latter processing a para-phenoxyphenyl group;
4. Thiazolidine derivatives which show relevant inhibition in a reverse-phase HPLC assay with an NS3/4A fusion protein and NS5A/5B substrate (Sudo K. et al. *Antiviral Research* 1996, 32, 9), especially compound RD-1-6250, possessing a fused cinnamoyl moiety substituted with a long alkyl chain, RD4 6205 and RD4 6193;
5. Thiazolidines and benzanilides identified in Kakiuchi N. et al. *J. EBS Letters* 421, 217 and Takeshita N. et al. *Analytical Biochemistry* 1997, 247, 242;
6. A phenanthrenequinone possessing activity against HCV protease in a SDS-PAGE and autoradiography assay isolated from the fermentation culture broth of *Streptomyces* sp., Sch 68631 (Chu M. et al. *Tetrahedron Letters* 1996, 37, 7229), and Sch 351633, isolated from the fungus *Penicillium griscofuluum*, which demonstrates activity in a scintillation proximity assay (Chu M. et al., *Bioorganic and Medicinal Chemistry Letters* 9, 1949);
7. Selective NS3 inhibitors based on the macromolecule elgin c, isolated from leech (Qasim M. A. et al. *Biochemistry* 1997, 36, 1598);
8. HCV helicase inhibitors (Diana G. D. et al., U.S. Pat. No. 5,633,358 and Diana G. D. et al. PCT WO 97/36554);
9. HCV polymerase inhibitors such as nucleotide analogues, gliotoxin (Ferrari R. et al. *Journal of Virology* 1999, 73, 1649), and the natural product cerulenin (Lohmann V. et al. *Virology* 1998, 249, 108);
10. Antisense phosphorothioate oligodeoxynucleotides (S-ODN) complementary to at least a portion of a sequence of the HCV (Anderson et al. U.S. Pat. No. 6,174,868), and in particular the sequence stretches in the 5' non-coding region (NCR) (Alt M. et al. *Hepatology* 1995, 22, 707), or nucleotides 326-348 comprising the 3' end of the NCR and nucleotides 371-388 located in the core coding region of the HCV RNA (Alt M. et al. *Archives of Virology* 1997, 142, 589 and Galderisi U. et al., *Journal of Cellular Physiology* 1999, 81:2151);
11. Inhibitors of IRES-dependent translation (Ikeda N et al., Japanese Patent Pub. JP-08268890; Kai Y. et al. Japanese Patent Publication JP-10101591);
12. Nuclease-resistant ribozymes (Maccjak D. J. et al., *Hepatology* 1999, 30, abstract 995);
13. Amantadine, such as rimantadine (Smith, Abstract from Annual Meeting of the American Gastoenterological Association and AASLD, 1996);
14. Quinolones, such as ofloxacin, ciprofloxacin and levofloxacin (AASLD Abstracts, Hepatology, October 1994, Program Issue, 20 (4), pt. 2, abstract no. 293);
15. Nucleoside analogs (Ismaili et al. WO 01/60315; Storer WO 32153), including 2'-deoxy-L-nucleosides (Watanabe et al. WO 01/34618), and 1-(β-L-ribofuranosyl)-1,2,4-tri azole-3-carboxamide (Levovirin™) (Tam WO 01/46212); and 16. Other miscellaneous compounds including 1-aminoalkylcyclohexanes (Gold et al. U.S. Pat. No. 6,034,134), alkyl lipids (Chojkier et al. U.S. Pat. No. 5,922,757), vitamin E and other antioxidants (Chojkier et al. U.S. Pat. No. 5,922,757), squalene, bile acids (Ozeki et al. U.S. Pat. No. 5,846,964), N-(phosphonoacetyl)-L-aspartic acid, (Diana et al. U.S. Pat. No. 5,830,905), benzenedicarboxamides (Diana et al. U.S. Pat. No. 5,633,388), polyadenylic acid derivatives (Wang et al. U.S. Pat. No. 5,496,546), 2',3'-dideoxyinosine (Yarchoan et al. U.S. Pat. No. 5,026,687), benzimidazoles (Colacino et al. U.S. Pat. No. 5,891,874), glucamines (Mueller et al. WO 01/08672), substituted-1,5-imino-D-glucitol compounds (Mueller et al. WO 00/47198).

Orthomyxoviridae

The Orthomyxoviridae is a group of segmented negative single-stranded RNA viruses with a genome size from 10-13.6 kb. They are enveloped viruses of approximately 80-120 nm. An overview of the Orthomyxoviridae taxonomy is available from the International Committee for Taxonomy of Viruses. The Orthomyxoviridae consists of three genera, which can be distinguished on the basis of antigenic differences between their nucleocapsid (NP) and matrix proteins (M).

1. Influenzavirus A, B. This genus contains influenza A and B viruses each of which contain eight distinct RNA segments. Influenza B viruses show little variability in their surface glycoproteins and only infect humans. On the other hand, influenza A viruses have great variability in their surface glycoproteins of influenza A viruses, and they can be divided into subtypes based on the antigenic nature of their hemagglutinin (HA) and neuroamidase (NA) glycoproteins and infect humans as well as swine, horses, seals, fowl, ducks and many other species of birds.

2. Influenzavirus C. This genus contains only one species, influenza C, which contains only seven distinct RNA segments. Influenza C only has a single multifunctional glycoprotein and infects mainly humans, but has also been isolated from swine in China.

3. Influenzavirus D. This genus contains influenza D, which is solely tick-borne viruses that are structurally and genetically similar to influenza A, B and C.

One of the most important Orthomyxoviridae infections in humans is caused by the influenza A virus. These viruses are highly contagious and cause acute respiratory illness that has plagued society in epidemic proportions since ancient times. One of the earliest recordings of an influenza A epidemic can be traced to Hippocrates in 412 BC. These epidemics are rather frequent and are often fatal to the elderly, however these epidemics are quite unpredictable. These viruses are unique respiratory tract viruses, in that they undergo significant antigenic variation. Both hemagglutinin (HA) and neuroamidase (NA) glycoproteins are capable of antigenic drifts and shifts. There are fourteen known hemagglutinin (H1-H14) glycoproteins and nine known neuroamidase (N1-N9) glycoproteins. For example, since the first human influenza virus was isolated in 1933, major antigenic shifts have occurred. In 1957, the H2N2 subtype (Asian influenza) replaced the H1N1 subtype (Spanish influenza). Currently, the primary subtypes of influenza are H1N1, which reappeared in 1977 and H3N2, which reappeared in 1968.

The vast majority of research on influenza virus gene expression and RNA replication has been carried out with the influenza A virus. The most striking feature of the influenza A virion is a layer of about 500 spikes radiating outward (10 to 14 nm) from the lipid envelope. These spikes are of two types: rod-shaped spikes of HA and mushroom-shaped spikes of NA. The ratio of HA and NA varies, but is usually 4-5 to 1. Each gene segment encodes its own proteins, with the exception of the seventh and eighth, which encodes $M_1$ and $M_2$, and $NS_1$ and $NS_2$ respectively. The first 12 nucleotides at the 3'-end and the first 13 nucleotides at the 5'-end of each vRNA segment are conserved in all eight RNA segments. The first gene to have its nucleotide sequence determined was HA. Since then, all 14 known HA antigenic subtypes and many variants within the subtypes have been determined.

In infected cells, the vRNAs are both transcribed into mRNAs and replicated. The synthesis of mRNA is distinct, in that the RNA is primed by 5' capped fragments derived from newly synthesized host-cell RNA polymerase II transcripts. The mRNA chain elongates until a stretch of uridine residues is reached 15-22 nucleotides before the 5'-ends of the vRNAs where transcription ends and polyadenylate is added to the mRNAs. For replication to occur, an alternative type of transcription is required that results in the production of full-length copies of the vRNAs. The full-length transcripts are initiated without a primer and are not terminated at the poly(A) site used during mRNA synthesis. The second step in replication is the copying of the template RNAs into vRNAs. This synthesis also occurs without a primer, since the vRNAs contain 5'-triphosphorylated ends. All three types of virus-specific RNAs mRNA, template RNA and vRNA—are synthesized in the nucleus.

Examples of antiviral agents that have been identified as active against the influenza A virus include:
1. Actinomycin D (Barry, R. D. et al. "Participation of deoxyribonucleic acid in the multiplication of influenza virus" *Nature*, 1962, 194, 1139-1140);
2. Amantadine (Van Voris, L. P. et al. "Antivirals for the chemoprophylaxis and treatment of influenza" *Semin Respir Infect*, 1992, 7, 61-70);
3. 4-Amino- or 4-guanidino-2-deoxy-2,3-didehydro-D-N-acetylneuroaminic acid-4-amino- or 4-guanidino-Neu 5 Ac2en (von Itzstein, M. et al. "Rational design of potent sialidase-based inhibitors of influenza virus replication" *Nature*, 1993, 363, 418-423);
4. Ribavirin (Van Voris, L. P. et al. "Antivirals for the chemoprophylaxis and treatment of influenza" *Semin Respir Infect*, 1992, 7, 61-70);
5. Interferon (Came, P. E. et al. "Antiviral activity of an interferon-inducing synthetic polymer" *Proc Soc Exp Biol Med*, 1969, 131, 443-446; Gerone, P. J. et al. "Inhibition of respiratory virus infections of mice with aeresols of synthetic double-stranded ribonucleic acid" *Infect Immun*, 1971, 3, 323-327; Takano, K. et al. "Passive interferon protection in mouse influenza" *J Infect Dis*, 1991, 164, 969-972);
6. Inactivated influenza A and B virus vaccines ("Clinical studies on influenza vaccine—1978" *Rev Infect Dis*, 1983, 5, 721-764; Galasso, G. T. et al. "Clinical studies on influenza vaccine—1976" *J Infect Dis*, 1977, 136 (suppl), S341-S746; Jennings, R. et al. "Responses of volunteers to inactivated influenza virus vaccines" *J Hyg*, 1981, 86, 1-16; Kilbourne, E. D. "Inactivated influenza vaccine" In: Plothin S A, Mortimer E A, eds. *Vaccines* Philadelphia: Saunders, 1988, 420-434; Meyer, H. M., Jr. et al. "Review of existion vaccines for influenza" *Am J Clin Pathol*, 1978, 70, 146-152; "Mortality and Morbidity Weekly Report. Prevention and control of Influenza: Part I, Vaccines. Recommendations of the Advisory Committee on Immunization Practices (ACIP)" *MMWR*, 1993, 42 (RR-6), 1-14; Palache, A. M. et al. "Antibody response after influenza immunization with various vaccine doses: A double-blind, placebo-controlled, multi-centre, dose-response study in elderly nursing-home residents and young volunteers" *Vaccine*, 1993, 11, 3-9; Potter, C. W. "Inactivated influenza virus vaccine" In: Beare A S, ed. *Basic and applied influenza research*, Boca Raton, Fla.: CRC Press, 1982, 119-158).

Paramyxoviridae

The Paramyxoviridae is a group of negative single-stranded RNA viruses with a genome size from 16-20 kb. They are enveloped viruses of approximately 150-300 nm. An overview of the Paramyxoviridae taxonomy is available from the International Committee for Taxonomy of Viruses. The Paramyxoviridae consists of two subfamilies.
1. Paramyxovirinae. This subfamily contains three genera:
    a) Paramyxovirus. This genus is represented by Sendai virus and including human parainfluenza viruses 1 and 3;
    b) Rubulavirus. This genus is represented by the mumps virus, simian virus 5, Newcastle disease virus and the human parainfluenza viruses 2 and 4;
    c) Morbillivirus. This genus is represented by the measles virus; and
2. Pneumovirinae. This subfamily encode a larger number of mRNAs than the other sub-family (ten, compared with six or seven) and contains only one genera:
    a) Pneumovirus. This genus is best represented by the respiratory syncytial virus (RSV), but also includes bovine (BRSV), ovine RSV (ORSC), caprine RSV (CRSV), pneumonia virus of mice (PVM) and turkey rhinotracheitis virus (TRTV).

One of the most important Pneumovirinae infections in humans is caused by the respiratory syncytial virus (RSV). RSV is the most important cause of viral lower respiratory tract disease in infants and children worldwide. In most areas, RSV outranks all other microbial pathogens as a cause of pneumonia and bronchiolitis in infants under one year of age. It has also been found that RSV infection is an important agent of disease in immunosuppressed adults and in the elderly. Additionally, BRSV has been shown to be an economically important disease in cattle.

The 3'-end of genomic RSV RNA consists of a 44-nucleotide extragenic leader region that is presumed to contain the major viral promoter. The leader region is followed by the ten viral genes, which is followed by a 155-nucleotide extragenic trailer region. Eighty eight percent of the genomic RNA is accounted for by the ORFs for the ten major proteins. Each gene begins with a conserved nine-nucleotide gene-start signal. For each gene, transcription begins at the first nucleotide of the signal. Each gene terminates with a semi-conserved 12 to 13 nucleotide gene-end signal that directs transcriptional termination and polyadenylation. The first nine genes are non-overlapping and are separated by intergenic regions that range in size from 1 to 52 nucleotides. The intergenic regions do not contain any conserved sequence motifs or any obvious features of secondary structure. The last two RSV genes overlap by 68 nucleotides. Thus, one of the gene-start signals is located inside of, rather than after the other gene.

Examples of antiviral agents that have been identified as active against RSV include:
1. Ribavirin (Hruska, J. F. et al. "In vivo inhibition of respiratory syncytial virus by ribavirin" *Antimicrob Agents Chemother*, 1982, 21, 125-130); and 2. Purified human intravenous IgG-IVIG (Prince, G. A. et al. "Effectiveness of topically administered neutralizing antibodies in experimental immunotherapy of respiratory syncytial virus infection in cotton rats" *J Virol*, 1987, 61, 1851-1954; Prince, G. A. et al. "Immunoprophylaxis and immunotherapy of respiratory syncytial virus infection in cotton rats" *Infect Immun*, 1982, 42, 81-87).

Abnormal Cellular Proliferation

Cellular differentiation, growth, function and death are regulated by a complex network of mechanisms at the molecular level in a multicellular organism. In the healthy animal or human, these mechanisms allow the cell to carry out its designed function and then die at a programmed rate.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Approximately 2% of the population in the United States have psoriasis, occurring in about 3% of Caucasian Americans, in about 1% of African Americans, and rarely in native Americans. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. *Nature*, 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr., *The New England Journal of Medicine*, 1990, 322: 1277-1289), and to be caused by autoantibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

A tumor, also called a neoplasm, is a new growth of tissue in which the multiplication of cells is uncontrolled and progressive. A benign tumor is one that lacks the properties of invasion and metastasis and is usually surrounded by a fibrous capsule. A malignant tumor (i.e., cancer) is one that is capable of both invasion and metastasis. Malignant tumors also show a greater degree of anaplasia (i.e., loss of differentiation of cells and of their orientation to one another and to their axial framework) than benign tumors.

Approximately 1.2 million Americans are diagnosed with cancer each year, 8,000 of which are children. In addition, 500,000 Americans die from cancer each year in the United States alone. Prostate and lung cancers are the leading causes of death in men while breast and lung cancer are the leading causes of death in women. It is estimated that cancer-related costs account for about 10 percent of the total amount spent on disease treatment in the United States (CNN.Cancer.Factshttp://www.cnn.com/HEALTH/9511/conquer_cancer/facts/index.html, page 2 of 2, Jul. 18, 1999).

Proliferative disorders are currently treated by a variety of classes of compounds including alkylating agents, antimetabolites, natural products, enzymes, biological response modifiers, miscellaneous agents, radiopharmaceuticals (for example, Y-90 tagged to hormones or antibodies), hormones and antagonists, such as those listed below.

Alkylating Agents

Nitrogen Mustards: Mechlorethamine (Hodgkin's disease, non-Hodgkin's lymphomas), Cyclophosphamide, Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphoctic leukemia, primary macroglobulinemia, Hodgkin's disease, non-Hodgkin's lymphomas).

Ethylenimines and Methylmelamines: Hexamethylmelamine (ovary), Thiotepa (bladder, breast, ovary).

Alkyl Sulfonates: Busulfan (chronic granuloytic leukemia).

Nitrosoureas: Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (STR) (malignant pancreatic insulinoma, malignant carcinoin).

Triazenes: Dacarbazine (DTIC; dimethyltriazenoimidazole-carboxamide) (malignant melanoma, Hodgkin's disease, soft-tissue sarcomas).

Antimetabolites

Folic Acid Analogs: Methotrexate (amethopterin) (acute lymphocytic leukemia, choriocarcinoma, mycosis fungoides, breast, head and neck, lung, osteogenic sarcoma).

Pyrimidine Analogs: Fluorouracil (5-fluorouracil; 5-FU) Floxuridine (fluorodeoxyuridine; FUdR) (breast, colon, stomach, pancreas, ovary, head and neck, urinary bladder, premalignant skin lesions) (topical), Cytarabine (cytosine arabinoside) (acute granulocytic and acute lymphocytic leukemias).

Purine Analogs and Related Inhibitors: Mercaptopurine (6-mercaptopurine; 6-MP) (acute lymphocytic, acute granulocytic and chronic granulocytic leukemia), Thioguanine (6-thioguanine: TG) (acute granulocytic, acute lymphocytic and chronic granulocytic leukemia), Pentostatin (2'-deoxycyoformycin) (hairy cell leukemia, mycosis fungoides, chronic lymphocytic leukemia).

Vinca Alkaloids: Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung).

Epipodophylotoxins: Etoposide (testis, small-cell lung and other lung, breast, Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

Natural Products

Antibiotics: Dactinomycin (actinonmycin D) (choriocarcinoma, Wilms' tumor rhabdomyosarcoma, testis, Kaposi's sarcoma), Daunorubicin (daunomycin; rubidomycin) (acute granulocytic and acute lymphocytic leukemias), Doxorubicin (soft tissue, osteogenic, and other sarcomas; Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcema), Mitomycin (mitomycin C) (stomach, cervix, colon, breast, pancreas, bladder, head and neck).

Enzymes: L-Asparaginase (acute lymphocytic leukemia).

Biological Response Modifiers: Interferon-alfa (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

Miscellaneous Agents

Platinum Coordination Complexes: Cisplatin (cis-DDP) Carboplatin (testis, ovary, bladder, head and neck, lung, thyroid, cervix, endometrium, neuroblastoma, osteogenic sarcoma).

Anthracenedione: Mixtozantrone (acute granulocytic leukemia, breast).

Substituted Urea: Hydroxyurea (chronic granulocytic leukemia, polycythemia vera, essential thrombocytosis, malignant melanoma).

Methylhydrazine Derivative: Procarbazine (N-methylhydrazine, MIH) (Hodgkin's disease).

Adrenocortical Suppressant: Mitotane (o,p'-DDD) (adrenal cortex), Amino-glutethimide (breast).

Adrenorticosteriods: Prednisone (acute and chronic lymphocytic leukemias, non-Hodgkin's lymphomas, Hodgkin's disease, breast).

Progestins: Hydroxprogesterone caproate, Medroxyprogesterone acetate, Megestrol acetate (endometrium, breast).

Anti-Angiogenesis Agents

Angiostatin, Endostatin.

Hormones and Antagonists

Estrogens: Diethylstibestrol Ethinyl estradiol (breast, prostate)

Antiestrogen: Tamoxifen (breast).

Androgens: Testosterone propionate Fluxomyesterone (breast).

Antiandrogen: Flutamide (prostate).

Gonadotropin-Releasing Hormone Analog: Leuprolide (prostate).

Toxicity associated with therapy for abnormally proliferating cells, including cancer, is due in part to a lack of selectivity of the drug for diseased versus normal cells. To overcome this limitation, therapeutic strategies that increase the specificity and thus reduce the toxicity of drugs for the treatment of proliferative disorders are being explored. One such strategy that is being aggressively pursued is drug targeting.

In view of the severity of these diseases and their pervasiveness in animals, including humans, it is an object of the present invention to provide a compound, method and composition for the treatment of a host, including animals and especially humans, infected with any of the viruses described above, including flavivirus or pestivirus, influenza virus or Respiratory Syncytial Virus ("RSV").

It is another object of the present invention to provide a method and composition for the treatment of a host, including animals and especially humans, with abnormal cellular proliferation.

It is a further object to provide a method and composition for the treatment of a host, including animals and especially humans, infected with hepatitis C or BVDV.

It is a further object to provide a method and composition for the treatment of a host, including animals and especially humans, infected with influenza.

It is a further object to provide a method and composition for the treatment of a host, including animals and especially humans, infected with RSV.

It is a further object to provide a method and composition for the treatment of a host, including animals and especially humans, with a tumor, including a malignant tumor.

It is yet another object of the present invention to provide a more effective process to quantify viral load, and in particular of BVDV or HCV load, in a host, including animals, especially humans.

SUMMARY OF THE INVENTION

The present invention provides a β-D or β-L nucleoside of formula (I)-(XXIII) or its pharmaceutically acceptable salt or prodrug for the treatment of a host infected with a virus belonging to the Flaviviridae, Orthomyxoviridae and Paramyxoviridae family. Alternatively, the β-D or β-L nucleoside (I)-(XXIII) or its pharmaceutically acceptable salt or prodrug can be used for the treatment of abnormal cellular proliferation.

Specifically, the invention also includes methods for treating or preventing the following:

(a) a Flaviviridae infection, including all members of the Hepacivirus genus (HCV), Pestivirus genus (BVDV, CSFV, BDV), or Flavivirus genus (Dengue virus, Japanese encephalitis virus group (including West Nile Virus), and Yellow Fever virus);

(b) an Orthomyxoviridae infection, including all members of the Influenza A, B genus, in particular influenza A and all relevant subtypes—including H1N1 and H3N2—and Influenza B;

(c) a Paramyxoviridae infection including Respiratory Syncytial Virus (RSV) infection; and (d) abnormal cellular proliferation, including malignant tumors.

In one embodiment, the anti-virally or anti-proliferatively effective nucleoside is a β-D nucleoside of the general formula (I) or (II):

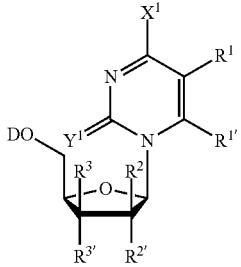
[I-a]

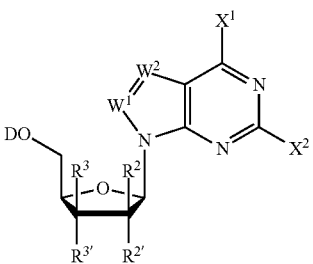
[I-b]

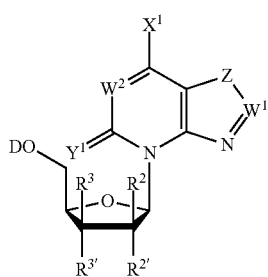
[I-c]

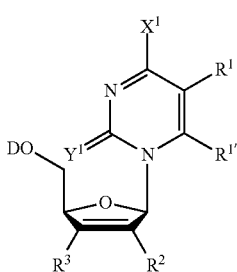
[II-a]

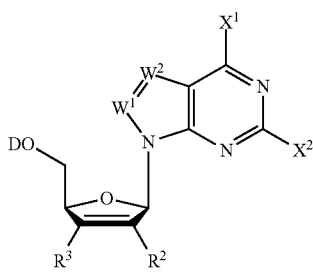
[II-b]

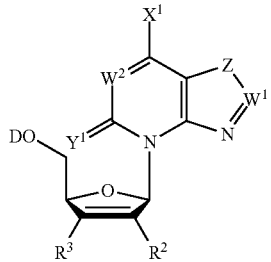
[II-c]

or its pharmaceutically acceptable salt or prodrug thereof, wherein:

each D is hydrogen, alkyl, acyl, monophosphate, diphosphate, triphosphate, monophosphate ester, diphosphate ester, triphosphate ester, phospholipid or amino acid;

each $W^1$ and $W^2$ is independently CH or N;

each $X^1$ and $X^2$ is independently hydrogen, halogen (F, Cl, Br or I), $NH_2$, $NHR^4$, $NR^4R^{4'}$, $NHOR^4$, $NR^4NR^{4'}R^{4''}$, OH, $OR^4$, SH or $SR^4$;

each $Y^1$ is O, S or Se;

each Z is $CH_2$ or NH;

each $R^1$ and $R^{1'}$ is independently hydrogen, lower alkyl, lower alkenyl, lower alkynyl, aryl, alkylaryl, halogen (F, Cl, Br or I), $NH_2$, $NHR^5$, $NR^5R^{5'}$, $NHOR^5$, $NR^5NHR^{5'}$, $NR^5NR^{5'}R^{5''}$, OH, $OR^5$, SH, $SR^5$, $NO_2$, NO, $CH_2OH$, $CH_2OR^5$, $CO_2H$, $CO_2R^5$, $CONH_2$, $CONHR^5$, $CONR^5R^{5'}$ or CN;

each $R^2$ and $R^{2'}$ independently is hydrogen or halogen (F, Cl, Br or I), OH, SH, $OCH_3$, $SCH_3$, $NH_2$, $NHCH_3$, $CH=CH_2$, CN, $CH_2NH_2$, $CH_2OH$, $CO_2H$.

each $R^3$ and $R^{3'}$ independently is hydrogen or halogen (F, Cl, Br or I), OH, SH, $OCH_3$, $SCH_3$, $NH_2$, $NHCH_3$, $CH_3$, $C_2H_3$, $CH=CH_2$, CN, $CH_2NH_2$, $CH_2OH$, $CO_2H$.

each $R^4$, $R^{4'}$, $R^{4''}$, $R^5$, $R^{5'}$ and $R^{5''}$ independently is hydrogen, lower alkyl, lower alkenyl, aryl, or arylalkyl such as unsubstituted or substituted phenyl or benzyl;

such that for each nucleoside of the general formula (I) or (II), at least one of $R^2$ and $R^{2'}$ is hydrogen and at least one of $R^3$ and $R^{3'}$ is hydrogen.

In another embodiment of the invention, anti-virally or anti-proliferatively effective nucleoside is a β-L nucleoside of the general formula (III) or (IV):

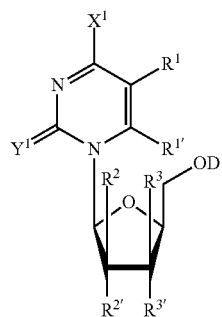
[III-a]

-continued

[III-b]

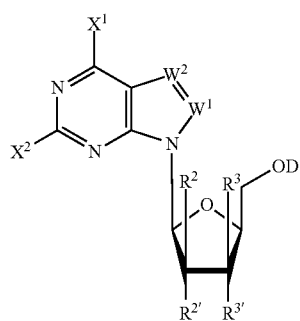

[III-c]

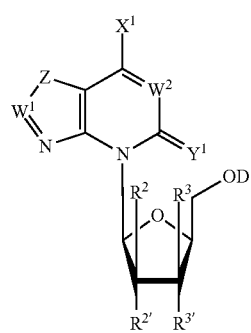

[IV-a]

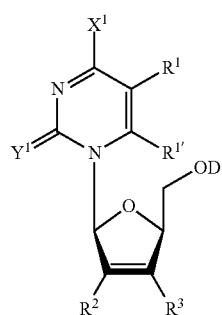

[IV-b]

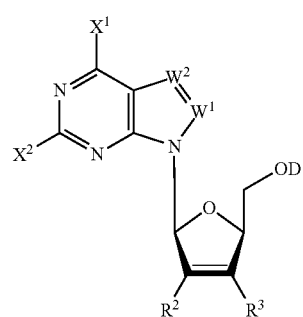

[IV-c]

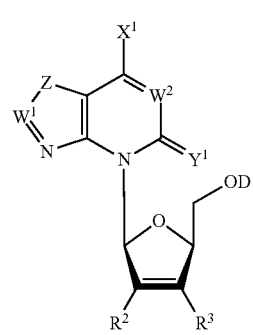

or its pharmaceutically acceptable salt or prodrug thereof, wherein:

each D, $W^1$, $W^2$, $X^1$, $X^2$, $Y^1$, Z, $R^1$, $R^{1'}$, $R^2$, $R^{2'}$, $R^3$ and $R^{3'}$ is the same as defined previously;

such that for each nucleoside of the general formula (III) or (IV), at least one of $R^2$ and $R^{2'}$ is hydrogen and at least one of $R^3$ and $R^{3'}$ is hydrogen.

In one embodiment of the invention, the anti-virally or anti-proliferatively effective nucleoside is a β-D-carba-sugar nucleoside of the general formula (V) to (VII):

-continued

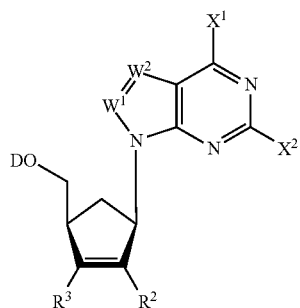
[VI-b]

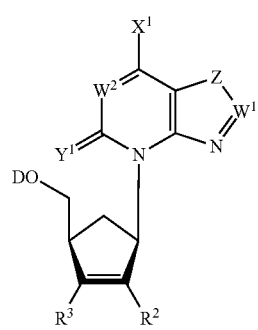
[VI-c]

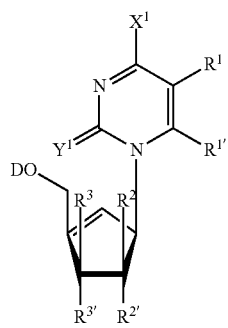
[VII-a]

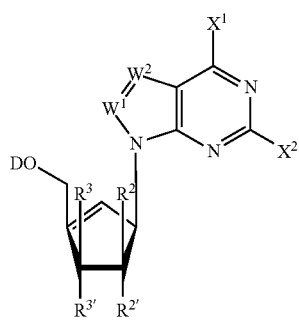
[VII-b]

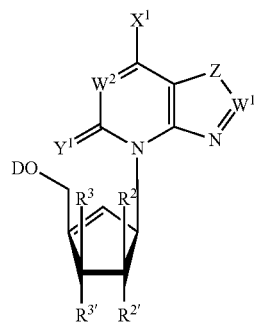
[VII-c]

or its pharmaceutically acceptable salt or prodrug thereof, wherein:

each D, $W^1$, $W^2$, $X^1$, $X^2$, $Y^1$, Z, $R^1$, $R^{1'}$, $R^2$, $R^{2'}$, $R^3$ and $R^{3'}$ is the same as defined previously;

such that for each nucleoside of the general formula (V) or (VI), at least one of $R^2$ and $R^{2'}$ is hydrogen and at least one of $R^3$ and $R^{3'}$ is hydrogen.

In one embodiment, anti-virally or anti-proliferatively effective nucleoside is a β-L-carba-sugar nucleoside of the general formula (VIII) to (X):

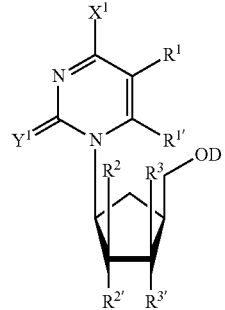
[VIII-a]

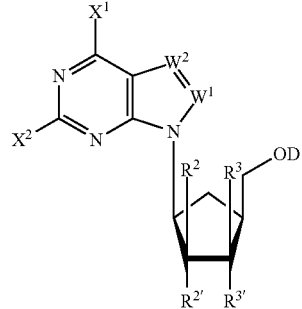
[VIII-b]

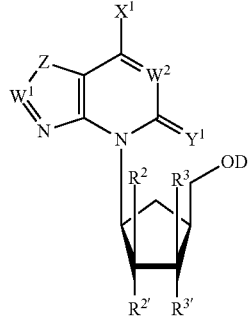
[VIII-c]

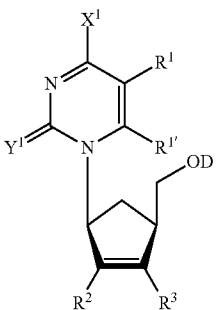
[IX-a]

-continued

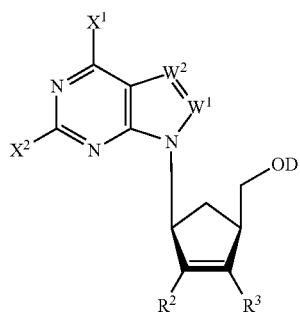
[IX-b]

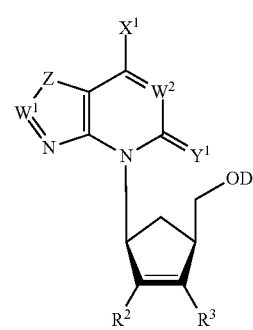
[IX-c]

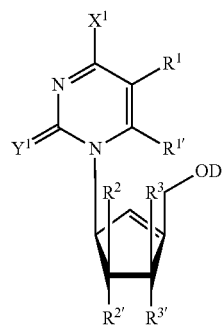
[X-a]

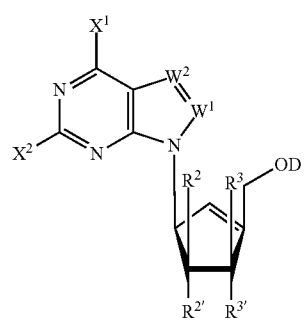
[X-b]

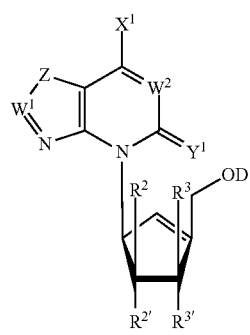
[X-c]

or its pharmaceutically acceptable salt or prodrug thereof, wherein:

each D, $W^1$, $W^2$, $X^1$, $X^2$, $Y^1$, Z, $R^1$, $R^{1'}$, $R^2$, $R_{2'}$, $R^3$ and $R^{3'}$ is the same as defined previously;

such that for each nucleoside of the general formula (VIII) or (IX), at least one of $R^2$ and $R^{2'}$ is hydrogen and at least one of $R^3$ and $R^{3'}$ is hydrogen.

In further embodiment of the invention, the anti-virally or anti-proliferatively effective β-D or β-L-nucleoside is of the general formula (XI) or (XII), respectively:

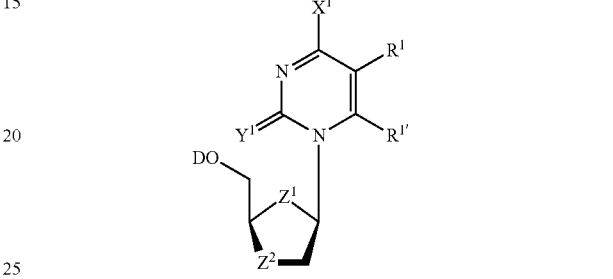
[XI-a]

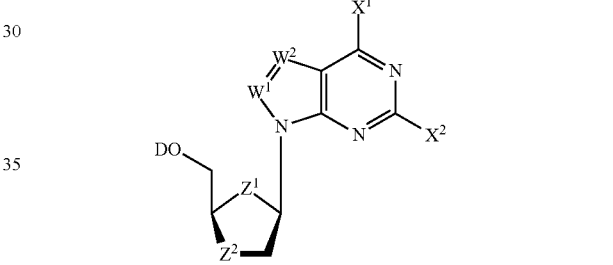
[XI-b]

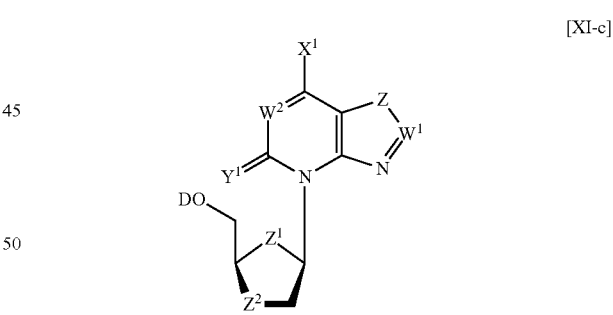
[XI-c]

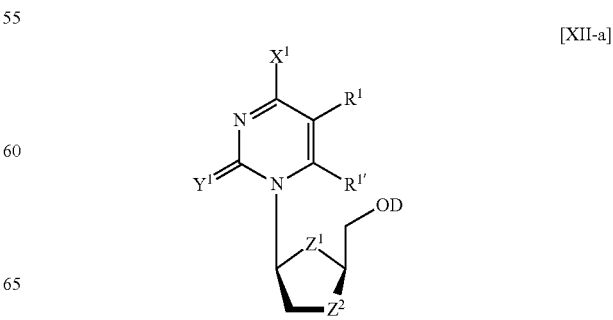
[XII-a]

-continued

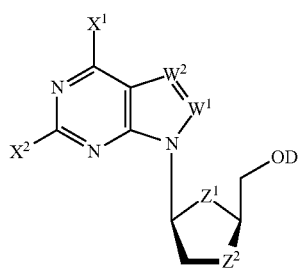
[XII-b]

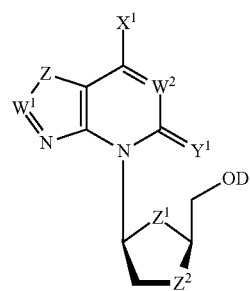
[XII-c]

or its pharmaceutically acceptable salt or prodrug thereof, wherein:

each D, $W^1$, $W^2$, $X^1$, $X^2$, Z, $R^1$, $R^{1'}$, $R^2$, $R^{2'}$, $R^3$ and $R^{3'}$ is the same as defined previously;

each $Z^1$ and $Z^2$ independently is O, S, $CH_2$, $NR^6$ or Se;

each $R^6$ is hydrogen, lower alkyl or lower acyl.

In a further embodiment of this invention, the anti-virally or anti-proliferatively effective β-D or β-L-nucleoside, though preferably β-D, is of the general formula (XIII):

[XIII-a]

[XIII-b]

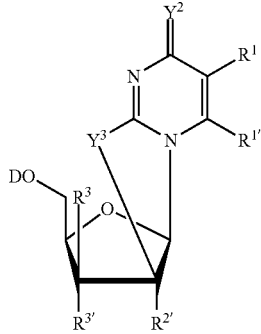
[XIII-c]

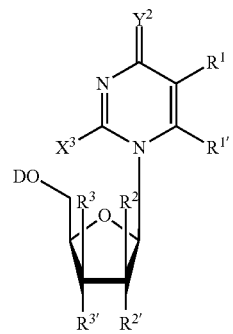
[XIII-d]

or its pharmaceutically acceptable salt or prodrug thereof, wherein:

each D, $R^1$, $R^{1'}$, $R^2$, $R^{2'}$, $R^3$ and $R^{3'}$ is the same as defined previously;

each $Y^2$ is O, S, NH or $NR^7$;

each $Y^3$ is O, S, NH or $NR^8$;

each $X^3$ is $OR^9$ or $SR^9$; and each $R^7$, $R^8$ and $R^9$ is hydrogen, lower alkyl of $C_1$-$C_6$, arylalkyl or aryl;

such that for each nucleoside of the general formula (XIII-d), at least one of $R^2$ and $R^{2'}$ is hydrogen and at least one of $R^3$ and $R^{3'}$ is hydrogen.

In another embodiment, the anti-virally or anti-proliferatively effective compound is a β-D or β-L-nucleoside, though preferably β-D, resulting from the addition of a small molecule, such as alkyl hypochlorite, alkyl hypobromite, hypobromous acid or acyl halide to an appropriate pyrimidine nucleoside, forming a nucleoside of the formula (XIV):

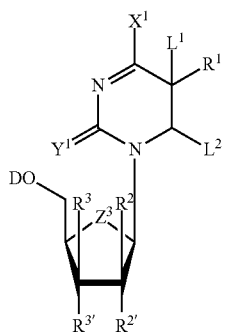
[XIV]

or its pharmaceutically acceptable salt or prodrug thereof, wherein:

each D, $X^1$, $Y^1$, $Z^1$, $R^1$, $R^2$, $R^{2'}$, $R^3$ and $R^{3'}$ is the same as defined previously;

each $L^1$ is hydrogen, Cl or Br,
each $L^2$ is OH, $OCH_3$, $OC_2H_5$, $OC_3H_7$, $OCF_3$, OAc or OBz;
each $Z^3$ can be O or $CH_2$.

In another embodiment, the anti-virally or anti-proliferatively effective nucleoside is a dimeric nucleoside (each nucleoside being in either the β-D or β-L configuration) of general formula (XV), in which the two nucleosides are linked through a disulfide bond:

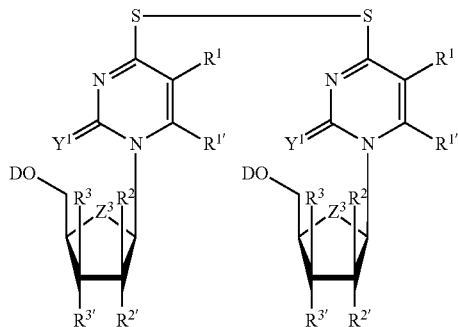

[XV-a]

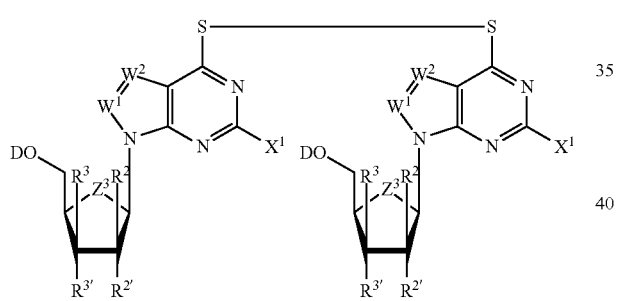

[XV-b]

or its pharmaceutically acceptable salt or prodrug thereof, wherein:

each D, $W^1$, $W^2$, $Y^1$, $Z^3$, $R^1$, $R^{1'}$, $R^2$, $R^{2'}$, $R^3$ and $R^{3'}$ is the same as defined previously.

In one embodiment, the anti-virally or anti-proliferatively effective nucleoside is a β-D or β-L C-nucleoside of the general formula (XVI):

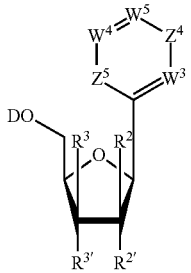

[XVI-a]

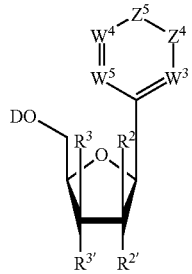

[XVI-b]

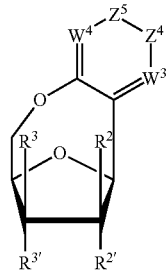

[XVI-c]

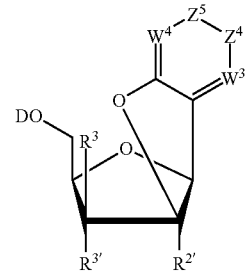

[XVI-d]

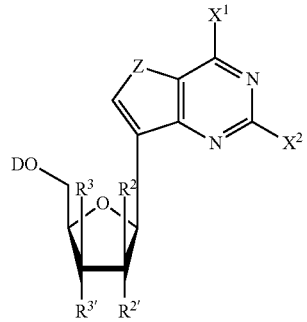

[XVI-e]

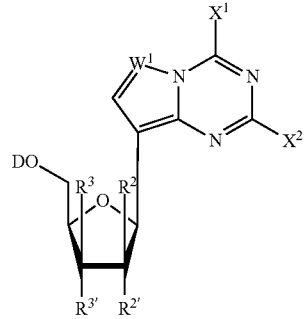

[XVI-f]

or its pharmaceutically acceptable salt or prodrug thereof, wherein:

each D, $W^1$, $X^1$, $X^2$, $Y^1$, Z, $R^1$, $R^2$, $R^{2'}$, $R^3$ and $R^{3'}$ is the same as defined previously;

each $W^3$ is independently N, CH or $CR^1$;

each $W^4$ and $W^5$ is independently N, CH, $CX^1$ or $CR^{1'}$; and
each $Z^4$ and $Z^5$ is independently NH or $C(=Y^1)$;
such that if e and $Z^5$ are covalently bound, then $Z^4$ is not $C(=Y^1)$ when $Z^5$ is $C(=Y^1)$; and
there are no more than three ring nitrogens.

In one embodiment, the anti-virally or anti-proliferatively effective nucleoside is a β-D or β-L-branched-chain sugar nucleoside of the general formula (XVII):

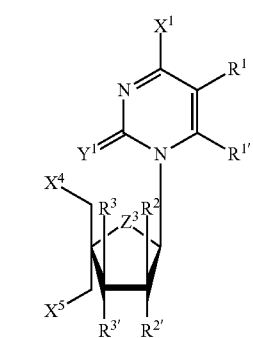
[XVII-a]

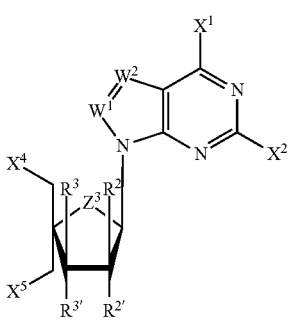
[XVII-b]

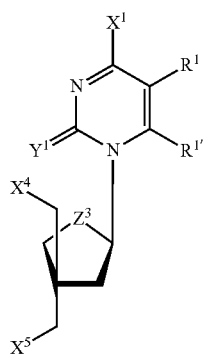
[XVII-c]

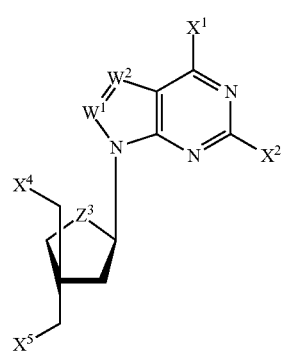
[XVII-d]

or its pharmaceutically acceptable salt or prodrug thereof, wherein:

each D, $W^1$, $W^2$, $X^1$, $X^2$, $Y^1$, $Z^3$, $R^1$, $R^{1'}$, $R^2$, $R^{2'}$, $R^3$ and $R^{3'}$ is the same as defined previously;
each $X^4$ and $X^5$ is independently hydrogen, halogen (F, Cl, Br or I), $N_3$, $NH_2$, $NHR^8$, $NR^8R^{8'}$, OH, $OR^8$, SH or $SR^8$; and
each $R^8$ and $R^{8'}$ is independently hydrogen, lower alkyl, lower alkenyl, aryl or arylalkyl, such as an unsubstituted or substituted phenyl or benzyl;
such that for each nucleoside of the general formula (XVII-a) or (XVII-b), $X^4$ is not OH or $OR^8$.

In one embodiment, the anti-virally or anti-proliferatively effective nucleoside is a α-D or α-L-nucleoside of the general formula (XVIII):

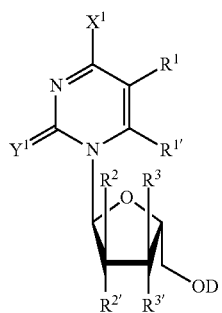
[XVIII-a]

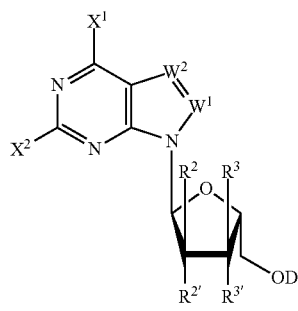
[XVIII-b]

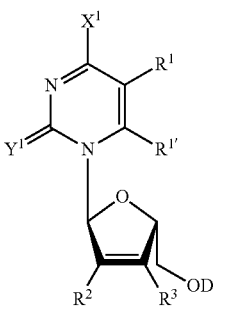
[XVIII-c]

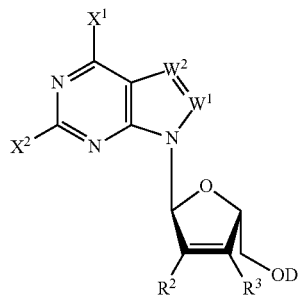
[XVIII-d]

or its pharmaceutically acceptable salt or prodrug thereof, wherein:

each D, $W^1$, $W^2$, $X^1$, $X^2$, $Y^1$, $R^1$, $R^{1'}$, $R^2$, $R^{2'}$, $R^3$ and $R^{3'}$ is the same as defined previously;

In a sub-embodiment of the present invention, the anti-virally or anti-proliferatively effective β-D or β-L nucleoside is of the formula (XIX):

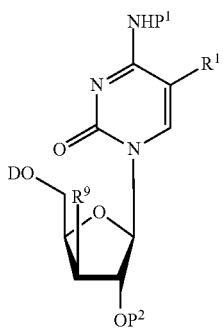

[XIX]

or its pharmaceutically acceptable salt or prodrug thereof, wherein:

each D, $R^1$, $R^4$ and $R^{4'}$ is the same as defined previously;

each $R^9$ is hydrogen, halogen (F, Cl, Br or I) or $OP^3$;

each $P^1$ is hydrogen, lower alkyl, lower alkenyl, aryl, arylalkyl (such as an unsubstituted or substituted phenyl or benzyl), OH, $OR^4$, $NH_2$, $NHR^4$ or $NR^4R^{4'}$; and each $P^2$ and $P^3$ is independently hydrogen, alkyl, acyl, -Ms, -Ts, monophosphate, diphosphate, triphosphate, mono-phosphate ester, diphosphate ester, triphosphate ester, phospholipid or amino acid, though preferably hydrogen.

In a particular sub-embodiment of the present invention, the anti-virally or anti-proliferatively effective β-D or β-L nucleoside of the formula (XIX) is the following:

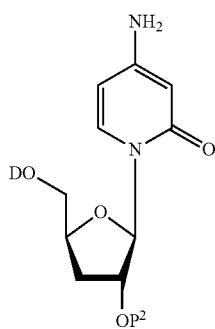

or its pharmaceutically acceptable salt or prodrug thereof, wherein:

each D and $P^2$ is the same as defined previously. In a preferred embodiment, D and $P^2$ are independently hydrogen.

In another sub-embodiment of the present invention, the anti-virally or anti-proliferatively effective β-D or β-L nucleoside is of the formula (XX):

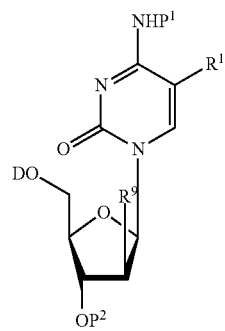

[XX]

or its pharmaceutically acceptable salt or prodrug thereof, wherein:

each D, $P^1$, $P^2$, $P^3$, $R^1$, $R^4$, $R^{4'}$ and $R^9$ is the same as defined previously.

In another sub-embodiment of the present invention, the anti-virally or anti-proliferatively effective β-D or β-L nucleoside is of the formula (XXI):

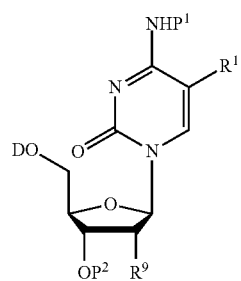

[XXI]

or its pharmaceutically acceptable salt or prodrug thereof, wherein:

each D, $P^1$, $P^2$, $P^3$, $R^1$, $R^4$ and $R^{4'}$ is the same as defined previously.

In a particular sub-embodiment of the present invention, the anti-virally or anti-proliferatively effective β-D or β-L nucleoside of the formula (XXI) is the following:

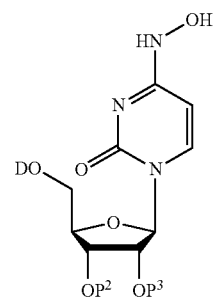

or its pharmaceutically acceptable salt or prodrug thereof, wherein:

each D, $P^2$ and $P^3$ is the same as defined previously. In a preferred embodiment, D, $P^2$ and $P^3$ are independently hydrogen.

In another sub-embodiment of the present invention, the anti-virally or anti-proliferatively effective β-D or β-L nucleoside is of the formula (XXII):

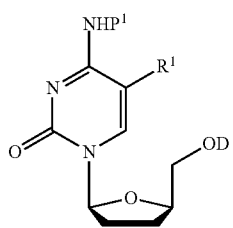

[XXII]

or its pharmaceutically acceptable salt or prodrug thereof, wherein:

each D, $P^1$ and $R^1$ is the same as defined previously. In a preferred embodiment, D and $P^2$ are independently hydrogen.

In a particular sub-embodiment of the present invention, the anti-virally or anti-proliferatively effective β-D or β-L nucleoside, though preferably β-L, of the formula (XXII) is the following:

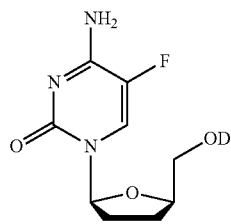

or its pharmaceutically acceptable salt or prodrug thereof, wherein:

D is the same as defined previously, and preferably H.

In another sub-embodiment of the present invention, the anti-virally or anti-proliferatively effective β-D or β-L nucleoside is of the formula (XXIII):

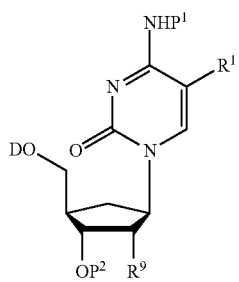

[XXIII]

or its pharmaceutically acceptable salt or prodrug thereof, wherein:

each D, $P^1$, $P^2$, $P^3$, $R^1$, $R^4$ and $R^{4'}$ is the same as defined previously.

In a particular sub-embodiment of the present invention, the anti-virally or anti-proliferatively effective β-D or β-L nucleoside of the formula (XXIII) is the following:

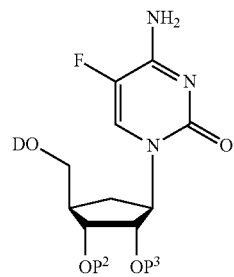

or its pharmaceutically acceptable salt or prodrug thereof, wherein:

each D, $P^2$ and $P^3$ is the same as defined previously. In a preferred embodiment, D, $P^2$ and $P^3$ are independently hydrogen.

In one embodiment, the nucleoside has an $EC_{50}$ (effective concentration to achieve 50% viral inhibition) when tested in an appropriate cell-based assay, of less than 15 micromolar, and more particularly, less than 10 or 5 micromolar. In a preferred embodiment, the nucleoside is enantiomerically enriched.

The present invention also includes at least the following features:

(a) use of a β-D nucleoside or β-L nucleoside of formula (I)-(XXIII), as described herein, or its pharmaceutically acceptable salt or prodrug thereof in a medical therapy, i.e. as an antiviral or antitumor/anticancer agent, for example for the treatment or prophylaxis of a Flaviviridae infections, including hepatitis C infection;

(b) use of a β-D nucleoside or β-L nucleoside of formula (I)-(XXIII), as described herein, or its pharmaceutically acceptable salt or prodrug thereof in the manufacture of a medicament for treatment of a Flaviviridae infection, including hepatitis C infection;

(c) a pharmaceutical composition that include an antivirally effective amount of a β-D nucleoside or β-L nucleoside of formula (I)-(XXIII), as described herein, or its pharmaceutically acceptable salt or prodrug thereof together with a pharmaceutically acceptable carrier or diluent according to the present invention;

(d) a pharmaceutical composition with a β-D nucleoside or β-L nucleoside of formula (I)-(XXIII), as described herein, or its pharmaceutically acceptable salt or prodrug thereof in combination with one or more other antivirally effective agents; and (e) process for the preparation of β-D nucleoside or β-L nucleoside of formula (I)-(XXIII), as described herein, and their pharmaceutically acceptable salts and prodrugs thereof.

The activity and toxicity of the compounds described herein can be evaluated according to any known procedure. An efficient process to quantify the viral load in a host using real-time polymerase chain reaction ("RT-PCR") is provided below. The process involves the use of a quenched fluorescent probe molecule, which can be hybridized to the target viral DNA or RNA. Upon exonucleolytic degradation, a detectable fluorescent signal can be monitored. Using this technique, the RT-PCR amplified DNA or RNA can be detected in real time by monitoring the presence of fluorescence signals.

This specification demonstrates:

(a) a process to quantitate viral load in real time using RT-PCR, as described herein;

(b) a process to quantitate viral load of a Flaviviridae in a host, including BVDV and HCV, in a host in real time using the RT-PCR, as described herein;
(c) a process to quantitate viral load of BVDV in a MDBK cell line or a host sample in real time using the RT-PCR, as described herein;
(d) a probe molecule designed to fluoresce upon exonucleolytic degradation and to be complementary to the BVDV NADL NS5B region, as described herein; and
(e) a probe molecule with a sequence of 5'-6-fam-AAATC-CTCCTAACAAGCGGGTTCCAGG-tamara-3' (Sequence ID No 1) and primers with a sequence of sense: 5'-AGCCTTCAGTTTCTTGCTGATGT-3'(Sequence ID No 2) and antisense: 5'-TGTTGCGAAAGCAC-CAACAG-3' (Sequence ID No 3);
(f) a process to quantitate viral load of HCV in a host derived sample or a cell line in real time using the RT-PCR, as described herein;
(g) a probe molecule designed to fluoresce upon exonucleolytic degradation and to be complementary to the HCV 5'-uncoding region, as described herein; and
(h) a probe molecule designed to fluoresce upon exonucleolytic degradation and to be complementary to the HCV coding region, as described herein; and
(i) a probe molecule designed to fluoresce upon exonucleolytic degradation and to be complementary to the HCV 3'-uncoding region, as described herein; and
(j) a probe molecule with a sequence of 5'-6-fam-CCTC-CAGGACCCCCCCTCCC-tamara-3' (Sequence ID No 4) and primers with a sequence of sense: 5'-AGCCATG-GCGTTAGTA(T/C)GAGTGT-3' (Sequence ID No 5) and antisense: 5'-TTCCGCAGACCACTATGG-3' (Sequence ID No 6).

BRIEF DESCRIPTION OF THE FIGURES

FIG. 1 is an illustration of the increase in plaque forming units with increasing concentration of bovine viral diarrhea virus ("BVDV") in cell culture as described in Example 51. FIG. 1 establishes that the method of Example 51 provides reliable quantification of BVDV over a four log PFU/mL of virus.

FIG. 2 is an illustration of the BVDV replication cycle in MDBK cells to determine the optimal harvesting time (in hours post infection versus the log of plaque forming units ("PFU"), i.e. 22 hours after infection, which roughly corresponds to approximately one replication cycle, where the amount of virus produced is equal to the amount of virus inoculated into the cell, as described in Example 52.

FIG. 3 is a bar chart graph showing the ability of certain test compounds to inhibit the number of plaque forming units, as described in Example 40 against BVDV.

FIG. 5 provides the structure of various non-limiting examples of nucleosides of the present invention, as well as the known nucleoside, ribavirin, which is used as a comparative example in the text.

DETAILED DESCRIPTION OF THE INVENTION

Figure 4:
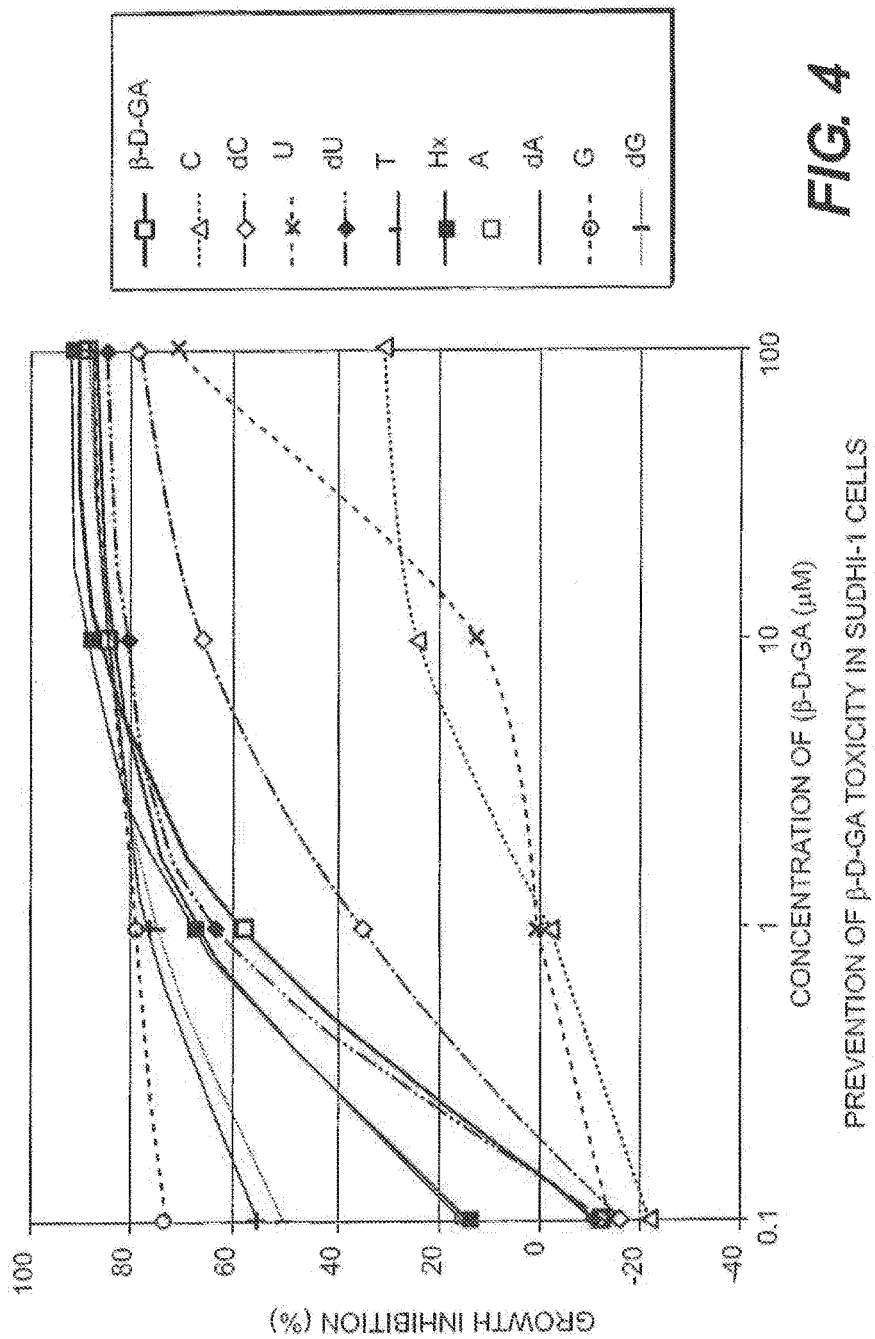
FIG. 4 is a line graph illustrating that the prevention of cytotoxicity of a "carba-sugar" nucleoside in CEM cells (human T-cell lymphoma) and in SUDHL-1 cells (human anaplastic T-cell lymphoma cell line) can be accomplished by co-administration of natural nucleosides, namely cytidine and uridine.

The present invention provides a nucleoside of the general formula (I)-(XXIII) or its pharmaceutically acceptable salt or prodrug for the treatment of a host infected with a virus belonging to the Flaviviridae, the Orthomyxoviridae, or the Paramyxoviridae family. Alternatively, the nucleoside of the general formula (I)-(XXIII) or its pharmaceutically acceptable salt or prodrug can be used for the treatment of abnormal cellular proliferation.

In one embodiment, a method for the treatment or prophylaxis of an antiviral or antiproliferative agent, for example for the treatment or prophylaxis of a viral infections, including Flaviviridae infections, including hepatitis C infection, influenza virus infection, including influenza A (such as H1N1 and H3N2) and influenza B and RSV, as well as abnormal cellular proliferation that includes the administration of an anti-virally or anti-proliferatively effective amount of a nucleoside of the present invention, or its pharmaceutically acceptable salt or prodrug thereof is provided.

In another embodiment, a method for the treatment or prophylaxis of an antiviral or antiproliferative agent, for example for the treatment or prophylaxis of a Flaviviridae infection that includes the administration of an antivirally amount of a nucleoside of the present invention, or its pharmaceutically acceptable salt or prodrug thereof in the manufacture of a medicament for treatment is provided.

In another embodiment, a method for the treatment or prophylaxis of an antiviral or antiproliferative agent, for example for the treatment or prophylaxis of an Influenza virus infection that includes the administration of an antivirally effective amount of a nucleoside of the present invention, or its pharmaceutically acceptable salt or prodrug thereof in the manufacture of a medicament for treatment is provided.

In another embodiment, a method for the treatment or prophylaxis of an antiviral or antiproliferative agent, for example for the treatment or prophylaxis of a RSV infection that includes the administration of an antivirally effective amount of the present invention, or its pharmaceutically acceptable salt or prodrug thereof in the manufacture of a medicament for treatment is provided.

In another embodiment, a method for the treatment or prophylaxis of an antiviral or antiproliferative agent, for example for the treatment or prophylaxis of a disease characterized by abnormal cellular proliferation that includes the administration of an anti-proliferatively effective amount of a nucleoside of the present invention.

In another embodiment, the invention is the use of one of the compounds described herein in the manufacture of a medicament for the treatment of a viral infection or abnormal cellular proliferation, as provided herein.

In another embodiment, the invention is the use of one of the compounds described herein in the treatment of a host exhibiting a viral infection or abnormal cellular proliferation, as provided herein.

In another embodiment, a pharmaceutical composition that includes an antivirally or anti-proliferatively effective amount of a nucleoside of the present invention, or its pharmaceutically acceptable salt or prodrug thereof together with a pharmaceutically acceptable carrier or diluent according to the present invention is provided.

In another embodiment, a pharmaceutical composition with a nucleoside of the present invention, or its pharmaceutically acceptable salt or prodrug thereof in combination with one or more other antivirally or anti-proliferatively effective agents is provided.

In another embodiment, a process for the preparation of the nucleosides of the present invention, and its pharmaceutically acceptable salt and prodrug thereof is provided.

In an additional embodiment, a method of treating a mammal having a virus-associated disorder which comprises administering to the mammal a pharmaceutically effective amount of a nucleoside of the present invention, or their pharmaceutically acceptable salts or prodrugs thereof, is provided.

In an additional embodiment, a method of treating a mammal having disorder associated with abnormal cellular proliferation, which comprises administering to the mammal a pharmaceutically effective amount of a nucleoside of the present invention, or their pharmaceutically acceptable salts or prodrugs thereof, is provided.

In particular, the invention includes the described compounds in methods for treating or preventing, or uses for the treatment or prophylaxis of, or uses in the manufacture of a medicament for following:

(a) a Flaviviridae infection, including all members of the Hepacivirus genus (HCV), Pestivirus genus (BVDV, CSFV, BDV), or Flavivirus genus (Dengue virus, Japanese encephalitis virus group (including West Nile Virus), and Yellow Fever virus);
(b) an Orthomyxoviridae infection, including all members of the Influenza A, B genus, in particular influenza A and all relevant subtypes including H1N1 and H3N2 and Influenza B;
(c) a Paramyxoviridae infection, including Respiratory Syncytial Virus (RSV) infection; and
(d) abnormal cellular proliferation, including malignant tumors.

I. COMPOUNDS OF THE INVENTION

In one embodiment, the anti-virally or anti-proliferatively effective nucleoside is a β-D nucleoside of the general formula (I) or (II):

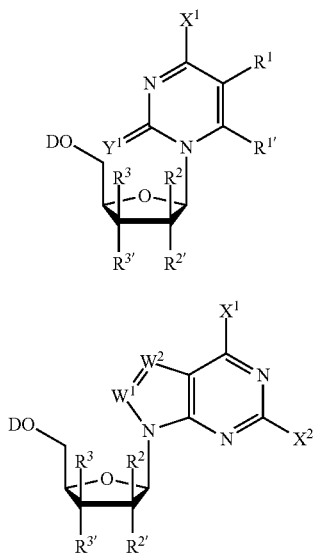

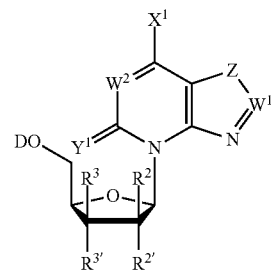

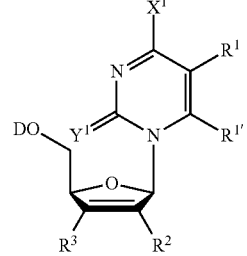

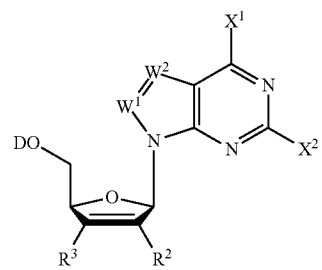

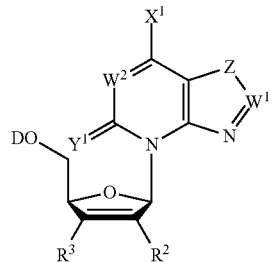

or its pharmaceutically acceptable salt or prodrug thereof, wherein:
each D is hydrogen, alkyl, acyl, monophosphate, diphosphate, triphosphate, monophosphate ester, diphosphate ester, triphosphate ester, phospholipid or amino acid, though preferably hydrogen;
each $W^1$ and $W^2$ is independently CH or N;
each $X^1$ and $X^2$ is independently hydrogen, halogen (F, Cl, Br or I), $NH_2$, $NHR^4$, $NR^4R^{4'}$, $NHOR^4$, $NR^4NR^{4'}R^{4''}$, OH, $OR^4$, SH or $SR^4$;
each $Y^1$ is O, S or Se;
each Z is $CH_2$ or NH;
each $R^1$ and $R^{1'}$ is independently hydrogen, lower alkyl, lower alkenyl, lower alkynyl, aryl, alkylaryl, halogen (F, Cl, Br or I), $NH_2$, $NHR^5$, $NR^5R^{5'}$, $NHOR^5$, $NR^5NHR^{5'}$, $NR^5NR^{5'}R^{5''}$, OH, $OR^5$, SH, $SR^5$, $NO_2$, NO, $CH_2OH$, $CH_2OR^5$, $CO_2H$, $CO_2R^5$, $CONH_2$, $CONHR^5$, $CONR^5R^{5'}$ or CN;
each $R^2$ and $R^{2'}$ independently is hydrogen or halogen (F, Cl, Br or I), OH, SH, $OCH_3$, $SCH_3$, $NH_2$, $NHCH_3$, $CH=CH_2$, CN, $CH_2NH_2$, $CH_2OH$, $CO_2H$.

each $R^3$ and $R^{3'}$ independently is hydrogen or halogen (F, Cl, Br or I), OH, SH, $OCH_3$, $SCH_3$, $NH_2$, $NHCH_3$, $CH_3$, $C_2H_5$, $CH=CH_2$, CN, $CH_2NH_2$, $CH_2OH$, $CO_2H$.

each $R^4$, $R^{4'}$, $R^{4''}$, $R^5$, $R^{5'}$ and $R^{5''}$ independently is hydrogen, lower alkyl, lower alkenyl, aryl, or arylalkyl such as unsubstituted or substituted phenyl or benzyl;

such that for each nucleoside of the general formula (I) or (II), at least one of $R^2$ and $R^{2'}$ is hydrogen and at least one of $R^3$ and $R^{3'}$ is hydrogen.

In another embodiment of the invention, anti-virally or anti-proliferatively effective nucleoside is a β-L nucleoside of the general formula (III) or (IV):

[III-a]
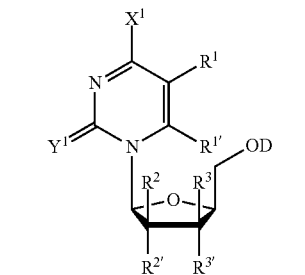

[III-b]
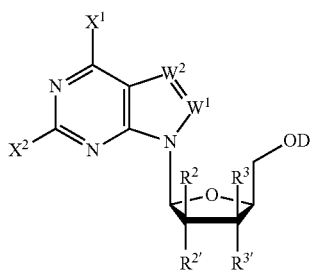

[III-c]
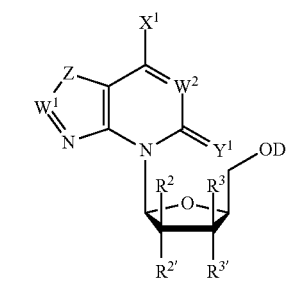

[IV-a]
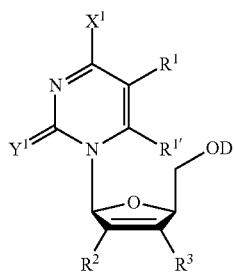

[IV-b]
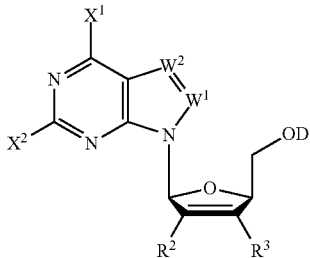

[IV-c]
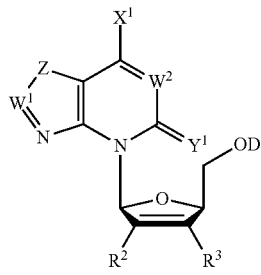

or its pharmaceutically acceptable salt or prodrug thereof, wherein:

each D, $W^1$, $W^2$, $X^1$, $X^2$, $Y^1$, Z, $R^1$, $R^{1'}$, $R^2$, $R^{2'}$, $R^3$ and $R^{3'}$ is the same as defined previously;

such that for each nucleoside of the general formula (III) or (IV), at least one of $R^2$ and $R^{2'}$ is hydrogen and at least one of $R^3$ and $R^{3'}$ is hydrogen.

In one embodiment of the invention, the anti-virally or anti-proliferatively effective nucleoside is a β-D-carba-sugar nucleoside of the general formula (V) to (VII):

[V-a]
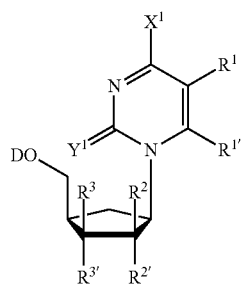

[V-b]
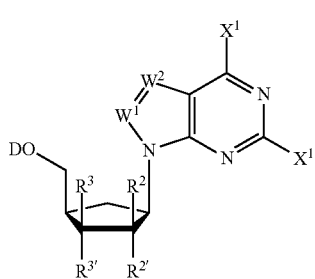

[V-c]
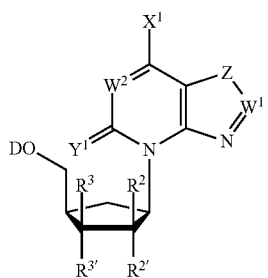

[VI-a]
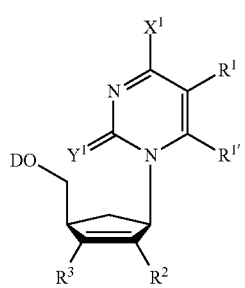

[VI-b]
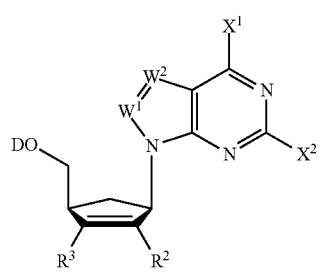

[VI-c]
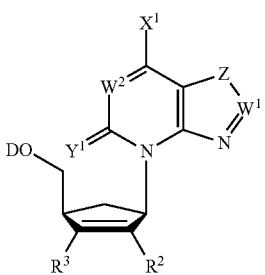

[VII-a]
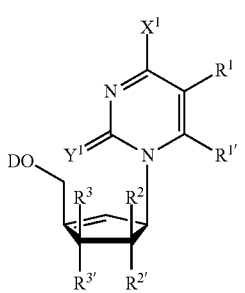

[VII-b]
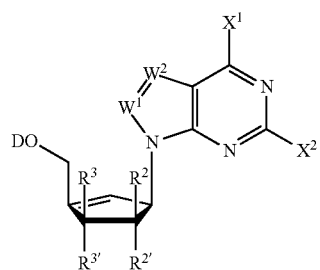

[VII-c]
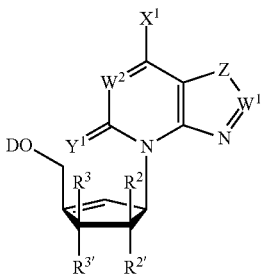

or its pharmaceutically acceptable salt or prodrug thereof, wherein:

each D, $W^1$, $W^2$, $X^1$, $X^2$, $Y^1$, Z, $R^1$, $R^{1'}$, $R^2$, $R^{2'}$, $R^3$ and $R^{3'}$ is the same as defined previously;

such that for each nucleoside of the general formula (V) or (VI), at least one of $R^2$ and $R^{2'}$ is hydrogen and at least one of $R^3$ and $R^{3'}$ is hydrogen.

In one embodiment, anti-virally or anti-proliferatively effective nucleoside is a β-L-carba-sugar nucleoside of the general formula (VIII) to (X):

[VIII-a]
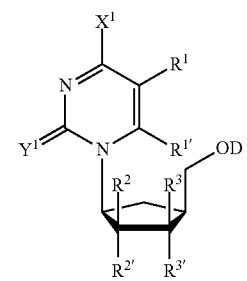

[VIII-b]
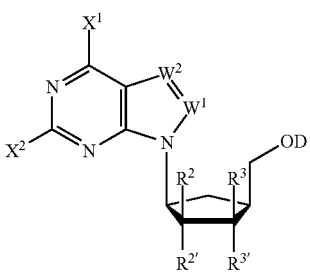

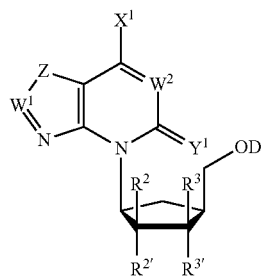
[VIII-c]

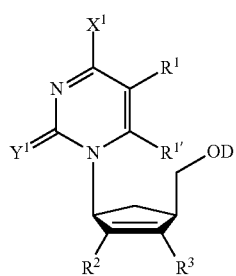
[IX-a]

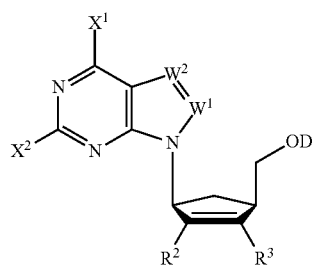
[IX-b]

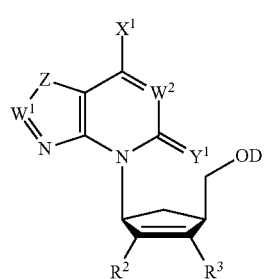
[IX-c]

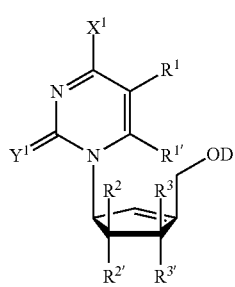
[X-a]

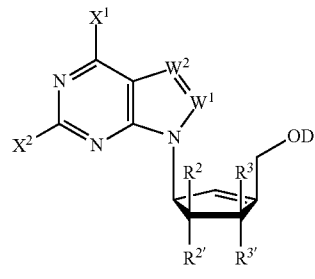
[X-b]

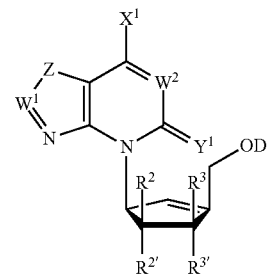
[X-c]

or its pharmaceutically acceptable salt or prodrug thereof, wherein:

each D, $W^1$, $W^2$, $X^1$, $X^2$, $Y^1$, Z, $R^1$, $R^{1'}$, $R^2$, $R^{2'}$, $R^3$ and $R^{3'}$ is the same as defined previously;

such that for each nucleoside of the general formula (VIII) or (IX), at least one of $R^2$ and $R^{2'}$ is hydrogen and at least one of $R^3$ and $R^{3'}$ is hydrogen.

In further embodiment of the invention, the anti-virally or anti-proliferatively effective β-D or β-L-nucleoside is of the general formula (XI) or (XII), respectively:

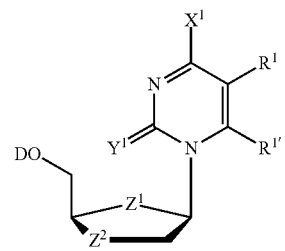
[XI-a]

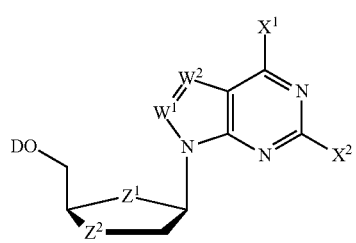
[XI-b]

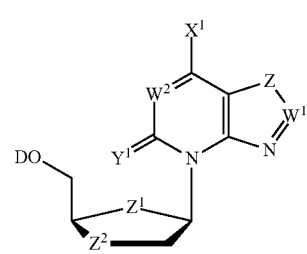
[XI-c]

-continued

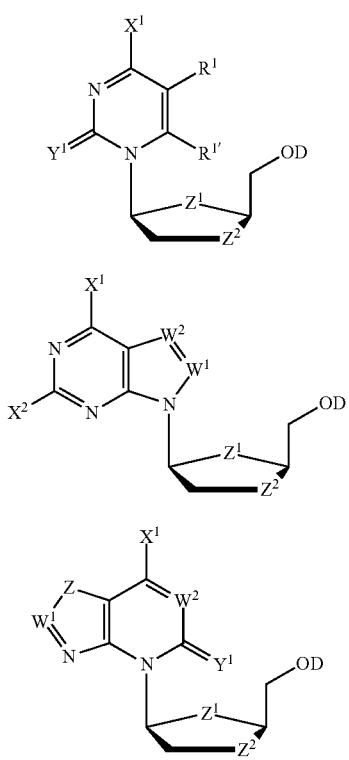

[XII-a]

[XII-b]

[XII-c]

or its pharmaceutically acceptable salt or prodrug thereof, wherein:

each D, $W^1$, $W^2$, $X^1$, $X^2$, $Y^1$, Z, $R^1$, $R^{1'}$, $R^2$, $R^{2'}$, $R^3$ and $R^{3'}$ is the same as defined previously;

each $Z^1$ and $Z^2$ independently is O, S, $NR^6$ or Se;

each $R^6$ is hydrogen, lower alkyl or lower acyl.

In a further embodiment of this invention, the anti-virally or anti-proliferatively effective β-D or β-L-nucleoside, though preferably β-D, is of the general formula (XIII):

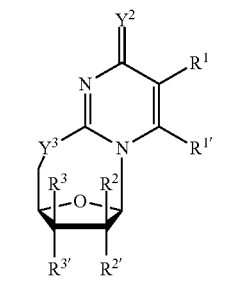

[XIII-a]

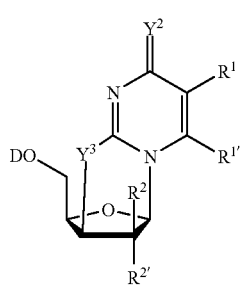

[XIII-b]

-continued

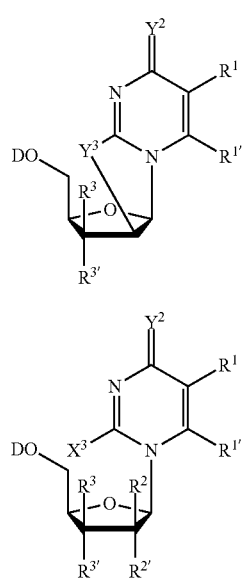

[XIII-c]

[XIII-d]

or its pharmaceutically acceptable salt or prodrug thereof, wherein:

each D, $R^1$, $R^{1'}$, $R^2$, $R^{2'}$, $R^3$ and $R^{3'}$ is the same as defined previously;

each $Y^2$ is O, S, NH or $NR^7$;

each $Y^3$ is O, S, NH or $NR^8$;

each $X^3$ is $OR^9$ or $SR^9$; and each $R^7$, $R^8$ and $R^9$ is hydrogen, lower alkyl of $C_1$-$C_6$, arylalkyl or aryl;

such that for each nucleoside of the general formula (XIII-d), at least one of $R^2$ and $R^{2'}$ is hydrogen and at least one of $R^3$ and $R^{3'}$ is hydrogen.

In another embodiment, the anti-virally or anti-proliferatively effective is a β-D or β-L-nucleoside, though preferably β-D, resulting from the addition of a small molecule, such as alkyl hypochlorite, alkyl hypobromite, hypobromous acid or acyl halide to an appropriate pyrimidine nucleoside, forming a nucleoside of the formula (XIV):

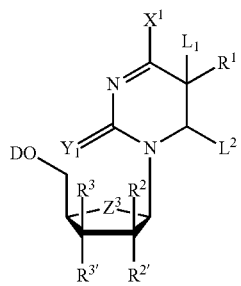

[XIV]

or its pharmaceutically acceptable salt or prodrug thereof, wherein:

each D, $X^1$, $Y^1$, $Z^1$, $R^1$, $R^2$, $R^{2'}$, $R^3$ and $R^{3'}$ is the same as defined previously;

each $L^1$ is hydrogen, Cl or Br;

each $L^2$ is OH, $OCH_3$, $OC_2H_5$, $OC_3H_7$, $OCF_3$, OAc or OBz;

each $Z^3$ can be O or $CH_2$.

In another embodiment, the anti-virally or anti-proliferatively effective nucleoside is a dimeric nucleoside (each nucleoside being in either the β-D or β-L configuration) of general formula (XV), in which the two nucleosides are linked through a disulfide bond:

[XV-a]

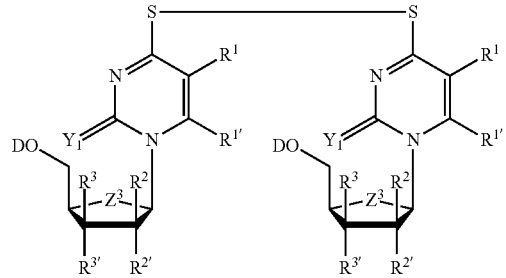

[XV-b]

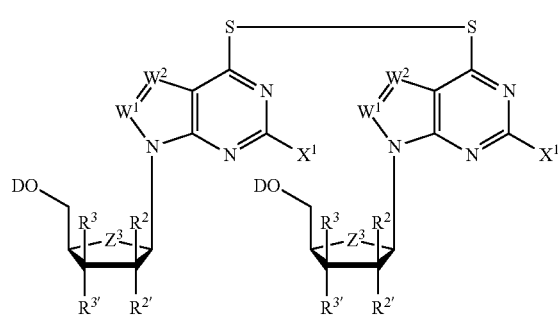

or its pharmaceutically acceptable salt or prodrug thereof, wherein:

each D, $W^1$, $W^2$, $X^1$, $Y^1$, $Z^3$, $R^1$, $R^{1'}$, $R^2$, $R^{2'}$, $R^3$ and $R^{3'}$ is the same as defined previously.

In one embodiment, the anti-virally or anti-proliferatively effective nucleoside is a β-D or β-L C-nucleoside of the general formula (XVI):

[XVI-a]

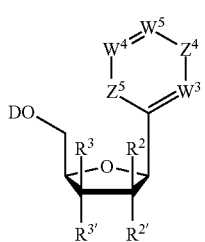

[XVI-b]

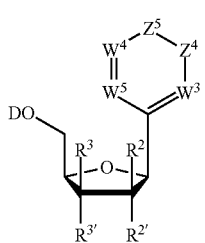

[XVI-c]

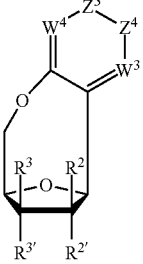

[XVI-d]

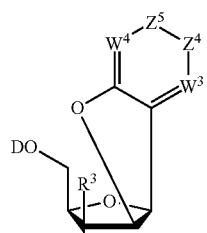

[XVI-e]

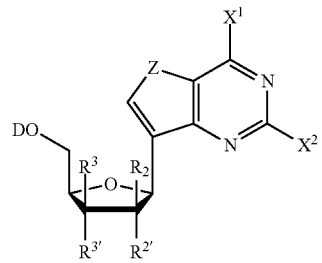

[XVI-f]

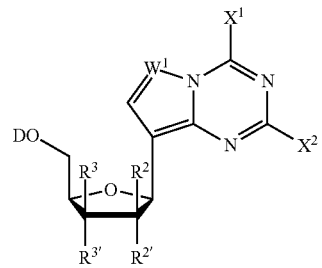

or its pharmaceutically acceptable salt or prodrug thereof, wherein:

each D, $W^1$, $X^1$, $X^2$, $Y^1$, Z, $R^1$, $R^2$, $R^{2'}$, $R^3$ and $R^{3'}$ is the same as defined previously;

each $W^3$ is independently N, CH or $CR^1$;

each $W^4$ and $W^5$ is independently N, CH, $CX^1$ or $CR^{1'}$; and each $Z^4$ and $Z^5$ is independently NH or $C(=Y^1)$;

such that if $Z^4$ and $Z^5$ are covalently bound, then $Z^4$ is not $C(=Y^1)$ when $Z^5$ is $C(=Y^1)$; and there are no more than three ring-nitrogens.

In one embodiment, the anti-virally or anti-proliferatively effective nucleoside is a β-D or β-L-branched-chain sugar nucleoside of the general formula (XVII):

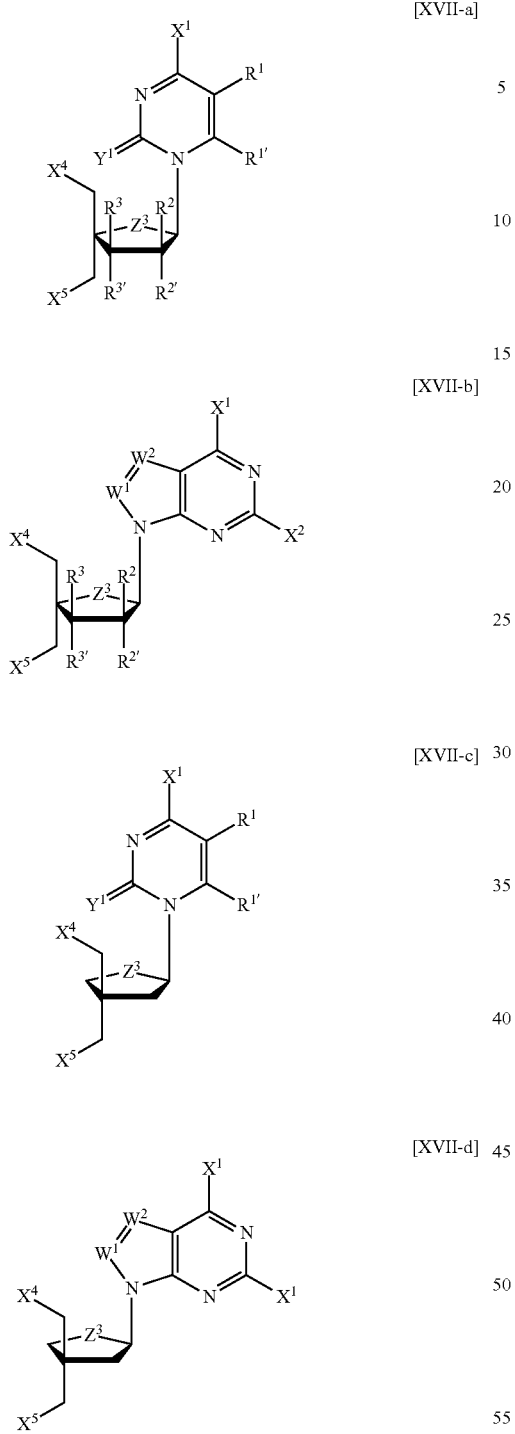

[XVII-a]

[XVII-b]

[XVII-c]

[XVII-d]

or its pharmaceutically acceptable salt or prodrug thereof, wherein:

each D, $W^1$, $W^2$, $X^1$, $X^2$, $Y^1$, $Z^3$, $R^1$, $R^2$, $R^{2'}$, $R^3$ and $R^{3'}$ is the same as defined previously;

each $X^4$ and $X^5$ is independently hydrogen, halogen (F, Cl, Br or I), $N_3$, $NH_2$, $NHR^8$, $NR^8R^{8'}$, OH, $OR^8$, SH or $SR^8$; and each $R^8$ and $R^{8'}$ is independently hydrogen, lower alkyl, lower alkenyl, aryl or arylalkyl, such as an unsubstituted or substituted phenyl or benzyl;

such that for each nucleoside of the general formula (XVII-a) or (XVII-b), $X^4$ is not OH or $OR^8$.

In one embodiment, the anti-virally or anti-proliferatively effective nucleoside is a α-D or α-L-nucleoside of the general formula (XVIII):

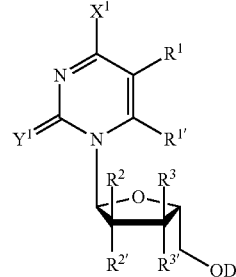

[XVIII-a]

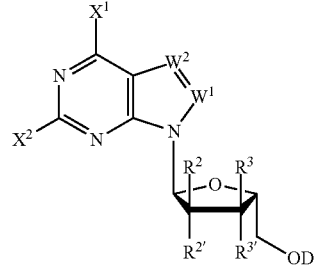

[XVIII-b]

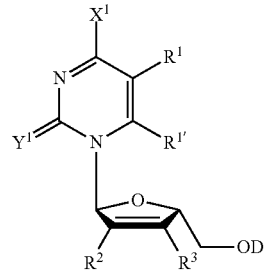

[XVIII-c]

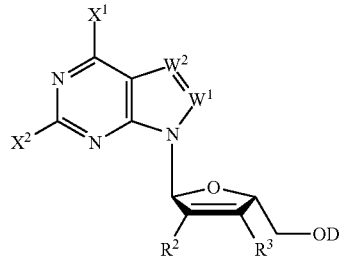

[XVIII-d]

or its pharmaceutically acceptable salt or prodrug thereof, wherein:

each D, $W^1$, $W^2$, $X^1$, $X^2$, $Y^1$, $R^1$, $R^{1'}$, $R^2$, $R^{2'}$, $R^3$ and $R^{3'}$ is the same as defined previously;

In a sub-embodiment of the present invention, the anti-virally or anti-proliferatively effective β-D or β-L nucleoside is of the formula (XIX):

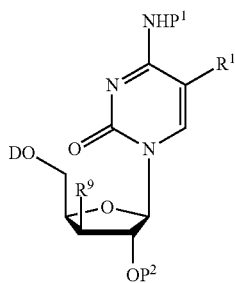

[XIX]

or its pharmaceutically acceptable salt or prodrug thereof, wherein:
each D, $R^1$, $R^4$ and $R^{4'}$ is the same as defined previously;
each $R^9$ is hydrogen, halogen (F, Cl, Br or I) or $OP^3$;
each $P^1$ is hydrogen, lower alkyl, lower alkenyl, aryl, arylalkyl (such as an unsubstituted or substituted phenyl or benzyl), OH, $OR^4$, $NH_2$, $NHR^4$ or $NR^4R^{4'}$; and
each $P^2$ and $P^3$ is independently hydrogen, alkyl, acyl, -Ms, -Ts, monophosphate, diphosphate, triphosphate, mono-phosphate ester, diphosphate ester, triphosphate ester, phospholipid or amino acid, though preferably hydrogen.

In a particular sub-embodiment of the present invention, the anti-virally or anti-proliferatively effective β-D or β-L nucleoside of the formula (XIX) is the following:

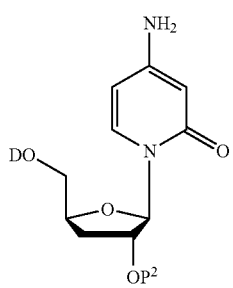

or its pharmaceutically acceptable salt or prodrug thereof, wherein:
each D and $P^2$ is the same as defined previously. In a preferred embodiment, D and $P^2$ are independently hydrogen.

In another sub-embodiment of the present invention, the anti-virally or anti-proliferatively effective β-D or β-L nucleoside is of the formula (XX):

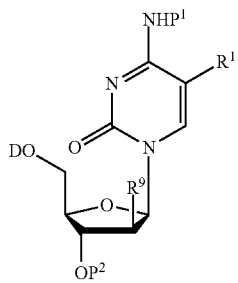

[XX]

or its pharmaceutically acceptable salt or prodrug thereof, wherein:

each D, $P^1$, $P^2$, $P^3$, $R^1$, $R^4$, $R^{4'}$ and $R^9$ is the same as defined previously.

In another sub-embodiment of the present invention, the anti-virally or anti-proliferatively effective β-D or β-L nucleoside is of the formula (XXI):

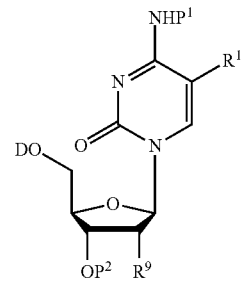

[XXI]

or its pharmaceutically acceptable salt or prodrug thereof, wherein:
each D, $P^1$, $P^2$, $P^3$, $R^1$, $R^4$ and $R^{4'}$ is the same as defined previously.

In a particular sub-embodiment of the present invention, the anti-virally or anti-proliferatively effective β-D or β-L nucleoside of the formula (XXI) is the following:

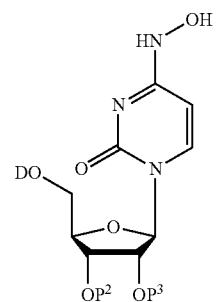

or its pharmaceutically acceptable salt or prodrug thereof, wherein:
each D, $P^2$ and $P^3$ is the same as defined previously. In a preferred embodiment, D, $P^2$ and $P^3$ are independently hydrogen.

In another embodiment, N-hydroxycytosine is used as the base attached to any of the sugar or carba-sugar moieties described in this application, as if each were fully described a separate specific embodiment.

In another sub-embodiment of the present invention, the anti-virally or anti-proliferatively effective β-D or β-L nucleoside is of the formula (XXII):

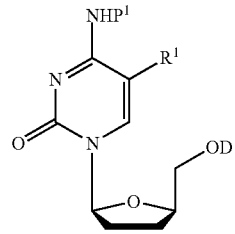

[XXII]

or its pharmaceutically acceptable salt or prodrug thereof, wherein:

each D, $P^1$ and $R^1$ is the same as defined previously. In a preferred embodiment, D and $P^2$ are independently hydrogen.

In a particular sub-embodiment of the present invention, the anti-virally or anti-proliferatively effective β-D or β-L nucleoside, though preferably β-L, of the formula (XXII) is the following:

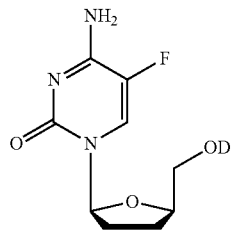

or its pharmaceutically acceptable salt or prodrug thereof, wherein:
D is the same as defined previously, and preferably H.

In another sub-embodiment of the present invention, the anti-virally or anti-proliferatively effective β-D or β-L nucleoside is of the formula (XXIII):

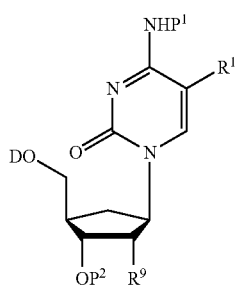

[XXIII]

or its pharmaceutically acceptable salt or prodrug thereof, wherein:

each D, $P^1$, $P^2$, $P^3$, $R^1$, $R^4$ and $R^{4'}$ is the same as defined previously.

In a particular sub-embodiment of the present invention, the anti-virally or anti-proliferatively effective β-D or β-L nucleoside of the formula (XXIII) is the following:

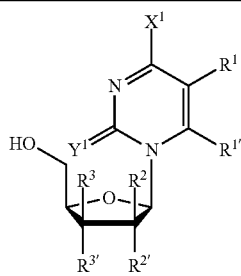

or its pharmaceutically acceptable salt or prodrug thereof, wherein:

each D, $P^2$ and $P^3$ is the same as defined previously. In a preferred embodiment, D, $P^2$ and $P^3$ are independently hydrogen.

In a preferred embodiment, the β-D and β-L nucleosides of general formula (I-a) and (III-a) are represented by the non-limiting examples provided in Table 1.

TABLE 1

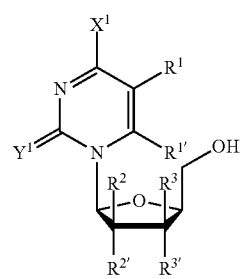

[I-a]

[III-a]

TABLE 1-continued

| ID | X$^1$ | Y$^1$ | R$^1$ | R$^{1'}$ | R$^2$ | R$^{2'}$ | R$^3$ | R$^{3'}$ |
|---|---|---|---|---|---|---|---|---|
| AA | NH$_2$ | O | H | H | OH | H | H | OH |
| AB | NH$_2$ | O | H | H | OH | H | H | I |
| AC | NH$_2$ | O | H | H | OH | H | H | Cl |
| AD | NH$_2$ | O | H | H | OH | H | H | Br |
| AE | NH$_2$ | O | H | H | OH | H | H | S—CN |
| AF | NH$_2$ | O | H | H | OH | H | H | N$_3$ |
| AG | NH$_2$ | O | H | H | H | Cl | H | OH |
| AH | NH$_2$ | O | H | H | H | Br | H | OH |
| AI | NH$_2$ | O | H | H | H | OH | Br | H |
| AJ | NH$_2$ | O | H | H | H | OH | H | H |
| AK | NH$_2$ | O | H | H | H | OH | O—Ms | H |
| AL | NH$_2$ | O | H | H | H | OH | O—Ts | H |
| AM | NH$_2$ | O | H | H | O—Ms | H | H | OH |
| AN | NH$_2$ | O | H | H | Cl | H | H | OH |
| AO | NH$_2$ | O | D | D | OH | H | H | OH |
| AP | NH$_2$ | O | F | H | OH | H | H | OH |
| AQ | NH$_2$ | O | F | H | H | OH | H | OH |
| AR | NH$_2$ | O | F | H | H | OH | H | H |
| AS | NH$_2$ | O | F | H | H | OH | Cl | H |
| AT | NH$_2$ | O | F | H | H | OH | Br | H |
| AU | NH$_2$ | O | F | H | H | Cl | H | OH |
| AV | NH$_2$ | O | F | H | H | OH | O—Ts | H |
| AW | NH$_2$ | O | F | H | H | OH | O—Ms | H |
| AX | NH$_2$ | O | Cl | H | H | OH | O—Ms | H |
| AY | NH$_2$ | O | Br | H | H | OH | O—Ms | H |
| AZ | NH$_2$ | O | Br | H | H | OH | O—Ts | H |
| BA | NH$_2$ | O | Br | H | H | OH | Cl | H |
| BB | NH$_2$ | O | Br | H | H | OH | H | OH |
| BC | NH$_2$ | O | Br | H | OH | H | H | OH |
| BD | NH$_2$ | O | I | H | H | OH | O—Ms | H |
| BE | NH$_2$ | O | I | H | H | OH | Br | H |
| BF | NH$_2$ | O | I | H | H | OH | O—Ts | H |
| BG | NH$_2$ | O | I | H | H | Cl | H | OH |
| BH | NH$_2$ | O | I | H | Br | H | H | OH |
| BI | NH$_2$ | O | OH | H | OH | H | H | OH |
| BJ | NH$_2$ | O | NH$_2$ | H | H | OH | H | OH |
| BK | NH$_2$ | O | CH$_3$ | H | H | OH | Cl | H |
| BL | NH$_2$ | NH | H | H | OH | H | H | OH |
| BM | NH$_2$ | S | H | H | H | Se-phenyl | H | H |
| BN | NH-(2-Ph—Et) | O | H | H | OH | H | H | OH |
| BO | NH—COCH$_3$ | O | H | H | OH | H | H | OH |
| BP | NH—NH$_2$ | O | H | H | OH | H | H | OH |
| BQ | NH—NH$_2$ | O | F | H | OH | H | H | OH |
| BR | NH—NH$_2$ | O | CH$_3$ | H | H | OH | H | OH |
| BS | NH—OH | O | H | H | H | OH | H | OH |
| BT | NH—OH | O | F | H | H | OH | H | OH |
| BU | NH—OH | O | Br | H | H | OH | H | OH |
| BV | NH—OH | O | I | H | H | OH | H | OH |
| BW | NH—OH | O | H | H | OH | H | H | OH |
| BX | OH | O | OH | H | OH | H | H | OH |
| BY | OH | O | NH$_2$ | H | H | OH | H | OH |
| BZ | OH | O | F | H | OH | H | H | OH |
| CA | OH | O | F | H | H | O—Ts | H | OH |
| CB | OH | O | F | H | H | O—Ms | H | O—Ms |
| CC | OH | O | F | H | H | OH | H | OH |
| CD | OH | O | F | H | H | OH | H | O—Ts |
| CE | OH | O | F | H | H | H | H | OH |
| CF | O—Et | O | H | H | H | O—Bz | H | O—Bz |
| CG | S—CH$_3$ | O | H | H | H | F | H | OH |
| CH | SH | O | H | H | H | OH | H | OH |
| CI | SH | O | F | H | H | OH | H | OH |
| CJ | N$_3$ | O | H | H | H | H | H | H |
| CK | NH-(2-Ph—Et) | O | H | H | H | OH | H | OH |
| CL | OH | O | OH | H | H | OH | H | OH |
| CM | OH | O | H | H | H | OH | H | H |

In a preferred embodiment, the β-D and β-L nucleosides of general formula (I-b) and (III-b) are represented by the non-limiting examples provided in Table 2.

TABLE 2

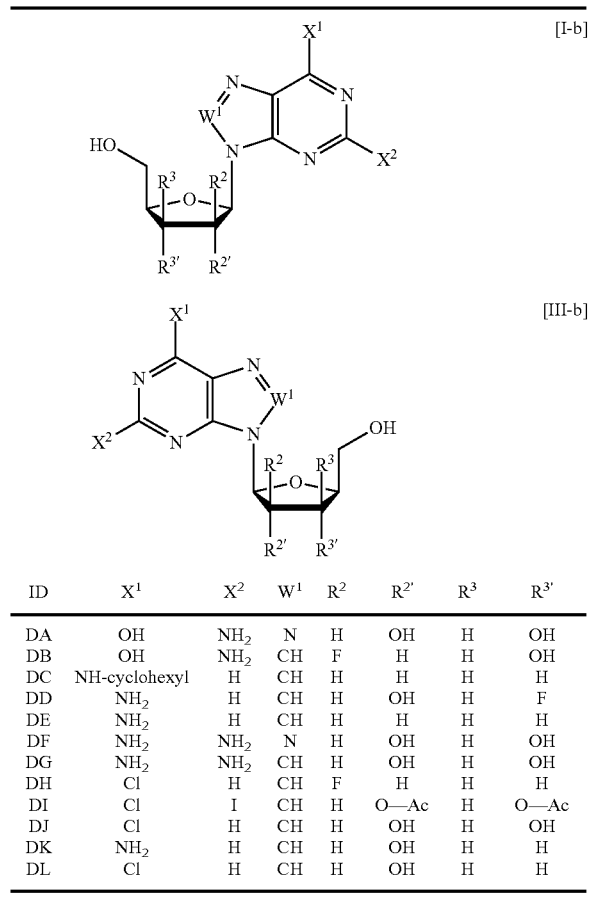

| ID | X¹ | X² | W¹ | R² | R²' | R³ | R³' |
|---|---|---|---|---|---|---|---|
| DA | OH | $NH_2$ | N | H | OH | H | OH |
| DB | OH | $NH_2$ | CH | F | H | H | OH |
| DC | NH-cyclohexyl | H | CH | H | H | H | H |
| DD | $NH_2$ | H | CH | H | OH | H | F |
| DE | $NH_2$ | H | CH | H | H | H | H |
| DF | $NH_2$ | $NH_2$ | N | H | OH | H | OH |
| DG | $NH_2$ | $NH_2$ | CH | H | OH | H | OH |
| DH | Cl | H | CH | F | H | H | H |
| DI | Cl | I | CH | H | O—Ac | H | O—Ac |
| DJ | Cl | H | CH | H | OH | H | OH |
| DK | $NH_2$ | H | CH | H | OH | H | H |
| DL | Cl | H | CH | H | OH | H | H |

In a preferred embodiment, the β-D and β-L nucleosides of general formula (II-a) and (IV-a) are represented by the non-limiting examples provided in Table 3.

TABLE 3

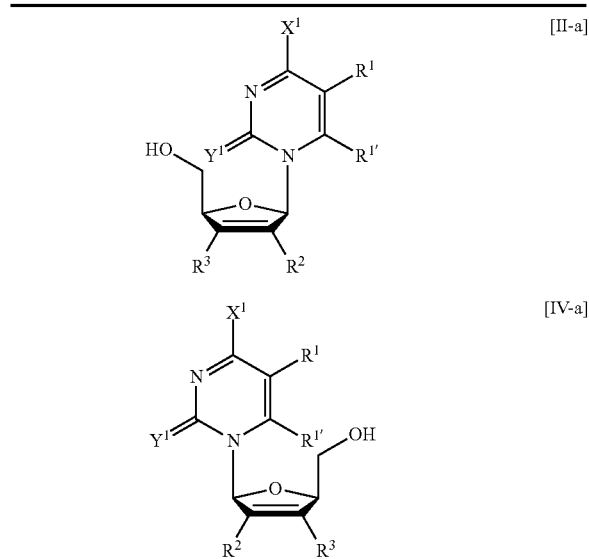

TABLE 3-continued

| ID | X¹ | Y¹ | R¹ | R¹' | R² | R³ |
|---|---|---|---|---|---|---|
| EA | NH—Bz-(m-$NO_2$) | O | F | H | H | H |
| EB | NH—Bz-(o-$NO_2$) | O | F | H | H | H |
| EC | $NH_2$ | O | F | H | F | H |

In a preferred embodiment, the β-D and β-L nucleosides of general formula (II-b) and (IV-b) are represented by the non-limiting examples provided in Table 4.

TABLE 4

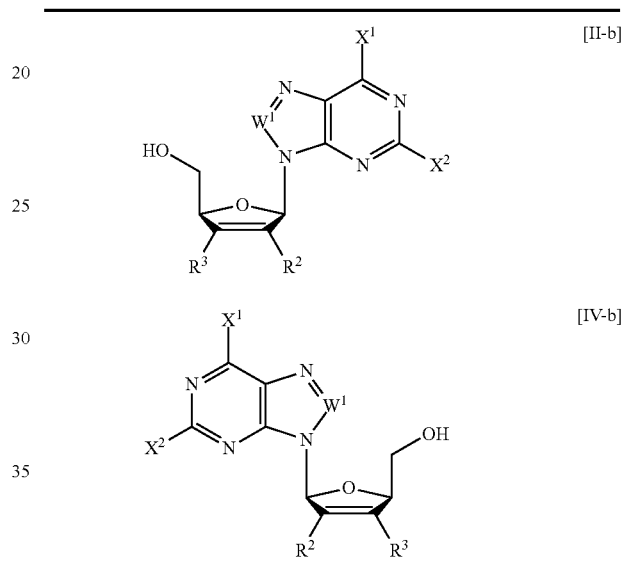

| ID | X¹ | X² | W¹ | R² | R³ |
|---|---|---|---|---|---|
| FA | Cl | H | CH | F | H |
| FB | OH | H | CH | H | H |
| FC | $NH_2$ | F | CH | H | H |
| FD | $NH_2$ | F | CH | F | H |
| FE | $NH_2$ | H | CH | H | H |
| FF | OH | $NH_2$ | CH | H | H |
| FG | OH | H | CH | H | H |

In a preferred embodiment, the β-D and β-L nucleosides of general formula (V-a) and (VIII-a) are represented by the non-limiting examples provided in Table 5.

TABLE 5

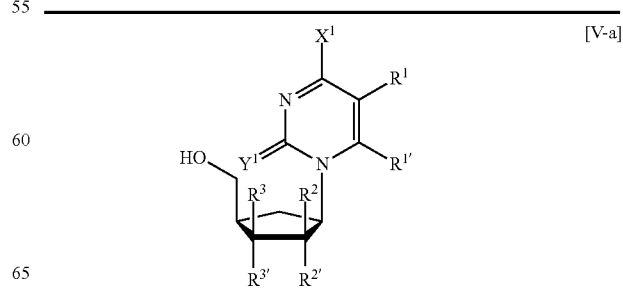

TABLE 5-continued

[VIII-a]

| ID | X¹ | Y¹ | R¹ | R¹' | R² | R²' | R³ | R³' |
|----|-----|-----|-----|-----|-----|------|-----|------|
| GA | NH$_2$ | O | F | H | H | OH | H | OH |
| GB | OH | H | CH$_3$ | H | H | H | H | H |
| GC | OH | O | H | H | H | H | H | H |
| GD | NH$_2$ | O | H | H | H | OH | H | OH |
| GE | NH$_2$ | O | H | H | H | H | H | H |
| GF | OH | O | F | H | H | OH | H | OH |
| GG | NH$_2$ | O | I | H | H | H | H | H |
| GH | NH$_2$ | O | I | H | H | OH | H | OH |
| GI | NH$_2$ | O | Cl | H | H | OH | H | OH |

In a preferred embodiment, the β-D and β-L nucleosides of general formula (VII-a) and (X-a) are represented by the non-limiting examples provided in Table 6.

TABLE 6

[VII-a]

[X-a]

| ID | X¹ | Y¹ | R¹ | R¹' | R² | R²' | R³ | R³' |
|----|-----|-----|-----|-----|-----|------|-----|------|
| HA | NH$_2$ | O | H | H | H | OH | H | OH |
| HB | NH$_2$ | O | F | H | H | OH | H | OH |
| HC | NH—OH | O | H | H | H | OH | H | OH |

In a preferred embodiment, the β-D and β-L nucleosides of general formula (VII-b) and (X-b) are represented by the non-limiting examples provided in Table 7.

TABLE 7

[VII-b]

[X-b]

| ID | X¹ | X² | W¹ | R² | R²' | R³ | R³' |
|----|-----|-----|-----|-----|------|-----|------|
| IA | NH$_2$ | H | CH | H | OH | H | OH |

In a preferred embodiment, the β-D or β-L nucleosides of general formula (XI-a) or (XII-a) are represented by the non-limiting examples provided in Table 8.

TABLE 8

[XI-a]

[XII-a]

| ID | X¹ | Y¹ | Z¹ | Z² | R¹ | R¹' |
|----|-----|-----|-----|-----|-----|------|
| JA | NH$_2$ | O | O | O | H | H |
| JB | NH$_2$ | O | O | S | F | H |
| JC | NH$_2$ | O | O | O | F | H |

In a preferred embodiment, the β-L nucleosides of general formula (XII-b) are represented by the non-limiting examples provided in Table 9.

TABLE 9

[XI-b]

| ID | $X^1$ | $X^2$ | $W^1$ | $Z^1$ | $Z^2$ |
|---|---|---|---|---|---|
| KA | Cl | H | CH | O | S |
| KB | Cl | $NH_2$ | CH | O | S |
| KC | $NH_2$ | F | CH | O | S |
| KD | OH | H | CH | O | O |

In a preferred embodiment, the β-D nucleosides of general formula (XIII-a) are represented by the non-limiting examples provided in Table 10.

TABLE 10

[XIII-a]

| ID | $Y^2$ | $Y^3$ | $R^1$ | $R^{1'}$ | $R^2$ | $R^{2'}$ | $R^3$ | $R^{3'}$ |
|---|---|---|---|---|---|---|---|---|
| LA | O | O | F | H | H | OH | H | OH |

In a preferred embodiment, the β-D nucleosides of general formula (XIII-c) are represented by the non-limiting examples provided in Table 11.

TABLE 11

[XIII-c]

TABLE 11-continued

| ID | $Y^2$ | $Y^3$ | $R^1$ | $R^{1'}$ | $R^3$ | $R^{3'}$ |
|---|---|---|---|---|---|---|
| MA | O | O | F | H | H | OH |
| MB | O | O | F | H | H | O—Ms |
| MC | NH | O | H | H | H | O—Ms |
| MD | NH | O | H | H | H | O—Ac |
| ME | NH | O | H | H | H | OH |
| MF | NH | O | F | H | H | OH |
| MG | NH | O | F | H | H | O—Ac |

In a preferred embodiment, the β-D nucleosides of general formula (XIII-d) are represented by the non-limiting examples provided in Table 12.

TABLE 12

[XIII-d]

| ID | $Y^2$ | $X^3$ | $R^1$ | $R^{1'}$ | $R^2$ | $R^{2'}$ | $R^3$ | $R^{3'}$ |
|---|---|---|---|---|---|---|---|---|
| NA | O | O—$CH_3$ | H | H | H | O—Ac | H | O—Ac |

In a preferred embodiment, the β-D nucleosides of general formula (XIV) are represented by the non-limiting examples provided in Table 13.

TABLE 13

[XIV]

| ID | $X^1$ | $Y^1$ | $R^1$ | $R^{1'}$ | $R^2$ | $R^{2'}$ | $R^3$ | $R^{3'}$ | $L^1$ | $L^2$ |
|---|---|---|---|---|---|---|---|---|---|---|
| OA | $NH_2$ | O | NH—OH | OH | OH | H | H | OH | H | OH |
| OB | OH | O | O | F | H | OH | H | OH | Cl | O—$CH_3$ |
| OC | OH | O | O | H | H | OH | H | OH | Br | O—$CH_3$ |
| OD | OH | O | O | F | H | OH | H | OH | Br | O—$COCH_3$ |
| OE | OH | O | O | F | H | OH | H | OH | Br | O—$CH_3$ |
| OF | OH | O | O | F | H | OH | H | OH | Br | O—Et |
| OG | OH | O | O | Cl | H | OH | H | OH | Br | O—$CH_3$ |

In a preferred embodiment, the nucleosides of general formula (XV-a) are represented by the non-limiting examples provided in Table 14.

TABLE 14

[XV-a]

(Structure of formula [XV-a])

| ID | Y¹ | Z³ | R¹ | R¹' | R² | R²' | R³ | R³' |
|---|---|---|---|---|---|---|---|---|
| PA | O | O | H | H | H | OH | H | OH |

In a preferred embodiment, the nucleosides of general formula (XV-b) are represented by the non-limiting examples provided in Table 15.

TABLE 15

[XV-b]

(Structure of formula [XV-b])

| ID | X¹ | W¹ | Z³ | R² | R²' | R³ | R³' |
|---|---|---|---|---|---|---|---|
| QA | NH₂ | CH | O | H | OH | H | OH |

In a preferred embodiment, the nucleosides of general formula (XVI-a) are represented by the non-limiting examples provided in Table 16.

TABLE 16

[XVI-a]

(Structure of formula [XVI-a])

| ID | W³ | Z⁴ | W⁵ | W⁴ | Z⁵ | R² | R²' | R³ | R³' |
|---|---|---|---|---|---|---|---|---|---|
| RA | CH | NCH₃ | C—OH | N | C=O | H | OH | H | O—Ts |
| RB | CH | NH | C—NH₂ | N | C=O | H | OH | H | OH |
| RC | CH | NH | C—NHAc | N | C=O | H | OH | H | OH |
| RD | CH | NH | C—OH | N | C=O | H | OH | H | OH |
| RE | CH | NCH₃ | C—NH₂ | N | C=O | H | OH | H | OH |
| RF | CH | NH | C—NHBz | N | C=O | H | OH | H | OH |
| RG | CH | C=O | C—NH₂ | C—SH | NH | H | OH | H | OH |
| RH | CH | NH | C—OH | N | C=O | H | Cl | H | OH |
| RI | CH | NH | C—NH₂ | N | C=O | H | Br | H | OH |

In a preferred embodiment, the nucleosides of general formula (XVI-c) are represented by the non-limiting examples provided in Table 17.

TABLE 17

[XVI-c]

(Structure of formula [XVI-c])

| ID | W³ | Z⁴ | Z⁵ | W⁴ | R² | R²' | R³ | R³' |
|---|---|---|---|---|---|---|---|---|
| SA | CH | N—CH₃ | C=O | N | H | OH | H | O—Ac |

In a preferred embodiment, the nucleosides of general formula (XVI-d) are represented by the non-limiting examples provided in Table 18.

TABLE 18

[XVI-d]

(Structure of formula [XVI-d])

| ID | W³ | Z⁴ | Z⁵ | W⁴ | R³ | R³' |
|---|---|---|---|---|---|---|
| TA | CH | N | C=NH | N | H | OH |

In a preferred embodiment, the nucleosides of general formula (XVI-f) are represented by the non-limiting examples provided in Table 19.

TABLE 19

[XVI-f]

(Structure of formula [XVI-f])

| ID | X¹ | X² | W¹ | R² | R²' | R³ | R³' |
|---|---|---|---|---|---|---|---|
| UA | NH₂ | H | N | H | OH | H | OH |

In a preferred embodiment, the nucleosides of general formula (XVII-d) are represented by the non-limiting examples provided in Table 20.

TABLE 20

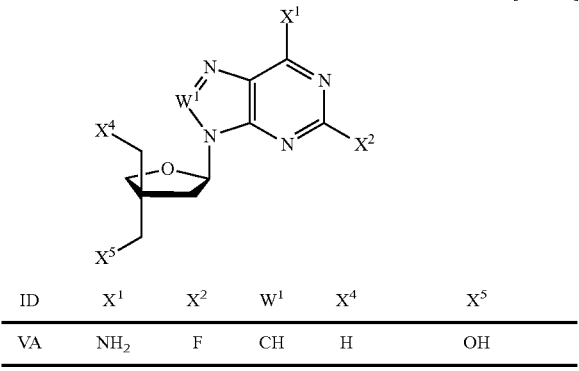

[XVII-d]

| ID | X$^1$ | X$^2$ | W$^1$ | X$^4$ | X$^5$ |
|---|---|---|---|---|---|
| VA | NH$_2$ | F | CH | H | OH |

In one embodiment, the nucleoside has an EC$_{50}$ (effective concentration to achieve 50% viral inhibition) when tested in an appropriate cell-based assay, of less than 15 micromolar, and more particularly, less than 10 or 5 micromolar. In a preferred embodiment, the nucleoside is enantiomerically enriched.

II. STEREOISOMERISM AND POLYMORPHISM

Compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

As shown below, a nucleoside contains at least two critical chiral carbon atoms (*). In general, the substituents on the chiral carbons [the specified purine or pyrimidine base (referred to as the C1 substituent when using the sugar ring intermediate numbering) and a CH$_2$OH (referred to as the C4 substituent)] of the nucleoside can be either cis (on the same side) or trans (on opposite sides) with respect to the sugar ring system. Both the cis and trans racemates consist of a pair of optical isomers. Hence, each compound has four individual stereoisomers. The four stereoisomers are represented by the following configurations (when orienting the sugar moiety in a horizontal plane such that the —O-moiety is in back): (1) cis, with both groups "up", which is referred to as β-D; (2) the mirror image, i.e., cis, with both groups "down", which is the mirror image is referred to as β-L; (3) trans with the C4 substituent "up" and the C1 substituent "down" (referred to as α-D); and (4) trans with the C4 substituent "down" and the C1 substituent "up" (referred to as α-L). The two cis enantiomers together are referred to as a racemic mixture of β-enantiomers, and the two trans enantiomers are referred to as a racemic mixture of α-enantiomers.

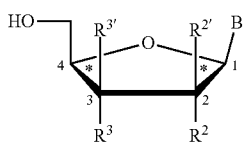

The four possible stereoisomers of the claimed compounds are illustrated below.

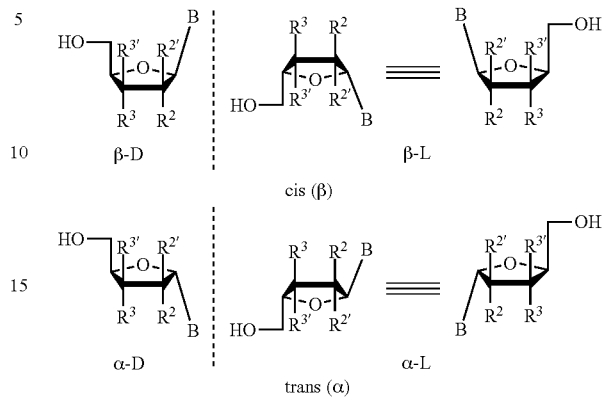

III. DEFINITIONS

The term "alkyl," as used herein, unless otherwise specified, refers to a saturated straight, branched, or cyclic, primary, secondary, or tertiary hydrocarbon, including but not limited to those of $C_1$ to $C_{16}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, azido, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "lower alkyl," as used herein, and unless otherwise specified, refers to a $C_1$ to $C_4$ saturated straight, branched, or if appropriate, a cyclic (for example, cyclopropyl) alkyl group, including both substituted and unsubstituted forms.

The term "alkylene" or "alkenyl" refers to a saturated hydrocarbyldiyl radical of straight or branched configuration, including but not limited to those that have from one to ten carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like. The alkylene group or other divalent moiety disclosed herein can be optionally substituted with one or more moieties selected from the group consisting of alkyl, halo, haloalkyl, hydroxyl, carboxyl, acyl, acyloxy, amino, amido, carboxyl derivatives, alkylamino, azido, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "aryl," as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of bromo, chloro, fluoro, iodo, hydroxyl, azido, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "aralkyl," as used herein, and unless otherwise specified, refers to an aryl group as defined above linked to the molecule through an alkyl group as defined above. The term "alkaryl" or "alkylaryl" as used herein, and unless otherwise specified, refers to an alkyl group as defined above linked to the molecule through an aryl group as defined above. In each of these groups, the alkyl group can be optionally substituted as describe above and the aryl group can be optionally substituted with one or more moieties selected from the group consisting of alkyl, halo, haloalkyl, hydroxyl, carboxyl, acyl, acyloxy, amino, amido, azido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included within the scope of the term aryl are rd phenyl; naphthyl; phenylmethyl; phenylethyl; 3,4,5-trihydroxyphenyl; 3,4,5-trimethoxyphenyl; 3,4,5-triethoxy-phenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-t-butylphenyl; 4-t-butylphenylmethyl and the like.

The term "alkylamino" or "arylamino" refers to an amino group that has one or two alkyl or aryl substituents, respectively.

The term "halogen," as used herein, includes fluorine, chlorine, bromine and iodine.

The term "enantiomerically enriched" is used throughout the specification to describe a nucleoside which includes at least about 95%, preferably at least 96%, more preferably at least 97%, even more preferably, at least 98%, and even more preferably at least about 99% or more of a single enantiomer of that nucleoside. When a nucleoside of a particular configuration (D or L) is referred to in this specification, it is presumed that the nucleoside is an enantiomerically enriched nucleoside, unless otherwise stated.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates (including chimpanzees) and humans. Relative to abnormal cellular proliferation, the term "host" refers to unicellular or multicellular organism in which abnormal cellular proliferation can be mimicked. The term host specifically refers to cells that abnormally proliferate, either from natural or unnatural causes (for example, from genetic mutation or genetic engineering, respectively), and animals, in particular, primates (including chimpanzees) and humans. In most animal applications of the present invention, the host is a human patient. Veterinary applications, in certain indications, however, are clearly anticipated by the present invention (such as bovine viral diarrhea virus in cattle, hog cholera virus in pigs, and border disease virus in sheep).

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

IV. PHARMACEUTICALLY ACCEPTABLE SALTS AND PRODRUGS

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hostetler, K. Y., D. D. Richman, D. A. Carson, L. M. Stuhmiller, G. M, T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuluniller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of ru the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, 11; Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

V. PHARMACEUTICAL COMPOSITIONS

Pharmaceutical compositions based upon a β-D or β-L compound of formula (I) (XXIII) or its pharmaceutically acceptable salt or prodrug can be prepared in a therapeutically effective amount for treating a Flaviviridae, Orthomyxoviridae or Paramyxoviridae viral infection or abnormal cellular proliferation, optionally in combination with a pharmaceutically acceptable additive, carrier or excipient. The therapeutically effective amount may vary with the infection or condition to be treated, its severity, the treatment regimen to be employed, the pharmacokinetics of the agent used, as well as the patient treated.

In one aspect according to the present invention, the compound according to the present invention is formulated preferably in admixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.).

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of Flaviviridae (including HCV), Orthomyxoviridae (including Influenza A and B), Paramyxoviridae (including RSV) infections or conditions related to abnormal cellular proliferation.

The amount of compound included within therapeutically active formulations, according to the present invention, is an effective amount for treating the infection or condition, in preferred embodiments, a Flaviviridae (including HCV), Orthomyxoviridae (including Influenza A and B), Paramyxoviridae (including RSV) infection or a condition related to abnormal cellular proliferation. In general, a therapeutically effective amount of the present compound in pharmaceutical dosage form usually ranges from about 0.1 mg/kg to about 100 mg/kg or more, depending upon the compound used, the condition or infection treated and the route of administration. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, Q.I.D., B.I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

In particularly preferred embodiments according to the present invention, the compounds and compositions are used to treat, prevent or delay the onset of Flaviviridae (including HCV), Orthomyxoviridae (including Influenza A and B), Paramyxoviridae (including RSV) infections or conditions related to abnormal cellular proliferation. Preferably, to treat, prevent or delay the onset of the infection or condition, the compositions will be administered in oral dosage form in amounts ranging from about 250 micrograms up to about 1 gram or more at least once a day, preferably, or up to four times a day. The present compounds are preferably administered orally, but may be administered parenterally, topically or in suppository form.

The compounds according to the present invention, because of their low toxicity to host cells in certain instances, may be advantageously employed prophylactically to prevent Flaviviridae (including HCV), Orthomyxoviridae (including Influenza A and B), Paramyxoviridae (including RSV) infections or conditions related to abnormal cellular proliferation or to prevent the occurrence of clinical symptoms associated with the viral infection or condition. Thus, the present invention also encompasses methods for the prophylactic treatment of viral infection, and in particular Flaviviridae (including HCV), Orthomyxoviridae (including Influenza A and B), Paramyxoviridae (including RSV) infections or of a condition related to abnormal cellular proliferation. In this aspect, according to the present invention, the present compositions are used to prevent or delay the onset of a Flaviviridae (including HCV), Orthomyxoviridae (including Influenza A and B), Paramyxoviridae (including RSV) infection or a condition related to abnormal cellular proliferation. This prophylactic method comprises administration to a patient in need of such treatment, or who is at risk for the development of the virus or condition, an amount of a compound according to the present invention effective for alleviating, preventing or delaying the onset of the viral infection or condition. In the prophylactic treatment according to the present invention, it is preferred that the antiviral or antiproliferative compound utilized should be low in toxicity and preferably non-toxic to the patient. It is particularly preferred in this aspect of the present invention that the compound that is used should be maximally effective against the virus or condition and should exhibit a minimum of toxicity to the patient. In the case of Flaviviridae (including HCV), Orthomyxoviridae (including Influenza A and B), Paramyxoviridae (including RSV) infections or conditions related to abnormal cellular proliferation, compounds according to the present invention, which may be used to treat these disease states, may be administered within the same dosage range for therapeutic treatment (i.e., about 250 micrograms up to 1 gram or more from one to four times per day for an oral dosage form) as a prophylactic agent to prevent the proliferation of a Flaviviridae (including HCV), Orthomyxoviridae (including Influenza A and B), Paramyxoviridae (including RSV) infections or conditions related to abnormal cellular proliferation, or alternatively, to prolong the onset of a Flaviviridae (including HCV), Orthomyxoviridae (including Influenza A and B), Paramyxoviridae (including RSV) infections or conditions related to abnormal cellular proliferation, which manifests itself in clinical symptoms.

In addition, compounds according to the present invention can be administered in combination or alternation with one or more antiviral, anti-HBV, anti-HCV or anti-herpetic agent or interferon, anti-cancer or antibacterial agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

This invention is further illustrated in the following sections. The Experimental Details section and Examples contained therein are set forth to aid in an understanding of the invention. This section is not intended to, and should not be interpreted to, limit in any way the invention set forth in the claims that follow thereafter.

VI. THERAPIES FOR THE TREATMENT OF FLAVIVIRIDAE INFECTION

It has been recognized that drug-resistant variants of viruses can emerge after prolonged treatment with an antiviral agent. Drug resistance most typically occurs by mutation of a gene that encodes for an enzyme used in the viral replication cycle, and most typically in the case of HCV, the RNA-dependent-RNA polymerase. It has been demonstrated that the efficacy of a drug against viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Examples of agents that have been identified as active against the hepatitis C virus, and thus can be used in combination or alternation with one or more nucleosides of general formula (I)-(XXIII) include:

(a) interferon and ribavirin (Battaglia, A. M. et al. *Ann. Pharmacother.* 2000, 34, 487; Berenguer, M. et al. *Antivir. Ther.* 1998, 3 (Suppl. 3), 125);

(b) Substrate-based NS3 protease inhibitors (Attwood et al. PCT WO 98/22496, 1998; Attwood et al. *Antiviral Chemistry and Chemotherapy* 1999, 10, 259; Attwood et al. German Patent Publication DE 19914474; Tung et al. PCT WO 98/17679), including alphaketoamides and hydrazinoureas, and inhibitors that terminate in an electrophile such as a boronic acid or phosphonate (Llinas-Brunet et. al. PCT WO 99/07734);

(c) Non-substrate-based inhibitors such as 2,4,6-trihydroxy-3-nitro-benzamide derivatives (Sudo K. et al., *Biochemical and Biophysical Research Communications*, 1997, 238, 643 and Sudo K. et al. *Antiviral Chemistry and Chemotherapy* 1998, 9, 186), including RD3-4082 and RD3-4078, the former substituted on the amide with a 14 carbon chain and the latter processing a para-phenoxyphenyl group;

(d) Thiazolidine derivatives which show relevant inhibition in a reverse-phase HPLC assay with an NS3/4A fusion protein and NS5A/5B substrate (Sudo K. et al. *Antiviral Research* 1996, 32, 9), especially compound RD-1-6250, possessing a fused cinnamoyl moiety substituted with a long alkyl chain, RD4 6205 and RD4 6193;

(e) Thiazolidines and benzanilides identified in Kakiuchi N. et al. *J. EBS Letters* 421, 217 and Takeshita N. et al., *Analytical Biochemistry* 1997, 247, 242;

(f) A phenanthrenequinone possessing activity against HCV protease in a SDS-PAGE and autoradiography assay isolated from the fermentation culture broth of *Streptomyces* sp., Sch 68631 (Chu M. et al., *Tetrahedron Letters* 1996, 37, 7229), and Sch 351633, isolated from the fungus *Penicillium griscofuluum*, which demonstrates activity in a scintillation proximity assay (Chu M. et al., *Bioorganic and Medicinal Chemistry Letters* 9, 1949);

(g) Selective NS3 inhibitors based on the macromolecule elgin c, isolated from leech (Qasim M. A. et al. *Biochemistry* 1997, 36, 1598);

(h) HCV helicase inhibitors (Diana G. D. et al., U.S. Pat. No. 5,633,358 and Diana G. D. et al. PCT WO 97/36554);

(i) HCV polymerase inhibitors such as nucleotide analogues, gliotoxin (Ferrari R. at al. *Journal of Virology* 1999, 73, 1649), and the natural product cerulenin (Lohmann V. et al. *Virology* 1998, 249, 108);

(j) Antisense phosphorothioate oligodeoxynucleotides (S-ODN) complementary to at least a portion of a sequence of the HCV (Anderson et al. U.S. Pat. No. 6,174,868), and in particular the sequence stretches in the 5' non-coding region (NCR) (Alt M. et al. *Hepatology* 1995, 22, 707), or nucleotides 326-348 comprising the 3' end of the NCR and nucleotides 371-388 located in the core coding region of the HCV RNA (Alt M. et al. *Archives of Virology* 1997, 142, 589 and Galderisi U. at al., *Journal of Cellular Physiology* 1999, 81:2151);

(k) Inhibitors of IRES-dependent translation (Ikeda N et al. Japanese Patent Pub. JP-08268890; Kai Y. at al. Japanese Patent Publication JP-10101591);

(l) Nuclease-resistant ribozymes (Maccjak D. J. et al., *Hepatology* 1999, 30, abstract 995);

(m) Amantadine, such as rimantadine (Smith, Abstract from Annual Meeting of the American Gastoenterological Association and AASLD, 1996);

(n) Quinolones, such as ofloxacin, ciprofloxacin and levofloxacin (AASLD Abstracts, Hepatology, October 1994, Program Issue, 20 (4), pt. 2, abstract no. 293);

(o) Nucleoside analogs (Ismaili et al. WO 01/60315; Storer WO 01/32153), including 2'-deoxy-L-nucleosides (Watanabe et al. WO 01/34618), and 1-(β-L-ribofuranosyl)-1,2,4-triazole-3-carboxamide (Levovirin™) (Tam WO 01/46212); and (p) Other miscellaneous compounds including 1-aminoalkylcyclohexanes (Gold et al. U.S. Pat. No. 6,034,134), alkyl lipids (Chojkier et al. U.S. Pat. No. 5,922,757), vitamin E and other antioxidants (Chojkier et al. U.S. Pat. No. 5,922,757), squalene, bile acids (Ozeki et al. U.S. Pat. No. 5,846,964), N-(phosphonoacetyl)-L-aspartic acid, (Diana et al. U.S. Pat. No. 5,830,905), benzenedicarboxamides (Diana et al. U.S. Pat. No. 5,633,388), polyadenylic acid derivatives (Wang et al. U.S. Pat. No. 5,496, 546), 2',3'-dideoxyinosine (Yarchoan et al. U.S. Pat. No. 5,026,687), benzimidazoles (Colacino et al. U.S. Pat. No. 5,891,874), glucamines (Mueller et al. WO 01/08672), substituted-1,5-imino-D-glucitol compounds (Mueller et al. WO 00/47198).

VII. THERAPIES FOR THE TREATMENT OF ORTHOMYXOVIRIDAE INFECTION

It has been recognized that drug-resistant variants of influenza can emerge after prolonged treatment with an antiviral agent. Drug resistance most typically occurs by mutation of a gene that encodes for an enzyme used in the viral replication cycle, resulting in antigenic shifts or drifts. It has been demonstrated that the efficacy of a drug against influenza infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Examples of agents that have been identified as active against the influenza virus, and thus can be used in combination or alternation with one or more nucleosides of general formula (I)-(XXIII) include:

(a) actinomycin D (Barry, R. D. et al. "Participation of deoxyribonucleic acid in the multiplication of influenza virus" *Nature,* 1962, 194, 1139-1140);
(b) amantadine (Van Voris, L. P. et al. "Antivirals for the chemoprophylaxis and treatment of influenza" *Semin Respir Infect,* 1992, 7, 61-70);
(c) 4-amino- or 4-guanidino-2-deoxy-2,3-didehydro-D-N-acetylneuroaminic acid 4-amino- or 4-guanidino-Neu 5 Ac2en (von Itzstein, M. et al. "Rational design of potent sialidase-based inhibitors of influenza virus replication" *Nature,* 1993, 363, 418-423);

(d) ribavirin (Van Voris, L. P. et al. "Antivirals for the chemoprophylaxis and treatment of influenza" *Semin Respir Infect,* 1992, 7, 61-70);
(e) interferon (Came, P. E. et al. "Antiviral activity of an interferon-inducing synthetic polymer" *Proc Soc Exp Biol Med,* 1969, 131, 443-446; Gerone, P. J. et al. "Inhibition of respiratory virus infections of mice with aeresols of synthetic double-stranded ribonucleic acid" *Infect Immun,* 1971, 3, 323-327; Takano, K. et al. "Passive interferon protection in mouse influenza" *J Infect Dis,* 1991, 164, 969-972);
(f) inactivated influenza A and B virus vaccines ("Clinical studies on influenza vaccine—1978" *Rev Infect Dis,* 1983, 5, 721-764; Galasso, G. T. et al. "Clinical studies on influenza vaccine 1976" *J Infect Dis,* 1977, 136 (suppl), S341-S746; Jennings, R. et al. "Responses of volunteers to inactivated influenza virus vaccines" *J Hyg,* 1981, 86, 1-16; Kilbourne, E. D. "Inactivated influenza vaccine" In: Plothin S A, Mortimer E A, eds. *Vaccines* Philadelphia: Saunders, 1988, 420-434; Meyer, H. M., Jr. et al. "Review of existion vaccines for influenza" *Am J Clin Pathol,* 1978, 70, 146-152; "Mortality and Morbidity Weekly Report. Prevention and control of Influenza: Part I, Vaccines. Recommendations of the Advisory Committee on Immunication Practices (ACIP)" *MMWR,* 1993, 42 (RR-6), 1-14; Palache, A. M. et al. "Antibody response after influenza immunization with various vaccine doses: A double-blind, placebo-controlled, multi-centre, dose-response study in elderly nursing-home residents and young volunteers" *Vaccine,* 1993, 11, 3-9; Potter, C. W. "Inactivated influenza virus vaccine" In: Beare A S, ed. *Basic and applied influeza research,* Boca Raton, Fla.: CRC Press, 1982, 119-158).

VIII. THERAPIES FOR THE TREATMENT OF PARAMYXOVIRIDAE INFECTION

It has been recognized that drug-resistant variants of RSV can emerge after prolonged treatment with an antiviral agent. Drug resistance most typically occurs by mutation of a gene that encodes for an enzyme used in the viral replication cycle. It has been demonstrated that the efficacy of a drug against RSV infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Examples of agents that have been identified as active against RSV, and thus can be used in combination or alternation with one or more nucleosides of general formula (I)-(XXIII) include:
(a) ribavirin (Hruska, J. F. et al. "In vivo inhibition of respiratory syncytial virus by ribavirin" *Antimicrob Agents Chemother,* 1982, 21, 125-130); and
(b) purified human intravenous IgG-IVIG (Prince, G. A. et al. "Effectiveness of topically administered neutralizing antibodies in experimental immunotherapy of respiratory syncytial virus infection in cotton rats" *J Virol,* 1987, 61, 1851-1954; Prince, G. A. et al. "Immunoprophylaxis and immunotherapy of respiratory syncytial virus infection in cotton rats" *Infect Immun,* 1982, 42, 81-87).

IX. THERAPIES FOR THE TREATMENT OF ABNORMAL CELLULAR PROLIFERATION

Examples of agents that have been identified as active against abnormal cellular proliferation, and thus can be used in combination or alternation with one or more nucleosides of general formula (I)-(XXIII) include:

A. Alkylating Agents

Nitrogen Mustards: Mechlorethamine (Hodgkin's disease, non-Hodgkin's lymphomas), Cyclophosphamide, Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphoctic leukemia, primary macroglobulinemia, Hodgkin's disease, non-Hodgkin's lymphomas).

Ethylenimines and Methylmelamines: Hexamethylmelamine (ovary), Thiotepa (bladder, breast, ovary).

Alkyl Sulfonates: Busulfan (chronic granuloytic leukemia).

Nitrosoureas: Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (STR) (malignant pancreatic insulinoma, malignant carcinoin).

Triazenes: Dacarbazine (DTIC; dimethyltriazenoimidazole-carboxamide) (malignant melanoma, Hodgkin's disease, soft-tissue sarcomas).

B. Antimetabolites

Folic Acid Analogs: Methotrexate (amethopterin) (acute lymphocytic leukemia, choriocarcinoma, mycosis fungoides, breast, head and neck, lung, osteogenic sarcoma).

Pyrimidine Analogs: Fluorouracil (5-fluorouracil; 5-FU) Floxuridine (fluorodeoxyuridine; FUdR) (breast, colon, stomach, pancreas, ovary, head and neck, urinary bladder, premalignant skin lesions) (topical), Cytarabine (cytosine arabinoside) (acute granulocytic and acute lymphocytic leukemias).

Purine Analogs and Related Inhibitors: Mercaptopurine (6-mercaptopurine; 6-MP) (acute lymphocytic, acute granulocytic and chronic granulocytic leukemia), Thioguanine (6-thioguanine: TG) (acute granulocytic, acute lymphocytic and chronic granulocytic leukemia), Pentostatin (2'-deoxycyoformycin) (hairy cell leukemia, mycosis fungoides, chronic lymphocytic leukemia).

Vinca Alkaloids: Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung).

Epipodophylotoxins: Etoposide (testis, small-cell lung and other lung, breast, Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

C. Natural Products

Antibiotics: Dactinomycin (actinonmycin D) (choriocarcinoma, Wilms' tumor rhabdomyosarcoma, testis, Kaposi's sarcoma), Daunorubicin (daunomycin; rubidomycin) (acute granulocytic and acute lymphocytic leukemias), Doxorubicin (soft tissue, osteogenic, and other sarcomas; Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcema), Mitomycin (mitomycin C) (stomach, cervix, colon, breast, pancreas, bladder, head and neck).

Enzymes: L-Asparaginase (acute lymphocytic leukemia).

Biological Response Modifiers: Interferon-alfa (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

D. Miscellaneous Agents

Platinum Coordination Complexes: Cisplatin (cis-DDP) Carboplatin (testis, ovary, bladder, head and neck, lung, thyroid, cervix, endometrium, neuroblastoma, osteogenic sarcoma).

Anthracenedione: Mixtozantrone (acute granulocytic leukemia, breast).

Substituted Urea: Hydroxyurea (chronic granulocytic leukemia, polycythemia vera, essential thrombocytosis, malignant melanoma).

Methylhydrazine Derivative: Procarbazine (N-methylhydrazine, MIH) (Hodgkin's disease).

Adrenocortical Suppressant: Mitotane (o,p'-DDD) (adrenal cortex), Aminoglutethimide (breast).

Adrenorticosteriods: Prednisone (acute and chronic lymphocytic leukemias, non-Hodgkin's lymphomas, Hodgkin's disease, breast).

Progestins: Hydroxprogesterone caproate, Medroxyprogesterone acetate, Megestrol acetate (endometrium, breast).

E. Antioangiogenesis Agents

Angiostatin, Endostatin.

F. Hormones and Antagonists

Estrogens: Diethylstibestrol Ethinyl estradiol (breast, prostate)

Antiestrogen: Tamoxifen (breast).

Androgens: Testosterone propionate Fluxomyesterone (breast).

Antiandrogen: Flutamide (prostate).

Gonadotropin-Releasing Hormone Analog: Leuprolide (prostate).

X. SYNTHETIC PROTOCOL

Compounds of formula (I)-(XXIII) can be synthesized by any means known in the art. In particular, the compounds can be made via three distinct routes: (a) from a pre-formed nucleoside, (b) condensation of a modified sugar or unmodified ribose with purine or pyrimidine, and (c) combination of the two routes. Since the 3-deoxy-D-erythropentofuranose structure is found in the nucleoside antibiotic, cordycepin, a number of total syntheses of this antibiotic have been reported during 1960s (see: Lee, W. W. et al. *J. Am. Chem. Soc.*, 1961, 83, 1906; Walton, E. et al. *J. Am. Chem. Soc.*, 1964, 86, 2952; Suhadolnik, R. J. et al. *Carbohydr. Res.*, 1968, 61, 545; Ikehara, M. et al. *Chem. Pharm. Bull.*, 1967, 15, 94; Kaneko, M. et al. *Chem. Pharm. Bull.* 1972, 20, 63). In a preferred embodiment of the invention, preparation of 3'-deoxy nucleosides from preformed nucleosides are performed in the following ways;

A. Compounds of Types Ia-c and IIIa-c.

(i) Synthesis from Pre-Formed Nucleosides:

From the teachings of Marumoto, R. et al. *Chem. Pharm. Bull.* 1974, 22, 128 where $N^4$-acetylcytidine is treated with acetyl bromide to give 2',5'-di-O-acetyl-3'-bromo-3'-deoxy-β-D-xylofuranosyl-cytosine (2, R=Ac), $N^4$-protected-cytidine nucleosides can be derivatized to form pyrimidine nucleosides (I-a) as shown in Scheme 1.

Scheme 1

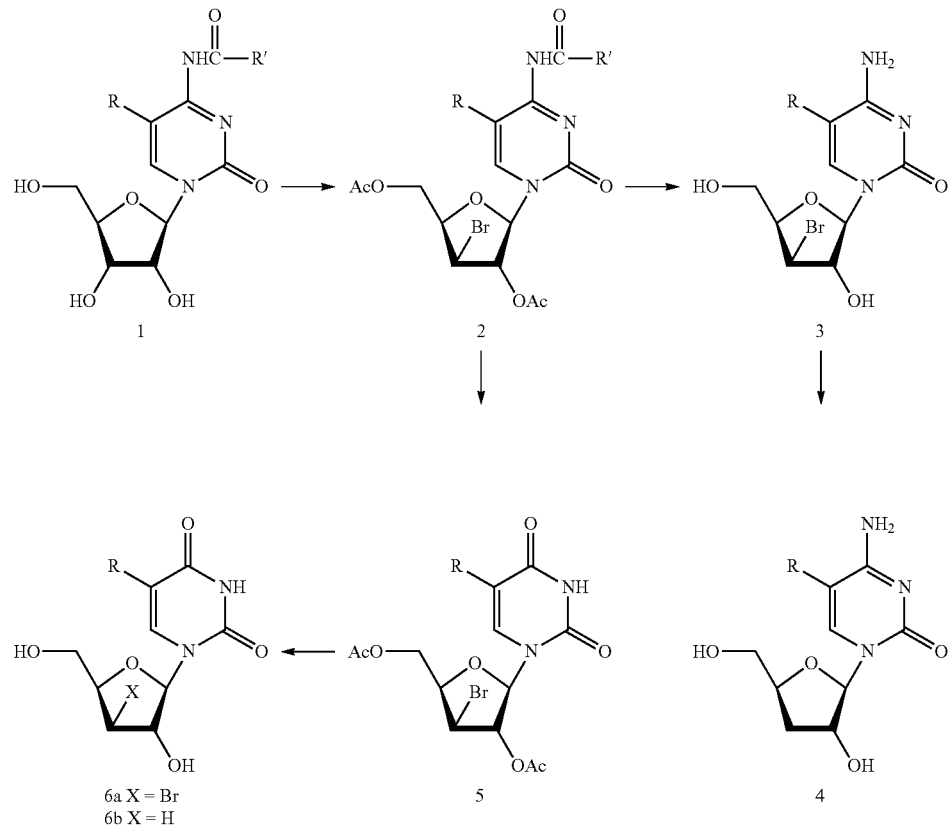

6a X = Br
6b X = H

An N⁴-protected-D-cytidine nucleoside 1 can be treated with an acid halide, such as acetyl bromide, to give the corresponding 3'-halo-xylo-nucleoside 2. Deacetylation of 2 to 3, followed reductive dehalogenation affords the desired 3'-deoxycytidine derivatives 4. Treatment of 2 with an acid, preferably boiling aqueous acetic acid, gives the corresponding protected uracil nucleoside 5, which can be readily converted into free 3'-bromo-xylo nucleoside 6a, from which 3'-deoxyuridine derivatives 6b can be obtained by reductive debromination. In a similar manner, starting from N⁴-protected-L-cytidine, the L-enantiomer (III-a) of 4 and 6 can be synthesized.

In an alternate embodiment for the preparation of nucleosides I-a, 2',5'-di-O-tritylation of a ribonucleoside gives 7 (R²'=R⁵'=Tr) which is converted into the corresponding 3'-O-mesylates 8 (Scheme 2). Treatment of 8 with diluted potassium or sodium hydroxide gives the corresponding xylo derivative 10 via anhydronucleoside 9, which, after de-O-tritylation, affords 12. Mesylation of 10, followed by de-O-tritylation yields the 3'-O-mesyl xylo-nucleoside. Upon treatment of 8 with lithium bromide or sodium iodide, the corresponding 3'-deoxy-3'-halogeno derivative 11 is formed via 9, which, after de-O-tritylation, followed by hydrogenolysis, is converted into the desired 3'-deoxyuridine derivative 6b. In a similar manner, starting from an L-ribonucleoside, the L-nucleoside (III-a) counterparts of 4 and 6 are synthesized.

An example for the preparation of type I-b compound, purine nucleoside, is the synthesis of 3'-deoxypurine nucleosides (Scheme 3). Ribonucleoside 13 is treated with 2-methoxyisobutyryl halide (X═Cl or Br) to give a mixture of 3'-halogeno-xylo-furanosyl and 2'-halogeno-arabinofuranosyl derivatives (14 and 15). Hydrogenolysis, followed by chromatographic separation affords the corresponding 3'-deoxynucleoside 17 along with the 2'-deoxynucleoside 16. Saponification of 17 gives the desired 3'-deoxynucleoside 20. Treatment of the reaction mixture of 14 and 15 with a base gives the single epoxide 18 in quantitative yield, which, upon treatment with ammonium or sodium iodide affords exclusively the 3'-xylo-iodide 19. Hydrogenolysis of 19 affords 20. Reduction of 18 with a reducing agent such as Raney nickel, lithium aluminum hydride or sodium borohydride also yields 20.

In a similar manner, starting from a purine L-ribonucleoside, the L-nucleoside counterpart of 20, which belongs to III-b, can be synthesized.

Scheme 2

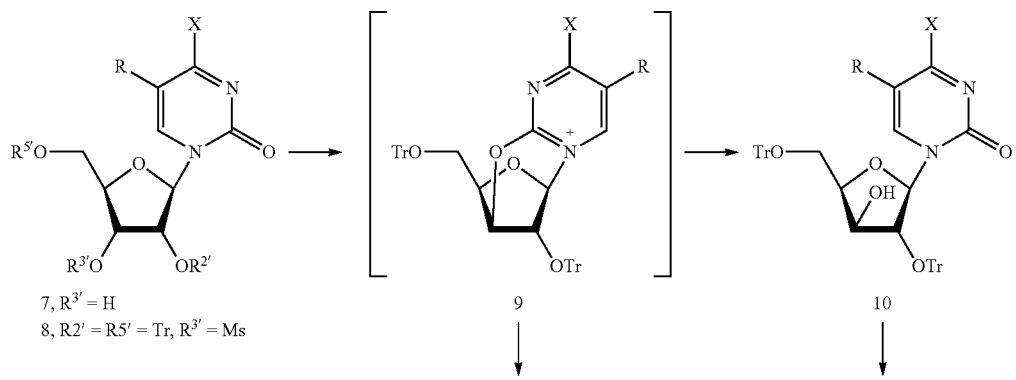

7, R³' = H
8, R2' = R5' = Tr, R³' = Ms

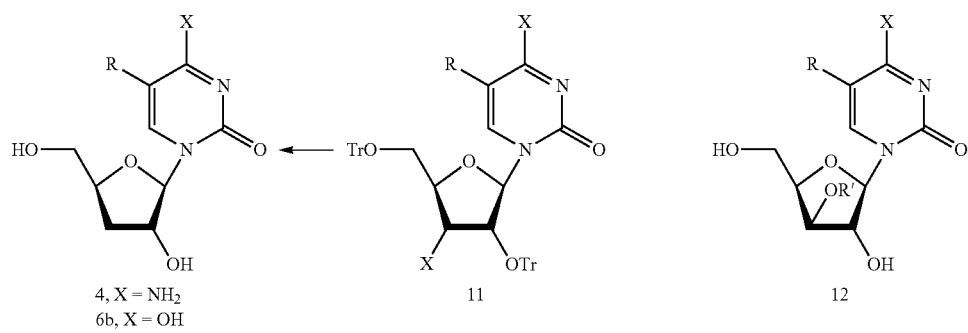

4, X = NH₂
6b, X = OH

11

12

Scheme 3

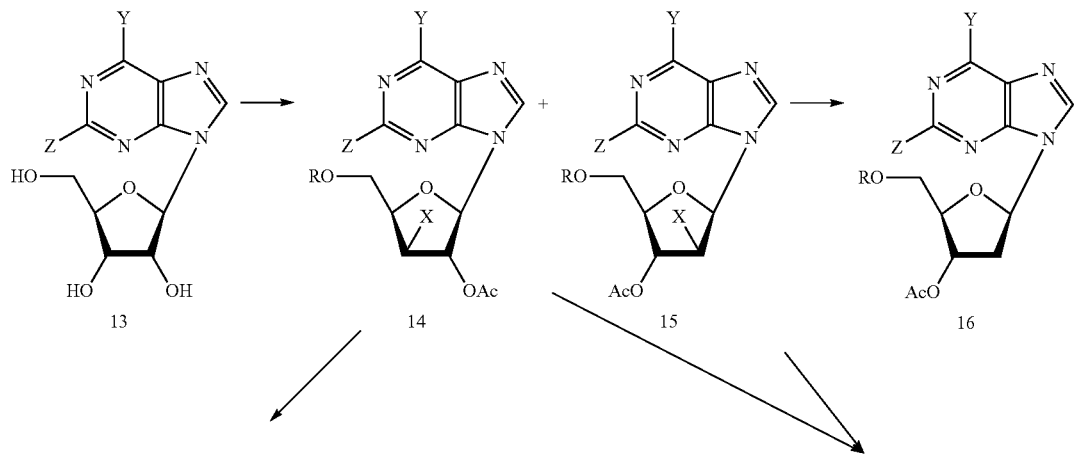

For the synthesis of a compound of formula I-c, the starting material is a 5-nitropyrimidine or pyridine nucleoside (Scheme 4). Treatment of 5-nitrouridine (21, vide supra) with azide ion in a solvent such as alcohol or dimethylformamide at a temperature range of from 20° C. to 100° C., preferably from 25° C. to 80° C. Nucleophilic attack of azide ion at C-6 of 21 results in the formation of aci-nitro salt 22 which cyclizes to 23. Neutralization of 23 furnishes the bicyclic nucleoside 24.

Scheme 4

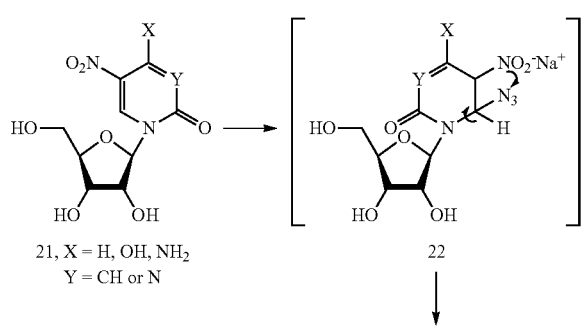

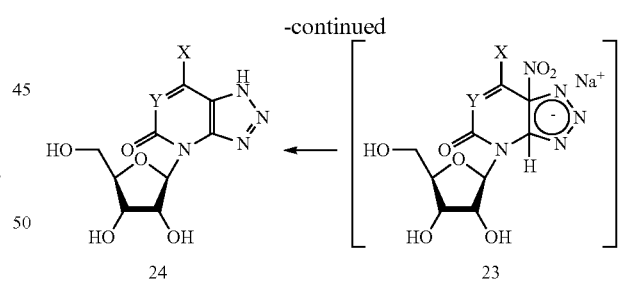

(ii) Synthesis by Condensation of an Appropriate Sugar with Base.

The appropriate sugar derivatives must be prepared for condensation with the selected base. Though there are several methods for the synthesis of 3-deoxy-D-erythropentofuranose (3-deoxy-D-ribofuranose) derivatives (see: Lee, W. W. et al. *J. Am. Chem. Soc.*, 1961, 83, 1906; Walton, E. et al. *J. Am. Chem. Soc.*, 1964, 86, 2952; Lin, T.-S. et al. *J. Med. Chem.*, 1991, 34, 693; Ozols, A. M. et al. *Synthesis*, 1980, 557), new methods were developed for the present invention as shown in Scheme 5.

Scheme 5

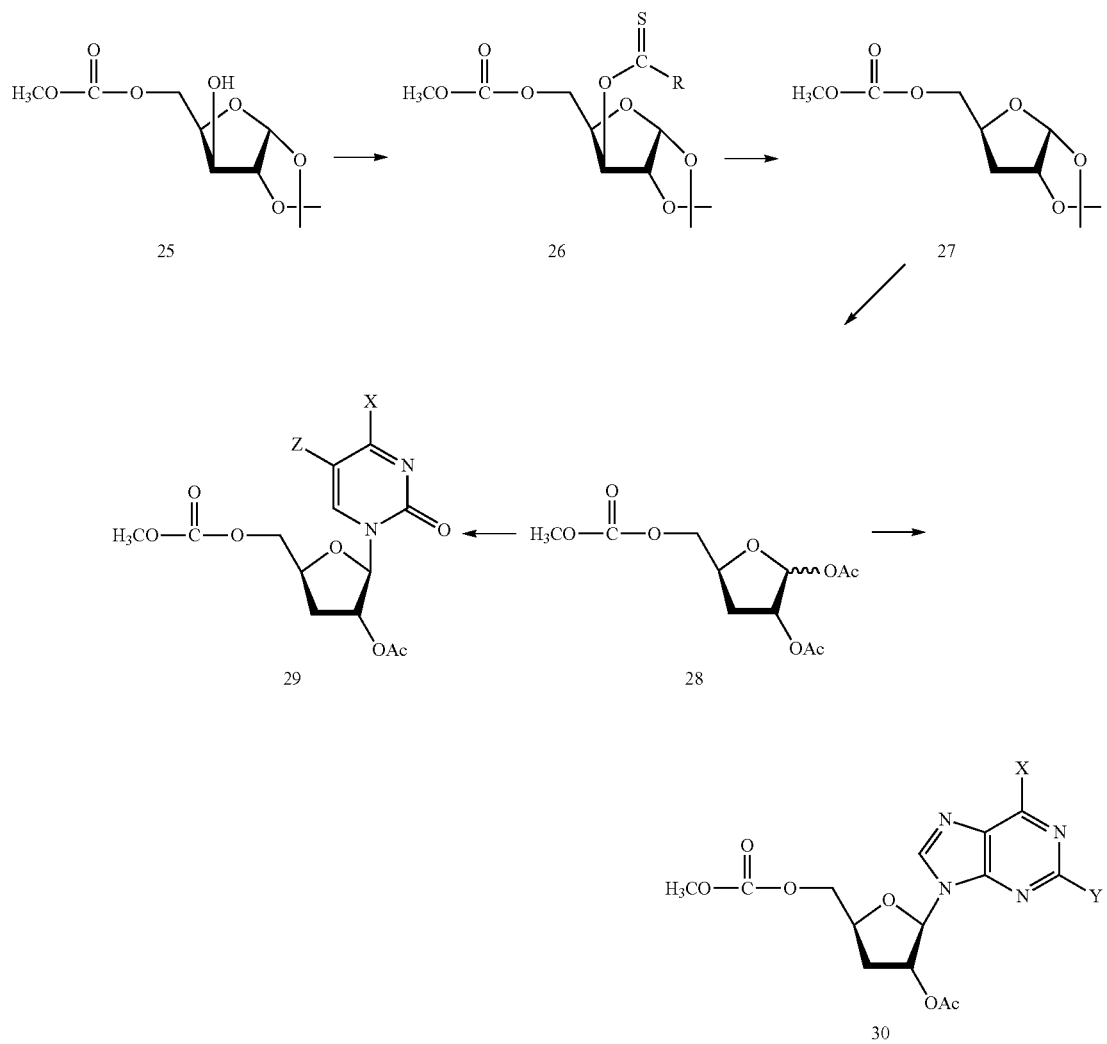

R = SCH₃, SC₂H₅, SCH₂Ph, N¹-imidazolyl, OPhe 1,2-O-Isopropylidene-5-O-methoxycarbonyl-α-D-xylofuranose (25) is converted into the corresponding 3-thiocarbonyl derivative 26, followed by free radical deoxygenation using trialkyltin hydride in the presence of a radical initiator, such as 2,2'-azobisisobutyronitrile. The deoxygenated product 27 is acylated with a mixture of acetic acid, acetic anhydride and sulfuric acid to give 28, which then is condensed with a silylated base using Vorbruggen's procedure (see: Niedballa, U. et al. *J. Org. Chem., a* 1976, 41, 2084; Vorbruggen, H. et al. *Chem. Ber.,* 1981, 114, 1234; Kazinerczuk, Z. et al. *J. Am. Chem. Soc.,* 1984, 106, 6379) to obtain the pyrimidine nucleoside 29 (Type I-a) or a related purine nucleoside (Type I-b). The 5-OH group can be alternatively protected with other acyl groups, such as benzoyls, p-nitrobenzoyls, p-chlorobenzoyls or p-methoxybenzoyls as well as other silyl groups, such as t-butyldimethylsilyl or t-butyldiphenyl groups. Similarly, L-xylose can be converted into the L-sugar counterpart of 25, which can be further derivatized to attain the L-nucleoside of 30.

Alternatively, as shown in Scheme 6, 1,2-O-isopropylidene-5-O-(t-butyldiphenylsilyl)-α-D-xylofuranose (31) can be sulfonylated with mesyl chloride, tosyl chloride or tresyl chloride in pyridine to obtain 32. After methanolysis of 32, the methyl xyloside 33 can be treated with a base, such as sodium methoxide in methanol, to afford the ribo-epoxide 34. Opening of the epoxide 34 with lithium aluminum hydride stereoselectively produces 3-deoxy sugar 36. Treatment of 34 with lithium bromide or sodium iodide in acetone or 2-butanone gives 3-halogeno-3-deoxy xyloside 35. Reductive dehalogenation of 35 affords 36. Removal of the 5'-silyl protecting group with a fluoride ion source, such as tri-n-butylammonium fluoride in tetrahydrofuran or triethylammonium hydrogen fluoride gives 37. Acylation of 37 with acetic anhydride and acetic acid in the presence of sulfuric acid gives tri-O-acetyl-3-deoxy-D-ribofuranose 38. Also, fluoride treatment converts 33 into 39, which, upon acetylation, affords 40. These acetylated sugars 38 and 40 can be condensed with pertrimethylsilylated pyrimidine or purine bases using Vorbrueggen's procedure to give the 3'-modified nucleoside. The t-butyldiphenylsilyl protecting group can be replaced by t-butyldimethylsilyl group.

Scheme 6

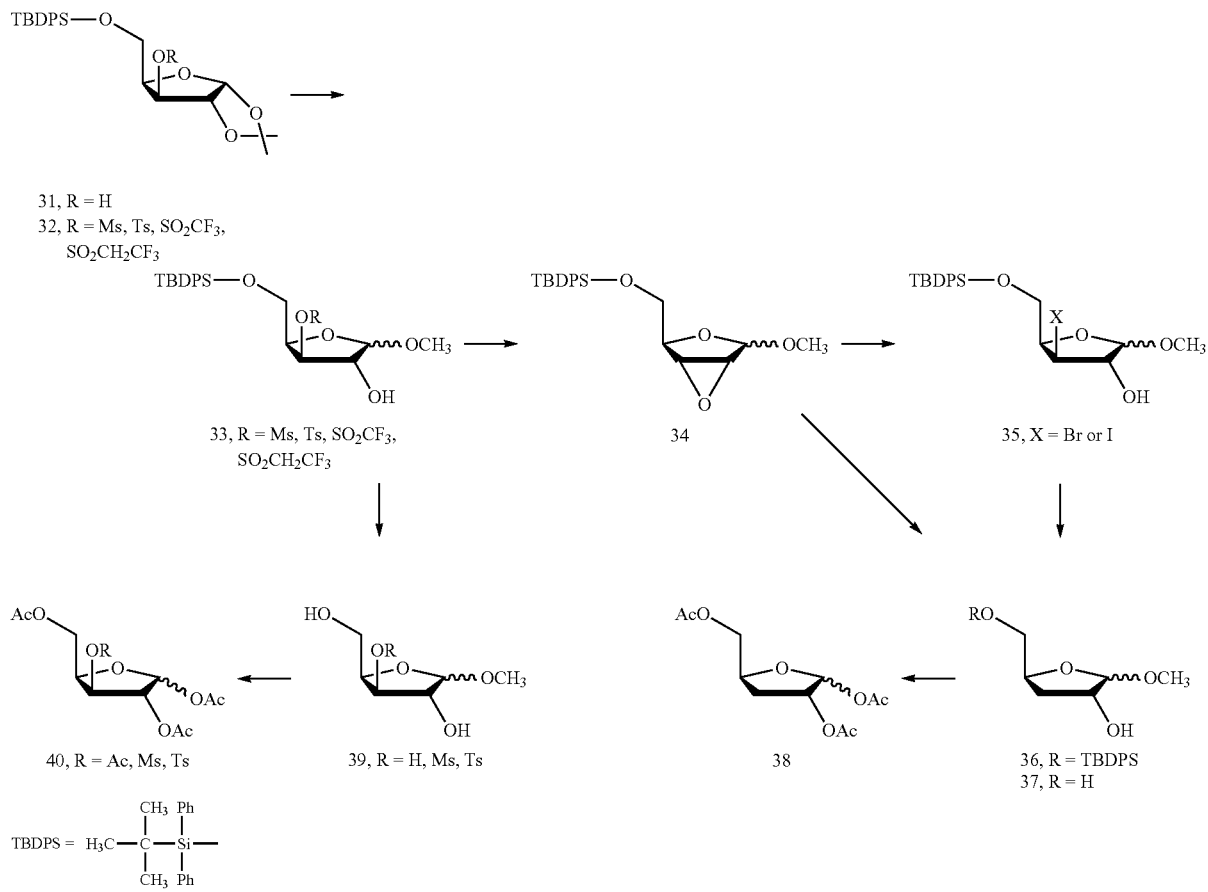

(Iii) Post Synthetic Modifications (1-6)

(a) Modification at C-4 of Pyrimidine Nucleosides (I-a and III-a)

After condensation of 28 or 38 with uracil or 5-substituted uracil, the protected 3'-deoxyuridine derivative (29, $R^{5'}$=CH$_3$OCO, $R^{2'}$=Ac or $R^{5'}$=$R^{2'}$=Ac) is treated with phosphorus pentasulfide in pyridine or Lawesson's reagent in toluene to give 4-thiouracil nucleoside 41, which, upon treatment with ammonia, is converted into 3'-deoxycytidine (43, $R_1$=$R_2$=H). Alternatively, methylation of 41 with methyliodide or dimethylsulfate in base gives the 4-S-methyl derivative 42. Displacement of the 4-S-methylgroup of 42 with various nucleophiles affords the corresponding $N^4$-substituted 3'-deoxycytidines 43. Also, 29 can be converted into the 4-(triazol-2-yl) derivative 44, which can be reacted with ammonia or various amines to give 43. Alternatively, treatment of 44 with various alcohols or phenols affords the corresponding 4-O-substituted-3' deoxyuridines.

Scheme 7

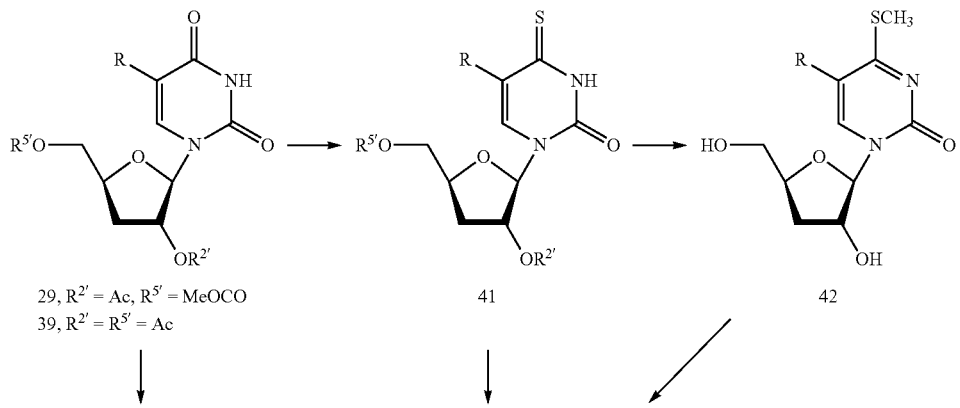

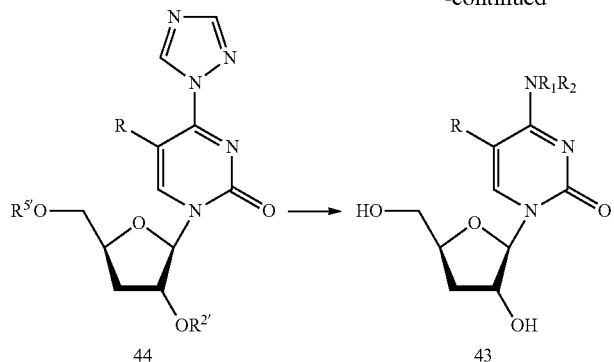

Alternatively, a uracil nucleoside, such as a sugar-protected uridine 45 (R=H) is converted into the 4-(methyl-imidazolium) 46 (Scheme 8) or 4-O-(2,4,6-triisopropylbenzenesulfonyl) intermediate 47 and then treated with a nucleophile, such as hydroxylamine, to give the corresponding C-4 modified nucleoside, such as $N^4$-hydroxy-cytidine (48, R=H).

In similar manners starting from the L-nucleoside counterparts, the corresponding III-a nucleosides are prepared.

(b) Modification at C-5 of Pyrimidine Nucleosides (I-a and III-a)

(i) Halogenation (Scheme 9)

3'-Deoxyuridine (6, R=H) can be fluorinated with fluorinating agents, some non-limiting examples include fluo- Scheme 8

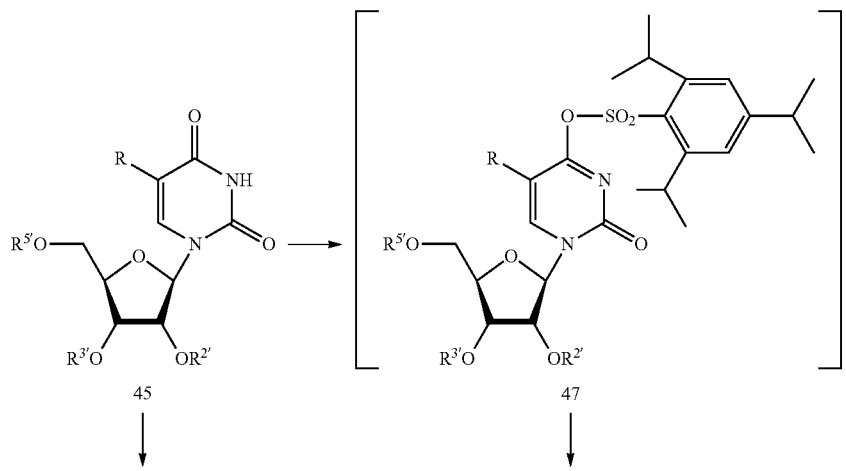

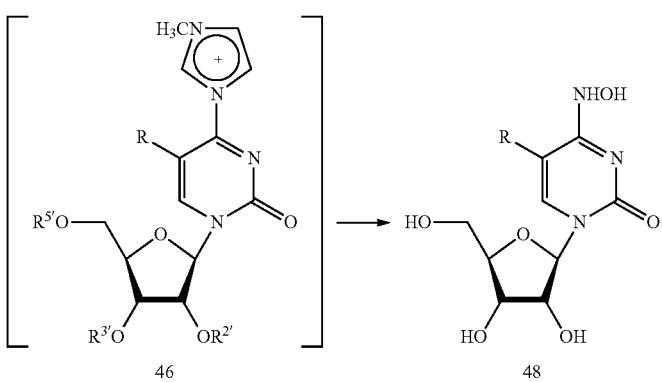

rine in acetic acid, selectfluor in an inert solvent or solvents such as tetrahydrofuran or cesium fluoroxisulfate in alcohol (see: Stovber, S. et al. *J. Chem. Soc. Chem. Commun.*, 1983, 563), to give 5-fluoro-3'-deoxyuridine (49). The 5-chloro, 5-bromo and 5-iodouridine derivatives (50-52) are obtained using the appropriate N-halogenosuccinimide. Treatment of 6 with bromine in water or iodine in acetic acid in the presence of an oxidizing agent such as nitric acid affords the 5-bromo- or 5-iodo-uracil nucleoside, respectively. The cytosine derivative 43 (R═H) also can be converted into the corresponding 5-halogeno derivative (44-56). 5-Fluoro-3'-deoxycytidine (53, R═H) is prepared by condensing 28 or 38 with 5-fluorocytosine, followed by saponification.

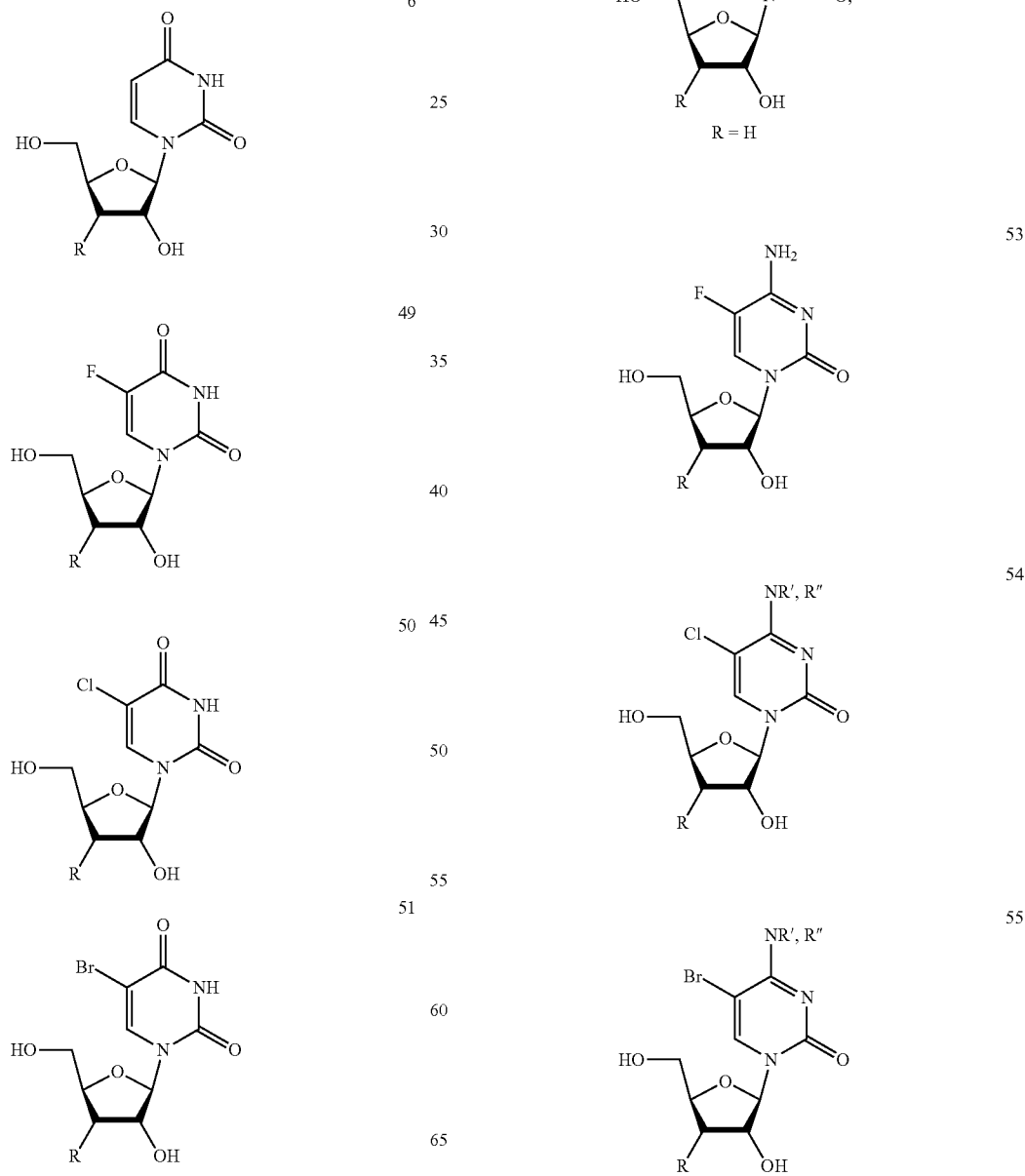

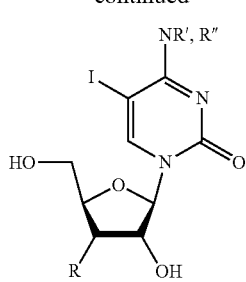

56

In similar manners starting from the L-nucleoside counterparts, the corresponding III-a nucleosides are prepared. Scheme 10 depicts the conversion of the brominated compound 51 into 5-hydroxy-3'-deoxyuridine (63) by treatment with sodium bicarbonate solution. Alkylation of 55 with an alkyl iodide with base affords 62. Prolonged reaction of 51 with an alkali metal cyanide gives the 5-cyano-uracil derivative 57, which can be hydrated to 5-carboxamide 58 and 5-carboxylic acid 59. Conversion of 59 into an alkyl ester 60, followed by reduction with sodium borohydride yields the 5-hydroxymethyl derivative 61. Compound 60 alternatively can be treated with dihydropyran and a catalytic amount of acid, such as hydrochloric, sulfuric or p-toluenesulfonic acid, to yield the 2',5'-di-O-protected nucleoside 64. Sodium borohydride reduction of 64 affords 65. Due to allylic nature of 65, treatment with mesyl chloride or tosyl chloride gives the 5-chloromethyl-uracil derivative 66. Alkoxide treatment of 66, followed by deprotection gives the corresponding 5-alkoxymethyl-3'-deoxyuridine (69). Similarly, reaction of various amines with 66 affords 67, which, upon mild acid hydrolysis, is converted into 68. Reaction with 66 and thiourea gives mercaptomethyl derivative (70, R=H), while treatment with sodium mercaptide gives thioalkyl derivative 70 (R=alkyl), which can be oxidized with hydrogen peroxide to the corresponding sulfone (71). In similar manners starting from the L-nucleoside counterparts, the corresponding III-a nucleosides are prepared.

Scheme 10

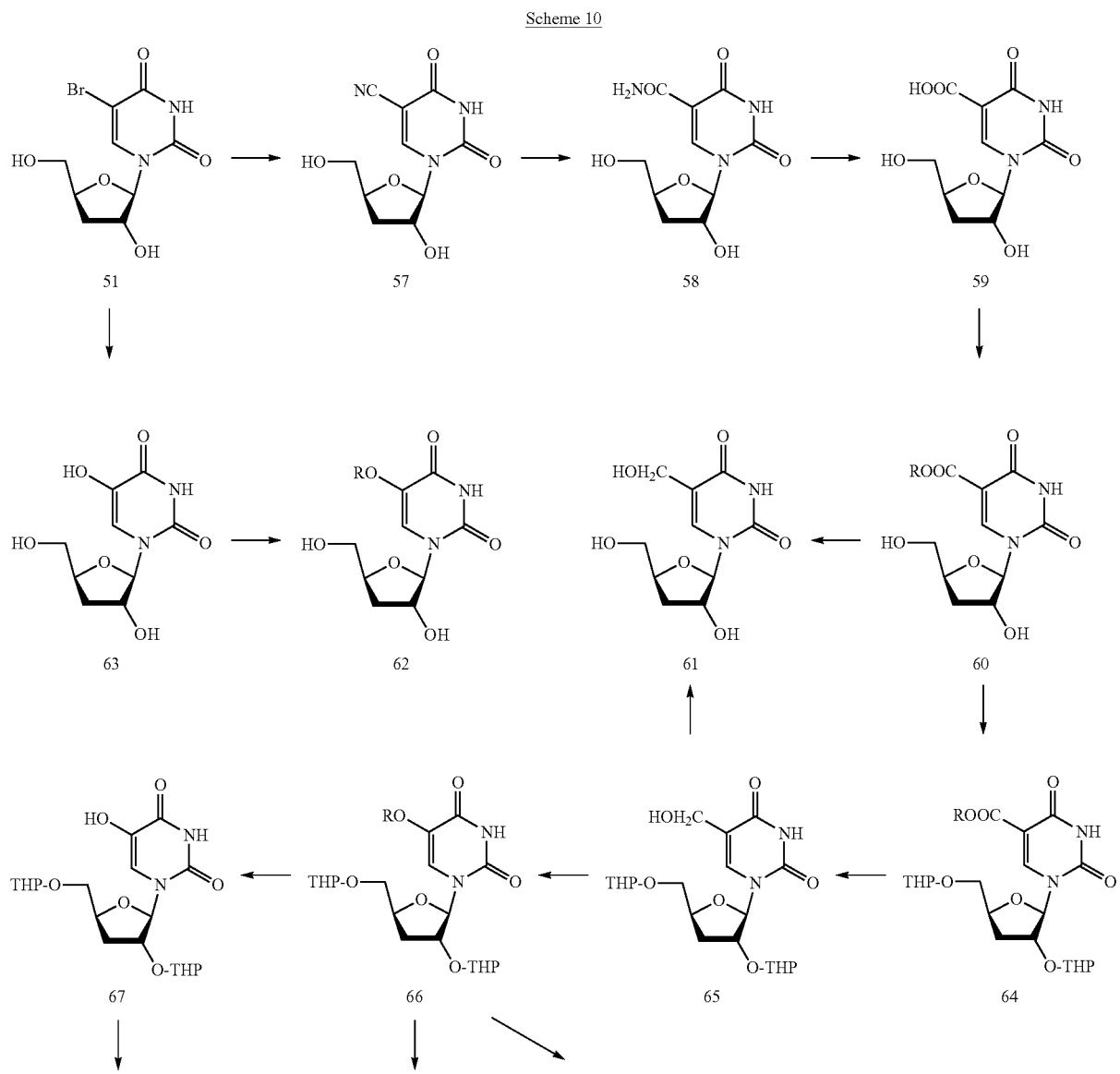

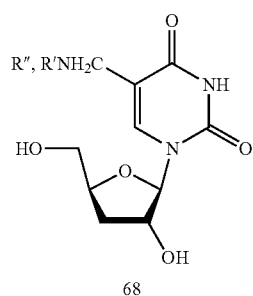
68

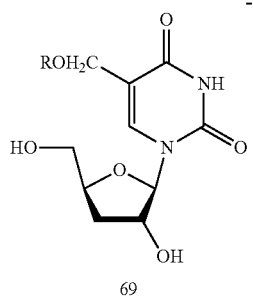
69

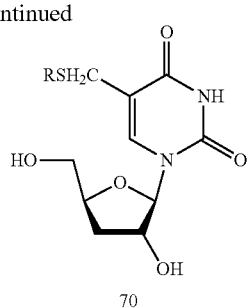
70

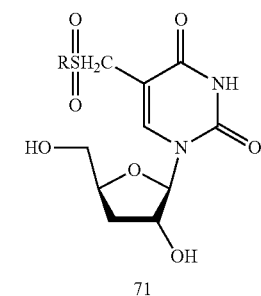
71

(ii) Nitration (Scheme 11)

Treatment of uridine 6 with nitronium tetrafluoroborate in sulfolane (see: Huang, G.-F. et al. *J. Org. Chem.*, 1977, 42, 3821; Huang, G.-F. et al. *J. Carbohyd. Nucleosides Nucleotides*, 1978, 5, 317) affords the corresponding 5-nitro derivative 72. Catalytic hydrogenation of the nitro-nucleoside 72 gives the corresponding 5-amino derivative 73. Diazotization of 73 with nitrous acid gives the 5-diazo-3'-deoxyuridine (74), which, upon hydrolysis, can be converted into the 1,2,3-triazole 75. Similar conversions of 5-aminouridine into ribosilyltriazole have been reported (see: Roberts, M. et al. *J. Am. Chem. Soc.*, 1952, 74, 668; Thurber, T. C. et al. *J. Am. Chem. Soc.*, 1973, 95, 3081; *J. Org. Chem.*, 1976, 41, 1041). Reaction of 72 with sodium azide in dimethylformamide affords the triazolopyrimidine (8-azapurine) nucleoside 76.

In similar manners starting from the L-nucleoside counterparts, the corresponding III-a nucleosides are prepared.

A similar sequence of reactions is shown in Scheme 12, starting from 3'-deoxycytidine 4 gives 5-nitro-3'-deoxycytidine (77), followed by 5-amino-3'-deoxycytidine (78). However, treatment of 78 with nitrous acid results in the formation of another 8-azapurine nucleoside 79. The same sequence of reactions can be applied to the corresponding L-nucleosides III-a.

Scheme 12

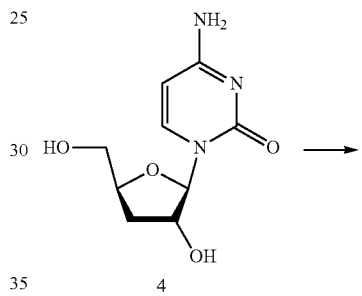
4

Scheme 11

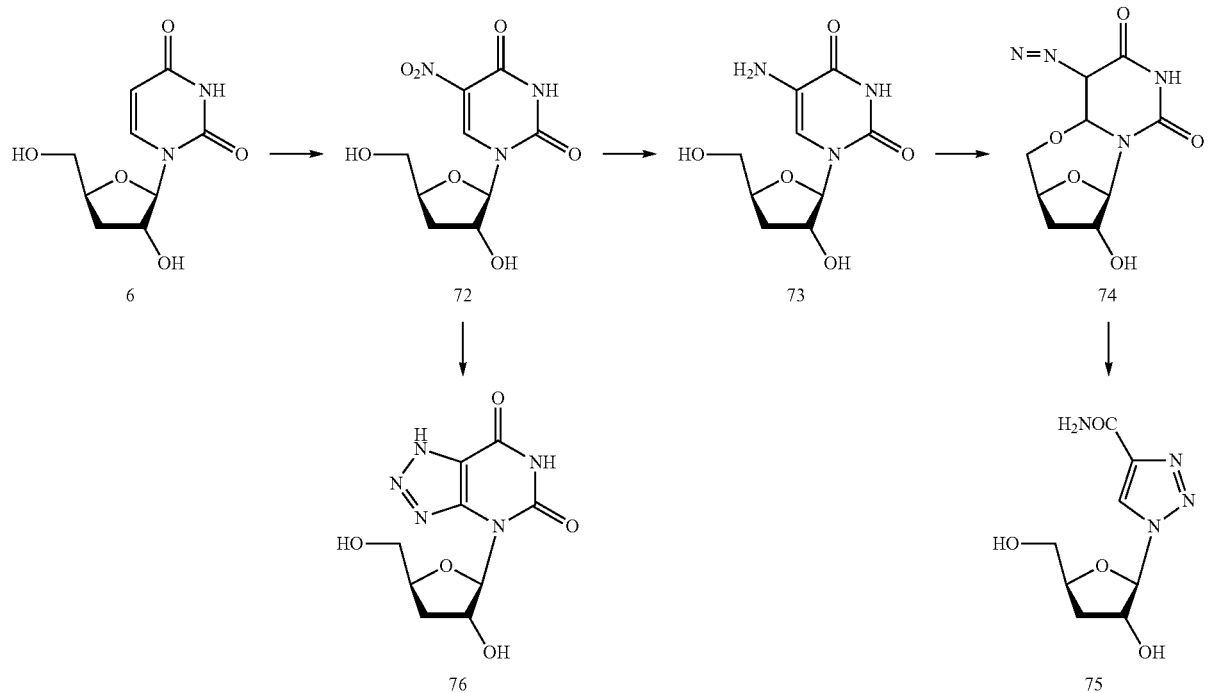

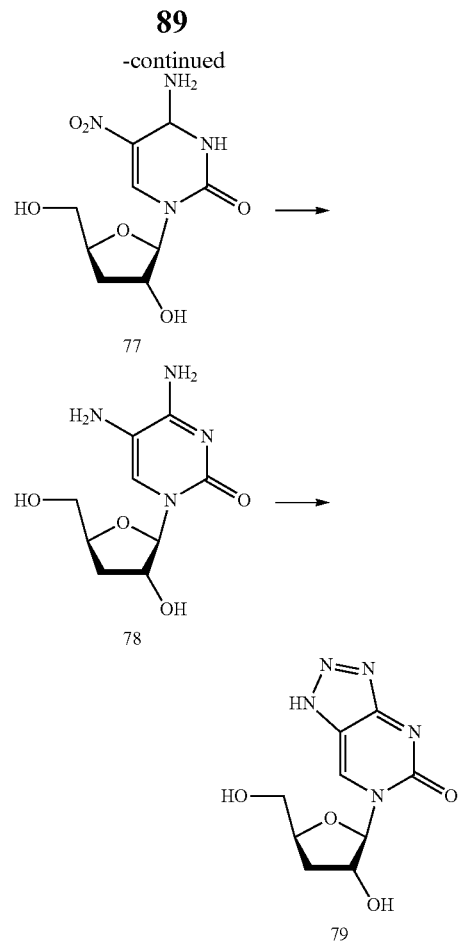

77

78

79

(iii) Hydroxymethylation

Treatment of 6 (R=H, $R^{5'}$=$R^{3'}$=$R^{3''}$H) with formaldehyde in base such as aqueous potassium hydroxide or sodium hydroxide gives 5-hydroxymethyl-3'-deoxyuridine (80) as shown in Scheme 13, which is converted into 5-ethoxymethyl-3'-deoxyuridine (81, X=OCH$_2$CH$_3$) by treatment with ethanolic hydrogen chloride. Compound 80 ($R^{5'}$=$R^{3'}$=TBDPS) can also be prepared from the thymine derivative 6 (R=CH$_3$, $R^{5'}$=$R^{3'}$=TBDPS) by photochemical bromination to 81 (X=Br), followed by hydrolysis (Matulic-Adamic, J. et al. *Chem. Pharm. Bull.*, 1988, 36, 1554). Compound 80 is converted into 5-chloromethyl derivative (81, X=Cl) by action of hydrochloric acid or 5-fluoromethyl derivative (81, X=F) by treatment with diethylaminosulfur trifluoride (DAST). Oxidation of 80 ($R^{5'}$=$R^{2'}$=TBDPS, $R^{3''}$=H) with manganese dioxide affords the 5-formyl derivative 82, which is a good substrate for various reactions including Wittig, Wittig-Horner, Grignard or Reformatsky reaction. For example, treatment of 82 with ethoxymethylene triphenylphosphorane [EtOC(=O)CH=PPh$_3$] gives 5-(2-ethoxycarbonypethylene-3'-deoxyuridine derivative (83), which can be converted into 5-ethylene-, 5-(2-chloroethylene)- or 5-(2-bromoethylene)-3'-deoxyuridine derivative (85) by way of the 5-(ethylene-2-carboxylic acid) derivative 84. 5-Difluoromethyl derivative 86 can be obtained by treatment of 82 with DAST. These synthetic pathways are shown in Scheme 13.

The same sequence of reactions can be applied to the corresponding L-nucleosides III-a.

Scheme 13

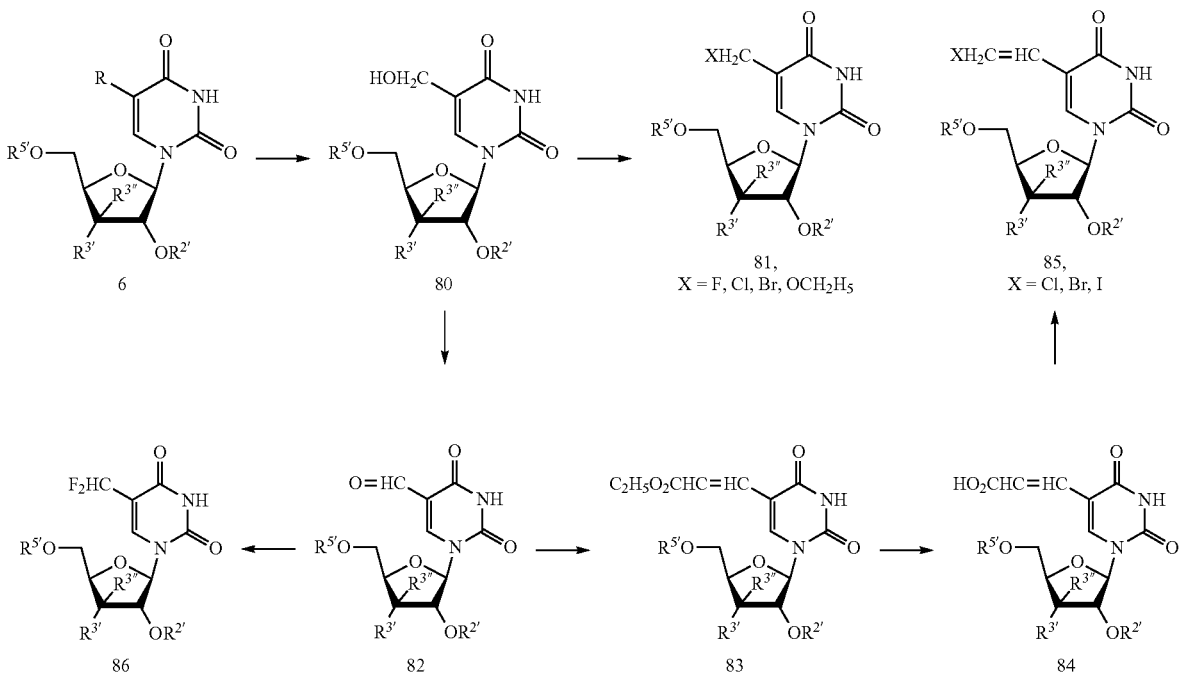

(iv) Metallation

In aqueous buffer, 6 or 4 can be treated with mercuric acetate, followed by sodium chloride, to give the corresponding 5-chloromercuri derivative 87 or 91, respectively (Scheme 14), in quantitative yield. Reaction of 87 or 91 with iodine in ethanol gives the 5-iodo derivative 52 or 56, respectively. Compound 52 can be converted to 5-ethynyl derivatives 88 by reaction with 1-alkynes and bis(triphenylphosphine)palladium chloride $(Ph_3P)_2PdCl_2$ in the presence of cuprous iodide and triethylamine. Treatment with trifluoroiodomethane and powdered copper, on the other hand, converts 52 into 5-trifluoromethyl-3'-deoxyuridine 89. Treatment of 87 with lithium palladium chloride $(Li_2PdCl_4)$ and allyl chloride affords 5-allyl-3'-deoxyuridine (90). Methyl acrylate reacts with 87 or 91 in the presence of $Li_2PdCl_2$ to give 5-(E)-(2-methoxy-carbonyl)vinyl-3'-deoxyuridine (83) or -cytidine (92), respectively. Saponification of 83 to 84, followed by N-halogenosuccinimide yields 5-(E)-halogenovinyluracil nucleoside 85 (X=Cl, Br or I). Thermal decarboxylation of 84 gives 5-vinyluracil derivative 85 (X=H). Compound 85 (X=H) can also be prepared by treatment of 52 with vinyl acetate in the presence of palladium acetate-triphenylphosphine complex. Similarly, 91 can be converted into the corresponding acrylate derivative 92, which, after hydrolysis to 93, is reacted with N-halogenosuccinimide to give 5-(E)-(2-halogenovinyl)-3'-deoxycytidines (94). It should be noted that catalytic hydrogenation of 5-vinyl derivatives gives the corresponding 5-ethyl-pyrimidine nucleosides. Hydration of 5-ethynyl-3'-deoxyuridine (88, R=H) with diluted sulfuric acid gives 5-acetyl-3'-deoxyuridine in high yield.

In a similar manner but starting from the L-nucleoside counterparts, the corresponding III-a nucleosides are prepared.

Scheme 14

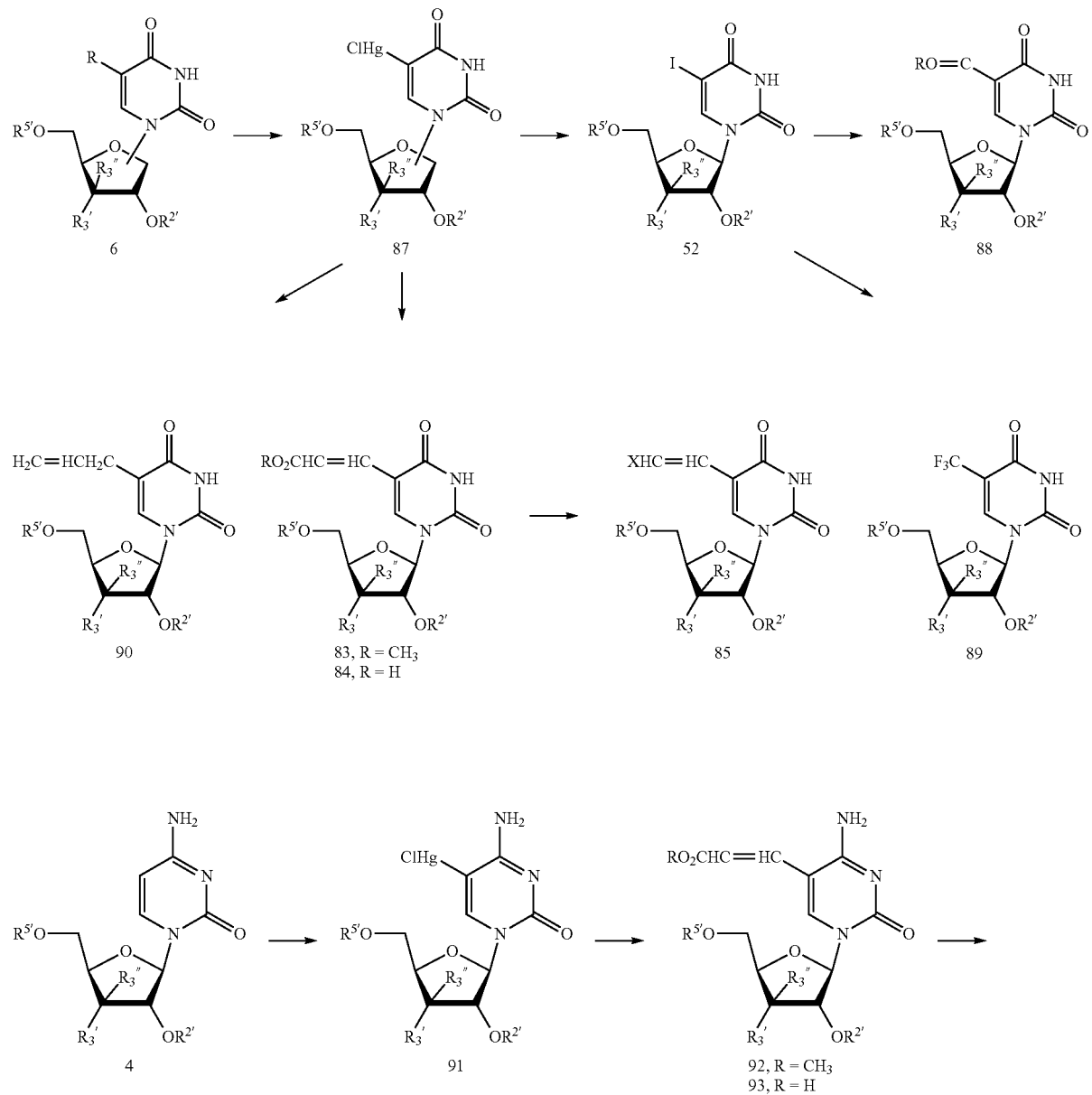

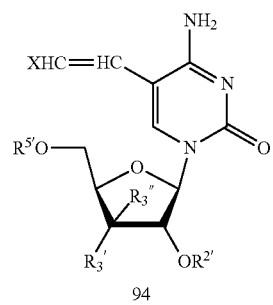

(c) Modification at C-6 of Pyrimidine Nucleosides (I-a and III-a)

Treatment of 5-bromo-3'-deoxyuridine (51, Scheme 15) with sodium or potassium cyanide in dimethylformamide at room temperature affords 6-cyano-3'-deoxyuridine (95) in high yield. Further treatment at elevated temperature converts 95 into the 5-cyano isomer 59. Hydrolysis of 95 furnishes 3'-deoxyorotidine 96. Methanolysis of 95 gives the methyl ester 97, which, upon amminolysis, is converted into 98, wherein R' is lower alkyl of from $C_1$ to $C_6$ or benzyl or phenyl group. Reduction of 97 with sodium borohydride affords 6-hydroxymethyl derivative 99, which is converted into 6-chloromethyluracil nucleoside 100 by action of hydrochloric acid. Reaction with various amines, 100 is converted into the corresponding 6-aminomethyl-3'-deoxyuridine (101). A similar sequence of reactions starting from 3'-deoxycytidine (55) gives 3'-deoxycytidin-6-yl-carboxylic acid (103) or its methyl ester 104 via the 6-cyano intermediate 102. Various 6-carbox-amidocytosine nucleosides 105 can be obtained by treatment of 104 with the corresponding amines. Borohydride reduction of 104 affords 6-hydroxymethyl derivative 106 which can be converted into 6-chloromethyl-3'-deoxycytidine 107 by action of hydrochloric acid. Compound 107 can be converted into the corresponding 6-aminomethyl-3'-deoxycytidine (108) by reaction with various amines. The same sequence of reactions can be applied to the corresponding L-nucleosides

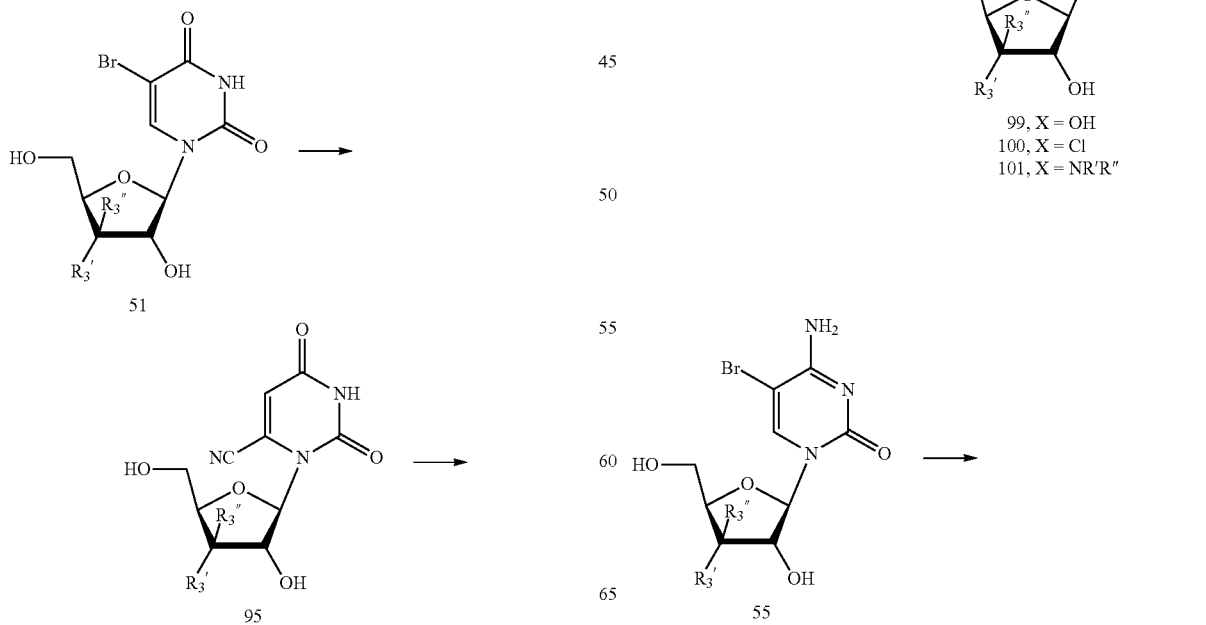

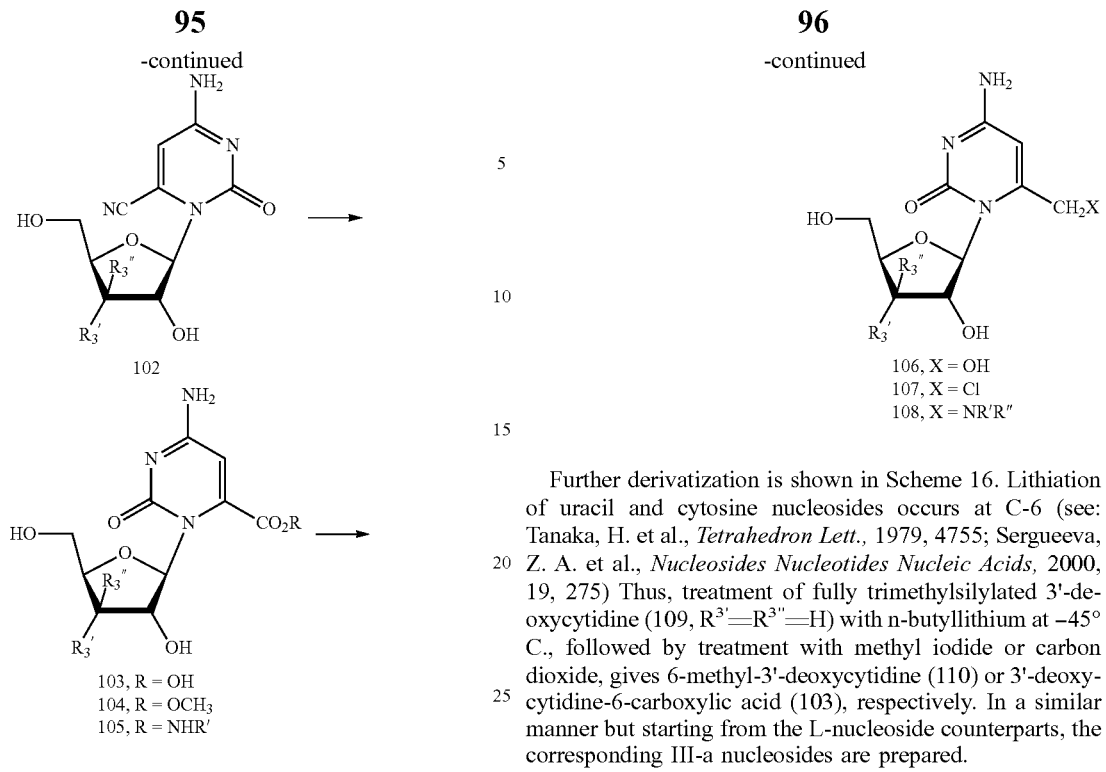

Further derivatization is shown in Scheme 16. Lithiation of uracil and cytosine nucleosides occurs at C-6 (see: Tanaka, H. et al., *Tetrahedron Lett.*, 1979, 4755; Sergueeva, Z. A. et al., *Nucleosides Nucleotides Nucleic Acids*, 2000, 19, 275) Thus, treatment of fully trimethylsilylated 3'-deoxycytidine (109, $R^{3'}=R^{3''}=H$) with n-butyllithium at −45° C., followed by treatment with methyl iodide or carbon dioxide, gives 6-methyl-3'-deoxycytidine (110) or 3'-deoxycytidine-6-carboxylic acid (103), respectively. In a similar manner but starting from the L-nucleoside counterparts, the corresponding III-a nucleosides are prepared.

Scheme 16

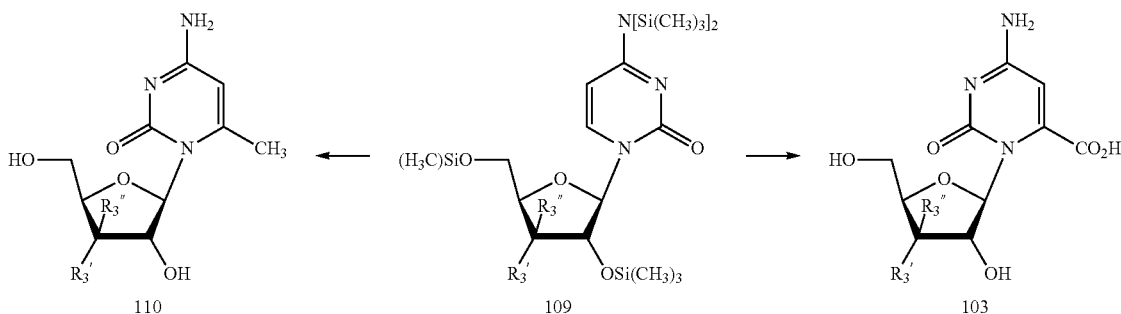

Treatment of 2',5'-di-O-(tetrahydropyran-2-yl)-3'-deoxyuridine (6, $R^2=R^{5'}=THP$, $R^{3'}=R^{3''}=H$) with lithium diisopropylamide in tetrahydrofuran at −78° C. and =subsequent reaction with alkyl halide result in the formation of 6-alkyl-3'-deoxyuridines (111). Oxidation of 111 (n=0) with selenium dioxide gives 3'-deoxyuridine-6-carboxaldehyde (112), which, upon treatment with nitromethane in the presence of base gives the nitroalkene 113. Compound 112 reacts with various Wittig reagents to give the corresponding olefins 114-117. Also, Grignard treatment of 112 gives 6-hydroxyalkyl derivatives 121. Oxidation of 121 affords the corresponding 6-acyl derivatives 120 (R=alkyl). On the other hand lithiated 6 ($R^{5'}=R^{2'}=THP$, $R^{3'}=R^{3''}=H$) with benzaldehyde produces 6-hydroxybenzyl derivative 119 which is converted into 6-benzoyl-3'-deoxyuridine (120, R=Ph) by mild oxidation. Also, reaction of lithiated 6 with diphenyldisulfide affords 6-phenylthio-3'-deoxyuridine 118, as shown in Scheme 17.

In a similar manner but starting from the L-nucleoside counterparts, the corresponding III-a nucleosides are prepared.

Scheme 17

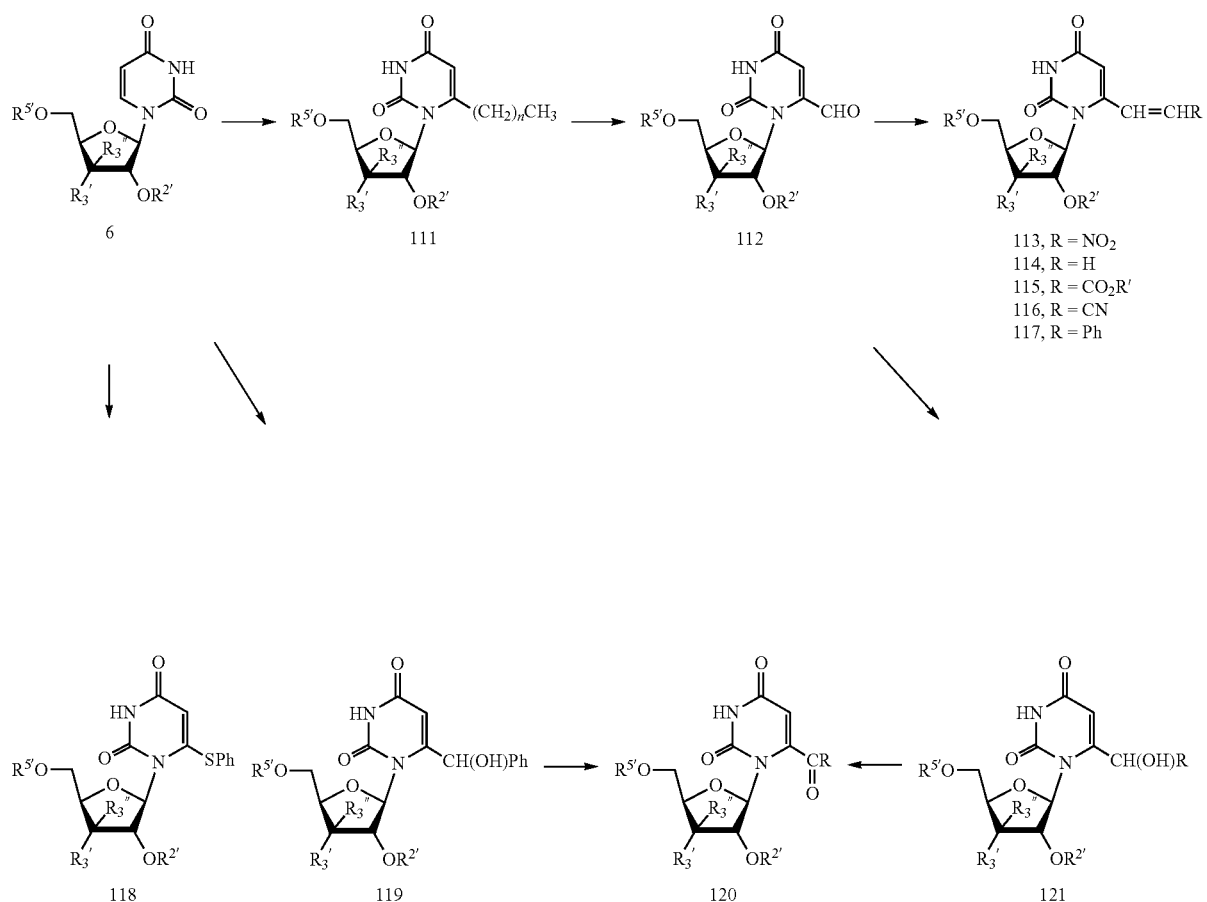

(d) Modification at C-6 of Purine Nucleosides (I-b and III-b)

Compound 28 or 38 is converted into halogenase 122 (Scheme 18) by treatment with hydrogen chloride or hydrogen bromide in acetic acid or hydrogen bromide in dichloromethane and condensed with 6-chloropurine by the sodio procedure in acetonitrile affords 3'-deoxynucleoside 123. Aqueous sodium or potassium hydroxide treatment of 123 gives 3'-deoxyinosine (124). Treatment of 123 with sodium methoxide in methanol affords 6-O-methyl-3'-deoxyinosine (125). Mild saponification, followed by catalytic hydrogenolysis of 123 results in the production of 3'-deoxynebularine (126). Thiourea reacts with 123 to give 6-thiopurine nucleoside 127, which is S-alkylated to 128. Compounds 123, 127 and 128 readily react with various amines, hydroxylamine, hydrazine and aminoalcohols to give 3'-deoxyadenosine analogues 129-133. Treatment of 123 with sodium azide gives 6-azidopurine nucleoside 134.

The same sequence of reactions can be applied to the corresponding L-nucleosides III-b.

Scheme 18

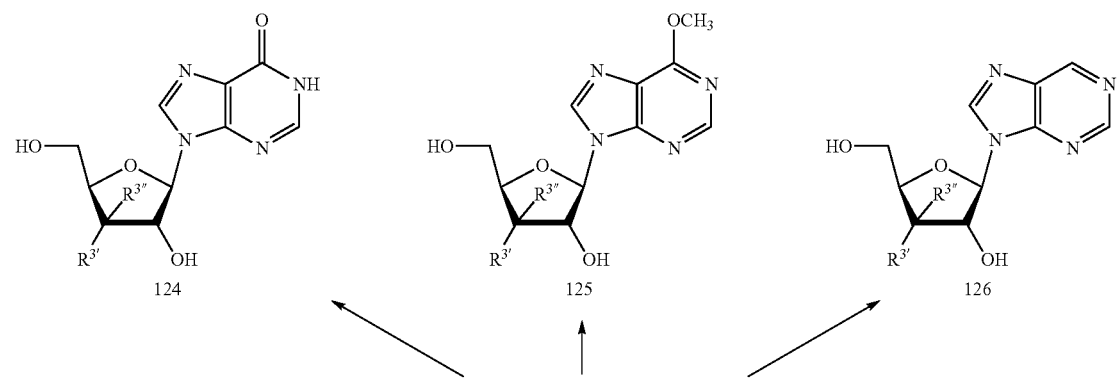

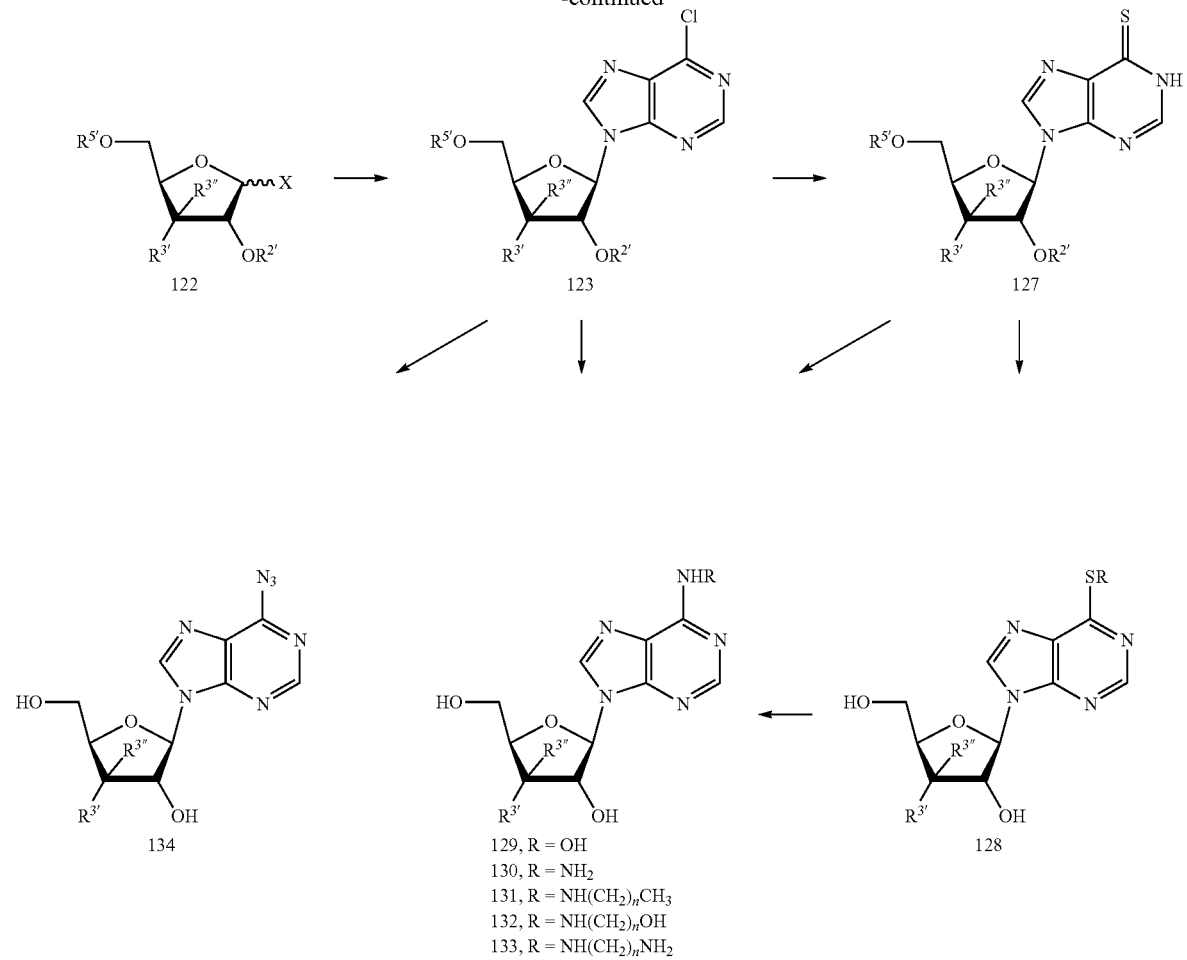

These compounds can also be synthesized by nitrous acid treatment of 6-hydrazidopurine nucleoside 130. Reduction of 129, 130 or 134 gives 3'-deoxyadenosine (i.e., cordycepin). Compound 125 or cordycepin are expected to be converted in vivo into 124 by action of adenosine deaminase. 6-Unsubstituted purine nucleoside 126 may be oxidized in vivo to 124.

Condensation of 122 with 2-substituted-6-chloropurine gives the 2-substituted analogue of 123. The 6-chloro functionality can be converted into various functional groups by nucleophilic substitution reactions. Thus, 2-amino-6-chloropurine is converted into 135 (Scheme 19), which can be converted various 2-aminopurine nucleosides (136-147). It should be noted that the 2,6-diamino- (141) and 2-aminopurine (138) nucleosides are potential precursors for 3'-deoxy-guanosine (136). In a similar manner but starting from the L-nucleoside counterparts, the corresponding III-b nucleosides are prepared.

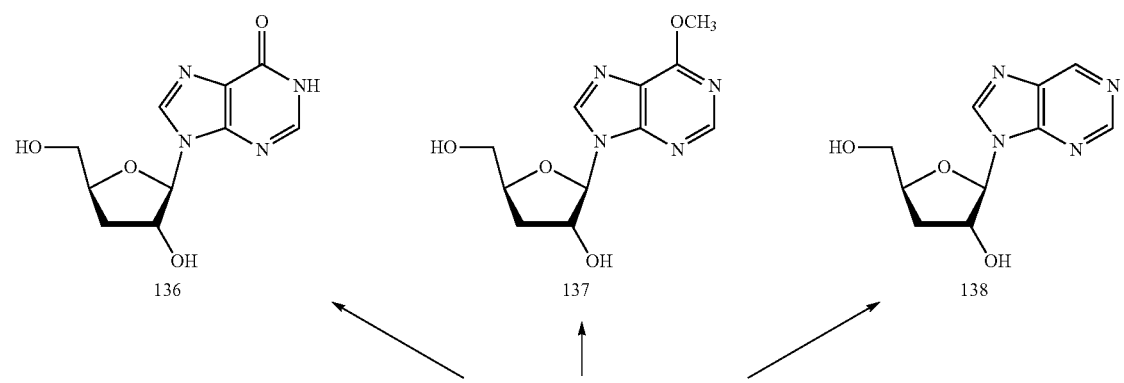

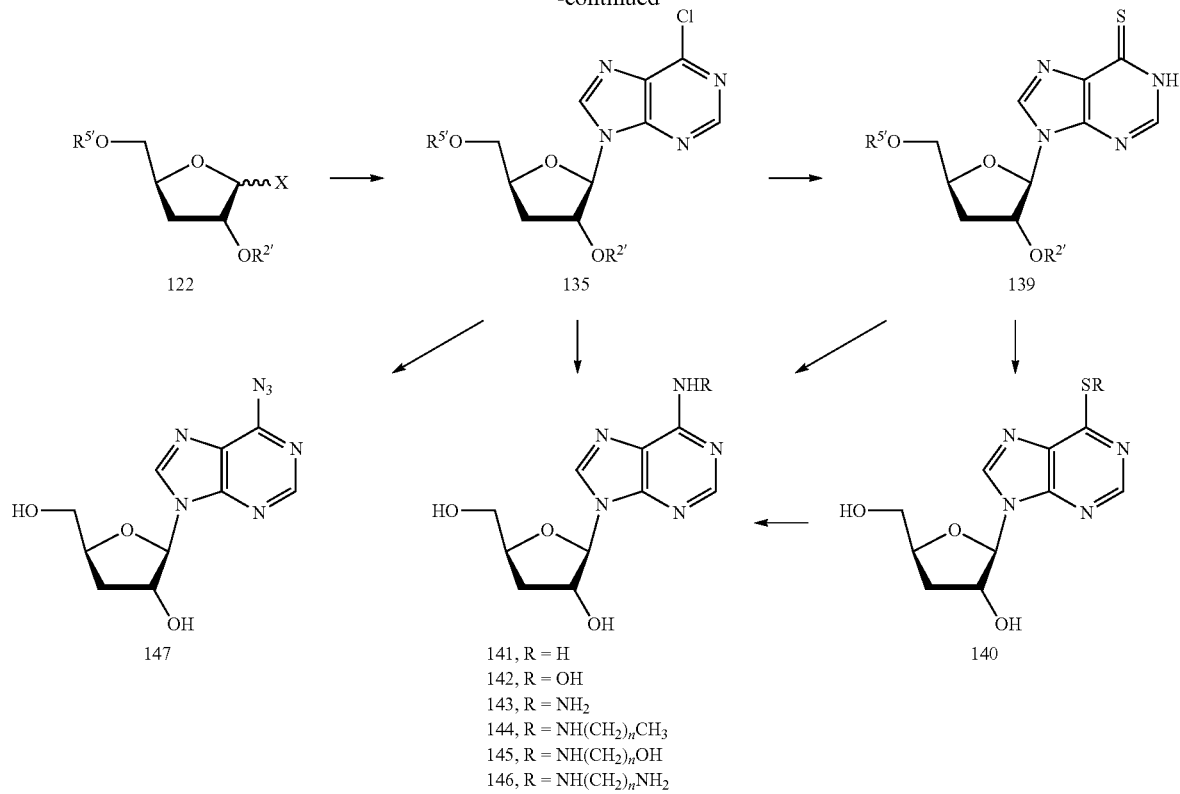
In a similar manner, 2-oxo-, 2-methoxy-, 2-thio-, 2-alkylmercapto-, 2-methyl-, 2-methyl-amino- or 2-dimethyl-amino-purine nucleosides (148-154) are synthesized (Scheme 20). Also, in a similar manner but using the corresponding L-nucleosides, compounds of III-b type are prepared.
Scheme 20
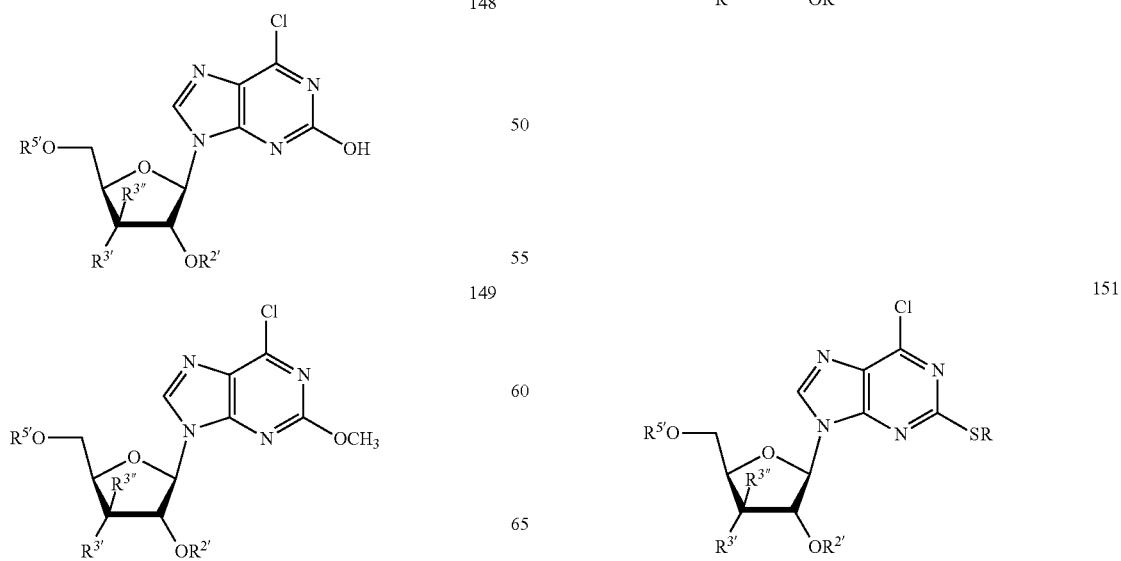

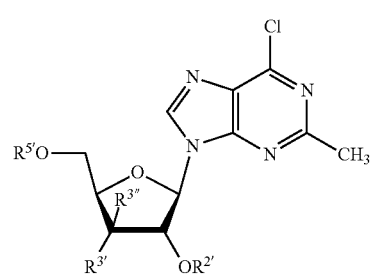

152

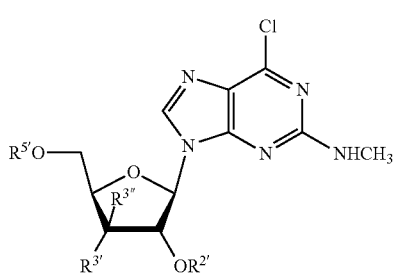

153

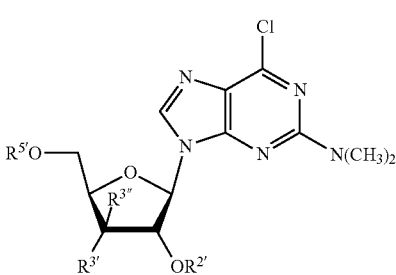

154

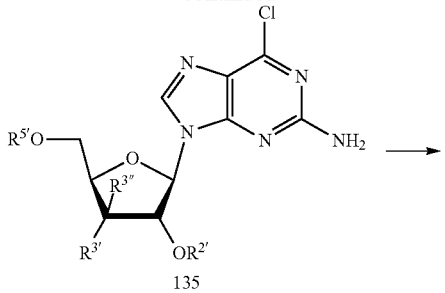

135

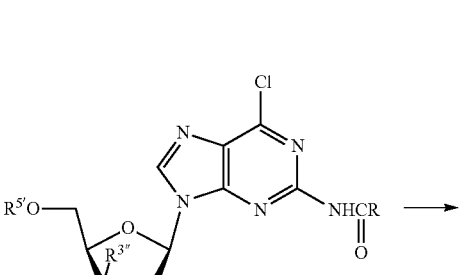

155

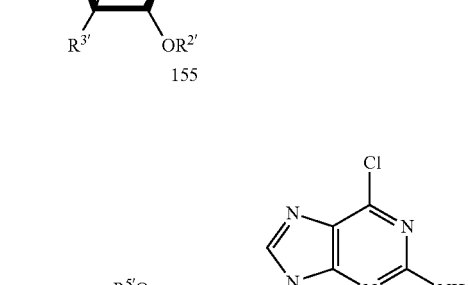

156

(e) Modification at C-2 of Purine Nucleosides (I-b and III-b).)

The 2-amino group of 135-147 can be modified to obtain 155 (Scheme 21) by acylation with various alkanoyl or aroyl halides. Then, 155 can further be derivatized into the corresponding 2-alkylamino or 2-arylamino derivative 156 by reduction with a borane-amine complex (Sergueeva, Z. A. et al. *Nucleosides Nucleotides Nucleic Acids,* 2000, 19, 275). Alternatively, the 2-amino group of compound 135 can be substituted by undergoing a Schiemann reaction, diazotizing in the presence of fluoroborate, followed by thermal decomposition, to give 2-fluoro-6-chloropurine nucleoside 157. Furthermore, the 6-chloro substituent of these nucleosides can be displaced with various nucleophilic reagents as described above. It should be noted that the presence of 2-fluoro substituent protects the 6-amino group from adenosine deaminase attack.

Scheme 21

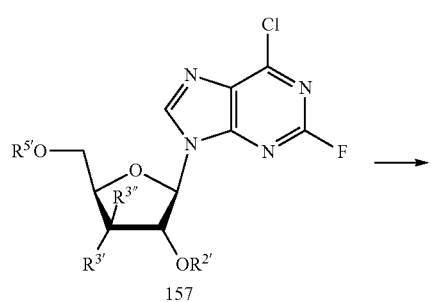

157

(f) Modification at C-8 of Purine Nucleosides (I-b)

It should be noted that modification of the 8-position of purine nucleosides is important as the substitution at this position alters the preferred conformation of the nucleosides to be syn.

Cordycepin (158, $R^{3'}=R^{3''}=H$), 3'-deoxyinosine (124, $R^{3'}=R^{3''}=H$) and 3'-deoxyguanosine (136, $R^{3'}=R^{3''}=H$) can be brominated at the C-8 position by treatment with bromine in acetic acid in the presence of sodium acetate to 159-161 (Scheme 22). The C-8 bromine substituent in 159-161 can be replaced with sulfur by the action of thiourea to obtain 162-164, which can be alkylated or aralkylated with alkyl or aralkyl halide in a polar solvent, such as water, alcohol or dimethylformamide, in the presence of base, such as sodium or potassium carbonate, to give 165-167. The methylmercapto derivative 165-167 (R=methyl) can be oxidized to the corresponding sulfone 168-170. Upon treatment of these sulfones with various amines, the corresponding 8-amino derivatives 171-173 are obtained. Many of the 8-amino derivatives can be obtained directly from 159-161 by treatment with amines. Also, 159 can be converted into the 8-oxo derivative 174 by treatment with sodium acetate in acetic anhydride, followed by hydrolysis. O-Alkylation of 174 with triethyloxonium fluoroborate gives 8-ethoxycordycepin 175.

Scheme 22

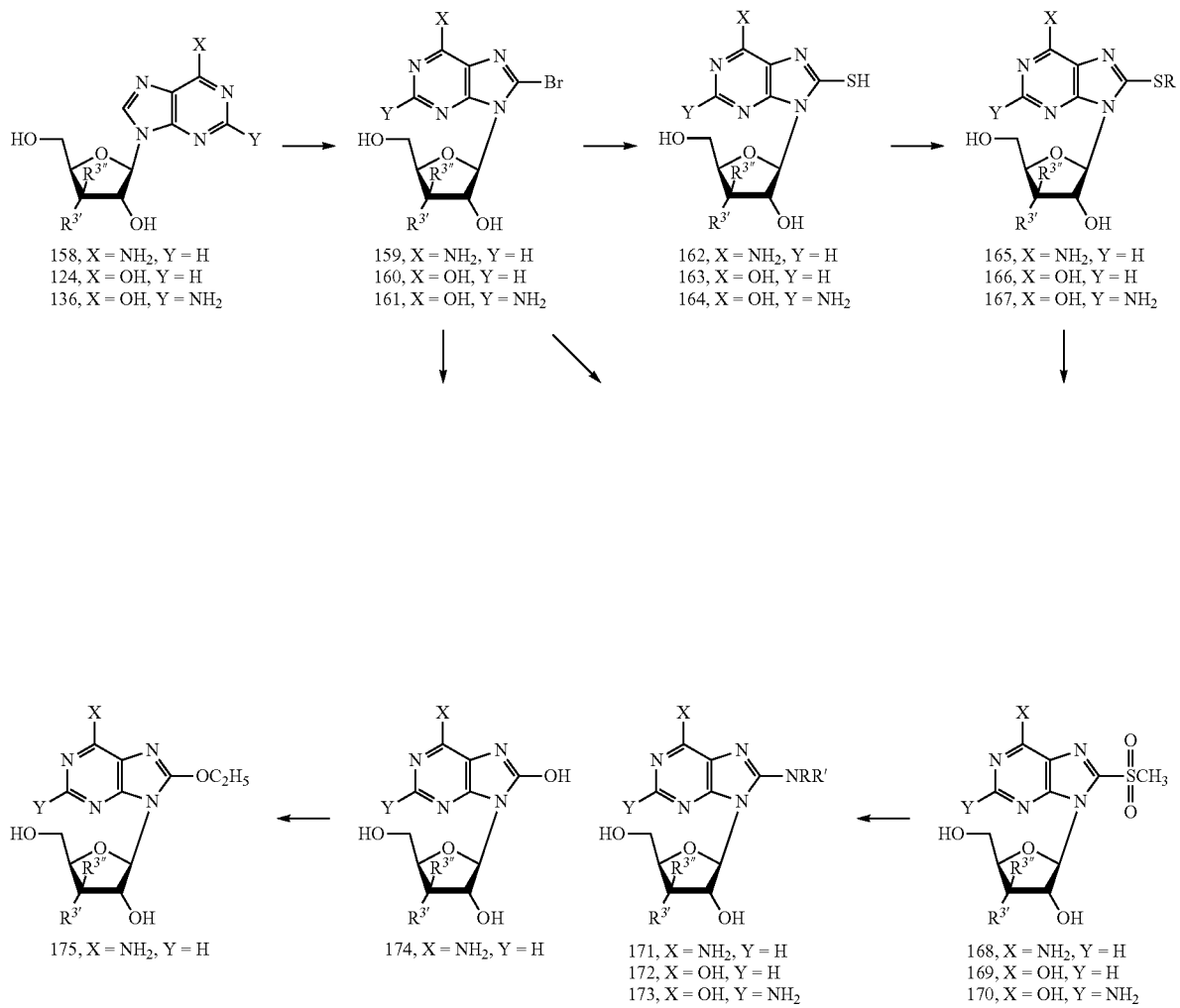

8-Alkyl derivatives 176 (Scheme 23) are prepared from 123 ($R^{5'}=R^{2'}=$THP) by treatment with lithium diisopropylamide in tetrahydrofuran below −70° C., followed by alkyl halide treatment. This method was successfully used in other ribonucleosides (Tanaka, H. et al. *Chem. Pharm. Bull.*, 1983, 31, 787) but never been applied to 3'-deoxynucleosides. When carbon dioxide is used instead of alkyl halide, purine nucleoside 8-carboxylic acid 177 is obtained. Esterification to 178, followed by ammonolysis gives amide 181, which is dehydrated to 8-cyanopurine nucleoside 182. Reduction of 178 with borane-dimethylsulfide affords the alcohol 179. Mild oxidation with dimethylsulfoxide and oxalic chloride affords aldehyde 180. Compounds 179 and 180 are versatile intermediates for various modifications.

Scheme 23

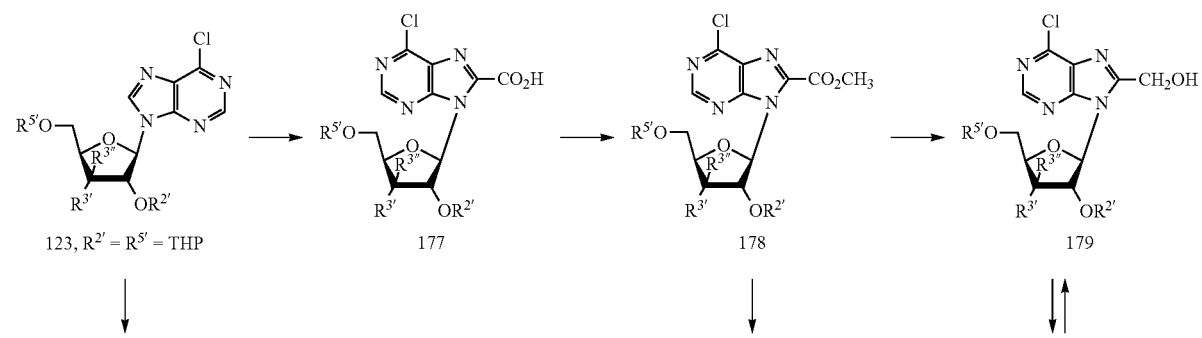

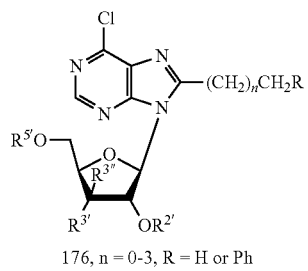
176, n = 0-3, R = H or Ph

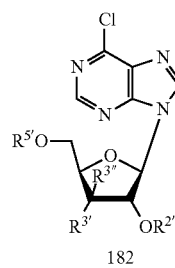
182

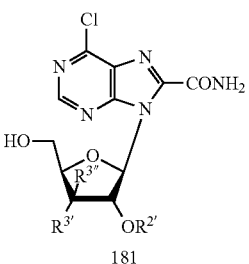
181

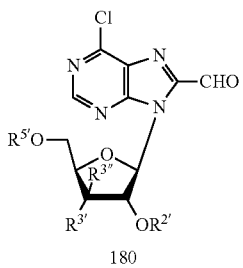
180

B. Compounds of Types IIa-c and IVa-c.
(i) Synthesis from Pre-Formed Nucleosides:

Several methods are available to introduce a 2',3'-unsaturation into a preformed nucleosides. An example is shown in Scheme 24.

Selective O-silylation of nucleoside 7, preferably with t-butyldimethylsilyl halide or t-butyldiphenylsilyl halide, in base, preferably in pyridine at from 0° C. to 80° C., preferably at room temperature, followed by sulfonylation, preferably with mesyl chloride or tosyl chloride in base, preferably in pyridine at from 0° C. to 80° C., preferably at room temperature, gives 8 in high yield, which can be readily converted into the lyxo-epoxide 183 by treatment with base. Reaction of 183 with halide ion, preferably iodide ion, such as treatment with sodium iodide in acetone or methylethylketone gives exclusively the trans-iodohydrin 184, X=I). Mesylation of 184 gives in high yield of the olifin 186 via 185. Compound 185 can be isolated in poor yield after short reaction time. De-O-silyation of 186 with fluoride, such as tetrabutyl ammonium fluoride affords the desired olefin 187, type II-a nucleoside, in high yield.

Scheme 24

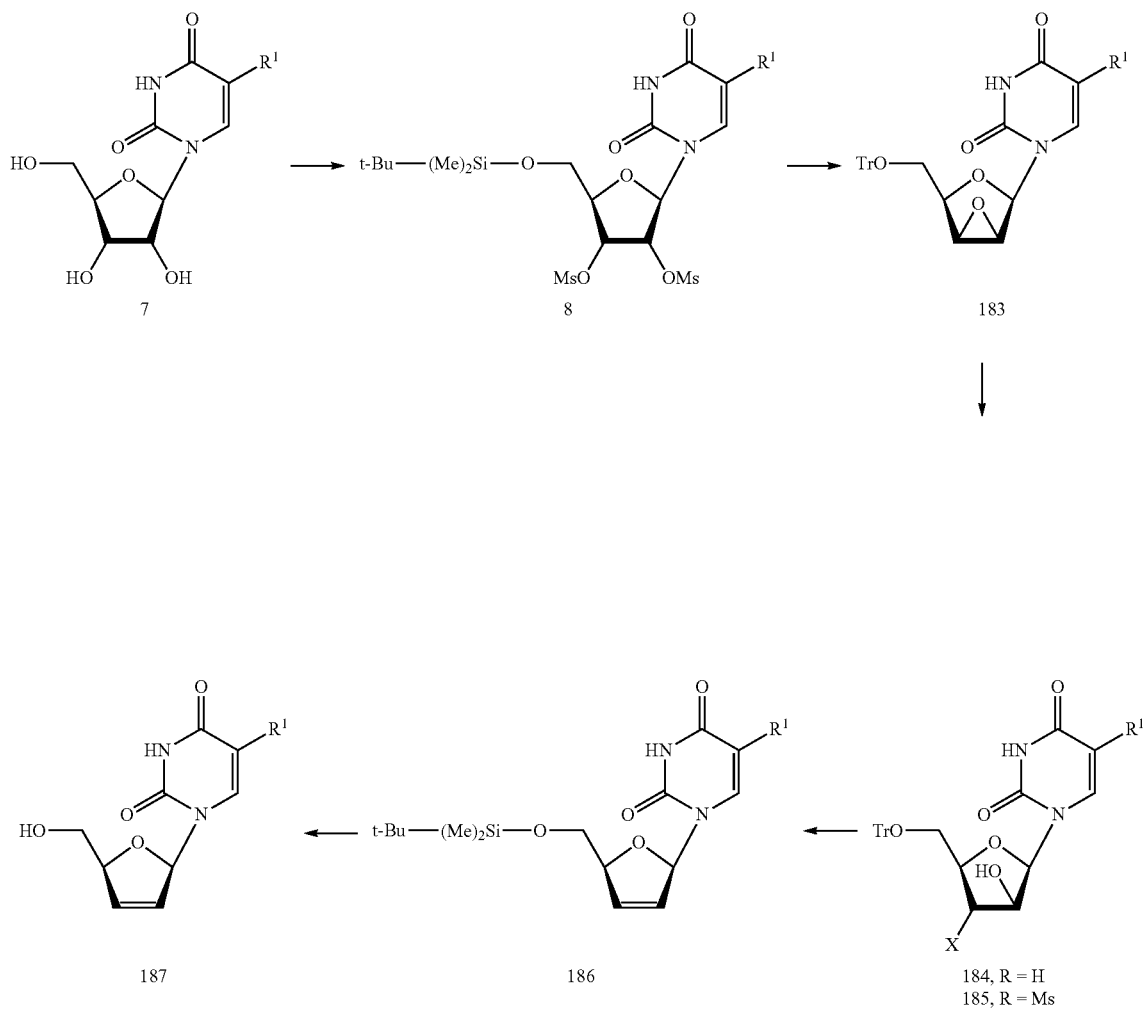

187     186     184, R = H
                                     185, R = Ms

Starting from 2'-deoxy nucleosides, e.g., 188 (Scheme 25), the type II-a olefinic sugar nucleoside also can be prepared. Sulfonylation of 188, preferably with mesyl chloride in pyridine at temperature range from −10° C. to 80° C., preferably at room temperature, gives the di-O-mesylate 189, which, upon treatment with aqueous base such as sodium hydroxide solution gives 3',5'-anhydrosugar nucleoside 190. The latter nucleoside can be readily converted into the desired 187 in high yield by treatment with strong, anhydrous base, such as with potassium tert-butoxide in dimethylsulfoxide at temperature range of from −10° C. to 80° C., preferably at room temperature for 10 minutes to overnight, preferably 1.5 to 3 hours.

Scheme 25

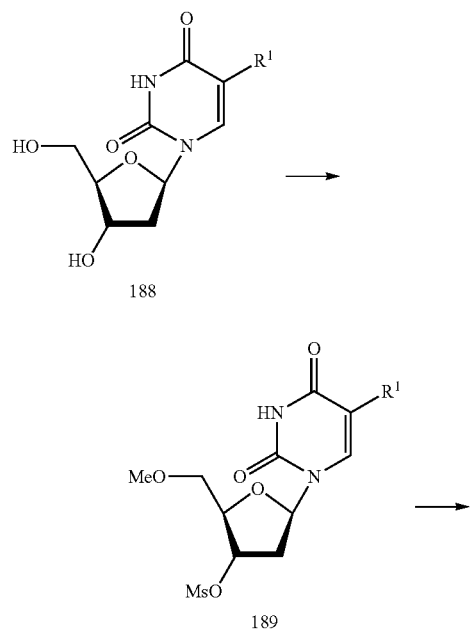

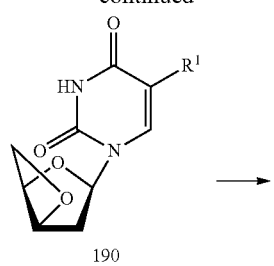

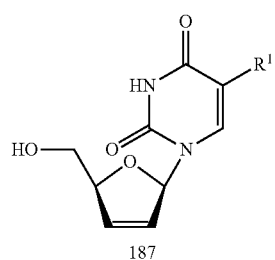

An example for preparation of 2'-substituted olefinic sugar nucleoside of type II-a is given in Scheme 26. 1-(2'-Deoxy-2'-fluoro-β-D-arabinofuranosyl)thymine (191) is selectively protected, preferably with trityl chloride or t-butyldimethylsilyl chloride or t-butyldiphenylsilyl chloride, in pyridine to give 192. Sulfonylation of 192, preferably with mesyl chloride in pyridine, gives the mesylate 193, which, upon treatment with non-nucleophilic base, such as DBU or DBN in anhydrous inert solvent, such as methylene chloride, affords 2,3'-anhydro nucleoside 194. This compound is readily converted into 2'-fluoro-olefinic sugar nucleoside 195 upon treatment with potassium t-butoxide in dimethylsulfoxide. De-protection of 195 gives the desired 2'-fluorinated II-a type nucleoside 196. 5'-O-Silyl protection gives better overall yield than trityl protection.

Scheme 26

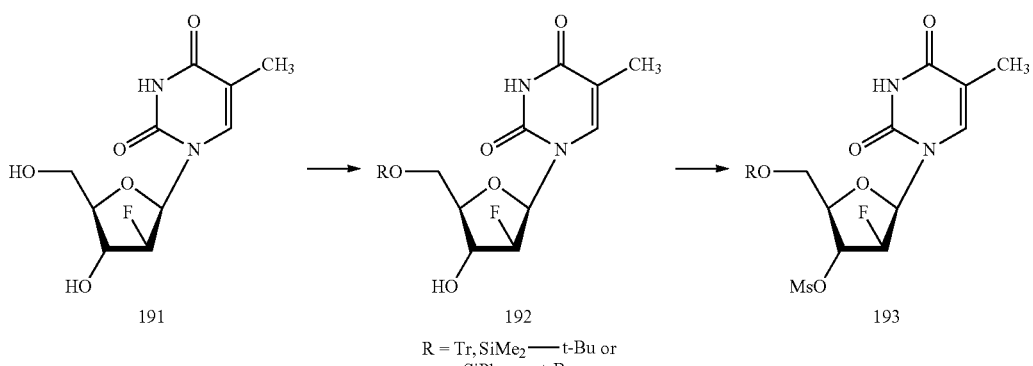

R = Tr, SiMe$_2$——t-Bu or SiPh$_2$——t-Bu

111

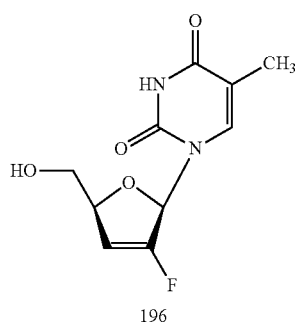

196

112

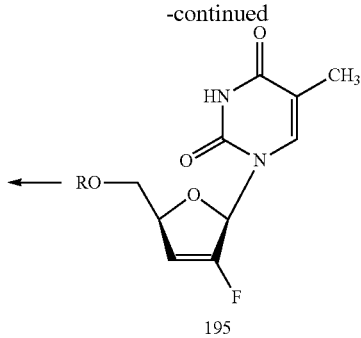

195

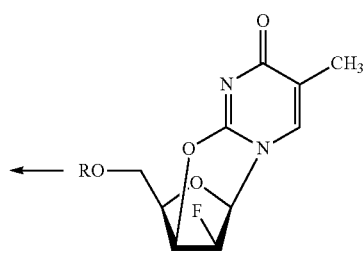

194

All these reactions can be applied to the corresponding pyrimidine L-nucleosides for the preparation of IV-a type nucleosides.

Nucleosides of type II-b can be prepared readily from 197 (Scheme 27). Selective protection of 197 at the 5'-position, e.g., with t-butyldimethylsilyl or t-butyldiphenylsilyl group affords 198. Sulfonylation with tosyl halide or mesyl halide in base such as in pyridine affords the protected olefinic nucleoside 199. De-O-silylation of 199 with fluoride, such as tetrabutyl ammonium fluoride affords the desired olefin 200, type II-b nucleoside, in high yield.

Alternatively, treatment of 15 (see Scheme 3) with chromous acetate gives, after deprotection with base 200 in good yield.

Scheme 27

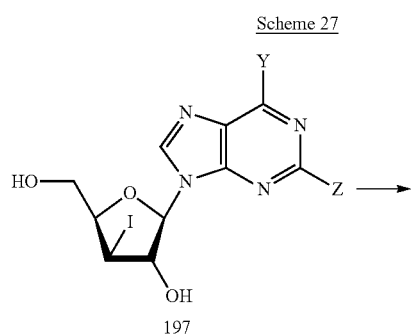

197

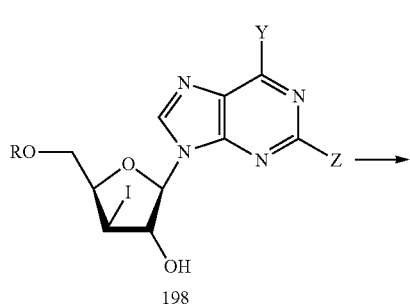

198

-continued

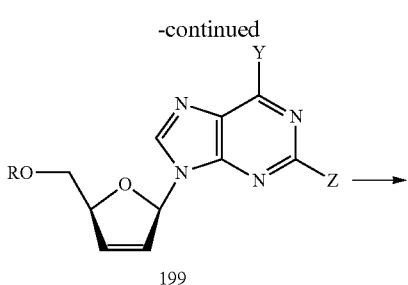

199

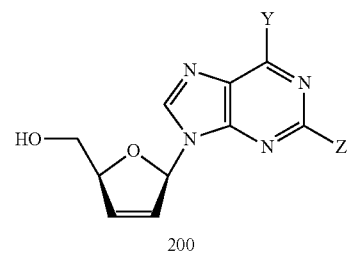

200

By the same procedure but using purine L-nucleosides, the corresponding olefinic sugar L-nucleosides of type IV-b can be obtained.

(ii) Synthesis by Condensation of Base and Unsaturated Sugar Derivative

Commercially available 4-hydroxymethyl-2-pentenone (201, Scheme 28) is silylated, preferably with t-butyldimethylsilyl halide in base, preferably in pyridine, to give 202, which is reduced with borohydride to 203. After acetylation, the product 204 is condensed with silylated base, e.g., 5-substituted uracil. A complicated mixture is obtained in which the anomeric nucleosides (205) are the major components. After chromatographic separation of the anomers 206 and 207, followed by desilylation of each anomer affords the β-nucleoside 208 (type II-a) and α-nucleoside 209 (type XVIII-c), respectively.

Scheme 28

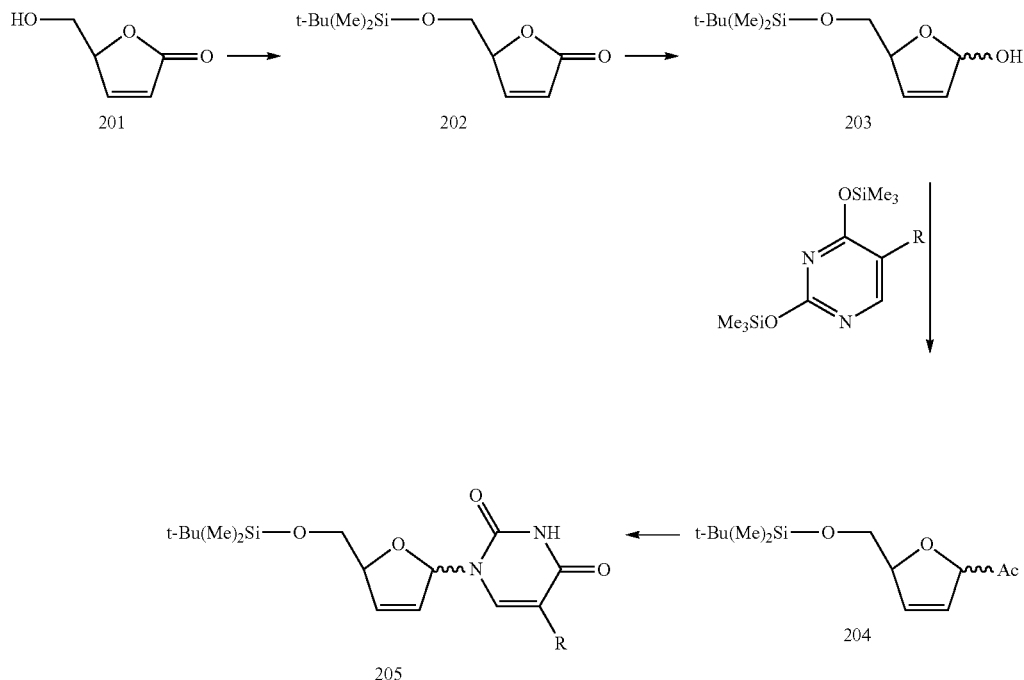

Mother example is shown in Scheme 29. 2-Fluoro-lactone 212 can be prepared by Wittig condensation of aldehyde 210 with Ph₃P=CFCO₂Et. Silyl protection and DIBAH reduction, followed by acetylation of the product affords 213. Condensation of 213 with silylated purine, such as 6-chloropurine, in the presence of Lewis acid, such as trimethylsilyl triflate or tin tetrachloride, in an inert solvent, such as methylene or ethylene chloride gives anomeric mixture 214. These anomers are separated on a silica gel column. After desilylation of each component, the corresponding β-nucleoside 215 (type II-b) and α-nucleoside 216 (type XVIII-d) can be obtained.

Scheme 29

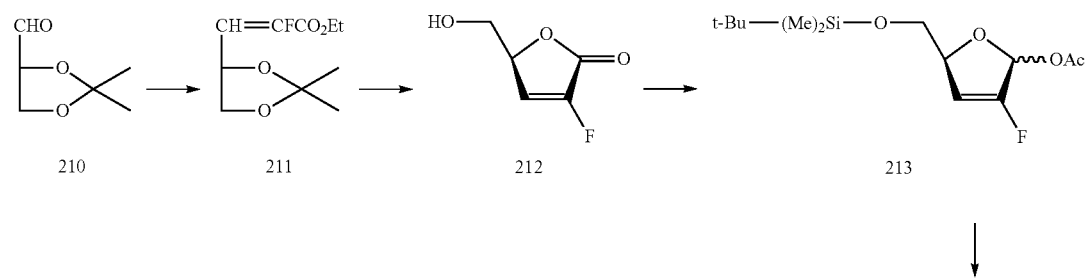

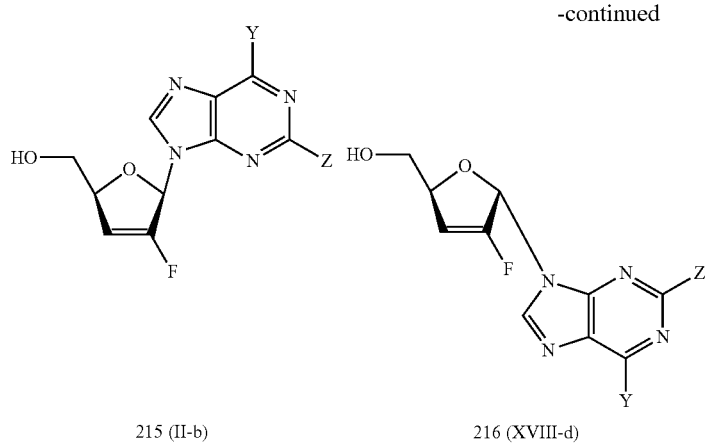 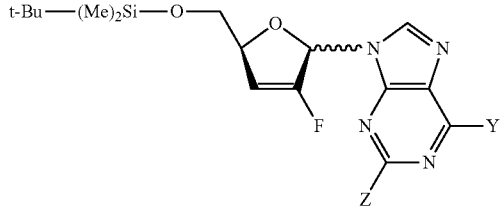

215 (II-b)  216 (XVIII-d)  214

C. Synthesis of Carba-Sugar Nucleosides (V-X)

Only carba-nucleosides so far found in nature are adenine nucleosides, i.e., aristeromycin and neplanocins, and they are either extremely expensive or commercially not available. Thus, these types of nucleosides are chemically synthesized from scratch. The carba-sugar derivative is prepared first and then the heterocyclic aglycon is constructed on the sugar to prepare carba-sugar nucleosides or in the case of purine nucleoside, the base is directly condensed with the carba-sugar.

Scheme 30 illustrates the synthesis of 5-fluoro-carba-cytidine (227, Type V-a). The carba-sugar intermediate 219 can be synthesized by any means known in the art. It is disclosed by Ali et al. (*Tetrahedron Letters*, 1990, 31, 1509) that D-ribonolactone 217 is converted into the pentanone intermediate 218. The ketone 218 can then be reduced by any known reducing agent, preferably sodium borohydride in methanol at 0° C. for 1 hour to afford alcohol 219. Sulfonylation of 219, preferably with mesyl chloride in methylene chloride in the presence of triethylamine at 0° C. for 2 hours gives 220, which is then treated with sodium azide in DMF at 140° C. overnight to give 221. The azide 221 can readily be reduced with any known reducing agent, e.g., Ph₃P (Staudinger procedure) or catalytic hydrogenolysis, preferably over palladium on carbon. The resulting amine 222 is subjected to Warrener-Shaw reaction with β-methoxyacryloylisocyanate in DMF, followed by ammonium hydroxide treatment to form protected carba-uridine 224 via the linear intermediate 223. Protected 5-fluoro-carba-uridine (225) can be obtained by fluorination of 224 with any fluorinating agent. Preferably, the fluorinating agent is fluorine in acetic acid. After quenching the reaction with base, preferably triethylamine. Conversion of uracil nucleoside 225 into protected carba-5-fluorocytidine (226) can be achieved in a similar manner as described with Scheme 7. The protecting groups of 226 are removed with acid, preferably with trifluoroacetic acid/water (2:1 v/v) at 50° C. for 3 hours, to give 227.

Sulfonylation of 219 with triflyl chloride in methylene chloride in the presence of triethylamine gives triflate, which, upon reaction with purine base, such as adenine, and sodium hydride in an inert solvent, such as acetonitrile or DMF directly affords the corresponding purine nucleoside (V-b type).

By using the same procedure but starting from L-ribonolactone, the corresponding L-nucleosides counterparts (type VIII nucleosides) can be obtained.

Scheme 30

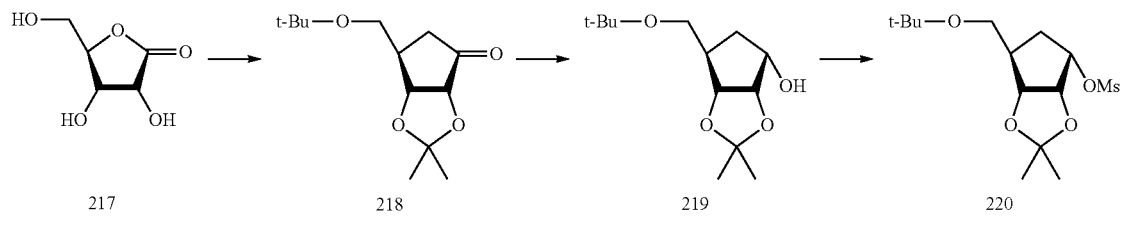

217  218  219  220

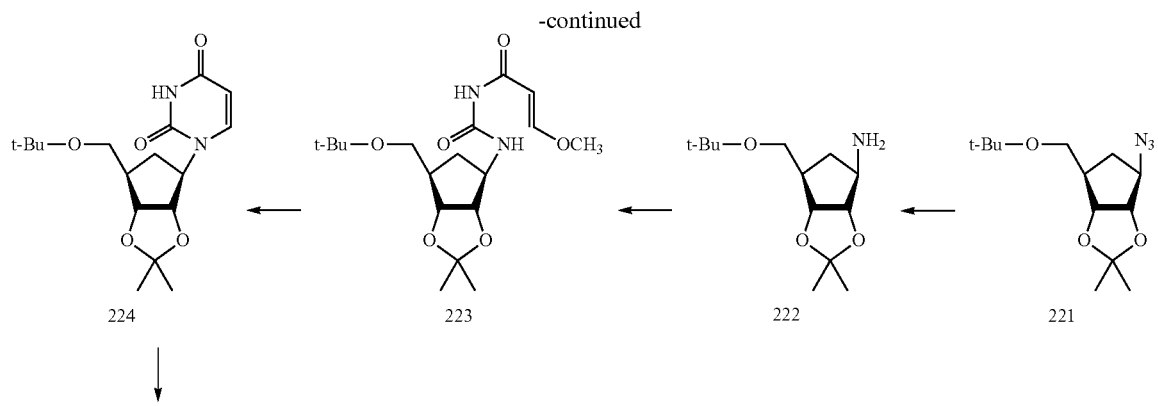

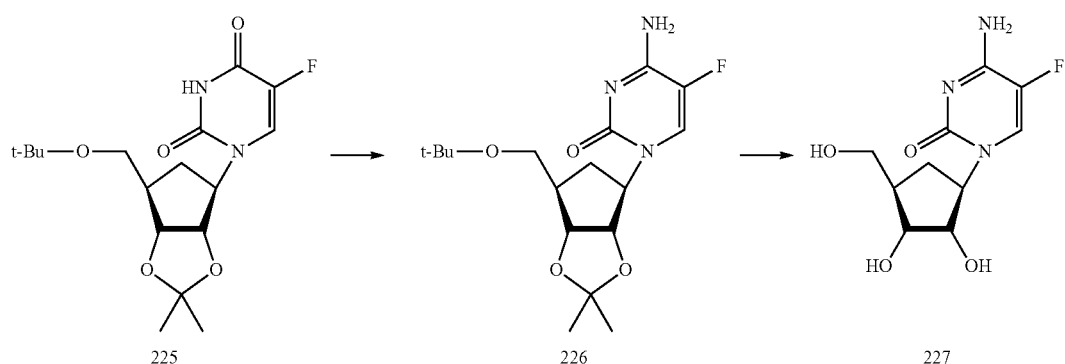

Alternatively, commercially available (1R)-(−)-azabicyclo[2.2.1]hept-5-en-3-one (228, Scheme 31) is converted into 2,3-dihydroxy-lactam 229 by osmium tetroxide oxidation. After methanolysis of 229 with methanolic hydrogen chloride, the product 230 is treated with 2,2-dimethoxypropane in acetone or 1,1-dimethoxycyclohexane in cyclohexanol to give a ketal, e.g., 231, which is reduced to 232 with sodium borohydride. The aminoalcohol 232 is converted into 2',3'-O-cyclohexylidene-carba-uridine by reaction with β-methoxyacryloylisocyanate, followed by ammonia treatment. Acid treatment, preferably with trifluoroacetic acid in methanol, gives carba-uridine (233). carba-5-Fluorocytidine (227) can be obtained readily from 233 by the well-known means in the art.

Scheme 31

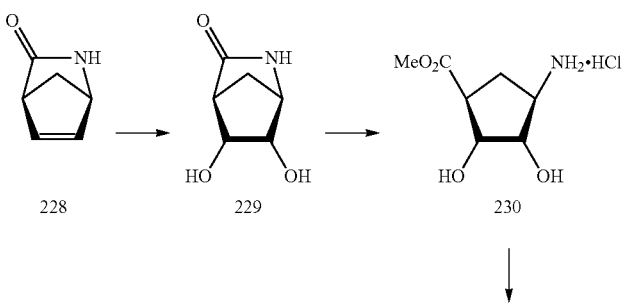

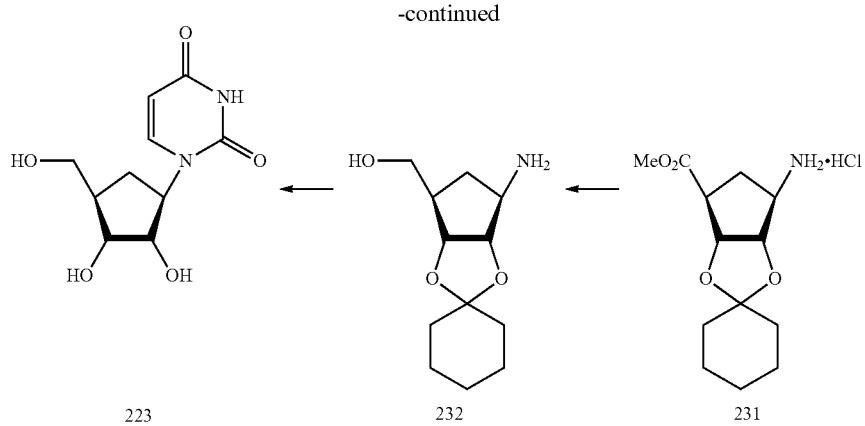

In a similar sequence of reactions but starting from the other optical isomer, (1R)-(+)-azabicyclo[2.2.1]hept-5-en-3-one, the corresponding L-nucleoside analogue (type VIII) can be obtained.

Nucleoside of type VI is prepared from nucleoside of type V. An example is shown in Scheme 32. Aristeromycin (234) or any carba-ribonucleoside is converted into the corresponding N-[(dimethylamino)methylene]-5'-O-trityl derivative 235 by treatment with dimethylformamide dimethylacetal in DMF, followed by tritylation. Reaction of 235 with thiocarbonyldiimidazole gives 2',3'-O-thiocarbonate 236, which, upon radical reduction with tri-n-butyltin hydride in the presence of 2,2'-azobis(2-methylpropionitrile) affords olefin 237 along with 3'-deoxy- and 2'-deoxy-aristeromycine derivatives 238 and 239, respectively. These products can be readily separated on a silica gel column. Each of these produces the corresponding free nucleoside, 240, 241 and 242, respectively, upon acid treatment. This procedure is particularly suited for preparation of small amounts of several nucleosides in short time for screening.

By the same procedure but using type VIII nucleosides instead of type V, the corresponding L-nucleosides of type IX can be obtained.

Scheme 32

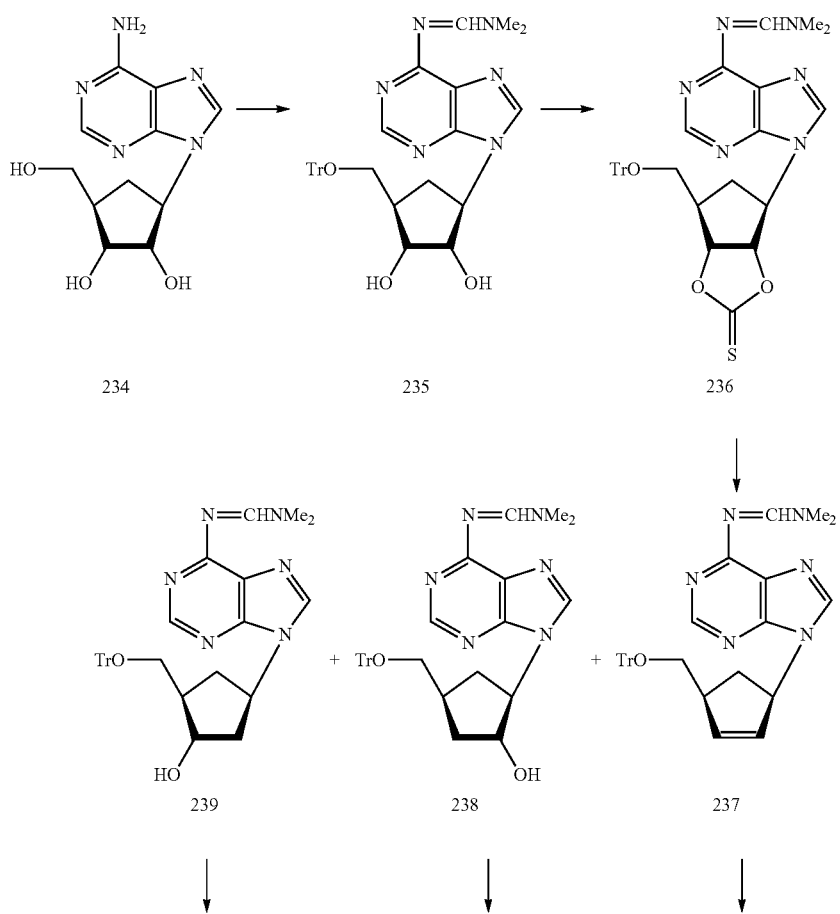

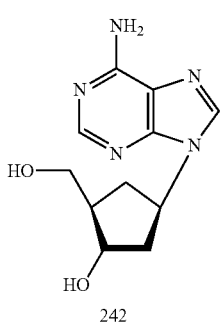
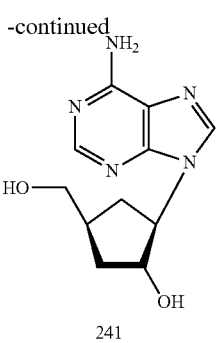
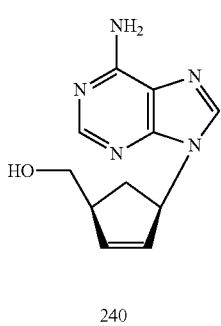

242  241  240

Stereoselective conversion of type V to type VI is also possible as shown in Scheme 33. 5-Fluoro-carba-uridine (233) is converted into the 5'-O-trityl-2',3'-di-O-mesyl derivative 243. Aqueous base treatment of 243 affords lyxo epoxide 245 via 2,2'-anhydro nucleoside intermediate 244. Epoxide ring-opening with sodium iodide in acetone or butanone gives trans iodohydrin 246, which, upon mesylation affords the olefin 248 via 247. De-O-tritylation of 247 furnishes 249. Instead of 5'-O-trityl protection, silyl protection with t-butyldimethylsilyl or t-butyldiphenylsilyl protection can also be used. Also, instead of mesylation, other sulfonylation using an agent, such as tosyl chloride, triflyl chloride or triflyl anhydride can be used.

By using the same procedure but using type VIII nucleosides instead of type V, the corresponding L-nucleosides of type IX can be obtained.

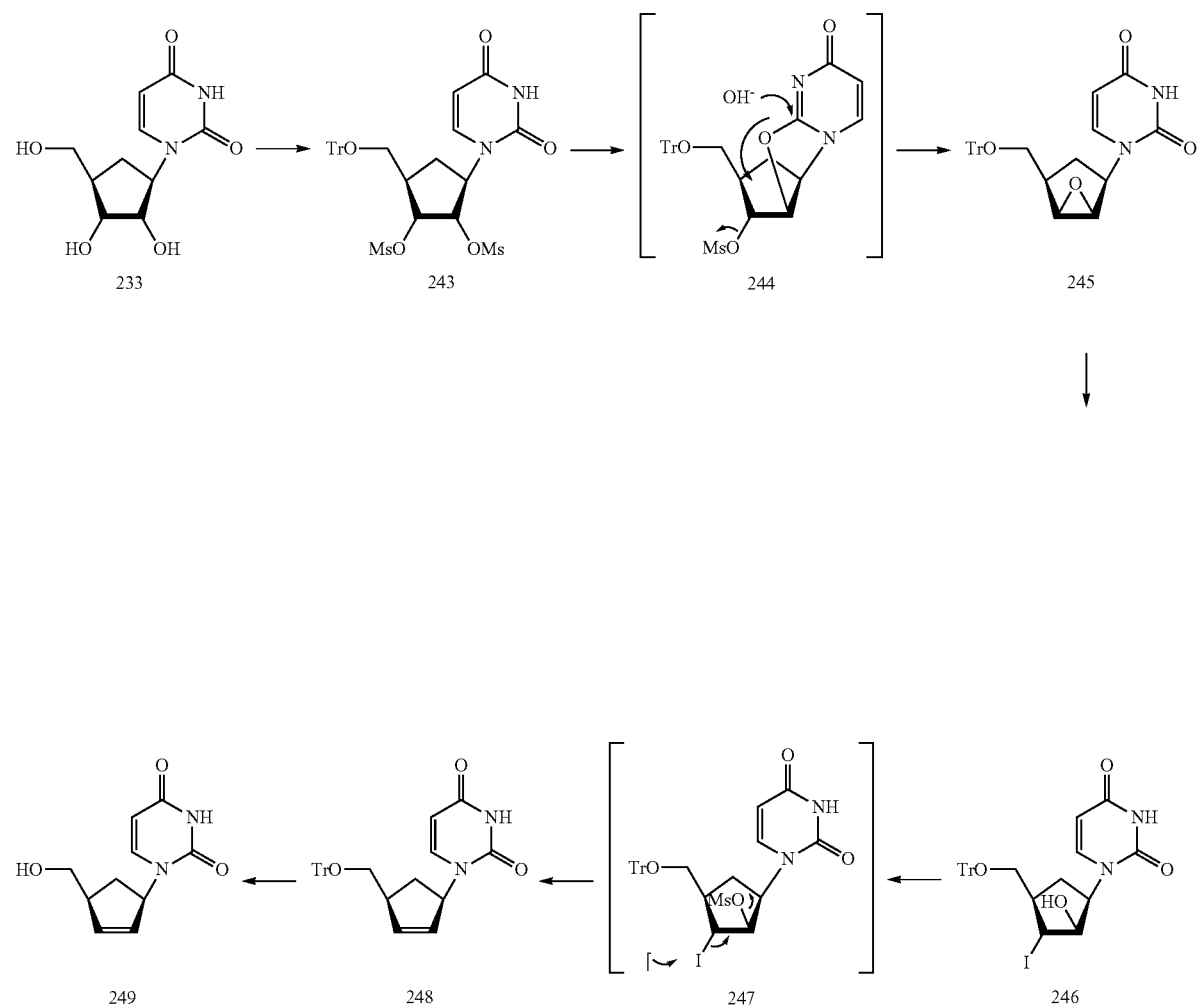

Scheme 33

Also, nucleosides of type VI-b can be synthesized starting from 2-cyclopenten-1-one (250, Scheme 34). Michael addition of t-butoxymethyllithiumcuprate [(t-BuOCH$_2$)$_2$CuLi] to 250 yields the adduct 251. Phenylselenation of 251 according to Wilson et al. (*Synthesis*, 1995, 1465) mainly occurs trans to t-butoxymethyl group to give 252. DIBAH reduction reduces the carbonyl group to hydroxyl group in a stereoselective manner to give 253. Sulfonylation, preferably with triflyl chloride or triflic anhydride in base, to 254, followed by condensation with sodio-purine, produced, e.g., adenine and NaH, in an inert solvent such as acetonitrile affords 255 in a stereoselective manner. Oxidation of the selenide 255 with hydrogen peroxide in pyridine smoothly converts 255 into the olefin 256. Mild acid treatment of 256 gives free nucleoside 240.

Alternatively, acetylation of 253, followed by condensation with silylated pyrimidine, such as tris(trimethylsilyl)-5-fluorocytosine in the presence of trimethylsilyl trifluoromethylsulfonate gives high yield of the corresponding pyrimidine nucleoside, from which VI-a type nucleoside can readily prepared by oxidation and acid removal of t-butyl group of the product.

By using the same procedure but using type VIII nucleosides instead of type V, the corresponding L-nucleosides of type IX can be obtained.

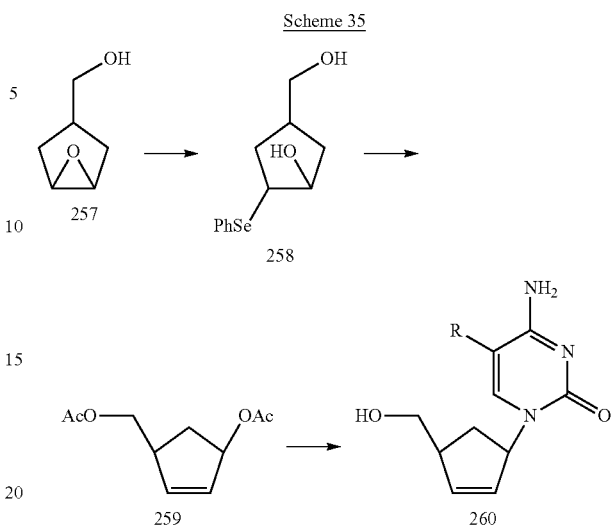

Scheme 36 shows the synthesis of 3,4-unsaturated carba nucleoside of type VII Wolfe et al (*J. Org. Chem.*, 1990, 55,

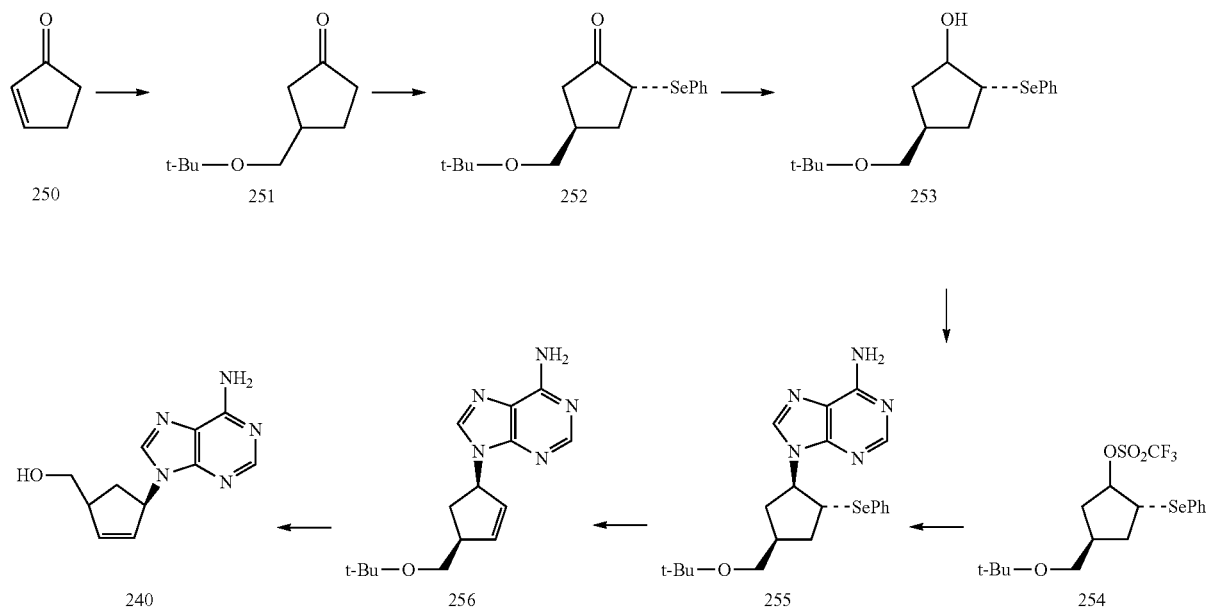

Scheme 34

Furthermore, racemic carba analogues of 2',3'-unsaturated nucleosides can be prepared by the procedure of Shi et al. (*J. Med. Chem.*, 1999, 42, 859) who achieved multi-step preparation of racemic cis-3,4-epoxy-cyclopentanemethanol 257 (Scheme 35) from ethyl cyclopentene-4-carboxylate. Opening of the epoxide with diphenyldiselenide affords 258, which, after acetylation followed by peroxide treatment, gives diacetate 259. Treatment of 259 with sodiopyrimidine, prepared by reaction of uracil or cytosine derivative with NaH in dimethylsulfoxide, in the presence of Pd(PPh$_3$)$_4$ in an inert solvent, e.g., tetrahydrofuran, gives 260 in 10-70% yield after deacetylation of the product.

4712) prepared 261 from D-ribonolactone. Quenching the Michael addition of t-butoxymethyl group to (261, Scheme 36) with sulfinyl chloride, followed by heating the product with calcium carbonate gives cyclopentenone 262. Reduction of 262 with DTBAH followed by sulfonylation affords 263. Condensation of 263 (preferably R=CF$_3$) with purine base with NaH as described earlier gives purine nucleoside VII-b, e.g., neplanocin A (264). Treatment of 263 (preferably R=Me) with NaN$_3$ gives 265 which can be readily converted into various pyrimidine nucleosides (VII-a) including 266 by the procedure already described with Scheme 30.

Starting from L-ribonolactone, the corresponding L-nucleoside counterparts (X-a and X-b) can be readily prepared.

Scheme 36

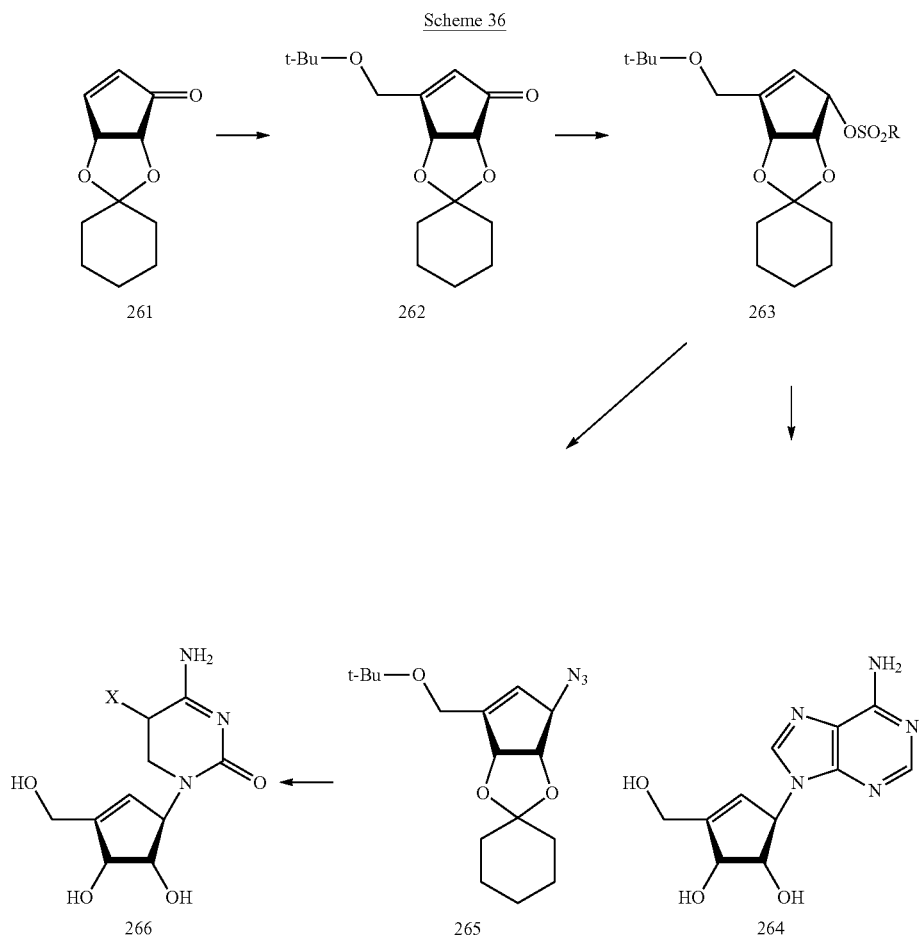

D. Synthesis of Nucleosides of Types XI and XII.

There are several methods are available for the synthesis of these types of nucleosides, Some nucleosides used in the present invention are prepared mainly in the following manner. 1-Mentylester of 2,2-dimethoxyacetic acid (267, Scheme 37) is condensed with thioglycolic acid to give a diastereomeric mixture 268, which can readily be separated on a silica gel column. Reduction of 268 with $NaBH_4$ in ethanol, followed by acetylation affords 269, which is condensed with silylated base in the presence of tin tetrachloride. Mainly the desired protected β-nucleoside is obtained and is purified by chromatography. De-O-acetylation affords the corresponding unprotected nucleoside 270. Also, 270 is obtained starting from 2,2-dimethoxyethyl ester of N-t-Boc-L-proline. This compound is treated with 3 equivalents of thioglycolic acid in methylene chloride in the presence of $MgSO_4$ and CAS to give 271 as a diastereomeric mixture, which is separated chromatographically. Reduction of each diastereomer of 271 with $Li(t-BuO)_3AlH$ in tetrahydrofuran and subsequent acetylation affords 272, which is condensed with silylated base, followed by deprotection of the product to give 270.

Scheme 37

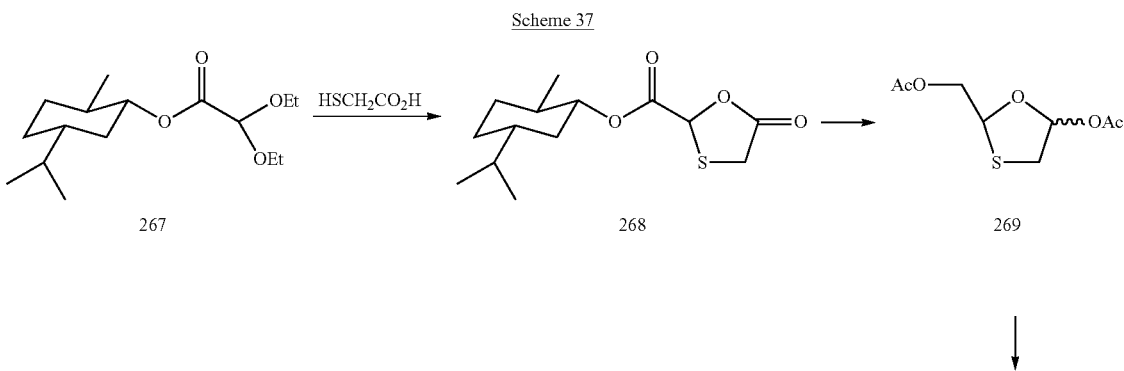

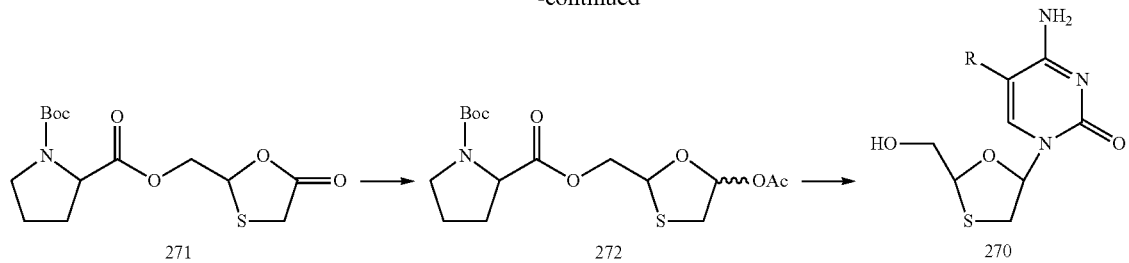

Nucleosides of type XIII used in this invention are prepared by using means known in the art. In a preferred embodiment, XIII-a type nucleosides are prepared in one or two-step synthesis reported (*Nucleic Acid Chem.*, 1978, 1, 272 and 343) by activating the 5'-OH by sulfonylation followed by base treatment or direct treatment of unprotected nucleosides with Ph3P and diethyl diazocarboxylate.

Preparation of nucleosides of type XIV used in the present invention are synthesized by methods somewhat analogous to those utilized for the synthesis of the corresponding 5-fluorodeoxyuridine adducts by Duschinsky et al. (*J. Med. Chem.*, 1967, 10, 47). Some examples are shown in Scheme 38 using 5-fluorouridine (273). Any pyrimidine nucleoside containing a strongly electron-withdrawing substituent at C-5 undergoes similar adduct formation. Treatment of 273 with bromine in methanol gives adduct 274 which can be reduced to 275 by catalytic hydrogenation. Treatment in water gives the bromohydrin 277 while action of bromine in acetic acid in the presence of acetic anhydride affords 276. The corresponding other adducts can be prepared by using other hypohalites, e.g., hypochlorite gives 278. Each of these adducts are diastereomeric mixture and are used for screening as such.

Scheme 38

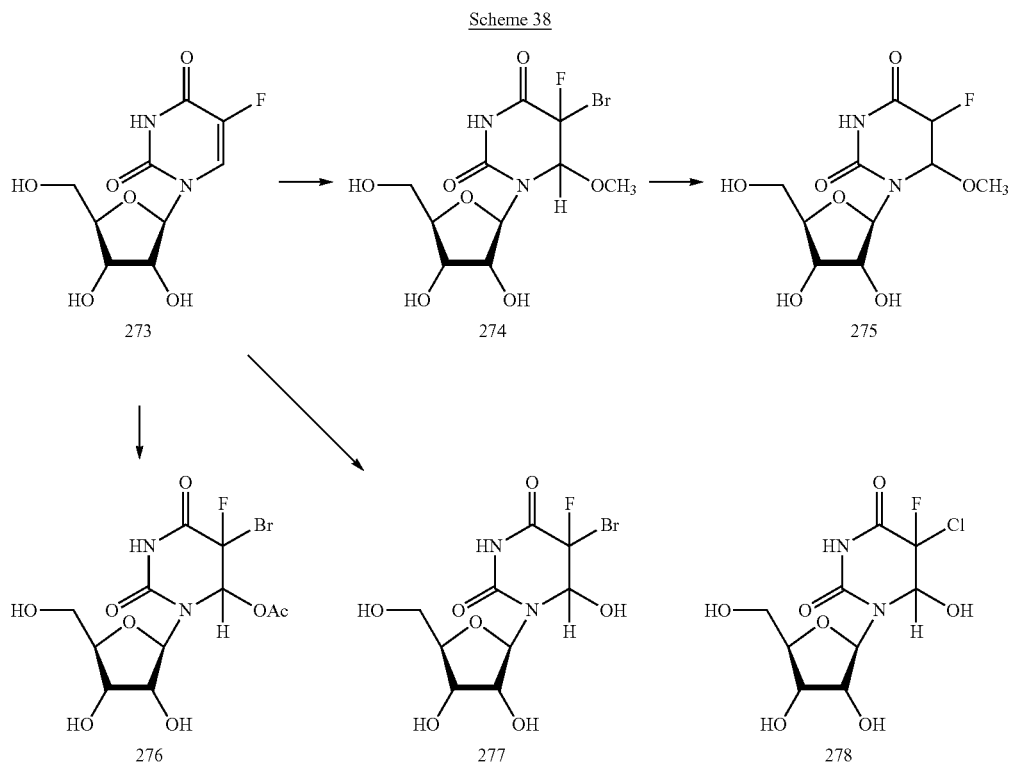

E. Nucleosides of Type XV-XVIII.

Nucleosides used in this invention are prepared by oxidation of 4-thiouridine and 6-thioinosine derivatives according to the well-known means in the art. Type XVI compounds are C-nucleosides. XVI-a nucleosides are synthesized from w-uridine by methods known in the art (Watanabe, "The Chemistry of C-Nucleosides", Townsend, L. B., Ed., In "*Chemistry of Nucleosides and Nucleotides*", Plenum, Publ., New York, Vol., 3, 421, 1994), or condensation of an aromatic compound to protected ribonolactone, followed by manipulation of the products (e.g., Kabat et al., *J. Med. Chem.*, 1987, 30, 924). Nucleosides XVI-b and XVI-c are prepared according to a modified procedure developed by Pankiewicz et al., (*Carbohydr. Res.*, 1984, 127, 227; *Nucleosides Nucleotides*, 1991, 10, 1333). The purine-type XVI-d C-nucleosides are synthesized according to the method reported by Chu et al., (*J. Heterocycl. Chem.*, 1980, 17, 1435). Nucleosides of type XVII used in this invention are synthesized either by cross-aldol reaction of 4'-formyl nucleosides with formaldehyde or condensation of preformed sugar with a base. Preparation of some of the type XVIII nucleosides have already discussed earlier.

The following working examples provide a further understanding of the method of the present invention. These examples are of illustrative purposes, and are not meant to limit the scope of the invention. Equivalent, similar or suitable solvents, reagents or reaction conditions may be substituted for those particular solvents, reagents or reaction conditions described without departing from the general scope of the method.

EXAMPLES

Melting points were determined in open capillary tubes on an Electrothermal digit melting point apparatus and are uncorrected. The UV absorption spectra were recorded on an Uvikon 931 (KONTRON) spectrophotometer in ethanol. $^1$H-NMR spectra were run at room temperature with a Varian Unity Plus 400 spectrometer. Chemical shifts are given in ppm downfield from internal tetramethylsilane as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive- (FAB>0) or negative- (FAB<0) ion mode on a JEOL DX 300 mass spectrometer The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analyses were performed by Atlantic Microlab Inc. (Norcross, Ga.). Analyses indicated by the symbols of the elements or functions were within ±0.4% of theoretical values. Thin layer chromatography was performed on Whatman PK5F silica gel plates, visualization of products being accomplished by UV absorbency followed by charring with 10% ethanolic sulfuric acid and heating. Column chromatography was carried out on Silica Gel (Fisher, S733-1) at atmospheric pressure.

Example 1

1-(2,5-Di-O-acetyl-3-bromo-3-deoxy-β-D-xylofuranosyl)-N$^4$-acetylcytosine (2, R=H)

To a suspension of N$^4$-acetylcytidine (5.7 g, 0.02 mol) in acetonitrile (300 mL) is added acetyl bromide (15 mL, 0.2 mol) over 30 minutes under reflux. The mixture is refluxed for 4 hours, and then concentrated in vacuo to dryness. The residue is dissolved in methylene chloride (150 mL) and washed with water (150 mL). The organic layer is dried (Na$_2$SO$_4$), evaporated, and the residue crystallized from ethanol to give 1-(2,5-Di-O-acetyl-3-bromo-3-deoxy-β-D-xylofuranosyl)-N$^4$-acetylcytosine (2, R=H, 3.4 g, 40%), mp 179-180° C. NMR (CDCl$_3$) δ: 10.2 (bs, 1H, NHAc), 8.1 (d, 1H, H-6, J$_{5,6}$=7.5 Hz), 7.5 (d, 1H, H-5, J$_{5,6}$=7.5 Hz), 6.0 (d, 1H, H-1', J$_{1',2'}$<1 Hz), 5.5 (d, 1H, H-2', J$_{1',2'}$<1, J$_{2',3'}$=0 Hz), 4.2-4.7 (m, 4H, H-3',4',5',5"), 2.0-2.4 (3s, 9H, 3Ac).

In a similar manner but using the corresponding N-acylated cytidine, the following nucleosides and their L-counterparts are prepared:
1-(2,5-Di-O-acetyl-3-bromo-3-deoxy-β-D-xylofuranosyl)-N$^4$-acetyl-5-fluorocytosine,
1-(2,5-Di-O-acetyl-3-bromo-3-deoxy-β-D-xylofuranosyl)-N$^4$-acetyl-5-chlororocytosine,
1-(2,5-Di-O-acetyl-3-bromo-3-deoxy-β-D-xylofuranosyl)-N$^4$-acetyl-5-bromocytosine,
1-(2,5-Di-O-acetyl-3-bromo-3-deoxy-β-D-xylofuranosyl)-N$^4$-acetyl-5-iodo cytosine,
1-(2,5-Di-O-acetyl-3-bromo-3-deoxy-β-D-xylofuranosyl)-N$^4$-acetyl-5-methylcytosine,
1-(2,5-Di-O-acetyl-3-bromo-3-deoxy-β-D-xylofuranosyl)-N$^4$-acetyl-5-ethylcytosine,
1-(2,5-Di-O-acetyl-3-bromo-3-deoxy-β-D-xylofuranosyl)-N$^4$-acetyl-5-n-propylcytosine,
1-(2,5-Di-O-acetyl-3-bromo-3-deoxy-β-D-xylofuranosyl)-N$^4$-acetyl-5-i-propylcytosine,
1-(2,5-Di-O-acetyl-3-bromo-3-deoxy-β-D-xylofuranosyl)-N$^4$-acetyl-5-vinylcytosine,
1-(2,5-Di-O-acetyl-3-bromo-3-deoxy-β-D-xylofuranosyl)-N$^4$-acetyl-5-(2-chlorovinyl)cytosine,
1-(2,5-Di-O-acetyl-3-bromo-3-deoxy-β-D-xylofuranosyl)-N$^4$-acetyl-5-(2-bromovinyl)cytosine,
1-(2,5-Di-O-acetyl-3-bromo-3-deoxy-β-D-xylofuranosyl)-N$^4$-acetyl-5-(2-iodovinyl)cytosine,
1-(2,5-Di-O-acetyl-3-bromo-3-deoxy-β-D-xylofuranosyl)-N$^4$-acetyl-5-(2-methoxylcarbonyl-vinyl)-cytosine,
1-(2,5-Di-O-acetyl-3-bromo-3-deoxy-β-D-xylofuranosyl)-N$^4$-acetyl-5-(2-hydroxycarbonyl-vinyl)-cytosine,
1-(2,5-Di-O-acetyl-3-bromo-3-deoxy-β-D-xylofuranosyl)-N$^4$-acetyl-5-phenylcytosine,
1-(2,5-Di-O-acetyl-3-bromo-3-deoxy-β-D-xylofuranosyl)-N$^4$-acetyl-5-benzylcytosine,
1-(2,5-Di-O-acetyl-3-bromo-3-deoxy-β-D-xylofuranosyl)-N$^4$-benzoylcytosine,
1-(2,5-Di-O-acetyl-3-bromo-3-deoxy-β-D-xylofuranosyl)-N$^4$-benzoyl-5-fluorocytosine,
1-(2,5-Di-O-acetyl-3-bromo-3-deoxy-β-D-xylofuranosyl)-N$^4$-benzoyl-5-chlororocytosine,
1-(2,5-Di-O-acetyl-3-bromo-3-deoxy-β-D-xylofuranosyl)-N$^4$-benzoyl-5-bromocytosine,
1-(2,5-Di-O-acetyl-3-bromo-3-deoxy-β-D-xylofuranosyl)-N$^4$-benzoyl-5-iodocytosine,
1-(2,5-Di-O-acetyl-3-bromo-3-deoxy-β-D-xylofuranosyl)-N$^4$-benzoyl-5-methylcytosine,
1-(2,5-Di-O-acetyl-3-bromo-3-deoxy-β-D-xylofuranosyl)-N$^4$-benzoyl-5-ethylcytosine,
1-(2,5-Di-O-acetyl-3-bromo-3-deoxy-β-D-xylofuranosyl)-N$^4$-benzoyl-5-n-propylcytosine,
1-(2,5-Di-O-acetyl-3-bromo-3-deoxy-β-D-xylofuranosyl)-N$^4$-benzoyl-5-i-propylcytosine,
1-(2,5-Di-O-acetyl-3-bromo-3-deoxy-β-D-xylofuranosyl)-N$^4$-benzoyl-5-vinylcytosine,
1-(2,5-Di-O-acetyl-3-bromo-3-deoxy-β-D-xylofuranosyl)-N$^4$-benzoyl-5-(2-chlorovinyl)cytosine,
1-(2,5-Di-O-acetyl-3-bromo-3-deoxy-β-D-xylofuranosyl)-N$^4$-benzoyl-5-(2-bromovinyl)cytosine,
1-(2,5-Di-O-acetyl-3-bromo-3-deoxy-β-D-xylofuranosyl)-N$^4$-benzoyl-5-(2-iodovinyl)cytosine,
1-(2,5-Di-O-acetyl-3-bromo-3-deoxy-β-D-xylofuranosyl)-N$^4$-benzoyl-5-(2-methoxylcarbonyl-vinyl)cytosine,
1-(2,5-Di-O-acetyl-3-bromo-3-deoxy-β-D-xylofuranosyl)-N$^4$-benzoyl-5-(2-hydroxycarbonyl-vinyl)cytosine,
1-(2,5-Di-O-acetyl-3-bromo-3-deoxy-β-D-xylofuranosyl)-N$^4$-benzoyl-5-phenylcytosine,
1-(2,5-Di-O-acetyl-3-bromo-3-deoxy-β-D-xylofuranosyl)-N$^4$-benzoyl-5-benzylcytosine,
1-(2,5-Di-O-acetyl-3-bromo-3-deoxy-β-D-xylofuranosyl)-N$^4$-anisoylcytosine, 1-(2,5-Di-O-acetyl-3-bromo-3-deoxy-β-D-xylofuranosyl)-N⁴-anisoyl-5-fluorocytosine,
1-(2,5-Di-O-acetyl-3-bromo-3-deoxy-β-D-xylofuranosyl)-N⁴-anisoyl-5-chlororocytosine,
1-(2,5-Di-O-acetyl-3-bromo-3-deoxy-β-D-xylofuranosyl)-N⁴-anisoyl-5-bromocytosine,
1-(2,5-Di-O-acetyl-3-bromo-3-deoxy-β-D-xylofuranosyl)-N⁴-anisoyl-5-iodocytosine,
1-(2,5-Di-O-acetyl-3-bromo-3-deoxy-β-D-xylofuranosyl)-N⁴-anisoyl-5-methylcytosine,
1-(2,5-Di-O-acetyl-3-bromo-3-deoxy-β-D-xylofuranosyl)-N⁴-anisoyl-5-ethylcytosine,
1-(2,5-Di-O-acetyl-3-bromo-3-deoxy-β-D-xylofuranosyl)-N⁴-anisoyl-5-n-propylcytosine,
1-(2,5-Di-O-acetyl-3-bromo-3-deoxy-β-D-xylofuranosyl)-N⁴-anisoyl-5-i-propylcytosine,
1-(2,5-Di-O-acetyl-3-bromo-3-deoxy-β-D-xylofuranosyl)-N⁴-anisoyl-5-vinylcytosine,
1-(2,5-Di-O-acetyl-3-bromo-3-deoxy-β-D-xylofuranosyl)-N⁴-anisoyl-5-(2-chlorovinyl)cytosine,
1-(2,5-Di-O-acetyl-3-bromo-3-deoxy-β-D-xylofuranosyl)-N⁴-anisoyl-5-(2-bromovinyl)cytosine,
1-(2,5-Di-O-acetyl-3-bromo-3-deoxy-β-D-xylofuranosyl)-N⁴-anisoyl-5-(2-iodovinyl)cytosine,
1-(2,5-Di-O-acetyl-3-bromo-3-deoxy-β-D-xylofuranosyl)-N⁴-anisoyl-5-(2-methoxylcarbonylvinyl)-cytosine,
1-(2,5-Di-O-acetyl-3-bromo-3-deoxy-β-D-xylofuranosyl)-N⁴-anisoyl-5-(2-hydroxycarbonyl-vinyl)-cytosine,
1-(2,5-Di-O-acetyl-3-bromo-3-deoxy-β-D-xylofuranosyl)-N⁴-anisoyl-5-phenylcytosine, and
1-(2,5-Di-O-acetyl-3-bromo-3-deoxy-β-D-xylofuranosyl)-N⁴-anisoyl-5-benzylcytosine.

Example 2

1-(2,5-Di-O-acetyl-3-deoxy-β-D-erythropentofuranosyl)-N⁴-acetylcytosine 1-(2,5-Di-O-acetyl-3-bromo-3-deoxy-β-D-xylofuranosyl)-N⁴-acetylcytosine (2.15 g, 5 mmol) in 50% aqueous methanol (100 mL) is hydrogenated in a Parr apparatus in the presence of powdered calcium carbonate (1 g) and Pd—BaSO₄ catalyst (0.5 g) at the initial pressure of 45 psi. The catalyst is removed by filtration, and the filtrate is concentrated in vacuo. The residue is crystallized from ethanol to give 1-(2,5-di-O-acetyl-3-deoxy-β-D-erythropentofuranosyl)-N⁴-acetylcytosine (3, R=H, 1.06 g, 60%), mp 174-177° C. ¹H NMR (CDCl₃) δ: 10.30 (bs, 1H, NHAc), 8.05 (d, 1H, H-6, J5,6=7.5 Hz), 7.43 (d, 1H, H-5, J5,6=7.5 Hz), 5.90 (d, 1H, H-1', J1',2'=1.0 Hz), 5.46 (m, 1H, H-2'), 4.30-4.80 (3H, m, H-4',5',5"), 2.10, 2.27 (2s, 9H, 3Ac), 1.60-2.00 (m, 2H, H-3',3").

In a similar manner but using the corresponding 3'-bromoxylo nucleosides, the following nucleosides and their L-counterparts are prepared:
1-(2,5-Di-O-acetyl-3-deoxy-β-D-erythropentofuranosyl)-N⁴-benzoylcytosine,
1-(2,5-Di-O-acetyl-3-deoxy-β-D-erythropentofuranosyl)-N⁴-benzoyl-5-methylcytosine,
1-(2,5-Di-O-acetyl-3-deoxy-β-D-erythropentofuranosyl)-N⁴-benzoyl-5-ethylcytosine,
1-(2,5-Di-O-acetyl-3-deoxy-β-D-erythropentofuranosyl)-N⁴-benzoyl-5-n-propylcytosine,
1-(2,5-Di-O-acetyl-3-deoxy-β-D-erythropentofuranosyl)-N⁴-benzoyl-5-i-propylcytosine,
1-(2,5-Di-O-acetyl-3-deoxy-β-D-erythropentofuranosyl)-N⁴-benzoyl-5-phenylcytosine,
1-(2,5-Di-O-acetyl-3-deoxy-β-D-erythropentofuranosyl)-N⁴-benzoyl-5-benzylcytosine,
1-(2,5-Di-O-acetyl-3-deoxy-β-D-erythropentofuranosyl)-N⁴-anisoylcytosine,
1-(2,5-Di-O-acetyl-3-deoxy-β-D-erythropentofuranosyl)-N⁴-anisoyl-5-methylcytosine,
1-(2,5-Di-O-acetyl-3-deoxy-β-D-erythropentofuranosyl)-N⁴-anisoyl-5-ethylcytosine,
1-(2,5-Di-O-acetyl-3-deoxy-β-D-erythropentofuranosyl)-N⁴-anisoyl-5-n-propylcytosine,
1-(2,5-Di-O-acetyl-3-deoxy-β-D-erythropentofuranosyl)-N⁴-anisoyl-5-i-propylcytosine,
1-(2,5-Di-O-acetyl-3-deoxy-β-D-erythropentofuranosyl)-N⁴-anisoyl-5-phenylcytosine and
1-(2,5-Di-O-acetyl-3-deoxy-β-D-erythropentofuranosyl)-N⁴-anisoyl-5-benzylcytosine.

Example 3

1-(3-Bromo-3-deoxy-β-D-xylofuranosyl)cytosine (3, R=H)

1-(2,5-Di-O-acetyl-3-bromo-3-deoxy-β-D-xylofuranosyl)-N⁴-acetylcytosine (4.31 g, 0.01 mol) is treated with saturated methanolic ammonia (100 mL) at 0° C. for 30 minutes, and then concentrated in vacuo below 35° C. The residue is crystallized from methanol to give 1-(3-bromo-3-deoxy-β-D-xylofuranosyl)cytosine (3, R=H). The UV and ¹H NMR (D₂O) are consistent with the xylo-structure In a similar manner but using the corresponding N-acylated cytidines, the following nucleosides and their L-counterparts are prepared:
1-(3-Bromo-3-deoxy-β-D-xylofuranosyl)-5-fluorocytosine,
1-(3-Bromo-3-deoxy-β-D-xylofuranosyl)-5-chlororocytosine,
1-(3-Bromo-3-deoxy-β-D-xylofuranosyl)-5-bromocytosine,
1-(3-Bromo-3-deoxy-β-D-xylofuranosyl)-5-iodocytosine,
1-(3-Bromo-3-deoxy-β-D-xylofuranosyl)-5-methylcytosine,
1-(3-Bromo-3-deoxy-β-D-xylofuranosyl)-5-ethylcytosine,
1-(3-Bromo-3-deoxy-β-D-xylofuranosyl)-5-n-propylcytosine,
1-(3-Bromo-3-deoxy-β-D-xylofuranosyl)-5-i-propylcytosine,
1-(3-Bromo-3-deoxy-β-D-xylofuranosyl)-5-vinylcytosine,
1-(3-Bromo-3-deoxy-β-D-xylofuranosyl)-5-(2-chlorovinyl)cytosine,
1-(3-Bromo-3-deoxy-β-D-xylofuranosyl)-5-(2-bromovinyl)cytosine,
1-(3-Bromo-3-deoxy-β-D-xylofuranosyl)-5-(2-iodovinyl)cytosine,
1-(3-Bromo-3-deoxy-β-D-xylofuranosyl)-5-(2-aminocarbonylvinyl)cytosine,
1-(3-Bromo-3-deoxy-β-D-xylofuranosyl)-5-(2-hydroxycarbonylvinyl)cytosine,
1-(3-Bromo-3-deoxy-β-D-xylofuranosyl)-5-phenylcytosine and
1-(3-Bromo-3-deoxy-β-D-xylofuranosyl)-5-benzylcytosine.

Example 4

3'-Deoxycytidine (4, R=H)

1-(2,5-Di-O-acetyl-3-deoxy-β-D-erythropentofuranosyl)-N⁴-acetylcytosine (3, R=H, 700 mg, 2 mmol) is dissolved in methanolic ammonia (20 mL, saturated at 0° C.) and the solution is kept overnight at room temperature. The solvent is removed by evaporation in vacuo, and the residue is dissolved in ethanol (20 mL), and then the pH of the solution is adjusted to 3 with 2N sulfuric acid. The precipitates are collected and crystallized from water-ethanol to give 3'-deoxycytidine (4) as hemisulfate (408 mg, 74%). Mp 202-203° C. (decomp). $^1$H NMR (D$_2$O) δ: 8.23 (d, 1H, H-6, $J_{5,6}$=8.0 Hz), 6.27 (d, 1H, H-5, $J_{5,6}$=8.0 Hz), 5.84 (d, 1H, $J_{1',2'}$=1.0 Hz), 4.6 (m, 1H, H-2'), 3.9 (m, 3H, H-4',5',5"), 1.95-2.15 (m, 2H, H-2',2").

In a similar manner but using the corresponding acylated 3'-deoxynucleosides, the following nucleosides and their L-counterparts are prepared: 3'-deoxy-5-methylcytidine, 3'-deoxy-5-ethylcytidine, 3'-deoxy-5-n-propylcytidine, 3'-deoxy-5-i-propylcytidine, 3'-deoxy-5-phenylcytidine, and 3'-deoxy-5-benzylcytidine.

Example 5

2',5'-Di-O-acetyl-3'-deoxyuridine

2',5'-Di-O-acetyl-3-deoxy-N$^4$-acetylcytidine (1.06 g, 3 mol) is dissolved in 70% acetic acid, and the solution is gently refluxed overnight. After concentration of the mixture in vacuo, the residue is crystallized from ethanol to give 2',5'-di-O-acetyl-3% deoxyuridine (660 mg, 96%). $^1$H NMR spectrum shows that it contains two acetyl groups, two methylene groups and two olefinic protons.

In a similar manner but using the corresponding 3'-deoxycytidines (4), the following 2',5'-di-O-acetyl-3'-deoxyuridines and their L-counterparts are prepared: 2',5'-Di-O-acetyl-3-deoxy-5-methyluridine, 2',5'-di-O-acetyl-3-deoxy-5-ethyluridine, O-acetyl-3-deoxy-5-n-propyluridine, 2',5'-di-O-acetyl-3-deoxy-5-i-propyluridine, 2',5'-di-O-acetyl-3-deoxy-5-phenyluridine and 2',5'-di-O-acetyl-3-deoxy-5-benzyluridine.

In a similar manner but using the corresponding 3'-deoxy cytosine nucleosides (2), the following uracil nucleosides and their L-counterparts are prepared:
2',5'-Di-O-acetyl-3-deoxy-5-fluorouridine,
2%5'-Di-O-acetyl-3-deoxy-5-chloro uridine,
2',5'-Di-O-acetyl-3-deoxy-5-bromouridine,
2',5'-Di-O-acetyl-3-deoxy-5-iodouridine,
2',5'-Di-O-acetyl-3-deoxy-5-methyluridine,
2',5'-Di-O-acetyl-3-deoxy-5-ethyluridine,
2',5'-Di-O-acetyl-3-deoxy-5-n-propyluridine,
2',5'-Di-O-acetyl-3-deoxy-5-i-propyluridine,
2',5'-Di-O-acetyl-3-deoxy-5-vinyluridine,
2',5'Di-O-acetyl-3-deoxy-5-(2-chlorovinyl)uridine,
2',5'-Di-O-acetyl-3-deoxy-5-(2-bromovinyl)uridine,
2',5'-Di-O-acetyl-3-deoxy-5-(2-iodovinyl)uridine,
2',5'-Di-O-acetyl-3-deoxy-5-(2-methoxylcarbonylvinyl)uridine,
2',5'-Di-O-acetyl-3-deoxy-5-(2-hydroxycarbonylvinyl)uridine,
2',5'-Di-O-acetyl-3-deoxy-5-phenyluridine and
2',5'-Di-O-acetyl-3-deoxy-5-benzyluridine.

Example 6

1-(2,5-Di-O-acetyl-3-bromo-3-deoxy-β-D-xylofuranosyl)uracil (5, R═H)

1-(2,5-Di-O-acetyl-3-bromo-3-deoxy-β-D-xylofuranosyl)-N$^4$-acetylcytosine (2, R═H, R'═CH$_3$) (4.31 g, 0.01 mol) is dissolved in 70% acetic acid, and the solution is gently refluxed for 4 hours. After concentration of the mixture in vacuo, the residue is crystallized from ethanol to give 2',5'-di-O-acetyl-3'-bromo-3'-deoxyuridine (5, 2.80 g, 91%). $^1$H NMR spectrum shows that it contains two acetyl groups, two methylene groups and two olefinic protons.

In a similar manner but using the corresponding 2',5'-di-O-acetyl-3'-bromo-3'-deoxy-N$^4$-acylcytidines (2), the following 1,5-di-O-acetyl-3'-bromo-3'-deoxyuridines and their L-counterparts are prepared:
1-(2,5-Di-O-acetyl-3-deoxy-β-D-xylofuranosyl)-5-fluorouracil,
1-(2,5-Di-O-acetyl-3-deoxy-β-D-xylofuranosyl)-5-chlorouracil,
1-(2,5-Di-O-acetyl-3-deoxy-β-D-xylofuranosyl)-5-bromouracil,
1-(2,5-Di-O-acetyl-3-deoxy-β-D-xylofuranosyl)-5-iodouracil,
1-(2,5-Di-O-acetyl-3-deoxy-β-D-xylofuranosyl)-5-methyluracil,
1-(2,5-Di-O-acetyl-3-deoxy-β-D-xylofuranosyl)-5-ethyluracil,
1-(2,5-Di-O-acetyl-3-deoxy-β-D-xylofuranosyl)-5-n-propyluracil,
1-(2,5-Di-O-acetyl-3-deoxy-β-D-xylofuranosyl)-5-i-propyluracil,
1-(2,5-Di-O-acetyl-3-deoxy-β-D-xylofuranosyl)-5-vinyluracil,
1-(2,5-Di-O-acetyl-3-deoxy-β-D-xylofuranosyl)-5-(2-chlorovinyl)uracil,
1-(2,5-Di-O-acetyl-3-deoxy-β-D-xylofuranosyl)-5-(2-bromovinyl)uracil,
1-(2,5-Di-O-acetyl-3-deoxy-β-D-xylofuranosyl)-5-(2-iodovinyl)uracil,
1-(2,5-Di-O-acetyl-3-deoxy-β-D-xylofuranosyl)-5-(2-methoxylcarbonylvinyl)uracil,
1-(2,5-Di-O-acetyl-3-deoxy-β-D-xylofuranosyl)-5-(2-hydroxycarbonylvinyl)uracil,
1-(2,5-Di-O-acetyl-3-deoxy-β-D-xylofuranosyl)-5-phenyluracil and
1-(2,5-Di-O-acetyl-3-deoxy-β-D-xylofuranosyl)-5-benzyluracil.

Example 7

3'-Deoxyuridine (6b, R═H)

2',5'-Di-O-acetyl-3'-deoxyuridine (1.06 g, 3 mol) is dissolved in methanolic ammonia (10 mL, saturated at 0° C.) overnight. After concentration of the mixture in vacuo, the residue is crystallized from ethanol to give 3'-deoxyuridine (6b, 660 mg, 96%).

In a similar manner but using the corresponding acylated 3'-deoxy-uracil nucleosides (6b) or their L-counterparts, the following nucleosides are prepared: 3-Deoxy-5-methyluridine, 3-deoxy-5-ethyluridine, 3-deoxy-5-n-propyluridine, 3-deoxy-5-i-propyl-uridine, 3-deoxy-5-phenyluridine, and 3-deoxy-5-benzyluridine.

Example 8

1-(3-Bromo-3-deoxy-β-D-xylofuranosyl)uracil (6a, R═H)

1-(2',5'-Di-O-acetyl-3'-bromo-3'-deoxy-β-D-xylofuranosyl)uracil (5, R═H) is dissolved in methanolic ammonia (10 mL, saturated at 0° C.). After 1 hour at 0° C., the mixture is concentrated in vacuo, and the residue is crystallized from ethanol to give 3'-bromo-3'-deoxyuridine (6a, 660 mg, 96%). The UV and $^1$H NMR are consistent with the structure.

In a similar manner but using the corresponding acylated 3'-bromo-xylosyluracils, the following nucleosides and their L-counterparts are prepared:
1-(3-Bromo-3-deoxy-β-D-xylofuranosyl)-5-fluorouracil,
1-(3-Bromo-3-deoxy-β-D-xylofuranosyl)-5-chlororouracil,
1-(3-Bromo-3-deoxy-β-D-xylofuranosyl)-5-bromouracil,
1-(3-Bromo-3-deoxy-β-D-xylofuranosyl)-5-iodouracil,
1-(3-Bromo-3-deoxy-β-D-xylofuranosyl)-5-methyluracil,
1-(3-Bromo-3-deoxy-β-D-xylofuranosyl)-5-ethyluracil,
1-(3-Bromo-3-deoxy-β-D-xylofuranosyl)-5-n-propyluracil,
1-(3-Bromo-3-deoxy-β-D-xylofuranosyl)-5-i-propyluracil,
1-(3-Bromo-3-deoxy-β-D-xylofuranosyl)-5-vinyluracil,
1-(3-Bromo-3-deoxy-β-D-xylofuranosyl)-5-(2-chlorovinyl)uracil,
1-(3-Bromo-3-deoxy-β-D-xylofuranosyl)-5-(2-bromovinyl)uracil,
1-(3-Bromo-3-deoxy-β-D-xylofuranosyl)-5-(2-iodovinyl)uracil,
1-(3-Bromo-3-deoxy-β-D-xylofuranosyl)-5-(2-aminocarbonylvinyl)uracil,
1-(3-Bromo-3-deoxy-β-D-xylofuranosyl)-5-(2-hydroxycarbonylvinyl)uracil,
1-(3-Bromo-3-deoxy-β-D-xylofuranosyl)-5-phenyluracil and
1-(3-Bromo-3-deoxy-β-D-xylofuranosyl)-5-benzyluracil.

Example 9

2',5'-Di-O-triphenylmethyluridine (7, R=H)

A mixture of uridine (24.4 g, 0.1 mol) and triphenylchloromethane (83.5 g, 0.3 mol) in anhydrous pyridine (250 mL) is stirred overnight at room temperature, and then is refluxed for 4 hours. After cooling to room temperature, the mixture is poured into water with vigorous stirring. The water is removed by decantation, and the gummy residue is treated with water, stirred and the water decanted. This process is repeated several times, after which the residue is treated with hot water (500 mL), stirred and the water decanted. This process is repeated twice. The residue is dissolved in methylene chloride, dried (Na$_2$SO$_4$), and concentrated in vacuo. The residue is dissolved in minimum amount of benzene, and the solution diluted with ethyl ether to turbidity, and the mixture left overnight at 15° C. The precipitates are collected and recrystallized from benzene-ethyl ether to give 7 (R=H) (22.8 g, 31%), mp 224-225° C. The combined filtrates are concentrated, and the residue dissolved in methylene chloride and chromatographed over a silica gel column using methylene chloride-ethanol (99:1 v/v), (98:2 v/v) and (97:3 v/v). Compound 7 is eluted first (10 g, 14%), followed by 3',5'-di-O-triphenylmethyluridine (31.0 g, 42.5%).

In a similar manner but using the corresponding nucleosides, the following 2',5'-di-O-protected and 3',5'-di-O-protected nucleosides and their L-counterparts are prepared:
2',5'-Di-O-triphenylmethyl-5-fluorouridine,
2',5'-Di-O-triphenylmethyl-5-chloro uridine,
2',5'-Di-O-triphenylmethyl-5-bromouridine,
2',5'-Di-O-triphenylmethyl-5-iodouridine,
2',5'-Di-O-triphenylmethyl-5-methyluridine,
2',5'-Di-O-triphenylmethyl-5-ethyluridine,
2',5'-Di-O-triphenylmethyl-5-n-propyluridine,
2',5'-Di-O-triphenylmethyl-5-i-propyluridine,
2',5'-Di-O-triphenylmethyl-5-vinyluridine,
2',5'-Di-O-triphenylmethyl-5-ethynyluridine,
2',5'-Di-O-triphenylmethyl-5-(2-chlorovinyl)uridine,
2',5'-Di-O-triphenylmethyl-5-(2-bromovinyl)uridine,
2',5'-Di-O-triphenylmethyl-5-(2-iodovinyl)uridine,
2',5'-Di-O-triphenylmethyl-5-(2-methoxylcarbonylvinyl)uridine,
2',5'-Di-O-triphenylmethyl-5-(2-hydroxycarbonylvinyl)uridine,
2',5'-Di-O-triphenylmethyl-5-phenyluridine,
2',5'-Di-O-triphenylmethyl-5-benzyluridine,
3',5'-Di-O-triphenylmethyl-5-fluorouridine,
3',5'-Di-O-triphenylmethyl-5-chlorouridine,
3',5'-Di-O-triphenylmethyl-5-bromouridine,
3',5'-Di-O-triphenylmethyl-5-iodouridine,
3',5'-Di-O-triphenylmethyl-5-methyluridine,
3',5'-Di-O-triphenylmethyl-5-ethyluridine,
3',5'-Di-O-triphenylmethyl-5-n-propyluridine,
3',5'-Di-O-triphenylmethyl-5-i-propyluridine,
3',5'-Di-O-triphenylmethyl-5-vinyluridine,
3',5'-Di-O-triphenylmethyl-5-ethynyluridine,
3',5'-Di-O-triphenylmethyl-5-(2-chlorovinyl)uridine,
3',51-Di-O-triphenylmethyl-5-(2-bromovinyl)uridine,
3',5'-Di-O-triphenylmethyl-5-(2-iodovinyl)uridine,
3',5'-Di-O-triphenylmethyl-5-(2-methoxylcarbonylvinyl)uridine,
3',5'-Di-O-triphenylmethyl-5-(2-hydroxycarbonylvinyl)uridine,
3',5'-Di-O-triphenylmethyl-5-phenyluridine and
3',5'-Di-O-triphenylmethyl-5-benzyluridine.

Example 10

3'-O-Mesyl-2,5'-di-O-triphenylmethyluridine (8, R=H)

To a cooled solution of 2',5'-di-O-triphenylmethyluridine (7, R=H, 7.28 g, 1 mmol) in pyridine (100 mL) is added drop wise mesyl chloride (1 mL), and the reaction is kept overnight at 4° C. The reaction is quenched by addition of ethanol (5 mL). After 2 hours of stirring at room temperature, the mixture is concentrated in vacuo. The residue is triturated with ethanol (250 mL), and the solid collected, and recrystallized from ethanol to give 8 (R=H) (7.45 g, 92%), mp 225-226° C.

In a similar manner but using the corresponding nucleosides, the following 2',5'-di-O-triphenylmethylated and 3',5'-di-O-triphenylmethylated nucleosides and their L-counterparts are prepared:
3'-O-Mesyl-2',5'-di-O-triphenylmethyl-5-fluorouridine,
3'-O-Mesyl-2',5'-di-O-triphenylmethyl-5-chlorouridine,
3'-O-Mesyl-2',5'-di-O-triphenylmethyl-5-bromouridine,
3'-O-Mesyl-2',5'-di-O-triphenylmethyl-5-iodouridine,
3'-O-Mesyl-2',5'-di-O-triphenylmethyl-5-methyluridine,
3'-O-Mesyl-2',5'-di-O-triphenylmethyl-5-ethyluridine,
3'-O-Mesyl-2',5'-di-O-triphenylmethyl-5-n-propyluridine,
3'-O-Mesyl-2',5'-di-O-triphenylmethyl-5-i-propyluridine,
3'-O-Mesyl-2',5'-di-O-triphenylmethyl-5-vinyluridine,
3'-O-Mesyl-2',5'-di-O-triphenylmethyl-5-ethynyluridine,
3'-O-Mesyl-2',5'-di-O-triphenylmethyl-5-(2-chlorovinyl)uridine,
3'-O-Mesyl-2',5'-di-O-triphenylmethyl-5-(2-bromovinyl)uridine,
3'-O-Mesyl-2',5'-di-O-triphenylmethyl-5-(2-iodovinyl)uridine,
3'-O-Mesyl-2',5'-di-O-triphenylmethyl-5-(2-methoxylcarbonylvinyl)uridine, 3'-O-Mesyl-2',5'-di-O-triphenylmethyl-5-(2-hydroxycarbonylvinyl)uridine,
3'-O-Mesyl-2',5'-di-O-triphenylmethyl-5-phenyluridine,
3'-O-Mesyl-2',5'-di-O-triphenylmethyl-5-benzyluridine,
2'-O-Mesyl-3',5'-di-O-triphenylmethyl-5-fluorouridine,
2'-O-Mesyl-3',5'-di-O-triphenylmethyl-5-chlorouridine,
2'-O-Mesyl-3',5'-di-O-triphenylmethyl-5-bromouridine,
2'-O-Mesyl-3',5'-di-O-triphenylmethyl-5-iodouridine,
2'-O-Mesyl-3',5'-di-O-triphenylmethyl-5-methyluridine,
2'-O-Mesyl-3',5'-di-O-triphenylmethyl-5-ethyluridine,
2'-O-Mesyl-3',5'-di-O-triphenylmethyl-5-n-propyluridine,
2'-O-Mesyl-3',5'-di-O-triphenylmethyl-5-i-propyluridine,
2'-O-Mesyl-3',5'-di-O-triphenylmethyl-5-vinyluridine,
2'-O-Mesyl-3',5'-di-O-triphenylmethyl-5-ethynyluridine,
2'-O-Mesyl-3',5'-di-O-triphenylmethyl-5-(2-chlorovinyl)uridine,
2'-O-Mesyl-3',5'-di-O-triphenylmethyl-5-(2-bromovinyl)uridine,
2'-O-Mesyl-3',5'-di-O-triphenylmethyl-5-(2-iodovinyl)uridine,
2'-O-Mesyl-3',5'-di-O-triphenylmethyl-5-(2-methoxylcarbonylvinyl)uridine,
2'-O-Mesyl-3',5'-di-O-triphenylmethyl-5-(2-hydroxycarbonylvinyl)uridine,
2'-O-Mesyl-3',5'-di-O-triphenylmethyl-5-phenyluridine and
2'-O-Mesyl-3',5'-di-O-triphenylmethyl-5-benzyluridine.

Example 11

2,3'-Anhydro-1-(2,5-di-O-triphenylmethyl-β-D-xylofuranosyl)uracil (9, R=H, X'=OH)

A mixture of 3'-O-mesyl-2',5'-di-O-triphenylmethyluridine (806 mg, 1 mmol), sodium benzoate (2 g) in dimethylformamide (40 mL) is heated at 130-140° C. overnight. The mixture is cooled to room temperature, and poured onto 1 L of water with stirring. The precipitates are collected by decantation and triturated with ethanol (100 mL) to give 3'-anhydro-1-(2,5-di-O-triphenylmethyl-β-D-xylofuranosyl)uracil (9, R=H, X'=OH), (500 mg, 75%), mp 237° C.

In a similar manner but using the corresponding 5-substituted 3'-O-mesyl-2',5'-di-O-triphenylmethyluridines (8), the following 2,3'-anhydro-di-O-triphenylmethylated nucleosides and their L-counterparts are prepared:
2,3'-Anhydro-1-(2,5-di-O-triphenylmethyl-β-D-xylofuranosyl)-5-fluorouracil.
2,3'-Anhydro-1-(2,5-di-O-triphenylmethyl-β-D-xylofuranosyl)-5-chlorouridine,
2,3'-Anhydro-1-(2,5-di-O-triphenylmethyl-β-D-xylofuranosyl)-5-bromouridine,
2,3'-Anhydro-1-(2,5-di-O-triphenylmethyl-β-D-xylofuranosyl)-5-iodouridine,
2,3% Anhydro-1-(2,5-di-O-triphenylmethyl-β-D-xylofuranosyl)-5-methyluridine,
2,3'-Anhydro-1-(2,5-di-O-triphenylmethyl-β-D-xylofuranosyl)-5-ethyluridine,
2,3'-Anhydro-1-(2,5-di-O-triphenylmethyl-β-D-xylofuranosyl)-5-n-propyluridine,
2,3'-Anhydro-1-(2,5-di-O-triphenylmethyl-β-D-xylofuranosyl)-5-i-propyluridine,
2,3'-Anhydro-1-(2,5-di-O-triphenylmethyl-β-D-xylofuranosyl)-5-vinyluridine,
2,3% Anhydro-1-(2,5-di-O-triphenylmethyl-β-D-xylofuranosyl)-5-ethynyluridine,
2,3'-Anhydro-1-(2,5-di-O-triphenylmethyl-β-D-xylofuranosyl)-5-(2-chlorovinyl)uridine,
2,3'-Anhydro-1-(2,5-di-O-triphenylmethyl-β-D-xylofuranosyl)-5-(2-bromovinyl)uridine,
2,3'-1-(2,5-di-O-triphenylmethyl-β-D-xylofuranosyl)-5-(2-iodovinyl)uridine,
2,3% Anhydro-1-(2,5-di-O-triphenylmethyl-β-D-xylofuranosyl)-5-(2-methoxylcarbonylvinyl)-uridine,
2,3'-Anhydro-1-(2,5-di-O-triphenylmethyl-β-D-xylofuranosyl)-5-(2-hydroxycarbonylvinyl)-uridine,
2,3% Anhydro-1-(2,5-di-O-triphenylmethyl-β-D-xylofuranosyl)-5-phenyluridine and
2,3'-Anhydro-1-(2,5-di-O-triphenylmethyl-β-D-xylofuranosyl)-5-benzyluridine.

In a similar manner but using the corresponding 5-substituted 2'-O-mesyl-3',5'-di-O-triphenylmethyluridines, the following 2,2'-anhydro-3',5'-di-O-triphenylmethylated nucleosides and their L-counterparts are prepared:
2,2'-Anhydro-1-(3,5-di-O-triphenylmethyl-β-D-arabinofuranosyl)-5-fluorouracil,
2,2'-Anhydro-1-(3,5-di-O-triphenylmethyl-β-D-arabinofuranosyl)-5-chlorouridine,
2,2'-Anhydro-1-(3,5-di-O-triphenylmethyl-β-D-arabinofuranosyl)-5-bromouridine,
2,2'-Anhydro-1-(3,5-di-O-triphenylmethyl-β-D-arabinofuranosyl)-5-iodouridine,
2,2'-Anhydro-1-(3,5-di-O-triphenylmethyl-β-D-arabinofuranosyl)-5-methyluridine,
2,2'-Anhydro-1-(3,5-di-O-triphenylmethyl-β-D-arabinofuranosyl)-5-ethyluridine,
2,2'-Anhydro-1-(3,5-di-O-triphenylmethyl-β-D-arabinofuranosyl)-5-n-propyluridine,
2,2'-Anhydro-1-(3,5-di-O-triphenylmethyl-β-D-arabinofuranosyl)-5-i-propyluridine,
2,2'-Anhydro-1-(3,5-di-O-triphenylmethyl-β-D-arabinofuranosyl)-5-vinyluridine,
2,2'-Anhydro-1-(3,5-di-O-triphenylmethyl-β-D-arabinofuranosyl)-5-ethynyluridine,
2,2'-Anhydro-1-(3,5-di-O-triphenylmethyl-β-D-arabinofuranosyl)-5-(2-chlorovinyl)uridine,
2,2'-Anhydro-1-(3,5-di-O-triphenylmethyl-β-D-arabinofuranosyl)-5-(2-bromovinyl)uridine,
2,2'-Anhydro-1-(3,5-di-O-triphenylmethyl-β-D-arabinofuranosyl)-5-(2-iodovinyl)uridine,
2,2'-Anhydro-1-(3,5-di-O-triphenylmethyl-β-D-arabinofuranosyl)-5-(2-methoxylcarbonylvinyl)-uridine,
2,2'-Anhydro-1-(3,5-di-O-triphenylmethyl-β-D-arabinofuranosyl)-5-(2-hydroxycarbonylvinyl)-uridine,
2,2'-Anhydro-1-(3,5-di-O-triphenylmethyl-β-D-arabinofuranosyl)-5-phenyluridine and
2,2'-Anhydro-1-(3,5-di-O-triphenylmethyl-β-D-arabinofuranosyl)-5-benzyluridine.

Example 12

3'-Deoxy-3'-iodo-2',5'-di-O-triphenylmethyluridine (11, R=H, X=1, X'=OH)

A mixture of 3'-O-mesyl-2',5'-di-O-triphenylmethyluridine (8, 1.61 g, 2 mmol), sodium iodide (3 g, 20 mmol) in 1,2-dimethoxyethane (40 mL) is heated at reflux overnight. The solvent is removed by evaporation in vacuo, the residue is dissolved in methylene chloride. The solution is washed successively with 5% sodium thiosulfate and water, dried over sodium sulfate, and concentrated to dryness in vacuo. The residue is chromatographed over a silica gel column using methylene chloride-ethyl ether (3:1 v/v) as the eluent to give 703 mg (42%) of 3'-deoxy-3'-iodo-2',5'-di-O-triphenylmethyluridine (11, R=H, X=I, X'=OH).

In a similar manner but using the corresponding 5-substituted 3'-O-mesyl-2',5'-di-O-triphenylmethyluridines (8), the following 3'-iodo derivatives are and their L-counterparts prepared:

3'-Deoxy-3'-iodo-2',5'-di-O-triphenylmethyl-5-fluorouridine,
3'-Deoxy-3'-iodo-2',5'-di-O-triphenylmethyl-5-chlorouridine,
3'-Deoxy-3'-iodo-2',5'-di-O-triphenylmethyl-5-bromouridine,
3'-Deoxy-3-iodo-2',5'-di-O-triphenylmethyl-5-iodouridine,
3'-Deoxy-3'-iodo-2',5'-di-O-triphenylmethyl-5-methyluridine,
3'-Deoxy-3'-iodo-2',5'-di-O-triphenylmethyl-5-ethyluridine,
3'-Deoxy-3'-iodo-2',5'-di-O-triphenylmethyl-5-n-propyluridine,
3'-Deoxy-3'-iodo-2',5'-di-O-triphenylmethyl-5-i-propyluridine,
3'-Deoxy-3'-iodo-2',5'-di-O-triphenylmethyl-5-vinyluridine,
3'-Deoxy-3'-iodo-2',5'-di-O-triphenylmethyl-5-ethynyluridine,
3'-Deoxy-3'-iodo-2',5'-di-O-triphenylmethyl-5-(2-chlorovinyl)uridine,
3'-Deoxy-3'-iodo-2',5'-di-O-triphenylmethyl-5-(2-bromovinyl)uridine,
3'-Deoxy-3'-iodo-2',5'-di-O-triphenylmethyl-5-(2-iodovinyl)uridine,
3'-Deoxy-3'-iodo-2',5'-di-O-triphenylmethyl-5-(2-methoxylcarbonylvinyl)uridine,
3'-Deoxy-3'-iodo-2',5'-di-O-triphenylmethyl-5-(2-hydroxycarbonylvinyl)uridine,
3'-Deoxy-3'-iodo-2',5'-di-O-triphenylmethyl-5-phenyluridine and
3'-Deoxy-3'-iodo-2',5'-di-O-triphenylmethyl-5-benzyluridine.

In a similar manner but using the corresponding 5-substituted 2'-O-mesyl-3',5'-di-O-triphenylmethyluridines, the following 2'-iodo derivatives and their L-counterparts are prepared:

2'-Deoxy-2'-iodo-3',5'-di-O-triphenylmethyl-5-fluorouridine,
2'-Deoxy-2'-iodo-3',5'-di-O-triphenylmethyl-5-chlorouridine,
2'-Deoxy-2'-iodo-3',5'-di-O-triphenylmethyl-5-bromouridine,
2'-Deoxy-2'-iodo-3',5'-di-O-triphenylmethyl-5-iodouridine,
2'-Deoxy-2'-iodo-3',5'-di-O-triphenylmethyl-5-methyluridine,
2'-Deoxy-2'-iodo-3',5'-di-O-triphenylmethyl-5-ethyluridine,
2'-Deoxy-2'-iodo-3',5'-di-triphenylmethyl-5-n-propyluridine,
2'-Deoxy-2'-iodo-3',5'-di-O-triphenylmethyl-5-i-propyluridine,
2'-Deoxy-2'-iodo-3',5'-di-O-triphenylmethyl-5-vinyluridine,
2'-Deoxy-2'-iodo-3',5'-di-O-triphenylmethyl-5-ethynyluridine,
2'-Deoxy-2'-iodo-3',5'-di-O-triphenylmethyl-5-(2-chlorovinyl)uridine,
2'-Deoxy-2'-iodo-3',5'-di-O-triphenylmethyl-5-(2-bromovinyl)uridine,
2'-Deoxy-2'-iodo-3',5'-di-O-triphenylmethyl-5-(2-iodovinyl)uridine,
2'-Deoxy-2'-iodo-3',5'-di-O-triphenylmethyl-5-(2-methoxylcarbonylvinyl)uridine,
2'-Deoxy-2'-iodo-3',5'-di-O-triphenylmethyl-5-(2-hydroxycarbonylvinyl)uridine,
2'-Deoxy-2'-iodo-3',5'-di-O-triphenylmethyl-5-phenyluridine and
2'-Deoxy-2'-iodo-3',5'-di-O-triphenylmethyl-5-benzyluridine.

Example 13

3'-Iodo-3'-deoxyuridine

3'-Deoxy-3'-iodo-2',5'-di-O-triphenylmethyluridine (840 mg, 1 mmol) (11, R=H, X=I, X'=OH) is dissolved in a 10:1 mixture of methylene chloride and trifluoroacetic acid (20 mL), and the mixture is kept at room temperature. The solvent is removed in vacuo, and the residue is triturated with ethyl ether (15 mL×2). The ether-insoluble residue is crystallized from methanol ether to give 3'-iodo-3'-deoxyuridine (312 mg, 88.1%).

In a similar manner but using the corresponding 5-substituted 3'-deoxy-3'-iodo-2',5'-di-O-triphenylmethyluridines, the following 3'-iodouridine derivatives and their L-counterparts are prepared: 3'-Deoxy-3'-iodo-5-fluorouridine, 3'-deoxy-3'-iodo-5-chlorouridine, 3'-deoxy-3'-iodo-5-bromo-uridine, 3'-deoxy-3'-iodo-5-iodouridine, 3'-deoxy-3'-iodo-5-methyl-uridine, 3'-deoxy-3'-iodo-5-ethyluridine, 3'-deoxy-3'-iodo-5-n-propyluridine, 3'-deoxy-3'-iodo-5-i-propyl-uridine, 3'-deoxy-3'-iodo-5-vinyluridine, 3'-deoxy-3'-iodo-5-ethynyluridine, 3' deoxy-3'-iodo-5-(2-chloro-vinyl)-uridine, 3'-deoxy-3'-iodo-5-(2-bromovinyl)uridine, 3'-deoxy-3'-iodo-5-(2-iodovinyl)uridine, 3'-deoxy-3'-iodo-5-(2-methoxylcarbonyl-vinyl)uridine, 3'-deoxy-3'-iodo-5-(2-hydroxy-carbonyl-vinyl)-uridine, 3'-deoxy-3'-iodo-5-phenyluridine, and 3'-deoxy-3'-iodo-5-benzyl-uridine.

In a similar manner but using the corresponding 5-substituted 2'-deoxy-2'-iodo-3',5'-di-O-triphenylmethyluridines, the following 2'-iodouridine derivatives and their L-counterparts are prepared: 2'-deoxy-2'-iodo-5-fluorouridine, 2'-deoxy-2'-iodo-5-chlorouridine, 2'-deoxy-2'-iodo-5-bromo-uridine, 2'-deoxy-2'-iodo-5-iodouridine, 2'-deoxy-2'-iodo-5-methyl-uridine, 2'-deoxy-2'-iodo-5-ethyluridine, 2'-deoxy-2'-iodo-5-n-propyluridine, 2'-deoxy-2'-iodo-5-i-propyl-uridine, 2'-deoxy-2'-iodo-5-vinyluridine, 2'-deoxy-2'-iodo-5-ethynyluridine, 2' deoxy-2'-iodo-5-(2-chlorovinyl)-uridine, 2'-deoxy-2'-iodo-5-(2-bromovinyl)uridine, 2'-deoxy-2'-iodo-5-(2-iodovinyl)uridine, 2'-deoxy-2'-iodo-5-(2-methoxylcarbonylvinyl)uridine, 2'-deoxy-2'-iodo-5-(2-hydroxycarbonyl-vinyl)-uridine, 2'-deoxy-2'-iodo-5-phenyluridine, and 2'-deoxy-2'-iodo-5-benzyluridine.

Example 14

9-(2-O-Acetyl-3-bromo-3-deoxy-β-D-xylofuranosyl)adenine (14, R=H, X=Br, Y=$NH_2$, Z=H)

Compound 14 (R=2,5,5-trimethyl-1,3-dioxolan-4-on-2-yl, X=Br, Y=$NH_2$, Z=H, 500 mg, 1 mmol) is dissolved in methanolic hydrogen chloride prepared by addition of 3 drops of acetyl chloride in 10 mL of methanol. After 30 minutes at room temperature, 3 mL of saturated sodium bicarbonate solution is added, and the mixture concentrated in vacuo to dryness. The residue is triturated with ethanol until supernatant does not show significant UV absorption at 260 nm. The ethanol extracts are concentrated, and the residue is crystallized from methanol to give the desired 14 (R=H, X=Br, Y=$NH_2$, Z=H), 325 g (87%). $^1$H NMR ($D_6$-DMSO) δ: 8.16, 8.32 (2s, H-2 and H-8), 6.10 (d, 1H, H-1', $J_{1',2'}$=3.9 Hz), 5.91 (dd, 1H, H-2', $J_{1',2'=3.9}$, $J_{2',3'=4.1}$ Hz), 5.85 (dd, 1H, H-3', J$_{2',3'}$=4.1, J$_{3',4'}$=5.1 Hz), 4.38 (dt, 1H, H-4', J$_{3',4'}$=5.1, ==5.0 Hz), 3.79 (dd, 2H, H-5',5"), 2.09 (s, 3H, Ac).

In a similar manner but using the corresponding purine nucleosides, the following 2'-O-acetyl-3'-bromo-3'-deoxy-D-xylo nucleosides (14) and their L-counterparts are prepared:

9-(2-O-Acetyl-3-bromo-3-deoxy-β-D-xylofuranosyl)guanine,
9-(2-O-Acetyl-3-bromo-3-deoxy-β-D-xylofuranosyl)-6-chloropurine,
9-(2-O-Acetyl-3-bromo-3-deoxy-β-D-xylofuranosyl)-2,6-dichloropurine,
9-(2-O-Acetyl-3-bromo-3-deoxy-β-D-xylofuranosyl)-2-amino-6-chloropurine,
9-(2-O-Acetyl-3-bromo-3-deoxy-β-D-xylofuranosyl)-6-methylthiopurine and
9-(2-O-Acetyl-3-bromo-3-deoxy-β-D-xylofuranosyl)-6-methoxypurine.

Example 15

9-[2-O-Acetyl-3-bromo-3-deoxy-5-O-(2,5,5-trimethyl-1,3-dioxolan-4-on-2-yl)-β-D-xylo-furanosyl] adenine (14, R=2,5,5-trimethyl-1,3-dioxalan-2-one-2-yl, X=Br, Y=NH$_2$, Z=H)

A mixture of adenosine (13, Y=NH$_2$, Z=H, 10 g, 0.037 mol) and α-acetoxy-iso-butyryl bromide (24 g, 0.117 mol) in acetonitrile (120 mL) is stirred at room temperature for 45 minutes. The solvent is removed in vacuo, and the residue is dissolved in ethyl acetate, washed with sodium bicarbonate solution and water, dried over sodium sulfate, and concentrated in vacuo. The residue is crystallized from methanol to give 6.5 g (35%) of 14 (X=Br, Y=NH$_2$, Z=H), mp 169-170° C. $^1$H NMR (D$_6$-DMSO) δ: 8.17, 8.26 (2s, 1H each, H-2 and H-6), 6.16 (d, 1H, H-1', J$_{1',2'}$=3.5 Hz), 5.94 (dd, 1H, H-2', J$_{1',2'}$=3.5 Hz, J$_{2',3'}$=3.0 Hz), 4.92 (dd, 1H, H-3', J$_{2',3'}$=3.0 Hz, J$_{3',4'}$=4.8 Hz), 4.54 (m, 1H, H-4'), 3.94 (m, 2H, H-5',5"), 2.10 (s, 31-1, Ac), 1.73, 1.58, 1.47 (3s, 3H each, CH$_3$ groups on 5'). The mother liquor of crystallization of 14 contains a mixture of 2'-bromo-2'-deoxy-D-arabinosyl isomer 15, as judged by $^1$H NMR.

In a similar manner but using the corresponding purine nucleosides, the following 3'-bromo-3'-deoxy derivatives (14) and their L-counterparts are prepared:
9-[2-O-Acetyl-3-bromo-3-deoxy-5-O-(2,5,5-trimethyl-1,3-dioxolan-4-on-2-yl)-β-D-xylofuranosyl]-guanine,
9-[2-O-Acetyl-3-bromo-3-deoxy-5-O-(2,5,5-trimethyl-1,3-dioxolan-4-on-2-yl)-β-D-xylo-furanosyl]-6-chloropurine,
9-[2-O-Acetyl-3-bromo-3-deoxy-5-O-(2,5,5-trimethyl-1,3-dioxolan-4-on-2-yl)-β-D-xylo-furanosyl]-2,6-dichloropurine,
9-[2-O-Acetyl-3-bromo-3-deoxy-5-O-(2,5,5-trimethyl-1,3-dioxolan-4-on-2-yl)-β-D-xylo-furanosyl]-2-amino-6-chloropurine,
9-[2-O-Acetyl-3-bromo-3-deoxy-5-O-(2,5,5-trimethyl-1,3-dioxolan-4-on-2-yl)-β-D-xylo-furanosyl]-6-methylthiopurine,
9-[2-O-Acetyl-3-bromo-3-deoxy-5-O-(2,5,5-trimethyl-1,3-dioxolan-4-on-2-yl)-β-D-xylo-furanosyl]-6-methoxypurine,
9-[3-O-Acetyl-2-bromo-2-deoxy-5-O-(2,5,5-trimethyl-1,3-dioxolan-4-on-2-yl)-β-D-arabino-furanosyl]guanine,
9-[3-O-Acetyl-2-bromo-2-deoxy-5-O-(2,5,5-trimethyl-1,3-dioxolan-4-on-2-yl)-β-D-arabino-furanosyl]-6-chloropurine,
9-[3-O-Acetyl-2-bromo-2-deoxy-5-O-(2,5,5-trimethyl-1,3-dioxolan-4-on-2-yl)-β-D-arabino-furanosyl]-2,6-dichloropurine,
9-[3-O-Acetyl-2-bromo-2-deoxy-5-O-(2,5,5-trimethyl-1,3-dioxolan-4-on-2-yl)-β-D-arabino-furanosyl]-2-amino-6-chloropurine,
9-[3-O-Acetyl-2-bromo-2-deoxy-5-O-(2,5,5-trimethyl-1,3-dioxolan-4-on-2-yl)-β-D-arabino-furanosyl]-6-methylthiopurine and (i) 9-[3-O-Acetyl-2-bromo-2-deoxy-5-O-(2,5,5-trimethyl-1,3-dioxolan-4-on-2-yl)-β-D-arabino-furanosyl]-6-methoxypurine Example 16

2',3'-Anhydroadenosine (18, Y=NH$_2$, Z=H)

9-[2-O-Acetyl-3-bromo-3-deoxy-5-O-(2,5,5-trimethyl-1, 3-dioxolan-4-on-2-yl)-β-D-xylo-furanosyl]adenine 14 (5.0 g, 0.01 mol) is treated with 1M sodium methoxide in methanol (20 mL) for 1 hour at room temperature. The mixture is neutralized with glacial acetic acid, and is kept refrigerator overnight. Crystalline 18 deposited is collected by filtration, 2.1 g (84%). $^1$H NMR spectrum of this sample is identical with the one prepared by an alternative procedure by Mendez, E. et al. *J. Virol.* 1998, 72, 4737.

In a similar manner but using the corresponding purine nucleosides, the following 2',3'-anhydro-D-ribo derivatives (18) and their L-counterparts are prepared: 2',3'-anhydroguanosine, 9-(2,3-anhydro-β-D-ribofuranosyl]-6-methylmercaptopurine, and 9-(2,3-anhydro-β-D-ribo-furanosyl]-2-amino-6-methoxypurine.

Example 17

9-(3-Deoxy-3-iodo-β-D-xylofuranosyl)adenine (19, X=I, Y=NH$_2$, Z=H)

A mixture of 18 (Y=NH$_2$, Z=H, 1 g, 4 mmol), sodium iodide (1.5 g, 10 mmol), sodium acetate (100 mg) and acetic acid (5 mL) in butanone (30 mL) is gently refluxed for 3 hours. Evaporation of the solvent in vacuo, and trituration of the residue with water afford 19 (X=I, Y=NH$_2$, Z=H), 1.2 g (80%). $^1$H NMR (D$_6$-DMSO) δ: 8.24, 8.34 (2s, 1H each, H-2 and H-8), 5.90 (d, 1H, H-1', J1',2'=4.7 Hz), 4.96 (dd, 1H, H-2', J1',2'=4.7, J2',3'=4.9 Hz), 4.60 (dd, 1H, H-3', J2', 3'=4.9, J3',4'=4.7 Hz), 4.80 (d, 2H, H-5',5"), 4.40 (m, 1H, H-4').

In a similar manner but using the corresponding 2',3'-anhydro-D-ribo purine nucleosides (14), the following 3'-deoxy-3'-iodo-D-xylo nucleosides and their L-counterparts are prepared:
9-(3-Deoxy-3-iodo-β-D-xylofuranosyl)guanine,
9-(3-Deoxy-3-iodo-β-D-xylofuranosyl)-6-methylmercaptopurine,
9-(3-Deoxy-3-iodo-β-D-xylofuranosyl)-6-methoxypurine,
9-(3-Deoxy-3-iodo-β-D-xylofuranosyl)-2-amino-6-methylmercaptopurine and
9-(3-Deoxy-3-iodo-β-D-xylofuranosyl)-2-amino-6-methoxypurine.

Example 18

3'-Deoxyadenosine (20, Y=NH$_2$, Z=H)

A solution of 19 (Y=NH$_2$, Z=H, 380 mg, 1 mmol) in methanol (75 mL) is shaken in an atmosphere of hydrogen in the presence of 5% Pd/BaSO$_4$ catalyst (100 mg) and triethylamine (1 mL) at the initial pressure of 3 atm overnight. After removal of the catalyst, the solvent is evaporated in vacuo, and the residue is crystallized from methanol to give 3'-deoxyadenosine 20 (Y=NH$_2$, Z=H), 200 mg (80%). The $^1$H NMR spectrum of this sample is identical with that of cordycepin.

In a similar manner but using the corresponding 3'-iodo-D-xylo purine nucleosides (19), the following 3'-deoxy-nucleosides and their L-counterparts are prepared: 9-(3-Deoxy-β-D-erythropentofuranosyl)guanine, 9-(3-deoxy-β-D-erythropentofuranosyl)-purine, 9-(3-deoxy-β-D-erythropentofuranosyl)-6-methoxypurine, 9-(3-deoxy-β-D-erythropento-furanosyl)-2-amino-purine and 9-(3-deoxy-β-D-erythropentofuranosyl)-2-amino-6-methoxypurine.

Example 19

3-(β-D-Ribofuranosyl)-8-azaxanthine (24, X=OH, Y=N)

To a solution of 5-nitrouridine (300 mg) in DMF (60 mL) is added sodium azide (100 mg), and the mixture is stirred overnight at room temperature. The solvent is removed in vacuo, and the residue is dissolved in minimal amount of hot water and the pH adjusted to 3-4 with diluted hydrochloric acid. The precipitates are recrystallized from water, mp 164-166° C. (dec). anal Calcd for C$_9$H$_{11}$N$_5$O$_6$H$_2$O: C, 35.64; H, 4.29; N, 23.1. Found: C, 35.96; H, 4.01; N, 23.43.

Example 20

1,2-O-Isopropylidene-5-O-methoxycarbonyl-3-O-phenoxythiocarbonyl-α-D-xylofuranose (26, R=Ph)

To a solution of 1,2-O-isopropylidene-5-O-methoxycarbonyl-α-D-xylofuranose (25, 25.0 g, 0.1 mol) and 4-dimethylaminopyridine (25 g, 0.2 mol) in dry pyridine (250 mL) is added drop wise a solution of phenyl chlorothionoformate (50 g, 0.3 mol) in acetonitrile (100 mL), and the reaction mixture is stirred at 50-60° C. for 24 hours. The solution is concentrated in vacuo, and the residue is partitioned between methylene chloride and water. The organic layer is washed successively with water, 0.1N sodium hydroxide, water, 0.1N hydrochloric acid and water, and dried over sodium sulfate, and concentrated in vacuo to give 26 (R=Ph) as a syrup in quantitative yield (38.2 g). This syrup is used directly in the next step.

Example 21

3-Deoxy-1,2-O-isopropylidene-5-O-methoxycarbonyl-α-D-erythropentofuranose (27)

A solution of tri-n-butyltin hydride (58 g, 0.2 mol) in toluene (300 mL) is added over a period of 3 hours to a refluxing solution of compound 26 (R=Ph) above (19.2 g, 50 mmol) and 2,2'-azobisisobutyronitrile (2.5 g, 15 mmol) in toluene (400 mL). The mixture is concentrated in vacuo, and the residue is dissolved in acetonitrile (300 mL), and the solution is extracted with petroleum ether (4×100 mL) to remove tri-n-butyltin derivatives. The acetonitrile layer is concentrated. The thin layer chromatography of the residue shows one major spot and $^1$H NMR spectrum indicates the presence of three methyl groups and no aromatic protons but contamination of a small amount of butyltin derivatives. Without further purification, this product is used in the next step.

Example 22

1,2-Di-O-acetyl-3-deoxy-5-O-methoxycarbonyl-D-erythropentofuranose (28)

To a stirred solution of 23 (2.32 g, 0.01 mol) in a mixture of acetic acid (60 mL) and acetic anhydride (6 mL) is added drop wise concentrated sulfuric acid (3 mL) with ice-cooling at such a rate that the temperature is maintained at 15-25° C. After standing overnight at room temperature, ice (250 g) is added to the solution, and then the mixture is extracted with methylene chloride (3×50 mL). The combined extracts are washed with saturated sodium bicarbonate solution (3×30 mL), dried over sodium sulfate, and concentrated in vacuo to give 28 (2.8 g, 100%) as an anomeric mixture. This compound is sufficiently pure to be used in the next step without further purification.

Example 23

1-(2-O-acetyl-3-deoxy-5-O-methoxycarbonyl-β-D-erythropentofuranosyl)-5-fluorouracil (29, X=OH, Z=F)

A mixture of 5-fluorouracil (2.6 g, 0.02 mol), ammonium sulfate (ca. 30 mg) in hexamethyldisilazane (15 mL) is refluxed until a clear solution is obtained. The solvent is removed in vacuo, and the residue is dissolved in 1,2-dichloroethane (20 mL), and 1,2-di-O-acetyl-3-deoxy-5-O-methoxycarbonyl-D-erythropentofuranose (28, 5.5 g, 0.02 mol) in 1,2-dichloroethane (20 mL) is added. To the solution is added tin tetrachloride (5.2 g, 0.02 mol), and the mixture is stirred overnight at room temperature, then is heated for 3 hours at 40-50° C. for 3 hours. Saturated sodium bicarbonate solution (40 mL) is added and stirred until carbon dioxide evolution ceases. The mixture is filtered through a Celite pad. The organic layer is separated, washed carefully with saturated sodium bicarbonate solution (20 mL×2) and water (20 mL×2), dried over sodium sulfate, and concentrated to dryness in vacuo. The residue is crystallized from ethanol to give 29 (4.3 g, 62%).

In a similar manner but using the corresponding pyrimidine bases, the following 2',5'-protected 3'-deoxy-nucleosides and their L-counterparts are prepared:
1-(2-O-Acetyl-3-deoxy-5-O-methoxycarbonyl-β-D-erythropentofuranosyl)-5-chlorouracil,
1-(2-O-Acetyl-3-deoxy-5-O-methoxycarbonyl-β-D-erythropentofuranosyl)-5-bromouracil,
1-(2-O-Acetyl-3-deoxy-5-O-methoxycarbonyl-β-D-erythropentofuranosyl)-5-iodouracil,
1-(2-O-Acetyl-3-deoxy-5-O-methoxycarbonyl-β-D-erythropentofuranosyl)-5-cyanouracil,
1-(2-O-Acetyl-3-deoxy-5-O-methoxycarbonyl-β-D-erythropentofuranosyl)-5-ethoxycarbonyl-uracil,
1-(2-O-Acetyl-3-deoxy-5-O-methoxycarbonyl-β-D-erythropentofuranosyl)-5-aminocarbonyl-uracil,
1-(2-O-Acetyl-3-deoxy-5-O-methoxycarbonyl-β-D-erythropentofuranosyl)-5-acetyluracil,
1-(2-O-Acetyl-3-deoxy-5-O-methoxycarbonyl-β-D-erythropentofuranosyl)-5-methyluracil,
1-(2-O-Acetyl-3-deoxy-5-O-methoxycarbonyl-β-D-erythropentofuranosyl)-5-ethyluracil, 1-(2-O-Acetyl-3-deoxy-5-O-methoxycarbonyl-β-D-erythropentofuranosyl)-5-n-propyluracil,
1-(2-O-Acetyl-3-deoxy-5-O-methoxycarbonyl-β-D-erythropentofuranosyl)-5-i-propyluracil,
1-(2-O-Acetyl-3-deoxy-5-O-methoxycarbonyl-β-D-erythropentofuranosyl)-5-vinyluracil,
1-(2-O-Acetyl-3-deoxy-5-O-methoxylcarbonyl-β-D-erythropentofuranosyl)-5-allyluracil,
1-(2-O-Acetyl-3-deoxy-5-O-methoxycarbonyl-β-D-erythropentofuranosyl)-5-ethynyluracil,
1-(2-O-Acetyl-3-deoxy-5-O-methoxycarbonyl-β-D-erythropentofuranosyl)-5-(2-chlorovinyl)-uracil,
1-(2-O-Acetyl-3-deoxy-5-O-methoxycarbonyl-β-D-erythropentofuranosyl)-5-(2-bromovinyl)-uracil,
1-(2-O-Acetyl-3-deoxy-5-O-methoxycarbonyl-β-D-erythropentofuranosyl)-5-(2-iodovinyl)-uracil,
1-(2-O-Acetyl-3-deoxy-5-O-methoxycarbonyl-β-D-erythropentofuranosyl)-5-(2-methoxylcarbonyl-vinyl)uracil,
1-(2-O-Acetyl-3-deoxy-5-O-methoxycarbonyl-β-D-erythropentofuranosyl)-5-(2-hydroxycarbonyl-vinyl)uracil,
1-(2-O-Acetyl-3-deoxy-5-O-methoxycarbonyl-β-D-erythropentofuranosyl)-5-phenyluracil,
1-(2-O-Acetyl-3-deoxy-5-O-methoxycarbonyl-β-D-erythropentofuranosyl)-5-benzyluracil,
1-(2-O-Acetyl-3-deoxy-5-O-methoxycarbonyl-β-D-erythropentofuranosyl)-5-fluorocytosine,
1-(2-O-Acetyl-3-deoxy-5-O-methoxycarbonyl-β-D-erythropentofuranosyl)-5-chlorocytosine,
1-(2-O-Acetyl-3-deoxy-5-O-methoxycarbonyl-β-D-erythropentofuranosyl)-5-bromocytosine,
1-(2-O-Acetyl-3-deoxy-5-O-methoxycarbonyl-β-D-erythropentofuranosyl)-5-iodocytosine,
1-(2-O-Acetyl-3-deoxy-5-O-methoxycarbonyl-β-D-erythropentofuranosyl)-5-cyanocytosine,
1-(2-O-Acetyl-3-deoxy-5-O-methoxycarbonyl-β-D-erythropentofuranosyl)-5-ethoxycarbonyl-cytosine,
1-(2-O-Acetyl-3-deoxy-5-O-methoxycarbonyl-β-D-erythropentofuranosyl)-5-aminocarbonyl-cytosine,
1-(2-O-Acetyl-3-deoxy-5-O-methoxycarbonyl-β-D-erythropentofuranosyl)-5-acetylcytosine,
1-(2-O-Acetyl-3-deoxy-5-O-methoxycarbonyl-β-D-erythropentofuranosyl)-5-methylcytosine,
1-(2-O-Acetyl-3-deoxy-5-O-methoxy carbonyl-β-D-erythropento furanosyl)-5-ethylcytosine,
1-(2-O-Acetyl-3-deoxy-5-O-methoxycarbonyl-β-D-erythropentofuranosyl)-5-n-propylcytosine,
1-(2-O-Acetyl-3-deoxy-5-O-methoxylcarbonyl-β-D-erythropentofuranosyl)-5-i-propylcytosine,
1-(2-O-Acetyl-3-deoxy-5-O-methoxycarbonyl-β-D-erythropentofuranosyl)-5-vinylcytosine,
1-(2-O-Acetyl-3-deoxy-5-O-methoxycarbonyl-β-D-erythropentofuranosyl)-5-allylcytosine,
1-(2-O-Acetyl-3-deoxy-5-O-methoxycarbonyl-β-D-erythropentofuranosyl)-5-ethynylcytosine,
1-(2-O-Acetyl-3-deoxy-5-O-methoxycarbonyl-β-D-erythropentofuranosyl)-5-(2-chlorovinyl)-cytosine,
1-(2-O-Acetyl-3-deoxy-5-O-methoxycarbonyl-β-D-erythropentofuranosyl)-5-(2-bromovinyl)-cytosine,
1-(2-O-Acetyl-3-deoxy-5-O-methoxycarbonyl-β-D-erythropentofuranosyl)-5-(2-iodovinyl)-cytosine,
1-(2-O-Acetyl-3-deoxy-5-O-methoxycarbonyl-β-D-erythropentofuranosyl)-5-(2-methoxylcarbonylvinyl)cytosine,
1-(2-O-Acetyl-3-deoxy-5-O-methoxycarbonyl-β-D-erythropentofuranosyl)-5-(2-hydroxy-carbonylvinyl)cytosine,
1-(2-O-Acetyl-3-deoxy-5-O-methoxycarbonyl-β-D-erythropentofuranosyl)-5-phenylcytosine and
1-(2-O-Acetyl-3-deoxy-5-O-methoxycarbonyl-β-D-erythropentofuranosyl)-5-benzylcytosine.

In a similar manner but using the corresponding pyrimidine and purine bases, the following 2',5'-di-O-acetyl 3'-deoxy-nucleosides and their L-counterparts are prepared:
1-(2,5-Di-O-acetyl-3-deoxy-β-D-erythropentofuranosyl)-5-chlorouracil,
1-(2,5-Di-O-acetyl-3-deoxy-β-D-erythropentofuranosyl)-5-bromouracil,
1-(2,5-Di-O-acetyl-3-deoxy-β-D-erythropentofuranosyl)-5-iodouracil,
1-(2,5-Di-O-acetyl-3-deoxy-β-D-erythropentofuranosyl)-5-cyanouracil,
1-(2,5-Di-O-acetyl-3-deoxy-β-D-erythropentofuranosyl)-5-ethoxycarbonyluracil,
1-(2,5-Di-O-acetyl-3-deoxy-β-D-erythropentofuranosyl)-5-aminocarbonyluracil,
1-(2,5-Di-O-acetyl-3-deoxy-β-D-erythropentofuranosyl)-5-acetyluracil,
1-(2,5-Di-O-acetyl-3-deoxy-β-D-erythropentofuranosyl)-5-methyluracil,
1-(2,5-Di-O-acetyl-3-deoxy-β-D-erythropentofuranosyl)-5-ethyluracil,
1-(2,5-Di-O-acetyl-3-deoxy-β-D-erythropentofuranosyl)-5-n-propyluracil,
1-(2,5-Di-O-acetyl-3-deoxy-β-D-erythropentofuranosyl)-5-i-propyluracil,
1-(2,5-Di-O-acetyl-3-deoxy-β-D-erythropentofuranosyl)-5-vinyluracil,
1-(2,5-Di-O-acetyl-3-deoxy-β-D-erythropentofuranosyl)-5-allyluracil,
1-(2,5-Di-O-acetyl-3-deoxy-β-D-erythropentofuranosyl)-5-ethynyluracil,
1-(2,5-Di-O-acetyl-3-deoxy-β-D-erythropentofuranosyl)-5-(2-chlorovinyl)uracil,
1-(2,5-Di-O-acetyl-3-deoxy-β-D-erythropentofuranosyl)-5-(2-bromovinyl)uracil,
1-(2,5-Di-O-acetyl-3-deoxy-β-D-erythropentofuranosyl)-5-(2-iodovinyl)uracil,
1-(2,5-Di-O-acetyl-3-deoxy-β-D-erythropentofuranosyl)-5-(2-methoxylcarbonylvinyl)uracil,
1-(2,5-Di-O-acetyl-3-deoxy-β-D-erythropentofuranosyl)-5-(2-hydroxycarbonylvinyl)uracil,
1-(2,5-Di-O-acetyl-3-deoxy-β-D-erythropentofuranosyl)-5-phenyluracil,
1-(2,5-Di-O-acetyl-3-deoxy-β-D-erythropentofuranosyl)-5-benzyluracil,
1-(2,5-Di-O-acetyl-3-deoxy-β-D-erythropento furanosyl)-5-fluorocytosine,
1-(2,5-Di-O-acetyl-3-deoxy-β-D-erythropentofuranosyl)-5-chlorocytosine,
1-(2,5-Di-O-acetyl-3-deoxy-β-D-erythropentofuranosyl)-5-bromocytosine,
1-(2,5-Di-O-acetyl-3-deoxy-β-D-erythropentofuranosyl)-5-iodocytosine,
1-(2,5-Di-O-acetyl-3-deoxy-β-D-erythropentofuranosyl)-5-cyanocytosine,
1-(2,5-Di-O-acetyl-3-deoxy-β-D-erythropentofuranosyl)-5-ethoxycarbonylcytosine,
1-(2,5-Di-O-acetyl-3-deoxy-β-D-erythropentofuranosyl)-5-aminocarbonylcytosine,
1-(2,5-Di-O-acetyl-3-deoxy-β-D-erythropentofuranosyl)-5-acetylcytosine,
1-(2,5-Di-O-acetyl-3-deoxy-β-D-erythropentofuranosyl)-5-methylcytosine,
1-(2,5-Di-O-acetyl-3-deoxy-β-D-erythropentofuranosyl)-5-ethylcytosine, 1-(2,5-Di-O-acetyl-3-deoxy-β-D-erythropentofuranosyl)-5-n-propylcytosine,
1-(2,5-Di-O-acetyl-3-deoxy-β-D-erythropentofuranosyl)-5-i-propylcytosine,
1-(2,5-Di-O-acetyl-3-deoxy-β-D-erythropentofuranosyl)-5-vinylcytosine,
1-(2,5-Di-O-acetyl-3-deoxy-β-D-erythropentofuranosyl)-5-allylcytosine,
1-(2,5-Di-O-acetyl-3-deoxy-β-D-erythropentofuranosyl)-5-ethynylcytosine,
1-(2,5-Di-O-acetyl-3-deoxy-β-D-erythropentofuranosyl)-5-(2-chlorovinyl)cytosine,
1-(2,5-Di-O-acetyl-3-deoxy-β-D-erythropentofuranosyl)-5-(2-bromovinyl)cytosine,
1-(2,5-Di-O-acetyl-3-deoxy-β-D-erythropento furanosyl)-5-(2-iodovinyl)cytosine,
1-(2,5-Di-O-acetyl-3-deoxy-β-D-erythropentofuranosyl)-5-(2-methoxylcarbonylvinyl)cytosine,
1-(2,5-Di-O-acetyl-3-deoxy-β-D-erythropentofuranosyl)-5-(2-hydroxycarbonylvinyl)cytosine,
1-(2,5-Di-O-acetyl-3-deoxy-β-D-erythropentofuranosyl)-5-phenylcytosine,
1-(2,5-Di-O-acetyl-3-deoxy-β-D-erythropentofuranosyl)-5-benzylcytosine,
1-(2,5-Di-O-acetyl-3-deoxy-β-D-erythropentofuranosyl)-$N^6$-benzoyladenine,
1-(2,5-Di-O-acetyl-3-deoxy-β-D-erythropentofuranosyl)-6-chloropurine,
1-(2,5-Di-O-acetyl-3-deoxy-β-D-erythropentofuranosyl)-2,6-dichloropurine,
1-(2,5-Di-O-acetyl-3-deoxy-β-D-erythropento furanosyl)-2-acetamido-6-chloropurine,
1-(2,5-Di-O-acetyl-3-deoxy-β-D-erythropentofuranosyl)-2-acetamido-6-methoxypurine,
1-(2,5-Di-O-acetyl-3-deoxy-β-D-erythropentofuranosyl)-6-methoxypurine and
1-(2,5-Di-O-acetyl-3-deoxy-β-D-erythropentofuranosyl)-6-methylmercaptopurine.

Example 24

1-(2-O-acetyl-3-deoxy-5-O-methoxycarbonyl-β-D-erythropentofuranosyl)-6-chloropurine (30, X=Cl, Y=H)

A mixture of 6-chloropurine (3.1 g, 0.02 mol), ammonium sulfate (ca. 30 mg) in hexamethyldisilazane (25 mL) is refluxed until a clear solution is obtained. The solvent is removed in vacuo, and the residue is dissolved in 1,2-dichloroethane (30 mL), and 1,2-di-O-acetyl-3-deoxy-5-O-methoxycarbonyl-D-erythropentofuranose (28, 5.5 g, 0.02 mol) in 1,2-dichloroethane (20 mL) is added. To the solution is added tin tetrachloride (5.2 g, 0.02 mol), and the mixture is stirred overnight at room temperature, then is heated for 3 hours at 40-50° C. for 3 hours. Saturated sodium bicarbonate solution (50 mL) is added and stirred until carbon dioxide evolution ceases. The mixture is filtered through a Celite pad. The organic layer is separated, washed carefully with saturated sodium bicarbonate solution (30 mL×2) and water (30 mL×2), dried over sodium sulfate, and concentrated to dryness in vacuo. The residue is crystallized from ethanol to give 30 (4.3 g, 62%).

In a similar manner but using the corresponding purine bases, the following 2',5'-protected 3'-deoxy-nucleosides and their L-counterparts are prepared:
1-(2-O-Acetyl-3-deoxy-5-O-methoxycarbonyl-β-D-erythropentofuranosyl)-$N^6$-benzoyladenine,
1-(2-O-Acetyl-3-deoxy-5-O-methoxycarbonyl-β-D-erythropentofuranosyl)-6-chloropurine,
1-(2-O-Acetyl-3-deoxy-5-O-methoxycarbonyl-β-D-erythropentofuranosyl)-2,6-dichloropurine,
1-(2-O-Acetyl-3-deoxy-5-O-methoxycarbonyl-β-D-erythropentofuranosyl)-2-acetamido-6-chloropurine,
1-(2-O-Acetyl-3-deoxy-5-O-methoxycarbonyl-β-D-erythropentofuranosyl)-2-acetamido-6-methoxypurine,
1-(2-O-Acetyl-3-deoxy-5-O-methoxycarbonyl-β-D-erythropentofuranosyl)-6-methoxypurine and
1-(2-O-Acetyl-3-deoxy-5-O-methoxycarbonyl-β-D-erythropentofuranosyl)-6-methylmercapto-purine.

Example 25

1,2-O-Isopropylidene-5-O-t-butyldiphenylsilyl-α-D-xylofuranose (31)

A mixture of 1,2-O-isopropylidene-α-D-xylofuranose (38.0 g, 0.2 mol), t-butyl-diphenylchlorosilane (70 g, 0.25 mol) and imidazole (21.5 g, 0.4 mol) in N,N-dimethylformamide (50 mL) is stirred at room temperature for 1 hour. The solvent is removed in vacuo, and the residue is dissolved in ethyl acetate (1 L), and extracted with water (300 mL×2) and brine (300 mL), dried over sodium sulfate, and concentrated to dryness in vacuo to give crude 31 (86 g, 100%), which is used directly in the next step without further purification.

Example 26

1,2-O-Isopropylidene-3-O-mesyl-5-O-t-butyldiphenylsilyl-α-D-xylofuranose (32, R=Ms)

Mesyl chloride (17 g, 0.15 mol) is added drop wise to a solution of crude 31 (43 g, 0.1 mol) in pyridine (100 mL), and the mixture is kept standing overnight at room temperature. Crashed ice (1 L) is added to the mixture, and the product is extracted with methylene chloride (300 mL×3). The extracts are combined, washed with water (300 mL×2) and brine (300 mL), dried over sodium sulfate, and concentrated in vacuo to dryness. Traces of pyridine are removed by repeated azeotropic distillation with toluene. The residue is dissolved in methylene chloride (500 mL) and washed with 0.1N hydrochloric acid (250 mL×2) and water, dried over sodium sulfate, and concentrated to dryness to give crude 32 (R=Ms), 50.1 g (99%). The $^1$H NMR spectrum of this material is sufficiently pure to be used directly in the next step.

Example 27

Methyl 3-O-mesyl-5-O-t-butyldiphenylsilyl-D-xylofuranoside (33, R=Ms)

A solution of crude 32 (50 g, 0.1 mol) in 1% anhydrous methanolic hydrogen chloride (1 L) is kept overnight at room temperature, and then evaporated in vacuo to a syrup which is partitioned between water (100 mL) and methylene chloride (150 mL). The organic layer is separated, washed with water (100 mL), dried over sodium sulfate, and concentrated in vacuo, giving crude 33, a syrup, weighing 48 g (100%). This material is not further purified but used directly in the next step.

Example 28

Methyl 2,3-anhydro-5-O-t-butyldiphenylsilyl-D-ribofuranoside (34)

Crude 33 (48 g, 0.1 mol) is dissolved in methylene chloride (100 mL) and treated with 2M methanolic sodium methoxide (60 mL), and refluxed for 2 hours. Insoluble salt is removed by filtration, and the filtrate is concentrated in vacuo to dryness. The residue is dissolved in methylene chloride (150 mL), washed with water (100 mL×2), dried over sodium sulfate, and concentrated to dryness to give crude 30 (38 g, 100%), which can be used directly in the next step without purification.

Example 29

Methyl 3-deoxy-3-iodo-5-O-t-butyldiphenylsilyl-D-ribofuranoside (35, X=I)

A mixture of 34 (38 g, 0.1 mol), sodium iodide (60 g, 0.4 mol), sodium acetate (0.6 g) and acetic acid (70 mL) in acetone (500 mL) is heated under reflux for 8 hours. The acetone is removed in vacuo, and the residue is partitioned between methylene chloride (500 mL) and water (250 mL). The organic layer is separated, washed with 250 mL each of water, 0.1 M sodium thiosulfate solution, water and dried over sodium sulfate. After removal of the solvent in vacuo, the residue is crystallized from ethanol to afford 31 g (60.5%) of 35 (X=I).

Example 30

Methyl 3-deoxy-5-O-t-butyldiphenylsilyl-D-erythro-pentofuranoside (37, from 35)

Compound 35 (X=I, 25.6 g, 0.05 mol) is hydrogenated in ethyl acetate (250 mL) with 5% palladium on charcoal (2 g). After the consumption of hydrogen ceased, the mixture is filtered, and the filtrate is washed with water (150 mL×2), dried over sodium sulfate, and concentrated to dryness to give crude 37 (19 g, quantitative yield) which is sufficiently pure to be used directly in the next step.

Example 31

Methyl 3-deoxy-5-O-t-butyldiphenylsilyl-D-erythro-pentofuranoside (36, from 34)

A suspension of lithium aluminum hydride (8.4 g, 0.2 mol) in dry ethyl ether (220 mL) is stirred under nitrogen atmosphere and cooled in an ice bath. To this suspension is added drop wise a solution of 34 (19 g, 0.05 mol) in dry tetrahydrofuran (250 mL) at such a rate that the temperature remains below 25° C. After 2 hours, another 1 g of lithium aluminum hydride is charged, and the mixture is stirred overnight at room temperature. The stirred mixture is cooled in an ice bath, and isopropanol (100 mL) is added drop wise, followed by acetone (50 mL). The mixture is concentrated in vacuo, and the residue is partitioned between ethyl ether (250 mL) and water (150 mL). Insoluble materials are filtered through Celite pad which is washed with ether. The ether layer is separated, washed successively with 0.2N hydrochloric acid (150 mL×2) and water (150 mL×2), dried over sodium sulfate, and then concentrated to dryness to give crude 36 (16.5 g, 87%).

Example 32

Methyl 3-deoxy-D-erythropentofuranoside (38)

To a solution of crude 36 (13 g, 0.03 mol) in tetrahydrofuran (320 mL) is added drop wise 1M solution of triethylammonium hydrogen fluoride (100 mL), and the mixture is stirred for 24 hours. The mixture is concentrated in vacuo, and the residue is dissolved in water (200 mL). Powdered calcium carbonate (20 g) is added, and the mixture is stirred overnight at room temperature, and then filtered. The filtrate is concentrated in vacuo to a syrup which is dissolved in chloroform (200 mL), filtered, and evaporated in vacuo to afford crude 38 (4.5 g, 100%).

Example 33

1,2,5-Tri-O-acetyl-3-deoxy-D-erythropentofuranose (38)

To a vigorously stirred mixture of crude methyl 3-deoxy-D-erythropentofuranoside 37 (4.5 g, 0.03 mol) and acetic acid (80 mL) is added acetic anhydride (40 mL), followed by sulfuric acid (4 mL), and the reaction mixture is stirred overnight at room temperature. The mixture is partitioned between methylene chloride (150 mL) and ice-water (400 mL). The water layer is extracted with methylene chloride (100 mL×2). The combined organic layers are washed twice with equal volumes of a saturated solution of sodium bicarbonate, once with water, dried over sodium sulfate, and concentrated to dryness in vacuo. Traces of acetic acid are removed by several azeotropic distillations with toluene to give crude 38 (5.1 g, 66%). The $^1$H NMR spectrum shows that the major constituent of this product contains 3 acetyl groups and is the β-anomer.

Example 34

1-(3-Deoxy-β-D-erythropentofuranosyl)-5-fluorouracil (3'-deoxy-5-fluorouridine, 6b, X=OH, R=F)

A mixture of an acetyl derivative of 39 (X=OH, Z=F, 3.3 g, 0.01 mol) and triethylamine (3 mL) in methanol (100 mL) is stirred overnight at room temperature. The mixture is concentrated in vacuo to dryness, and the residue is crystallized from ethanol to give 3'-deoxy-5-fluorouridine (2.0 g, 83%), mp 169-171° C. $^1$H NMR (D$_6$-DMSO) δ: 11.7 (bs, 1H, N$^3$—H, exchangeable), 8.44 (d, 1H, H-6, $J_{6,F}$=7.1 Hz), 5.7 (d, 1H, 2'-OH, exchangeable), 5.5 (narrow m, 1H, H-1'), 5.3 (t, 1H, 5'-OH, exchangeable), 4.1-4.5 (m, 2H, H-2' and 3.5-3.9 (m, 2H, H-5',5"), 1.6-2.2 (m, 2H, H-3',3").

In a similar manner but using the corresponding 2',5'-di-O-acetyl pyrimidine and purine nucleoside, the following 3'-deoxy-nucleosides and their L-counterparts are prepared:
1-(3-Deoxy-β-D-erythropentofuranosyl)-5-chlorouracil,
1-(3-Deoxy-(3-D-erythropentofuranosyl)-5-bromouracil,
1-(3-Deoxy-β-D-erythropentofuranosyl)-5-iodouracil,
1-(3-Deoxy-β-D-erythropentofuranosyl)-5-cyanouracil,
1-(3-Deoxy-β-D-erythropentofuranosyl)-5-ethoxycarbonyluracil,
1-(3-Deoxy-β-D-erythropentofuranosyl)-5-aminocarbonyluracil,
1-(3-Deoxy-β-D-erythropentofuranosyl)-5-acetyluracil,
1-(3-Deoxy-β-D-erythropentofuranosyl)-5-methyluracil,
1-(3-Deoxy-β-D-erythropentofuranosyl)-5-ethyluracil,
1-(3-Deoxy-β-D-erythropentofuranosyl)-5-n-propyluracil,
1-(3-Deoxy-β-D-erythropentofuranosyl)-5-i-propyluracil, 1-(3-Deoxy-β-D-erythropentofuranosyl)-5-vinyluracil,
1-(3-Deoxy-β-D-erythropentofuranosyl)-5-allyluracil,
1-(3-Deoxy-β-D-erythropentofuranosyl)-5-ethynyluracil,
1-(3-Deoxy-β-D-erythropentofuranosyl)-5-(2-chlorovinyl)uracil,
1-(3-Deoxy-β-D-erythropentofuranosyl)-5-(2-bromovinyl)uracil,
1-(3-Deoxy-β-D-erythropentofuranosyl)-5-(2-iodovinyl)uracil,
1-(3-Deoxy-β-D-erythropentofuranosyl)-5-(2-methoxylcarbonylvinyl)uracil,
1-(3-Deoxy-β-D-erythropentofuranosyl)-5-(2-hydroxycarbonylvinyl)uracil,
1-(3-Deoxy-β-D-erythropentofuranosyl)-5-phenyluracil,
1-(3-Deoxy-β-D-erythropentofuranosyl)-5-benzyluracil,
1-(3-Deoxy-β-D-erythropentofuranosyl)cytosine,
1-(3-Deoxy-β-D-erythropentofuranosyl)-5-fluorocytosine,
1-(3-Deoxy-β-D-erythropentofuranosyl)-5-chlorocytosine,
1-(3-Deoxy-β-D-erythropentofuranosyl)-5-bromocytosine,
1-(3-Deoxy-β-D-erythropentofuranosyl)-5-iodocytosine,
1-(3-Deoxy-β-D-erythropentofuranosyl)-5-cyanocytosine,
1-(3-Deoxy-β-D-erythropentofuranosyl)-5-ethoxycarbonylcytosine,
1-(3-Deoxy-β-D-erythropentofuranosyl)-5-aminocarbonylcytosine,
1-(3-Deoxy-β-D-erythropentofuranosyl)-5-acetylcytosine,
1-(3-Deoxy-β-D-erythropentofuranosyl)-5-methylcytosine,
1-(3-Deoxy-β-D-erythropentofuranosyl)-5-ethylcytosine,
1-(3-Deoxy-β-D-erythropentofuranosyl)-5-n-propylcytosine,
1-(3-Deoxy-β-D-erythropento furanosyl)-5-i-propylcytosine,
1-(3-Deoxy-β-D-erythropentofuranosyl)-5-vinylcytosine,
1-(3-Deoxy-β-D-erythropentofuranosyl)-5-allylcytosine,
1-(3-Deoxy-β-D-erythropentofuranosyl)-5-ethynylcytosine,
1-(3-Deoxy-β-D-erythropentofuranosyl)-5-(2-chlorovinyl)cytosine,
1-(3-Deoxy-β-D-erythropentofuranosyl)-5-(2-bromovinyl)cytosine,
1-(3-Deoxy-β-D-erythropentofuranosyl)-5-(2-iodovinyl)cytosine,
1-(3-Deoxy-β-D-erythropentofuranosyl)-5-(2-methoxylcarbonylvinyl)cytosine,
1-(3-Deoxy-β-D-erythropentofuranosyl)-5-(2-hydroxycarbonylvinyl)cytosine,
1-(3-Deoxy-β-D-erythropentofuranosyl)-5-phenylcytosine,
1-(3-Deoxy-β-D-erythropentofuranosyl)-5-benzylcytosine,
1-(3-Deoxy-β-D-erythropentofuranosyl)-2-chloroadenine,
1-(3-Deoxy-β-D-erythropentofuranosyl)-6-chloropurine,
1-(3-Deoxy-β-D-erythropentofuranosyl)-2,6-dichloropurine,
1-(3-Deoxy-β-D-erythropentofuranosyl)-2-acetamido-6-chloropurine,
1-(3-Deoxy-β-D-erythropentofuranosyl)-2-acetamido-6-methoxypurine,
1-(3-Deoxy-β-D-erythropentofuranosyl)-6-methoxypurine and
1-(3-Deoxy-β-D-erythropentofuranosyl)-6-methylmercaptopurine.

Example 35

1-(2,5-Di-O-acetyl-3-O-mesyl-β-D-xylofuranosyl)-5-fluorouracil

A mixture of 5-fluorouracil (0.02 mol), ammonium sulfate (ca. 30 mg) in hexamethyldisilazane (15 mL) is refluxed until a clear solution is obtained. The solvent is removed in vacuo, and the residue is dissolved in 1,2-dichloroethane (20 mL), and 1,2,5-tri-O-acetyl-3-O-mesyl-D-xylofuranose (5.5 g, 0.02 mol) in 1,2-dichloroethane (20 mL) is added. To the solution is added tin tetrachloride (5.2 g, 0.02 mol), and the mixture is stirred overnight at room temperature, then is heated for 3 hours at 40-50° C. for 3 hours. Saturated sodium bicarbonate solution (40 mL) is added and stirred until carbon dioxide evolution ceases. The mixture is filtered through a Celite pad. The organic layer is separated, washed carefully with saturated sodium bicarbonate solution (20 mL×2) and water (20 mL×2), dried over sodium sulfate, and concentrated to dryness in vacuo. The residue is crystallized from ethanol to give the title product (62%). The $^1$H NMR spectrum of this sample is compatible with the structure indicated.

In a similar manner but using the corresponding pyrimidine and purine bases, the following 2',5'-di-O-acetyl 3'-substituted xylo-nucleosides and their L-counterparts are prepared:

1-(2,5-Di-O-acetyl-3-O-mesyl-β-D-xylofuranosyl)-5-chlorouracil,
1-(2,5-Di-O-acetyl-3-O-mesyl-β-D-xylofuranosyl)-5-bromouracil,
1-(2,5-Di-O-acetyl-3-O-mesyl-β-D-xylofuranosyl)-5-iodouracil,
1-(2,5-Di-O-acetyl-3-O-mesyl-β-D-xylofuranosyl)-5-cyanouracil,
1-(2,5-Di-O-acetyl-3-O-mesyl-β-D-xylofuranosyl)-5-ethoxycarbonyluracil,
1-(2,5-Di-O-acetyl-3-O-mesyl-β-D-xylofuranosyl)-5-aminocarbonyluracil,
1-(2,5-Di-O-acetyl-3-O-mesyl-β-D-xylofuranosyl)-5-acetyluracil,
1-(2,5-Di-O-acetyl-3-O-mesyl-β-D-xylofuranosyl)-5-methyluracil,
1-(2,5-Di-O-acetyl-3-O-mesyl-β-D-xylofuranosyl)-5-ethyluracil,
1-(2,5-Di-O-acetyl-3-O-mesyl-β-D-xylofuranosyl)-5-n-propyluracil,
1-(2,5-Di-O-acetyl-3-O-mesyl-β-D-xylofuranosyl)-5-i-propyluracil,
1-(2,5-Di-O-acetyl-3-O-mesyl-β-D-xylofuranosyl)-5-vinyluracil,
1-(2,5-Di-O-acetyl-3-O-mesyl-β-D-xylofuranosyl)-5-allyluracil,
1-(2,5-Di-O-acetyl-3-O-mesyl-β-D-xylofuranosyl)-5-ethynyluracil,
1-(2,5-Di-O-acetyl-3-O-mesyl-β-D-xylofuranosyl)-5-(2-chlorovinyl)uracil,
1-(2,5-Di-O-acetyl-3-O-mesyl-β-D-xylofuranosyl)-5-(2-bromovinyl)uracil,
1-(2,5-Di-O-acetyl-3-O-mesyl-β-D-xylofuranosyl)-5-(2-iodovinyl)uracil,
1-(2,5-Di-O-acetyl-3-O-mesyl-β-D-xylofuranosyl)-5-(2-methoxylcarbonylvinyl)uracil,
1-(2,5-Di-O-acetyl-3-O-mesyl-β-D-xylofuranosyl)-5-(2-hydroxycarbonylvinyl)uracil,
1-(2,5-Di-O-acetyl-3-O-mesyl-β-D-xylofuranosyl)-5-phenyluracil,
1-(2,5-Di-O-acetyl-3-O-mesyl-β-D-xylofuranosyl)-5-benzyluracil,
1-(2,5-Di-O-acetyl-3-O-mesyl-β-D-xylofuranosyl)-5-fluorocytosine,
1-(2,5-Di-O-acetyl-3-O-mesyl-β-D-xylofuranosyl)-5-chlorocytosine, 1-(2,5-Di-O-acetyl-3-O-mesyl-β-D-xylofuranosyl)-5-bromocytosine,
1-(2,5-Di-O-acetyl-3-O-mesyl-β-D-xylofuranosyl)-5-iodocytosine,
1-(2,5-Di-O-acetyl-3-O-mesyl-β-D-xylofuranosyl)-5-cyanocytosine,
1-(2,5-Di-O-acetyl-3-O-mesyl-β-D-xylofuranosyl)-5-ethoxycarbonylcytosine,
1-(2,5-Di-O-acetyl-3-O-mesyl-β-D-xylofuranosyl)-5-aminocarbonylcytosine,
1-(2,5-Di-O-acetyl-3-O-mesyl-β-D-xylofuranosyl)-5-acetylcytosine,
1-(2,5-Di-O-acetyl-3-O-mesyl-β-D-xylofuranosyl)-5-methylcytosine,
1-(2,5-Di-O-acetyl-3-O-mesyl-β-D-xylofuranosyl)-5-ethylcytosine,
1-(2,5-Di-O-acetyl-3-O-mesyl-β-D-xylofuranosyl)-5-n-propylcytosine,
1-(2,5-Di-O-acetyl-3-O-mesyl-β-D-xylofuranosyl)-5-i-propylcytosine,
1-(2,5-Di-O-acetyl-3-O-mesyl-β-D-xylofuranosyl)-5-vinylcytosine,
1-(2,5-Di-O-acetyl-3-O-mesyl-β-D-xylofuranosyl)-5-allylcytosine,
1-(2,5-Di-O-acetyl-3-O-mesyl-β-D-xylofuranosyl)-5-ethynylcytosine,
1-(2,5-Di-O-acetyl-3-O-mesyl-β-D-xylofuranosyl)-5-(2-chlorovinyl)cytosine,
1-(2,5-Di-O-acetyl-3-O-mesyl-β-D-xylofuranosyl)-5-(2-bromovinyl)cytosine,
1-(2,5-Di-O-acetyl-3-O-mesyl-β-D-xylofuranosyl)-5-(2-iodovinyl)cytosine,
1-(2,5-Di-O-acetyl-3-O-mesyl-β-D-xylofuranosyl)-5-(2-methoxylcarbonylvinyl)cytosine,
1-(2,5-Di-O-acetyl-3-O-mesyl-β-D-xylofuranosyl)-5-(2-hydroxy carbonylvinyl)cytosine,
1-(2,5-Di-O-acetyl-3-O-mesyl-β-D-xylofuranosyl)-5-phenylcytosine,
1-(2,5-Di-O-acetyl-3-O-mesyl-β-D-xylofuranosyl)-5-benzylcytosine,
1-(2,5-Di-O-acetyl-3-O-mesyl-β-D-xylofuranosyl)-N$^6$-benzoyladenine,
1-(2,5-Di-O-acetyl-3-O-mesyl-β-D-xylofuranosyl)-6-chloropurine,
1-(2,5-Di-O-acetyl-3-O-mesyl-β-D-xylofuranosyl)-2,6-dichloropurine,
1-(2,5-Di-O-acetyl-3-O-mesyl-β-D-xylofuranosyl)-2-acetamido-6-chloropurine,
1-(2,5-Di-O-acetyl-3-O-mesyl-β-D-xylofuranosyl)-2-acetamido-6-methoxypurine,
1-(2,5-Di-O-acetyl-3-O-mesyl-β-D-xylofuranosyl)-6-methoxypurine,
1-(2,5-Di-O-acetyl-3-O-mesyl-β-D-xylofuranosyl)-6-methylmercaptopurine,
1-(2,5-Di-O-acetyl-3-O-tosyl-β-D-xylofuranosyl)-5-chlorouracil,
1-(2,5-Di-O-acetyl-3-O-tosyl-β-D-xylofuranosyl)-5-bromouracil,
1-(2,5-Di-O-acetyl-3-O-tosyl-β-D-xylofuranosyl)-5-iodouracil,
1-(2,5-Di-O-acetyl-3-O-tosyl-β-D-xylofuranosyl)-5-cyanouracil,
1-(2,5-Di-O-acetyl-3-O-tosyl-β-D-xylofuranosyl)-5-ethoxycarbonyluracil,
1-(2,5-Di-O-acetyl-3-O-tosyl-β-D-xylofuranosyl)-5-aminocarbonyluracil,
1-(2,5-Di-O-acetyl-3-O-tosyl-(3-D-xylofuranosyl)-5-acetyluracil,
1-(2,5-Di-O-acetyl-3-O-tosyl-β-D-xylofuranosyl)-5-methyluracil,
1-(2,5-Di-O-acetyl-3-O-tosyl-β-D-xylofuranosyl)-5-ethylaracil,
1-(2,5-Di-O-acetyl-3-O-tosyl-β-D-xylofuranosyl)-5-n-propyluracil,
1-(2,5-Di-O-acetyl-3-O-tosyl-β-D-xylofuranosyl)-5-i-propyluracil,
1-(2,5-Di-O-acetyl-3-O-tosyl-β-D-xylofuranosyl)-5-vinyluracil,
1-(2,5-Di-O-acetyl-3-O-tosyl-β-D-xylofuranosyl)-5-allyluracil,
1-(2,5-Di-O-acetyl-3-O-tosyl-β-D-xylofuranosyl)-5-ethynyluracil,
1-(2,5-Di-O-acetyl-3-O-tosyl-β-D-xylofuranosyl)-5-(2-chlorovinyl)uracil,
1-(2,5-Di-O-acetyl-3-O-tosyl-β-D-xylofuranosyl)-5-(2-bromovinyl)uracil,
1-(2,5-Di-O-acetyl-3-O-tosyl-β-D-xylofuranosyl)-5-(2-iodovinyl)uracil,
1-(2,5-Di-O-acetyl-3-O-tosyl-β-D-xylofuranosyl)-5-(2-methoxylcarbonylvinyl)uracil,
1-(2,5-Di-O-acetyl-3-O-tosyl-β-D-xylofuranosyl)-5-(2-hydroxycarbonylvinyl)uracil,
1-(2,5-Di-O-acetyl-3-O-tosyl-β-D-xylofuranosyl)-5-phenyluracil,
1-(2,5-Di-O-acetyl-3-O-tosyl-β-D-xylofuranosyl)-5-benzyluracil,
1-(2,5-Di-O-acetyl-3-O-tosyl-β-D-xylofuranosyl)-5-fluorocytosine,
1-(2,5-Di-O-acetyl-3-O-tosyl-β-D-xylofuranosyl)-5-chlorocytosine,
1-(2,5-Di-O-acetyl-3-O-tosyl-β-D-xylofuranosyl)-5-bromocytosine,
1-(2,5-Di-O-acetyl-3-O-tosyl-β-D-xylofuranosyl)-5-iodocytosine,
1-(2,5-Di-O-acetyl-3-O-tosyl-β-D-xylofuranosyl)-5-cyanocytosine,
1-(2,5-Di-O-acetyl-3-O-tosyl-β-D-xylofuranosyl)-5-ethoxycarbonylcytosine,
1-(2,5-Di-O-acetyl-3-O-tosyl-β-D-xylofuranosyl)-5-aminocarbonylcytosine,
1-(2,5-Di-O-acetyl-3-O-tosyl-β-D-xylofuranosyl)-5-acetylcytosine,
1-(2,5-Di-O-acetyl-3-O-tosyl-β-D-xylofuranosyl)-5-methylcytosine,
1-(2,5-Di-O-acetyl-3-O-tosyl-β-D-xylofuranosyl)-5-ethylcytosine,
1-(2,5-Di-O-acetyl-3-O-tosyl-β-D-xylofuranosyl)-5-n-propylcytosine,
1-(2,5-Di-O-acetyl-3-O-tosyl-β-D-xylofuranosyl)-5-i-propylcytosine,
1-(2,5-Di-O-acetyl-3-O-tosyl-β-D-xylofuranosyl)-5-vinylcytosine,
1-(2,5-Di-O-acetyl-3-O-tosyl-β-D-xylofuranosyl)-5-allylcytosine,
1-(2,5-Di-O-acetyl-3-O-tosyl-β-D-xylofuranosyl)-5-ethynylcytosine,
1-(2,5-Di-O-acetyl-3-O-tosyl-β-D-xylofuranosyl)-5-(2-chlorovinyl)cytosine,
1-(2,5-Di-O-acetyl-3-O-tosyl-β-D-xylofuranosyl)-5-(2-bromovinyl)cytosine,
1-(2,5-Di-O-acetyl-3-O-tosyl-β-D-xylofuranosyl)-5-(2-iodovinyl)cytosine, 1-(2,5-Di-O-acetyl-3-O-tosyl-β-D-xylofuranosyl)-5-(2-methoxylcarbonylvinyl)cytosine,
1-(2,5-Di-O-acetyl-3-O-tosyl-β-D-xylofuranosyl)-5-(2-hydroxycarbonylvinyl)cytosine,
1-(2,5-Di-O-acetyl-3-O-tosyl-β-D-xylofuranosyl)-5-phenylcytosine,
1-(2,5-Di-O-acetyl-3-O-tosyl-β-D-xylofuranosyl)-5-benzylcytosine,
1-(2,5-Di-O-acetyl-3-O-tosyl-β-D-xylofuranosyl)-N$^6$-benzoyladenine,
1-(2,5-Di-O-acetyl-3-O-tosyl-β-D-xylofuranosyl)-6-chloropurine,
1-(2,5-Di-O-acetyl-3-O-tosyl-3-D-xylofuranosyl)-2,6-dichloropurine,
1-(2,5-Di-O-acetyl-3-O-tosyl-β-D-xylofuranosyl)-2-acetamido-6-chloropurine,
1-(2,5-Di-O-acetyl-3-O-tosyl-β-D-xylopentofuranosyl)-2-acetamido-6-methoxypurine,
1-(2,5-Di-O-acetyl-3-O-tosyl-β-D-xylopentofuranosyl)-6-methoxypurine and
1-(2,5-Di-O-acetyl-3-O-tosyl-β-D-xylofuranosyl)-6-methylmercaptopurine.

Example 36

1-(2,3,5-Tri-O-acetyl-β-D-xylofuranosyl)thymine

A mixture of thymine (0.02 mol), ammonium sulfate (ca. 30 mg) in hexamethyldisilazane (15 mL) is refluxed until a clear solution is obtained. The solvent is removed in vacuo, and the residue is dissolved in 1,2-dichloroethane (20 mL), and 1,2,3,5-tri-O-acetyl-D-xylofuranose (5.5 g, 0.02 mol) in 1,2-dichloroethane (20 mL) is added. To the solution is added tin tetrachloride (5.2 g, 0.02 mol), and the mixture is stirred overnight at room temperature, then is heated for 3 hours at 40-50° C. for 3 hours. Saturated sodium bicarbonate solution (40 mL) is added and stirred until carbon dioxide evolution ceases. The mixture is filtered through a Celite pad. The organic layer is separated, washed carefully with saturated sodium bicarbonate solution (20 mL×2) and water (20 mL×2), dried over sodium sulfate, and concentrated to dryness in vacuo. The residue is crystallized from ethanol to give product (4.3 g, 62%). The $^1$H NMR spectrum of this sample is compatible with the structure indicated.

In a similar manner but using the corresponding pyrimidine and purine bases, the following 2',5'-di-O-acetyl 3'-substituted xylo-nucleosides and their L-counterparts are prepared:
1-(2,3,5-Tri-O-acetyl-3-D-xylofuranosyl)-5-fluorouracil,
1-(2,3,5-Tri-O-acetyl-β-D-xylofuranosyl)-5-chlorouracil,
1-(2,3,5-Tri-O-acetyl-β-D-xylofuranosyl)-5-bromouracil,
1-(2,3,5-Tri-O-acetyl-β-D-xylofuranosyl)-5-iodouracil,
1-(2,3,5-Tri-O-acetyl-β-D-xylofuranosyl)-5-cyanouracil,
1-(2,3,5-Tri-O-acetyl-β-D-xylofuranosyl)-5-ethoxycarbonyluracil,
1-(2,3,5-Tri-O-acetyl-β-D-xylofuranosyl)-5-aminocarbonyluracil,
1-(2,3,5-Tri-O-acetyl-β-D-xylofuranosyl)-5-acetyluracil,
1-(2,3,5-Tri-O-acetyl-β-D-xylofuranosyl)-5-methyluracil,
1-(2,3,5-Tri-O-acetyl-β-D-xylofuranosyl)-5-ethyluracil,
1-(2,3,5-Tri-O-acetyl-β-D-xylofuranosyl)-5-n-propyluracil,
1-(2,3,5-Tri-O-acetyl-β-D-xylofuranosyl)-5-i-propyluracil,
1-(2,3,5-Tri-O-acetyl-β-D-xylofuranosyl)-5-vinyluracil,
1-(2,3,5-Tri-O-acetyl-β-D-xylofuranosyl)-5-allyluracil,
1-(2,3,5-Tri-O-acetyl-β-D-xylofuranosyl)-5-ethynyluracil,
1-(2,3,5-Tri-O-acetyl-β-D-xylofuranosyl)-5-(2-chlorovinyl)uracil,
1-(2,3,5-Tri-O-acetyl-β-D-xylofuranosyl)-5-(2-bromovinyl)uracil,
1-(2,3,5-Tri-O-acetyl-β-D-xylofuranosyl)-5-(2-iodovinyl)uracil,
1-(2,3,5-Tri-O-acetyl-β-D-xylofuranosyl)-5-(2-methoxylcarbonylvinyl)uracil,
1-(2,3,5-Tri-O-acetyl-β-D-xylofuranosyl)-5-(2-hydroxycarbonylvinyl)uracil,
1-(2,3,5-Tri-O-acetyl-β-D-xylofuranosyl)-5-phenyluracil,
1-(2,3,5-Tri-O-acetyl-β-D-xylofuranosyl)-5-benzyluracil,
1-(2,3,5-Tri-O-acetyl-β-D-xylofuranosyl)-5-fluorocytosine,
1-(2,3,5-Tri-O-acetyl-β-D-xylofuranosyl)-5-chlorocytosine,
1-(2,3,5-Tri-O-acetyl-β-D-xylofuranosyl)-5-bromocytosine,
1-(2,3,5-Tri-O-acetyl-β-D-xylofuranosyl)-5-iodocytosine,
1-(2,3,5-Tri-O-acetyl-β-D-xylofuranosyl)-5-cyanocytosine,
1-(2,3,5-Tri-O-acetyl-β-D-xylofuranosyl)-5-ethoxycarbonylcytosine,
1-(2,3,5-Tri-O-acetyl-β-D-xylofuranosyl)-5-aminocarbonylcytosine,
1-(2,3,5-Tri-O-acetyl-β-D-xylofuranosyl)-5-acetylcytosine,
1-(2,3,5-Tri-O-acetyl-β-D-xylofuranosyl)-5-methylcytosine,
1-(2,3,5-Tri-O-acetyl-β-D-xylofuranosyl)-5-ethylcytosine,
1-(2,3,5-Tri-O-acetyl-β-D-xylofuranosyl)-5-n-propylcytosine,
1-(2,3,5-Tri-O-acetyl-β-D-xylofuranosyl)-5-i-propylcytosine,
1-(2,3,5-Tri-O-acetyl-β-D-xylofuranosyl)-5-vinylcytosine,
1-(2,3,5-Tri-O-acetyl-β-D-xylofuranosyl)-5-allylcytosine,
1-(2,3,5-Tri-O-acetyl-β-D-xylofuranosyl)-5-ethynylcytosine,
1-(2,3,5-Tri-O-acetyl-β-D-xylofuranosyl)-5-(2-chlorovinyl)cytosine,
1-(2,3,5-Tri-O-acetyl-β-D-xylofuranosyl)-5-(2-bromovinyl)cytosine,
1-(2,3,5-Tri-O-acetyl-β-D-xylofuranosyl)-5-
1-(2,3,5-Tri-O-acetyl-β-D-xylofuranosyl)-5-(2-methoxylcarbonylvinyl)cytosine,
1-(2,3,5-Tri-O-acetyl-β-D-xylofuranosyl)-5-phenylcytosine,
1-(2,3,5-Tri-O-acetyl-β-D-xylofuranosyl)-N$^6$-benzoyladenine,
1-(2,3,5-Tri-O-acetyl-β-D-xylofuranosyl)-6-chloropurine,
1-(2,3,5-Tri-O-acetyl-β-D-xylofuranosyl)-2,6-dichloropurine,
1-(2,3,5-Tri-O-acetyl-β-D-xylofuranosyl)-2-acetamido-6-chloropurine,
1-(2,3,5-Tri-O-acetyl-β-D-xylopentofuranosyl)-2-acetamido-6-methoxypurine,
1-(2,3,5-Tri-O-acetyl-β-D-xylopentofuranosyl)-6-methoxypurine and
1-(2,3,5-Tri-O-acetyl-β-D-xylofuranosyl)-6-methylmercaptopurine.

Example 37

1-(3-Deoxy-3-O-mesyl-β-D-xylofuranosyl)-5-fluorouracil

A mixture of 1-(2,5-Di-O-acetyl-3-O-mesyl-β-D-xylofuranosyl)-5-fluorouracil (4.24 g, 0.01 mol) in methanolic ammonia (100 mL) is stirred for 30 minutes at 0° C., and is concentrated in vacuo to dryness, and the residue is crystallized from ethanol to give 1-(3-deoxy-3-O-mesyl-β-D-xylofuranosyl)-5-fluorouracil (2.82 g, 83%). $^1$H NMR (D$_6$-DMSO) showed that there is no acetyl group but one mesyl group in the molecule.

In a similar manner but using the corresponding 2',5'-di-O-acetyl pyrimidine and purine nucleosides, the following 3'-O-mesyl-nucleosides and their L-counterparts are prepared:

1-(3-O-Mesyl-β-D-xylofuranosyl)-5-chlorouracil,
1-(3-O-Mesyl-β-D-xylofuranosyl)-5-bromouracil,
1-(3-O-Mesyl-β-D-xylofuranosyl)-5-iodouracil,
1-(3-O-Mesyl-β-D-xylofuranosyl)-5-cyanouracil,
1-(3-O-Mesyl-β-D-xylofuranosyl)-5-ethoxycarbonyluracil,
1-(3-O-Mesyl-β-D-xylofuranosyl)-5-aminocarbonyluracil,
1-(3-O-Mesyl-β-D-xylofuranosyl)-5-acetyluracil,
1-(3-O-Mesyl-β-D-xylofuranosyl)-5-methyluracil,
1-(3-O-Mesyl-β-D-xylofuranosyl)-5-ethyluracil,
1-(3-O-Mesyl-β-D-xylofuranosyl)-5-n-propyluracil,
1-(3-O-Mesyl-β-D-xylofuranosyl)-5-i-propyluracil,
1-(3-O-Mesyl-β-D-xylofuranosyl)-5-vinyluracil,
1-(3-O-Mesyl-β-D-xylofuranosyl)-5-allyluracil,
1-(3-O-Mesyl-β-D-xylofuranosyl)-5-ethynyluracil,
1-(3-O-Mesyl-β-D-xylofuranosyl)-5-(2-chlorovinyl)uracil,
1-(3-O-Mesyl-β-D-xylofuranosyl)-5-(2-bromovinyl)uracil,
1-(3-O-Mesyl-β-D-xylofuranosyl)-5-(2-iodovinyl)uracil,
1-(3-O-Mesyl-β-D-xylofuranosyl)-5-(2-methoxylcarbonylvinyl)uracil,
1-(3-O-Mesyl-β-D-xylofuranosyl)-5-(2-hydroxycarbonylvinyl)uracil,
1-(3-O-Mesyl-β-D-xylofuranosyl)-5-phenyluracil,
1-(3-O-Mesyl-β-D-xylofuranosyl)-5-benzyluracil,
1-(3-O-Mesyl-β-D-xylofuranosyl)cytosine,
1-(3-O-Mesyl-β-D-xylofuranosyl)-5-fluoro cytosine,
1-(3-O-Mesyl-β-D-xylofuranosyl)-5-chlorocytosine,
1-(3-O-Mesyl-β-D-xylofuranosyl)-5-bromocytosine,
1-(3-O-Mesyl-β-D-xylofuranosyl)-5-iodocytosine,
1-(3-O-Mesyl-β-D-xylofuranosyl)-5-cyanocytosine,
1-(3-O-Mesyl-3-D-xylofuranosyl)-5-ethoxycarbonylcytosine,
1-(3-O-Mesyl-β-D-xylofuranosyl)-5-aminocarbonylcytosine,
1-(3-O-Mesyl-β-D-xylofuranosyl)-5-acetylcytosine,
1-(3-O-Mesyl-β-D-xylofuranosyl)-5-methylcytosine,
1-(3-O-Mesyl-β-D-xylofuranosyl)-5-ethylcytosine,
1-(3-O-Mesyl-β-D-xylofuranosyl)-5-n-propylcytosine,
1-(3-O-Mesyl-β-D-xylofuranosyl)-5-i-propylcytosine,
1-(3-O-Mesyl-β-D-xylofuranosyl)-5-vinylcytosine,
1-(3-O-Mesyl-β-D-xylofuranosyl)-5-allylcytosine,
1-(3-O-Mesyl-β-D-xylofuranosyl)-5-ethynylcytosine,
1-(3-O-Mesyl-β-D-xylofuranosyl)-5-(2-chlorovinyl)cytosine,
1-(3-O-Mesyl-β-D-xylofuranosyl)-5-(2-bromovinyl)cytosine,
1-(3-O-Mesyl-β-D-xylofuranosyl)-5-(2-iodovinyl)cytosine,
1-(3-O-Mesyl-β-D-xylofuranosyl)-5-(2-methoxylcarbonylvinyl)cytosine,
1-(3-O-Mesyl-β-D-xylofuranosyl)-5-(2-hydroxycarbonylvinyl)cytosine,
1-(3-O-Mesyl-β-D-xylofuranosyl)-5-phenylcytosine,
1-(3-O-Mesyl-β-D-xylofuranosyl)-5-benzylcytosine,
1-(3-O-Mesyl-β-D-xylofuranosyl)-2-chloroadenine,
1-(3-O-Mesyl-β-D-xylofuranosyl)-6-chloropurine,
1-(3-O-Mesyl-β-D-xylofuranosyl)-2,6-dichloropurine,
1-(3-O-Mesyl-β-D-xylofuranosyl)-2-acetamido-6-chloropurine,
1-(3-O-Mesyl-β-D-xylofuranosyl)-2-acetamido-6-methoxypurine,
1-(3-O-Mesyl-β-D-xylofuranosyl)-6-methoxypurine and
1-(3-O-Mesyl-β-D-xylofuranosyl)-6-methylmercaptopurine.

Example 38

1-(β-D-Xylofuranosyl)-5-fluorouracil

A mixture of 1-(2,3,5-tri-O-acetyl-β-D-xylofuranosyl)-5-fluorouracil (3.88 g, 0.01 mol) and triethylamine (3 mL) in methanol (100 mL) is stirred overnight at room temperature. The mixture is concentrated in vacuo to dryness, and the residue is crystallized from ethanol to give 1-(β-D-xylofuranosyl)-5-fluorouracil (2.0 g, 76%). The UV and $^1$H NMR (Me$_2$SO-d6) spectra of this sample are consistent with the product structure.

In a similar manner but using the corresponding 2',5'-di-O-acetyl pyrimidine and purine bases, the following xylo-nucleosides and their L-counterparts are prepared:

1-(β-D-Xylofuranosyl)-5-chlorouracil,
1-(β-D-Xylofuranosyl)-5-bromouracil,
1-(β-D-Xylofuranosyl)-5-iodouracil,
1-(β-D-Xylofuranosyl)-5-cyanouracil,
1-(β-D-Xylofuranosyl)-5-ethoxycarbonyluracil,
1-(β-D-Xylofuranosyl)-5-aminocarbonyluracil,
1-(β-D-Xylofuranosyl)-5-acetyluracil,
1-(β-D-Xylofuranosyl)-5-methyluracil,
1-(β-D-Xylofuranosyl)-5-ethyluracil,
1-(β-D-Xylofuranosyl)-5-n-propyluracil,
1-(β-D-Xylofuranosyl)-5-i-propyluracil,
1-(β-D-Xylofuranosyl)-5-vinyluracil,
1-(β-D-Xylofuranosyl)-5-allyluracil,
1-(β-D-Xylofuranosyl)-5-ethynyluracil,
1-(β-D-Xylofuranosyl)-5-(2-chlorovinyl)uracil,
1-(β-D-Xylofuranosyl)-5-(2-bromovinyl)uracil,
1-(β-D-Xylofuranosyl)-5-(2-iodovinyl)uracil,
1-(β-D-Xylofuranosyl)-5-(2-methoxylcarbonylvinyl)uracil,
1-(β-D-Xylofuranosyl)-5-(2-hydroxycarbonylvinyl)uracil,
1-(β-D-Xylofuranosyl)-5-phenyluracil,
1-(β-D-Xylofuranosyl)-5-benzyluracil,
1-(β-D-Xylofuranosyl)cytosine,
1-(β-D-Xylofuranosyl)-5-fluorocytosine,
1-(β-D-Xylofuranosyl)-5-chlorocytosine,
1-(β-D-Xylofuranosyl)-5-bromocytosine,
1-(β-D-Xylo furanosyl)-5-iodocytosine,
1-(β-D-Xylofuranosyl)-5-cyanocytosine,
1-(β-D-Xylo furanosyl)-5-ethoxycarbonylcytosine,
1-(β-D-Xylo furanosyl)-5-aminocarbonylcytosine,
1-(β-D-Xylofuranosyl)-5-acetylcytosine,
1-(β-D-Xylofuranosyl)-5-methylcytosine,
1-(β-D-Xylo furanosyl)-5-ethylcytosine,
1-(β-D-Xylo furanosyl)-5-n-propylcytosine,
1-(β-D-Xylo furanosyl)-5-i-propylcytosine,
1-(β-D-Xylofuranosyl)-5-vinylcytosine,
1-(β-D-Xylofuranosyl)-5-allylcytosine,
1-(β-D-Xylofuranosyl)-5-ethynylcytosine,
1-(β-D-Xylofuranosyl)-5-(2-chlorovinyl)cytosine,
1-(β-D-Xylo furanosyl)-5-(2-bromovinyl)cytosine,
1-(β-D-Xylo furanosyl)-5-(2-iodovinyl)cytosine,
1-(β-D-Xylofuranosyl)-5-(2-methoxylcarbonylvinyl)cytosine,
1-β-D-Xylofuranosyl)-5-(2-hydroxycarbonylvinyl)cytosine,
1-(β-D-Xylofuranosyl)-5-phenylcytosine,
1-(β-D-Xylofuranosyl)-5-benzylcytosine,
1-(β-D-Xylofuranosyl)-2-chloroadenine,
1-(β-D-Xylofuranosyl)-6-chloropurine,
1-(β-D-Xylofuranosyl)-2,6-dichloropurine, 1-(β-D-Xylofuranosyl)-2-acetamido-6-chloropurine,
1-(β-D-Xylofuranosyl)-2-acetamido-6-methoxypurine,
1-(β-D-Xylofuranosyl)-6-methoxypurine and
1-(β-D-Xylofuranosyl)-6-methylmercaptopurine.

Example 39

2',3'-O-Isopropylidene-5'-O-triphenylmethyl-$N^4$-hydroxycytidine

To a stirred solution of 2',3'-O-isopropylidene-5-O-triphenylmethyluridine (1 g) in 50 mL of anhydrous acetonitrile and triethylamine (0.76 g) are added 2,4,6-triisopropylbenzenesulfonyl chloride (1.15 g) and DMAP (232 mg) at 0° C., and the reaction mixture is stirred for 1 day at room temperature. Hydroxylamine hydrochloride (263 mg) is then added, and the mixture is further stirred for 1 day at room temperature. The reaction is quenched by addition of water, and the product is extracted with chloroform (200 mL). The organic layer is washed with brine, dried over $MgSO_4$, and concentrated in vacuo. The residue is purified by silica gel column chromatography (5% MeOH in $CHCl_3$) to give 2',3'-O-isopropylidene-5'-O-trityl-$N^4$-hydroxy-cytidine (723 mg, 70%) as a white solid. Mp: 99-101° C. $^1$H NMR ($CDCl_3$) δ 1.34 (s, 3H), 1.56 (s, 3H), 3.40-3.73 (m, 2H), 4.26 (br s, 1H), 4.79-4.81 (m, 2H), 5.34 (d, J=8.12 Hz, 1H), 5.88 (br s, 1H), 6.88 m (d, J=8.12 Hz, 1H), 7.22-7.41 (m, 15H).

In a similar manner but using the corresponding 5-substituted uracil nucleosides, the following $N^4$-hydroxy-2',3'-O-isopropylidene-5'-O-triphenylmethylcytidine derivatives are synthesized:
2',3'-O-Isopropylidene-5'-O-triphenylmethyl-5-fluoro-$N^4$-hydroxycytidine,
2',3'-O-Isopropylidene-5'-O-triphenylmethyl-5-chloro-$N^4$-hydroxycytidine,
2',3'-O-Isopropylidene-5'-O-triphenylmethyl-5-bromo-$N^4$-hydroxycytidine,
2',3'-O-Isopropylidene-5'-O-triphenylmethyl-5-iodo-$N^4$-hydroxycytidine,
2',3'-O-Isopropylidene-5'-O-triphenylmethyl-5-methyl-$N^4$-hydroxycytidine,
2',3'-O-Isopropylidene-5'-O-triphenylmethyl-5-ethyl-$N^4$-hydroxycytidine,
2',3'-O-Isopropylidene-5'-O-triphenylmethyl-5-n-propyl-$N^4$-hydroxycytidine,
2',3'-O-Isopropylidene-5'-O-triphenylmethyl-5-i-propyl-$N^4$-hydroxycytidine,
2',3'-O-Isopropylidene-5'-O-triphenylmethyl-5-vinyl-$N^4$-hydroxycytidine,
2',3'-O-Isopropylidene-5'-O-triphenylmethyl-5-ethynyl-$N^4$-hydroxycytidine,
2',3'-O-Isopropylidene-5'-O-triphenylmethyl-5-(2-chlorovinyl)-$N^4$-hydroxycytidine,
2',3'-O-Isopropylidene-5'-O-triphenylmethyl-5-(2-bromovinyl)-$N^4$-hydroxycytidine,
2',3'-O-Isopropylidene-5'-O-triphenylmethyl-5-(2-iodovinyl)-$N^4$-hydroxycytidine,
2',3'-O-Isopropylidene-5'-O-triphenylmethyl-5-(2-methoxycarbonylvinyl)-$N^4$-hydroxycytidine,
2',3'-O-Isopropylidene-5'-O-triphenylmethyl-5-(2-hydroxycarbonylvinyl)-$N^4$-hydroxycytidine,
2',3'-O-Isopropylidene-5'-O-triphenylmethyl-5-phenyl-$N^4$-hydroxycytidine and
2',3'-O-Isopropylidene-5'-O-triphenylmethyl-5-benzyl-$N^4$-hydroxycytidine.

In a similar manner but using the corresponding 5-substituted 2',5'-di-O-acetyl-3'-deoxyuridines, the following $N^4$-hydroxy-2',5'-di-O-acetyl-3'-deoxycytidine derivatives are synthesized:
1-(2,5-Di-O-acetyl-3-deoxy-β-D-erythropentofuranosyl)-$N^4$-hydroxycytosine,
1-(2,5-Di-O-acetyl-3-deoxy-β-D-erythropentofuranosyl)-5-fluoro-$N^4$-hydroxycytosine,
1-(2,5-Di-O-acetyl-3-deoxy-β-D-erythropentofuranosyl)-5-chloro-$N^4$-hydroxycytosine,
1-(2,5-Di-O-acetyl-3-deoxy-β-D-erythropentofuranosyl)-5-bromo-$N^4$-hydroxycytosine,
1-(2,5-Di-O-acetyl-3-deoxy-β-D-erythropentofuranosyl)-5-iodo-$N^4$-hydroxycytosine,
1-(2,5-Di-O-acetyl-3-deoxy-β-D-erythropentofuranosyl)-5-cyano-$N^4$-hydroxycytosine,
1-(2,5-Di-O-acetyl-3-deoxy-β-D-erythropentofuranosyl)-5-ethoxycarbonyl-$N^4$-hydroxycytosine,
1-(2,5-Di-O-acetyl-3-deoxy-β-D-erythropentofuranosyl)-5-aminocarbonyl-$N^4$-hydroxycytosine,
1-(2,5-Di-O-acetyl-3-deoxy-β-D-erythropentofuranosyl)-5-acetyl-$N^4$-hydroxycytosine,
1-(2,5-Di-O-acetyl-3-deoxy-β-D-erythropentofuranosyl)-5-methyl-$N^4$-hydroxycytosine,
1-(2,5-Di-O-acetyl-3-deoxy-β-D-erythropentofuranosyl)-5-ethyl-$N^4$-hydroxycytosine,
1-(2,5-Di-O-acetyl-3-deoxy-β-D-erythropentofuranosyl)-5-n-propyl-$N^4$-hydroxycytosine,
1-(2,5-Di-O-acetyl-3-deoxy-β-D-erythropentofuranosyl)-5-i-propyl-$N^4$-hydroxycytosine,
1-(2,5-Di-O-acetyl-3-deoxy-β-D-erythropentofuranosyl)-5-vinyl-$N^4$-hydroxycytosine,
1-(2,5-Di-O-acetyl-3-deoxy-β-D-erythropentofuranosyl)-5-allyl-$N^4$-hydroxycytosine,
1-(2,5-Di-O-acetyl-3-deoxy-β-D-erythropentofuranosyl)-5-ethynyl-$N^4$-hydroxycytosine,
1-(2,5-Di-O-acetyl-3-deoxy-β-D-erythropentofuranosyl)-5-(2-chlorovinyl)-$N^4$-hydroxycytosine,
1-(2,5-Di-O-acetyl-3-deoxy-β-D-erythropentofuranosyl)-5-(2-bromovinyl)-$N^4$-hydroxycytosine,
1-(2,5-Di-O-acetyl-3-deoxy-β-D-erythropentofuranosyl)-5-(2-iodovinyl)-$N^4$-hydroxycytosine,
1-(2,5-Di-O-acetyl-3-deoxy-β-D-erythropentofuranosyl)-5-(2-methoxylcarbonylvinyl)-$N^4$-hydroxycytosine,
1-(2,5-Di-O-acetyl-3-deoxy-β-D-erythropentofuranosyl)-5-(2-hydroxycarbonylvinyl)-$N^4$-hydroxycytosine,
1-(2,5-Di-O-acetyl-3-deoxy-β-D-erythropentofuranosyl)-5-phenyl-$N^4$-hydroxycytosine and
1-(2,5-Di-O-acetyl-3-deoxy-β-D-erythropentofuranosyl)-5-benzyl-$N^4$-hydroxycytosine, In a similar manner but using the corresponding 5-substituted 3',5'-di-O-acetyl-2'-deoxyuridines, the following $N^4$-hydroxy-3',5'-di-O-acetyl-$N^4$-hydroxy-2'-deoxycytidine derivatives are synthesized:
3',5'-Di-O-acetyl-2'-deoxy-$N^4$-hydroxycytidine,
3',5'-Di-O-acetyl-2'-deoxy-5-fluoro-$N^4$-hydroxycytidine,
3',5'-Di-O-acetyl-2'-deoxy-5-chloro-$N^4$-hydroxycytidine,
3',5'-Di-O-acetyl-2'-deoxy-5-bromo-$N^4$-hydroxycytidine,
3',5'-Di-O-acetyl-2'-deoxy-5-iodo-$N^4$-hydroxycytosine,
3',5'-Di-O-acetyl-2'-deoxy-5-cyano-$N^4$-hydroxycytidine,
3',5'-Di-O-acetyl-2'-deoxy-5-ethoxycarbonyl-$N^4$-hydroxycytidine,
3',5'-Di-O-acetyl-2'-deoxy-5-aminocarbonyl-$N^4$-hydroxycytidine,
3',5'-Di-O-acetyl-2'-deoxy-5-acetyl-$N^4$-hydroxycytidine,
3',5'-Di-O-acetyl-2'-deoxy-5-methyl-$N^4$-hydroxycytidine,
3',5'-Di-O-acetyl-2'-deoxy-5-ethyl-$N^4$-hydroxycytosine, 3',5'-Di-O-acetyl-2'-deoxy-5-n-propyl-$N^4$-hydroxycytidine,
3',5'-Di-O-acetyl-2'-deoxy-5-i-propyl-$N^4$-hydroxycytidine,
3',5'-Di-O-acetyl-2'-deoxy-5-vinyl-$N^4$-hydroxycytidine,
3',5'-Di-O-acetyl-2'-deoxy-5-allyl-$N^4$-hydroxycytidine,
3',5'-Di-O-acetyl-2'-deoxy-5-ethynyl-$N^4$-hydroxycytidine,
3',5'-Di-O-acetyl-2'-deoxy-5-(2-chlorovinyl)-$N^4$-hydroxycytidine,
3',5'-Di-O-acetyl-2'-deoxy-5-(2-bromovinyl)-$N^4$-hydroxycytidine,
3',5'-Di-O-acetyl-2'-deoxy-5-(2-iodovinyl)-$N^4$-hydroxycytidine,
3',5'-Di-O-acetyl-2'-deoxy-5-(2-methoxylcarbonylvinyl)-$N^4$-hydroxycytidine,
3',5'-Di-O-acetyl-2'-deoxy-5-(2-hydroxycarbonylvinyl)-$N^4$-hydroxycytosine,
3',5'-Di-O-acetyl-2'-deoxy-5-phenyl-$N^4$-hydroxycytidine and
3',5'-Di-O-acetyl-2'-deoxy-5-benzyl-$N^4$-hydroxycytidine.

Example 40

$N^4$-Hydroxycytidine

2',3'-O-Isopropylidene-5'-O-trityl-$N^4$-hydroxycytidine (500 mg, 0.92 mmol) is dissolved in 50 mL of a mixture of trifluoroacetic acid and water (2:1, v/v), and the solution is stirred for 3 h at 50° C. After cooling to room temperature, the solvent is removed by evaporation and coevaporated with ethanol (3×20 mL). The residue is purified by silica gel column chromatography (20% MeOH in $CHCl_3$) to give $N^4$-hydroxycytidine (215 mg) as a white solid which is recrystallized from hot ethanol; mp. 173-176° C. NMR (DMSO-$d_5$) δ 3.66-3.71 (m, 2H), 3.93 (br s, 1H), 4.08-4.15 (m, 2H), 5.17-5.23 (m, 2H, $D_2O$ exchangeable), 5.43 (d, J=6.00 Hz, 1H, $D_2O$ exchangeable), 5.73 (d, J=8.16 Hz, 1H), 5.90 (d, J=8.12 Hz, 1H), 7.28 (d, J=8.40 Hz, 1H), 9.65 (s, 1H, $D_2O$ exchangeable), 10.15 (s, 1H, $D_2O$ exchangeable). Anal. Calcd for $C_9H13N3O_6$: C, 41.70; H, 5.05; N, 16.21. Found: C, 41.85; H, 5.14; N, 16.34.

In a similar manner but using the corresponding 5-substituted 2',3'-O-isopropylidene-5-O-triphenylmethyl-$N^4$-hydroxycytidine nucleosides, the following $N^4$-hydroxy-5-substituted cytidine are synthesized:
5-Fluoro-$N^4$-hydroxycytidine,
5-Chloro-$N^4$-hydroxycytidine,
5-Bromo-$N^4$-hydroxycytidine,
5-Iodo-$N^4$-hydroxycytidine,
5-Methyl-$N^4$-hydroxycytidine,
5-Ethyl-$N^4$-hydroxycytidine,
5-n-Propyl-$N^4$-hydroxycytidine,
5-i-Propyl-$N^4$-hydroxycytidine,
5-Vinyl-$N^4$-hydroxycytidine,
5-Ethynyl-$N^4$-hydroxycytidine,
5-(2-chlorovinyl)-$N^4$-hydroxycytidine,
5-(2-bromovinyl)-$N^4$-hydroxycytidine,
5-(2-iodovinyl)-$N^4$-hydroxycytidine,
5-(2-methoxycarbonylvinyl)-$N^4$-hydroxycytidine,
5-(2-hydroxycarbonylvinyl)-$N^4$-hydroxycytidine,
5-phenyl-$N^4$-hydroxycytidine and
5-benzyl-$N^4$-hydroxycytidine.

In a similar manner but using methanolic ammonia instead of trifluoroacetic acid, and the corresponding 5-substituted 1-(2,5-di-O-acetyl-3-deoxy-β-D-erythro-pentofuranosyl)-$N^4$-hydroxycytosine nucleosides, the following $N^4$-hydroxy-5-substituted 3'-deoxycytidine are synthesized:
5-Fluoro-3'-deoxy-$N^4$-hydroxycytidine,
5-Chloro-3'-deoxy-$N^4$-hydroxycytidine,
5-Bromo-3'-deoxy-$N^4$-hydroxycytidine,
5-Iodo-3'-deoxy-$N^4$-hydroxycytidine,
5-Methyl-3'-deoxy-$N^4$-hydroxycytidine,
5-Ethyl-3'-deoxy-$N^4$-hydroxycytidine,
5-n-Propyl-3'-deoxy-$N^4$-hydroxycytidine,
5-i-Propyl-3'-deoxy-$N^4$-hydroxycytidine,
5-Vinyl-3'-deoxy-$N^4$-hydroxycytidine,
5-Ethynyl-3'-deoxy-$N^4$-hydroxycytidine,
5-(2-chlorovinyl)-3'-deoxy-$N^4$-hydroxycytidine,
5-(2-bromovinyl)-3'-deoxy-$N^4$-hydroxycytidine,
5-(2-iodovinyl)-3'-deoxy-$N^4$-hydroxycytidine,
5-(2-methoxycarbonylvinyl)-3'-deoxy-$N^4$-hydroxycytidine,
5-(2-hydroxycarbonylvinyl)-3'-deoxy-$N^4$-hydroxycytidine,
5-phenyl-3'-deoxy-$N^4$-hydroxycytidine and
5-benzyl-3'-deoxy-$N^4$-hydroxycytidine.

In a similar manner but using methanolic ammonia instead of trifluoroacetic acid, and the corresponding 5-substituted 3',5'-di-O-acetyl-2'-deoxy-$N^4$-hydroxycytosine nucleosides, the following $N^4$-hydroxy-5-substituted 2'-deoxycytidine are synthesized:
5-Fluoro-2'-deoxy-$N^4$-hydroxycytidine,
5-Chloro-2'-deoxy-$N^4$-hydroxycytidine,
5-Bromo-2'-deoxy-$N^4$-hydroxycytidine,
5-Iodo-2'-deoxy-$N^4$-hydroxycytidine,
5-Methyl-2'-deoxy-$N^4$-hydroxycytidine,
5-Ethyl-2'-deoxy-$N^4$-hydroxycytidine,
5-n-Propyl-2'-deoxy-$N^4$-hydroxycytidine,
5-i-Propyl-2'-deoxy-$N^4$-hydroxycytidine,
5-Vinyl-2'-deoxy-$N^4$-hydroxycytidine,
5-Ethynyl-2'-deoxy-$N^4$-hydroxycytidine,
5-(2-chlorovinyl)-2'-deoxy-$N^4$-hydroxycytidine,
5-(2-bromovinyl)-2'-deoxy-$N^4$-hydroxycytidine,
5-(2-iodovinyl)-2'-deoxy-$N^4$-hydroxycytidine,
5-(2-methoxycarbonylvinyl)-2'-deoxy-$N^4$-hydroxycytidine,
5-(2-hydroxycarbonylvinyl)-2'-deoxy-$N^4$-hydroxycytidine,
5-phenyl-2'-deoxy-$N^4$-hydroxycytidine and
5-benzyl-2'-deoxy-$N^4$-hydroxycytidine.

Example 41

2,3'-Anhydro-1-(2-deoxy-2-fluoro-5-O-trityl-β-D-lyxofuranosyl)thymine (194, R=Tr)

A solution of 1-(2-deoxy-2-fluoro-3-O-mesyl-5-O-triphenylmethyl-β-D-arabino-furanosyl)thymine (193, R=Tr, 6.0 g) and DBU (3.0 mL) in methylene chloride (50 mL) is heated at reflux for 16 hours. After concentration of the mixture in vacuo, the residue is chromatographed on a silica gel column using chloroform as the eluent to give 4.4 g of 2,3'-anhydro-1-(2'-deoxy-2'-fluoro-5-O-trityl-β-D-lyxo furanosyl)thymine (194, R=Tr), mp 252-255° C. after recrystallization from methanol. $^1$H NMR (DMSO-$d_6$); δ 1.80 (s, 3H, Me), 4.61 (1H, m), 5.40 (dm, 1H), 5.89 (1H, ddd), 5.96 (1H, dd, H-1'), 7.30 (15H, Tr), 7.66 (s, 1H, H-6).

Example 42

1-(2,3-Dideoxy-2'-fluoro-5'-O-trityl-β-D-glycero-pento-2-enofuranosyl)-thymine (195, R=Tr)

A suspension of 194 (646 mg) and t-BuOK (270 mg) in DMSO (10 mL) is stirred at room temperature for 2 hours and then filtered. The filtrate is concentrated in vacuo and the residue is chromatographed on a silica gel column ($CHCl_3$/MeOH, 49:1 v/v) to give 600 mg of 195, mp. 176-180° C. (from EtOH). $^1$H NMR (DMSO-$d_6$) δ 1.27 (s, 3H, Me), 3.21 (m, 2’-1, H-5,5"), 4.98 (m, 1H, H-4'), 6.17 (t, 1H, H-1', J1',2'=J1',F=1.5 Hz), 6.81 (m, 1H, H-3'), 7.32 (m, 16H, H-6, Tr), 11.52 (s, 1H, NH exchangeable).

Example 43

1-(2,3-Dideoxy-2-fluoro-β-D-glycero-2-enofuranosyl)thymine (196)

A solution of 195 (600 mg) in 80% aqueous acetic acid (10 mL) is heated under reflux for 20 minutes and then concentrated to dryness in vacuo. The residue is chromatographed on a column of silica gel (CHCl$_3$/MeOH, 9:1 v/v) to give 100 mg of 196, mp 154-159° C. (from EtOH—H$_2$O). NMR (DMSO-d$_6$) δ 1.76 (s, 3H, Me), 3.61 (m, 2H, H-5',5"), 4.79 (m, 1H, H-4'), 5.15 (t, 1H, 5'-OH, exchangeable), 5.99 (m, 1H, H-1'), 6.76 (m, 1H, H-3'), 7.88 (s, 1H, H-6), 11.43 (s, 1H, NH, exchangeable).

Example 44

(1S,2S,3R,4R)-4-(tert-Butoxymethyl)-2,3-(isopropylidenedioxy)cyclopentan-1-ol (219)

To a solution of 4-(t-butoxymethyl)cyclopentane-2,3-diol (218, 5 g) and CeCl$_3$7H$_2$O (7.69 g) in methanol (80 mL) is added NaBH$_4$ (1.01 g) at 0° C., and the mixture is stirred for 1 hour at 0° C. The reaction is quenched by addition of cold water, and extracted with ethyl acetate (2×300 mL). The combined organic extracts are washed with brine (2×200 mL), dried over Na2SO4, and then concentrated in vacuo. The residue is chromatographed on a silica gel column (30% ethyl acetate in n-hexane) to give 219 (4.8 g, 95%) as a syrup. $^1$H-NMR (CDCl$_3$) δ 1.13 (s, 9H, t-Bu), 1.34 (s, 3H, Me), 1.48 (s, 3H, Me), 1.83 (m, 2H, 5a,b-H), 2.19 (m, 1H, 4-H), 2.44 (d, OH, exchangeable), 3.20 (dd, J=4.5, 8.8 Hz, 1H, 6a-H), 3.31 (dd, J=4.5, 8.8 Hz, 1H, 6b-H), 4.23 (m, 1H, 1-H), 4.44 (m, 2H, 2-H, 3-H). Anal. Calcd for C$_{13}$H$_{24}$O$_4$: C, 63.91; H, 9.90. Found: C, 64.09; H, 9.87.

Example 45

(1S,2S,3R,4R)-4-(tert-Butoxymethyl)-2,3-(isopropylidenedioxy)-1-mesyloxycyclopentane (220)

To a solution of 219 (6.50 g) and triethylamine (7.3 g) in methylene chloride (170 mL) is added mesyl chloride (4.73 g) dropwise at 0° C. After 45 minutes, water (270 mL) is added. The aqueous layer is extracted with methylene chloride (3×200 mL). The organic layers are combined, washed with brine (2×200 mL), dried over Na$_2$SO$_4$, and concentrated in vacuo to give crude 220, which is sufficiently pure to be used directly in the next step.

Example 46

(1R,2S,3R,4R)-1-Azido-4-(tert-butoxymethyl)-2,3-(isopropylidenedioxy)cyclopentane (221)

A mixture of 220 obtained above and sodium azide (17.3 g) in DMF (300 mL) is heated at 140° C. overnight with stirring. The mixture is filtered and the filtrate is concentrated in vacuo. The residue is partitioned between ethyl acetate (150 mL) and water (50 mL). The organic layer is dried over Na$_2$SO$_4$, concentrated in vacuo, and the residue is chromatographed on a silica gel column (1-4% gradient, ethyl acetate in n-hexane) to give 221 (5.9 g) as an oil. $^1$H NMR (CDCl$_3$) δ 1.18 (s, 9H, t-Bu), 1.30 (s, 3H, Me), 1.46 (s, 3H, Me), 1.71 (m, 1H, 5a-H), 2.29 (m, 2H, 4-H, 5b-H), 3.29 (dd, J=6.7, 8.8 Hz, 1H, 6a-H), 3.37 (dd, J=7.0, 8.8 Hz, 1H, 6b-H), 3.96 (m, 1H, 1-H), 4.40 (dd, J=2.3, 6.1 Hz, 1H, 3-H), 4.48 (dd, J=2.0, 6.1 Hz, 1H, 2-H). Anal. Calcd for C$_{13}$H$_{23}$N$_3$O$_3$.0.13EtOAc: C, 57.95; H, 8.65, N, 14.99. Found: C, 58.25; H, 8.71; N, 14.76.

Example 47

(1R,2S,3R,4R)-4-(tert-Butoxymethyl)-2,3-(isopropylidenedioxy)-1-cyclopentylamine (222)

A suspension of 221 (4.0 g) and 10% Pd/C (1.0 g) in anhydrous ethanol (140 mL) is shaken under 20 psi of H$_2$ for 5 hours. The mixture is filtered, and the filtrate is concentrated in vacuo to give crude 222 (3.6 g, quantitative), which is used directly in the next step without further purification. $^1$H NMR (CDCl$_3$) δ 1.18 (s, 9H, t-Bu), 1.28 (s, 3H, Me), 1.36 (m, 1H, 5a-H), 1.45 (s, 3H, Me), 1.89 (br s, 2H, NH$_2$), 2.24-2.36 (m, 2H, 4-H, 5b-H), 3.34-3.43 (m, 3H, 1-H, 6a,b-H), 4.21 (dd, J=2.6, 6.2 Hz, 1H, 3-H), 4.48 (dd, J=2.8, 6.2 Hz, 1H, 2-H). Anal. Calcd for C$_{13}$H$_{26}$NO$_3$ 0.16H$_2$O: C, 63.41; H, 10.37, N, 5.69. Found: C, 63.09; H, 10.16; N, 5.59.

Example 48

N-{[1R,2S,3R,4R)-4-(tert-Butoxymethyl)-2,3-(isopropylidenedioxy)cyclopentyl]-aminocarbonyl}-3-methoxy-2-propenamide (223)

A mixture of silver cyanate (7.60 g, dried in vacuo over phosphorus pentoxide in the dark at 100° C. for 3 hours), β-methoxyacryloyl chloride (2.64 g) in anhydrous benzene (30 mL) is heated under reflux for 30 minutes, and then is allowed to cool to room temperature. After precipitation is settled, 22.5 mL of the supernatant, which contains β-methoxyacryloyl isocyanate) is added during 15 minutes to a solution of 222 (3.0 g) in dry DMF (50 mL) at 15 to 20° C. under nitrogen. The mixture is stirred for 2 hours at 15° C. and then 10 more hours at room temperature under nitrogen. After concentration in vacuo and coevaporation with toluene (2×20 mL), the product 223 solidifies (4.0 g). $^1$H NMR (CDCl$_3$) δ 1.17 (s, 9H, t-Bu), 1.28 (s, 3H, Me), 1.47 (s, 3H, Me), 1.58 (m, 1H, 5' a-H), 2.28 (m, 1H, 4-H), 2.36-2.43 (m, 1H, 5' b-H), 3.33-3.42 (m, 2H, 6' a,b-H), 3.73 (s, 3H, OMe), 4.20 (m, 1H, 3'-H), 4.45 (m, 2H, 1'-H, 2'-H), 5.35 (d, J=12.3 Hz, 1H, 5-H), 7.67 (d, J=12.3 Hz, 1H, 6-H), 8.72 (br s, 1H, NH), 9.35 (br s, 1H, NH). Anal. Calcd for C$_{18}$H$_{30}$N$_2$O$_6$: C, 58.36; H, 8.16, N, 7.56. Found: C, 58.28; H, 8.16; N, 7.60.

Example 49

(1'R,2'S,3'R,4'R)-1-[4-(tert-Butoxymethyl)-2,3-isopropylidenedioxy)cyclopentan-1-yl]uracil (5'-tert-Butyl-2',3'-O-isopropylidene-carba-uridine, 224)

A solution of 223 (4.2 g) in ethanol (25 mL) and ammonium hydroxide (30% 11 mL) is heated at 100° C. in a steel bomb for 12 hours. After removal of the solvents, the residue is chromatographed over a silica gel column (ethylacetate-n-hexane, 1:1 v/v) to give 224 (3.21 g) as a white foam. UV (MeOH) λ$_{max}$ 266.0 nm. NMR (CDCl$_3$) δ 1.19 (s, 9H, t-Bu), 1.30 (s, 3H, Me), 1.54 (s, 3H, Me), 1.97 (m, 1H, 5' a-H), 2.32-2.41 (m, 2H, 4'-H, 5' b-H), 3.43-3.50 (m, 2H, 6' a,b-H), 4.48 (dd, J=4.1, 6.5 Hz, 1H, 3'-H), 4.65-4.75 (m, 2H, 1'-H, 2'-H), 5.72 (d, J=8.0 Hz, 1H, 5-H), 7.35 (d, J=8.0 Hz, 1H, 6-H), 8.63 (br s, 1H, NH). Anal. Calcd for $C_{17}H_{26}N_2O_5$: C, 60.34; H, 7.74, N, 8.28. Found: C, 60.06; H, 7.70; N, 8.14.

Example 50

(1'R,2'S,3'R,4'R)-1-[4-(tert-Butoxymethyl)-2,3-isopropylidenedioxy)cyclopentan-1-yl]-5-fluorouracil (5'-O-tert-Butyl-2',3'-O-isopropylidene-carba-5-fluorouridine, 225)

A fluorine-nitrogen mixture containing 5% of fluorine is bubbled carefully into a solution of 224 (2.50 g) in acetic acid (600 mL) for 30 minutes at room temperature. The mixture is stirred until no UV absorption is detected on TLC plate. The solvent is removed in vacuo, and the residue is coevaporated with acetic acid (20 mL) to dryness. The residue is treated with triethylamine for 1.5 hours at 50° C., and then concentrated in vacuo to dryness. The residue is purified by silica gel column chromatography (ethylacetate-n-hexane, 1:1 v/v) to give 225 (1.31 g) as a white foam. UV (MeOH) $\lambda_{max}$ 271.5 nm. NMR (CDCl$_3$) δ 1.22 (s, 9H, t-Bu), 1.31 (s, 3H, Me), 1.55 (s, 3H, Me), 1.85 (m, 1H, 5' a-H), 2.38-2.51 (m, 2H, 4'-H, 5' b-H), 3.44-3.52 (m, 2H, 6' a,b-H), 4.47 (dd, J=3.4, 6.2 Hz, 1H, 3'-H), 4.58 (t, J=6.0 Hz, 1H, 1'-H), 4.87 (dd, J=8.9, 14.5 Hz, 1H, 2'-H), 7.61 (d, J=6.1 Hz, 1H, 6-H), 8.77 (br s, 1H, NH). Anal. Calcd for $C_{17}H_{25}FN_2O_5 \cdot 0.25H_2O$: C, 56.58; H, 7.12, N, 7.76. Found: C, 56.20; H, 7.02; N, 7.50.

Example 51

(1'R,2'S,3'R,4'R)-1-[4-(tert-Butoxymethyl)-2,3-isopropylidenedioxy)cyclopentan-1-yl]-5-fluorocytosine (226). (5'-O-tert-Butyl-2',3'-O-isopropylidene-carba-5-fluorocytidine)

A mixture of 225 (350 mg), triethylamine (190 mg), 2,4,6-triisopropylbenzenesulfonyl chloride (590 mg) and DMAP (230 mg) in acetonitrile (50 mL) is stirred for 1 day at room temperature. Ammonium hydroxide solution (30%, 15 mL) is added, and the mixture is further stirred 5 hours. The reaction is quenched by addition of chloroform (250 mL) and water (10 mL). The organic layer is washed with brine, dried over Na$_2$SO$_4$, and concentrated in vacuo. The residue is purified by silica gel column chromatography (5% MeOH in CHCl$_3$, v/v) to give 226 (205 mg), mp 128-130° C. UV (MeOH) $\lambda_{max}$ 286.5 nm. $^1$H NMR (CDCl$_3$) δ 1.19 (s, 9H, t-Bu), 1.29 (s, 3H, Me), 1.53 (s, 3H, Me), 2.02 (dt, J=10.2, 12.8 Hz, 1H, 5' a-H), 2.32 (m, 1H, 4'-H), 2.42 (dt, J=8.0, 12.7 Hz, 1H, 5' b-H), 3.42 (dd, J=6.1, 8.7 Hz, 1H, 6' a-H), 3.52 (dd, J=4.1, 8.8 Hz, 1H, 6' b-H), 4.49 (dd, J=5.1, 6.3 Hz, 1H, 3'-H), 4.60 (m, 1H, 1'-H), 4.79 (dd, J=5.0, 6.4 Hz, 1H, 2'-H), 7.49 (d, J=6.1 Hz, 1H, 6-H). HR-FAB MS Obsd; m/z 356.1981. Calcd for $C_{17}H_{26}FN_3O_4$: m/z 356.1986 (M+1)$^+$.

Example 52

(1'R,2'S,3'R,4'R)-1-[2,3-Dihydroxy-4-(hydroxymethyl)cyclopentan-1-yl]-5-fluorocytosine (carba-5-fluorocytidine, 227)

A solution of 226 (180 mg) in a 2:1 (v/v) mixture of trifluoroacetic acid and water (40 mL) is stirred for 3 hours at 50° C. The solvents are removed in vacuo, and the residue is coevaporated with ethanol (2×30 mL), and purified on a silica gel column (MeOH—CHCl$_3$, 1:5 v/v) to give 227 (47.5 mg) as a foam. UV (H$_2$O) $\lambda_{max}$ 284 nm (e 5,876, pH 7), 293.5 nm (ε 7,440, pH 2), 284 5 nm (ε 5,883, pH 11). $^1$H NMR (DMSO-d$_6$) δ 1.19 (m, 1H, 5' a-H), 1.92 (m, 1H, 4' a-H), 2.00 (ddd, J=8.3, 8.7, 12.5 Hz, 1H, 5' b-H), 3.42 (m, 2H, 6' ab-H), 3.70 (dd, J=2.9, 5.3 Hz, 1H, 3' b-H), 3.98 (dd, J=5.2, 9.0 Hz, 1H, 2'-H), 4.10 (d, J=4.5, 1H, OH, exchangeable), 4.51 (br s, 1H, OH, exchangeable), 4.60 (dd, J=9.0, 18.2 Hz, 1H, 1'-H), 4.73 (d, J=6.1 Hz, 1H, OH, exchangeable), 7.33 (bs, 1H, exchangeable), 7.55 (bs, 1H, exchangeable), 7.98 (d, J=7.3 Hz, 1H, 6-H). HR-FAB MS Obsd; m/z 260.1054. Calcd for $C_{17}H_{26}FN_3O_4$: m/z 260.1047 (M+1)$^+$.

In a similar manner but using the corresponding 5-substituted derivatives, the following 5-substituted carba-nucleosides are prepared:
5-Chloro-carba-uridine,
5-Bromo-carba-uridine,
5-Iodo-carba-uridine,
5-Cyano-carba-uridine,
cara-Uridine-5-carboxylic acid,
5-Ethoxycarbonyl-carba-uridine,
carba-Uridine-5-carboxamide,
5-Hydroxymethyl-carba-uridine,
5-Nitro-carba-uridine,
5-Amino-carba-uridine
5-Chloro-carba-cytidine,
5-Bromo-carba-cytidine,
5-Iodo-carba-cytidine,
5-Cyano-carba-cytidine,
cara-Cytidine-5-carboxylic acid,
5-Ethoxycarbonyl-carba-cytidine,
carba-Cytidine-5-carboxamide,
5-Hydroxymethyl-carba-cytidine,
5-Nitro-carba-cytidine and
5-Amino-carba-cytidine.

XI. BIOLOGICAL METHODS

This invention further provides an efficient process to quantify the viral load in a host using quantitative real-time reverse-transcription polymerase chain reaction ("Q-RT-PCR"). The process involves using a quenched fluorescent probe molecule that can be hybridized to a target viral DNA or RNA. Therefore, upon exonucleolytic degradation, a detectable fluorescent signal can be monitored. Therefore, the RT-PCR amplified DNA or RNA can be detected in real time by monitoring the presence of fluorescence signals.

In a specific embodiment of the invention, the use of RT-PCR to quantitate the viral load of a Flaviviridae virus is provided.

In a more specific embodiment, the use of RT-PCR to quantitate the viral load of BVDV in a MDBK cell line or a host sample is provided.

In a further embodiment of the invention, a probe molecule designed to fluoresce upon exonucleolytic degradation and to be complementary to the BVDV NADL NS5B region is provided.

In a more specific embodiment of the invention, a probe molecule with a sequence of 5' 6-fam-AAATCCTC-CTAACAAGCGGGTTCCAGG-tamara 3' (Sequence ID No 1) and primers with a sequence of sense: 5'-AGCCTTCA-GTTTCTTGCTGATGT-3' (Sequence ID No 2) and antisense: 5'-TGTTGCGAAAGCACCAACAG-3' (Sequence ID No 3) is provided.

In a specific embodiment of the invention, the use of RT-PCR to quantitate viral load of HCV in a host derived sample or a cell line in real time is provided;

In a more specific embodiment of the invention, the use of RT-PCR, a probe molecule designed to fluoresce upon exonucleolytic degradation and to be complementary to the HCV genome is provided In a more specific embodiment of the invention, the use of RT-PCR, a probe molecule designed to fluoresce upon exonucleolytic degradation and to be complementary to the HCV 5' untranslated region is provided In a more specific embodiment of the invention, a probe molecule with a sequence of 5' 6-fam-CCTCCAGGAC-CCCCCCTCCC-tamara 3' (Sequence ID No 4) and primers with a sequence of sense: 5'-AGCCATGGCGTTAGTA(T/C)GAGTGT-3' (Sequence ID No 5) and antisense: 5'-TTC-CGCAGACCACTATGG-3' (Sequence ID No −6) is provided.

A. RNA Isolation and Quantitative RT-PCR Analysis

An effective process to quantify the viral load m a host, termed real-time polymerase chain reaction ("RT-PCR") is provided. The process involves using a Ft quenched fluorescent probe molecule that can be hybridized to viral DNA or RNA. Therefore, upon exonucleolytic degradation, a detectable fluorescent signal can be monitored. Therefore, the RT-PCR amplified DNA or RNA is detected in real time by monitoring the presence of fluorescence signals.

As one illustration of this method, in the case of BVDV in MDBK cells, in a first step, viral RNA is isolated from 140 μL of the cell culture supernatant by means of a commercially available column (Viral RNA extraction kit, QiaGen, CA). The viral RNA is then eluted from the column to yield a total volume of 60 μL, and subsequently amplified with a quantitative RT-PCR protocol using a suitable primer for the BVDV NADL strain. A quenched fluorescent probe molecule is hybridized to the BVDV DNA, which then undergoes exonucleolytic degradation resulting in a detectable fluorescent signal. Therefore, the RT-PCR amplified DNA was detected in real time by monitoring the presence of fluorescence signals. The TaqMan probe molecule (5'-6-fam-AAATCCTCCTAACAAGCGGGTTCCAGG-tamara 3' [Sequence ID No 1] and primers (sense: 5'-AGCCTTCA-GTTTCTTGCTGATGT-3' [Sequence ID No 2]; and antisense: 5'-TGTTGCGAAAGCACCAACAG-3' [Sequence ID No 3]) were designed with the aid of the Primer Express software (PE-Applied Biosystems) to be complementary to the BVDV NADL NS5B region. A total of 104 of RNA was analyzed in a 50 μL RT-PCR mixture. Reagents and conditions used in quantitative PCR were purchased from PE-Applied Biosystems. The standard curve that was created using the undiluted inoculum virus ranged from 6000 plaque forming units (PFU) to 0.6 PFU per RT-PCR mixture. A linear range of over 4-logs was routinely obtained.

A comparable approach can be taken to measure the amount of other Flaviviridae (more importantly HCV, YFV, Dengue, West Nile Virus and others) in a clinical sample or in a tissue culture sample. For example, the combination of HCV RNA purification with real-time RT-PCR using the following primers (5'-TTCCGCAGACCACTATGG-3' [Sequence ID No. 6] and 5'-AGCCATGGCGTTAGTAT-GAGTGT-3' [Sequence ID No. 7]) and probe (5'-6-fam-CCTCCAGGACCCCCCCTCCC-tamara-3' [Sequence ID No. 4]) resulted in a 7-log linear range of viral load detection.

B. Cell/Viral Materials

One of the best characterized members of the Pestivirus genus is BVDV. BVDV and HCV share at least three common features, which are the following: (1) they both undergo IRES-mediated translation; (2) NS4A cofactor is required by their NS3 serine protease; and (3) they undergo similar polyprotein processing within the non-structural region, especially at the NS5A and NS5B junction site.

The BVDV replication system was used for the discovery of anti-Flaviviridae compounds. The compounds described herein are active against Pestiviruses, Hepaciviruses and/or Flaviviruses.

Maldin-Darby bovine kidney (MDBK) cells were grown and maintained in a modified eagle medium (DMEM/F12; GibcoBRL), supplemented with 10% heat inactivated horse serum at 37° C. in a humidified, 5% $CO_2$, incubator.

Bovine viral diarrhea virus (BVDV), strain NADL, causes a cytopathogenic effect (CPE) after infection of these cells C. Antiviral Assay MDBK-cells, grown in DMEM/F12-10% horse serum (HS), were isolated in standard techniques using trypsin-EDTA. Cells were seeded in a 96-well plate at $5 \times 10^4$ cells/well, with test compound (20 micromolar (μM) concentration) to give a total volume of 100 microliters (μL). After one hour, the media was removed and the cells were infected at a multiplicity of infection (MOI) of 0.02 or 0.002 in a total volume of 50 μL for 45 minutes. Thereafter, the virus was removed and the cells were washed twice with 100 μL of assay media. Finally, the infected cells were incubated in a total volume of 100 μL containing the test compound at 10, 40 or 100 μM concentration. After 22 hours, the cell supernatant was collected by removing the cellular debris by low-speed centrifugation, and subsequently tested for the presence of virus in a quantitative manner.

D. Cytotoxicity Testing of Anti-Flaviviridae Compounds

The cytotoxicity testing as performed here is a standard technique. Briefly, cells are seeded in 96-well plates at various concentrations (dependent on cell type, duration of assay), typically at $5 \times 10^3$ cells per well, in the presence of increasing concentrations of the test compound (0, 1, 3, 10, 33, and 100 μM). After a three day-incubation, cell viability and mitochondrial activity are measured by adding the MTS-dye (Promega), followed by a 3 hours incubation. Afterwards the plates containing the dye are read at 490 nm. Such methodologies are well described and available from the manufacturer (Promega).

Example 53

The BVDV RT-PCR Quantification Standard Curve

The standard BVDV virus stock contained $2 \times 10^6$ PFU/mL, as determined by routine plaque assay (Mendez, E. et al. *J. Virol.* 1998, 72, 4737). Viral RNA was extracted from 140 μL of this inoculum material and eluted from a column using 60 μL of an elution buffer. This purified RNA material then was diluted stepwise from $10^{-1}$ to $10^{-5}$. Using the real-time RT-PCR amplification technique, 10 μL of each dilution was tested. The results of this dilution series are plotted in FIG. 1, relating PFU to concentration of standard. From this experiment, it is clear that this technology allows for reliable quantification over 4-logs of virus (from 6000 to 0.6 PFU/input in amplification mix). The lower limit of detection in this experiment is 0.6 PFU or −0.22 log PFU. Therefore, the real-time RT-PCR quantification values of test samples below this detection limit were considered non-reliable.

Example 54

The BVDV Replication Cycle in MDBK Cells

In order to measure the BVDV production in MDBK cells and to determine the optimal harvesting time over a certain period of time, cells were seeded at $5\times10^4$ cells/well and infected either with MOI=0.02 or MOI=0.002. After infection, the inoculum was removed and the cells were washed twice with culture medium. At different time points, the cell supernatant was harvested; and, the amount of virus was measured and compared to the original inoculum and the cell wash. At least 2 wash-steps were needed to remove the inoculum virus, as shown in FIG. 2. The amount of virus produced 22 hours after infection approximately equals the amount of virus used to inoculate the cells. Based on these results, the time required for one replication cycle of BVDV in MDBK cells was 22 hours. Note that the detection level set in these experiments was based on the lower limit of detection as determined by the standard curve.

Example 55

Evaluation of Antiviral Compounds Using RT-PCR

MDBK cells were seeded at $5\times10^4$ cells/well, infected with BVDV with a multiplicity of infection (MOI) equal to 0.02 and grown for 22 hours in the presence of a test compound. Cells that were not treated with a test compound were considered a negative control, while ribavirin served as a positive control. Viral RNA was extracted and analyzed by real time RT-PCR. A typical experiment, shown in FIG. 3, demonstrates that the negative control and the majority of the treated cells produced comparable amounts of virus (between 1.5 and 2 log PFU/input), effectively showing the test compounds as non-active. However, the cells treated with the positive control, ribavirin (RIB) or with 5-hydroxyuridine (β-D-CL) show an almost complete absence of viral RNA. RIB and β-D-CL reduce viral production by approximately 2 log PFU, or 99%, in the 22 hour reproduction period. The exact potency of these compounds cannot be deduced from this kind of experiment, since the detection limit in this experiment is set at −0.22 log PFU and only one cycle of viral replication occurs under the stated experimental conditions.

Potencies, or the effect concentration of compounds that inhibits virus production by 50% or 90% ($EC_{50}$ or $EC_{90}$ values, respectively), of anti-BVDV compounds were determined in a similar set of experiments, but over a broad range of test compound concentrations (0, 1, 3, 10, 33, 100 µM). The $EC_{90}$ value refers to the concentration necessary to obtain a 1-log reduction in viral production within a 22 hour period. Compounds that showed potent antiviral activity are listed in Table 21. This table gives the maximal viral load reduction observed at a given concentration 22 hours post infection.

TABLE 21

| BVDV viral load 22 hours post infection | | | |
|---|---|---|---|
| ID | n | conc. (µM) | Ave. Log Reduction |
| β-D-AA | 4 | 100 | 2.43 |
| β-D-AI | 3 | 100 | 1.52 |
| β-D-AJ | 3 | 100 | 1.34 |
| β-D-AK | 4 | 100 | 1.90 |
| β-D-AL | 3 | 100 | 1.55 |
| β-D-AN | 2 | 100 | 1.21 |
| β-D-AO | 2 | 100 | 2.24 |
| β-D-AP | 3 | 100 | 1.36 |
| β-D-AQ | 3 | 100 | 0.87 |
| β-D-AT | 4 | 100 | 1.42 |
| β-D-BE | 3 | 100 | 1.23 |
| β-D-BL | 2 | 100 | 1.20 |

TABLE 21-continued

| BVDV viral load 22 hours post infection | | | |
|---|---|---|---|
| ID | n | conc. (µM) | Ave. Log Reduction |
| β-D-BO | 3 | 100 | 0.80 |
| β-D-BS | 2 | 10 | 1.48 |
| β-D-CL | 6 | 40 | 3.10 |
| β-D-CM | 3 | 40 | 1.77 |
| β-D-DJ | 1 | 40 | 1.58 |
| β-D-DK | 2 | 100 | 2.17 |
| β-D-DL | 2 | 100 | 1.33 |
| β-D-HA | 1 | 100 | 2.87 |
| β-D-HB | 2 | 100 | 2.26 |
| β-D-MD | 1 | 100 | 2.16 |
| β-D-ME | 4 | 100 | 2.41 |
| β-D-MF | 4 | 100 | 1.41 |
| β-D-QA | 1 | 100 | 1.50 |
| β-D-TA | 1 | 100 | 1.30 |
| β-D-VA | 1 | 100 | 4.69 |
| β-L-FC | 2 | 100 | 2.39 |

Example 56

Alternate Cell Culture Systems for Determining Antiviral Activities

The assay described above can be adapted to the other members of the Flaviviridae by changing the cell system and the viral pathogen. Methodologies to determine the efficacy of these antiviral compounds include modifications of the standard techniques as described by Holbrook, M R et al. Virus Res. 2000, 69 (1), 31; Markland, W et al. Antimicrob. Agents. Chemother. 2000, 44 (4), 859; Diamond, M S et al., J. Virol. 2000, 74 (17), 7814; Jordan, I. et al. J. Infect. Dis. 2000, 182, 1214; Sreenivasan, V. et al. J. Viral. Methods 1993, 45 (1), 1; or Baginski, S G et al. Proc. Natl. Acad. Sci. U.S.A. 2000, 97 (14), 7981 or the real-time RT-PCR technology. Specifically, an HCV replicon system in HuH7 cells (Lohmann, V et al. Science, 1999, 285 (5424), 110) or modifications thereof (Rice et al. 2000, abstract Xth International Symposium for Viral Hepatitis and Liver Disease, Atlanta, Ga.) can be used.

Example 57

Cytotoxicity Testing of Candidate Compounds

The cytotoxicity testing as performed herein is a standard technique. Briefly, cells are seeded in 96-well plates at various concentrations (dependent on cell type, duration of assay), typically at $5\times10^3$ cells per well, in the presence of increasing concentrations of the test compound (0, 1, 3, 10, 33, and 100 µM). After three (Vero cells), or four (CEM cells), or five (PBM cells) day-incubation, cell viability and mitochondrial activity are measured by adding the MTT-dye (Promega), followed by a 8 hours incubation. Afterwards the plates containing the dye are fixed by adding a stop-solution followed by another eight hour incubation. Finally, absorbance is read at 570 nm. Such methodologies are well described and available from the manufacturer (Promega).

A relevant list of compounds tested in this methodology is listed in Table 22. While the tested compounds are generally not cytotoxic, compound B-D-GA showed a selective cytotoxic effect on CEM cells.

TABLE 22

Cytotoxicity* of V-a and VIIIa

| ID | PBM cells* | CEM Cells* | Vero Cells* |
|---|---|---|---|
| β-D-GA | >100 (11.3) | 1.9 | >57.4 |
| β-D-GF | >100 (−46.2) | >100 (11.2) | >100 (4.3) |
| β-L-GA | >100 (−113.2) | >100 (1.1) | >100 (27.9) |
| β-L-GB | >100 (33) | >100 (8.3) | ~171 |
| β-L-GC | >100 (−53.2) | >100 (−1.2) | >100 (−13.4) |
| β-L-GD | >100 (−12.9) | >100 (−79.7) | >100 (0.8) |
| β-L-GE | >100 (−59.7) | >100 (0.0) | >100 (10.6) |
| β-L-GF | >100 (−70.4) | >100 (35.1) | >100 (33.8) |
| β-L-GG | >100 (−34.6) | >100 (17.3) | >100 (33.6) |
| β-L-GH | >100 (−52.1) | >100 (19.7) | >100 (27.0) |
| β-L-GI | >100 (−47.8) | >100 (18.0) | >100 (31.9) |

*$IC_{50}$ in μM (% inhibition at 100 μM)

Example 58

Antiviral Testing of Candidate Compounds for Respiratory Viruses

During the course of these experiments, compounds from general formula (I) have been tested for their antiviral activities against a set of viruses infecting the upper respiratory tract. The methodologies used for these purposes are well described. The following protocols are standard operating procedures taken from the Virology Branch, Division of Microbiology and Infectious Diseases, NIAID, NIH.

A. Viruses and Cell-Lines Used in Primary Screen
(i) Influenza A and B
  Virus strains: A/Beijing/262/95 (H1N1) (Source CDC); A/Sydney/05/97 (H3N2) (source CDC); B/Beijing/184/93 (source: CDC).
  Cell line: Maldin Darby Canine Kidney (MDCK)
(ii) Respiratory Syncytial Virus (RSV)
  Virus strain A2 (source: ATCC).
  Cell Line African Green Monkey kidney (MA-104) cells
(iii) Parainfluenza Type 3 Virus
  Virus Strain: 14702 (source: isolate 5/95 Boivin, Montreal Canada)
  Cell line: African Green Monkey kidney (MA-104) cells
B. Methods for Antiviral Activity
(i) Inhibition of Viral Cytopathic Effect (CPE)
  This test is run in 96-well micro-titer plates. In this CPE inhibition test, four $log_{10}$ dilutions of each test compound will be added to 3 cups containing the cell mono-layer; within 5 min, the virus is then added and the plate sealed, incubated at 37° C. and CPE read microscopically when untreated infected controls develop a 3 to 4+ CPE (approximately 72 to 120 hours). A known positive control drug is evaluated in parallel with test drug in each test. This drug is Ribavirin for influenza, measles, RSV and para-influenza.
(ii) Increase in Neutral Red (NR) Dye Uptake.
  This test is run to validate the CPE inhibition seen in the initial test, and utilizes the same 96-well micro-plate after CPE has been red. Neutral red is added to the medium; cells not damaged by virus take up greater amount of dye, which is read on a computerized micro-plate reader. The method as described by McManus (Appl. Environment. Microbiol. 31:35-38, 1976) is used. An $EC_{50}$ is determined from this dye uptake.
(iii) Confirmatory Test: CPE-Visual and Virus Yield Assay
  Compounds considered active by CPE inhibition and by NR dye uptake will be retested using both CPE inhibition and effect on reduction of virus yield. Collected eluates from the initial testing are assayed for virus titer by serial dilution onto mono-layers of susceptible cells. Development of CPE in these cells is indicative for the presence of infectious virus The $EC_{90}$, which is the drug that inhibits the virus production by 1-log is determined from these data.

Table 23 summarizes the results of part of the antiviral testing. β-D-BS has potent anti-flaviviridae activity and potent in vitro antiviral capacities against influenza A and B, as well as some activities against RSV. There is no activity against Parainfluenza type 3 virus, illustrating that this compound is exerting a specific antiviral effect against certain classes of RNA viruses, but not all.

In addition, compound β-D-CL is a potent in-vitro anti-RSV compound with a selectivity index of 150.

TABLE 23

Antiviral effect on respiratory viruses

| | | β-D-AJ | β-D-BS | β-D-CL | β-D-DJ |
|---|---|---|---|---|---|
| Initial Test, Antiviral Screening with Respiratory Viruses by CPE Inhibition (Visual) | | | | | |
| Influenza A (H1N1) | $EC_{50}$ (μM) | 150 | 1.5 | >5 | >500 |
| | SI** | 2 | 50 | 0 | 0 |
| Influenza A (H3N2) | $EC_{50}$ (μM) | >500 | 1.5 | >5 | >500 |
| | SI** | 0 | 50 | 0 | 0 |
| Influenza B | $EC_{50}$ (μM) | 150 | 0.5 | >5 | 50 |
| | SI** | 2 | 150 | 0 | >10 |
| RSV* | $EC_{50}$ (μM) | >500 | 0.5 | 0.5 | 500 |
| | SI** | 0 | 80 | 150 | 0 |
| Parainfluenza Type 3 Virus | $EC_{50}$ (μM) | >500 | >500 | 90 | >500 |
| | SI** | 0 | 0 | 0 | 0 |
| Initial Test, Antiviral Screening with Respiratory Viruses by Neutral Red | | | | | |
| Influenza A (H1N1) | $EC_{50}$ (μM) | 150 | 1.2 | 8 | >500 |
| | SI** | >3.3 | 116 | 1.1 | 0 |
| Influenza A (H3N2) | $EC_{50}$ (μM) | >500 | 4 | >5 | >500 |
| | SI** | 0 | 20 | 0 | 0 |
| Influenza B | $EC_{50}$ (μM) | 150 | 1.2 | >5 | 110 |
| | SI** | >3.3 | 133 | 0 | >4.5 |
| RSV* | $EC_{50}$ (μM) | >500 | <0.5 | <0.5 | >500 |
| | SI** | 0 | >30 | >170 | 0 |
| Parainfluenza Type 3 Virus | $EC_{50}$ (μM) | >500 | 40 | 40 | 500 |
| | SI** | 0 | 1 | 1 | >1 |

| | | β-D-BS |
|---|---|---|
| Confirmatory Test, Antiviral Screening with Respiratory Viruses by Visual ($EC_{50}$) | | |
| Influenza A (H1N1) | $EC_{50}$ (μM) | 1.3 |
| | SI** | >246 |
| Influenza A (H3N2) | $EC_{50}$ (μM) | 0.5 |
| | SI** | >640 |
| Influenza B | $EC_{50}$ (μM) | 0.6 |
| | SI** | >533 |
| Confirmatory Test, Antiviral Screening with Respiratory Viruses by Yield ($EC_{90}$) | | |
| Influenza A (H1N1) | $EC_{50}$ (μM) | 0.4 |
| | SI** | >800 |
| Influenza A (H3N2) | $EC_{50}$ (μM) | 0.32 |
| | SI** | >1000 |
| Influenza B | $EC_{50}$ (μM) | 0.6 |
| | SI** | >533 |

*RSV: Respiratory Syncytial Virus A
**SI: Selectivity Index ($IC_{50}/EC_{90}$)

Example 59

Antiviral Testing of Candidate Compounds for Flaviviridae

A. The HCV Replicon System in Huh7 Cells.

Huh7 cells harboring the HCV replicon can be cultivated in DMEM media (high glucose, no pyruvate) containing 10% fetal bovine serum, 1× non-essential Amino Acids, Pen-Strep-Glu (100 units/liter, 100 microgram/liter, and 2.92 mg/liter, respectively) and 500 to 1000 microgram/milliliter G418. Antiviral screening assays can be done in the same media without G418 as follows: in order to keep cells in logarithmic growth phase, seed cells in a 96-well plate at low density, for example 1000 cells per well. Add the test compound immediate after seeding the cells and incubate for a period of 3 to 7 days at 37° C. in an incubator. Media is then removed, and the cells are prepared for total nucleic acid extraction (including replicon RNA and host RNA). Replicon RNA can then be amplified in a Q-RT-PCR protocol, and quantified accordingly. The observed differences in quantification of replicon RNA is one way to express the antiviral potency of the test compound. A typical experiment demonstrates that in the negative control and in the non-active compounds-settings a comparable amount of replicon is produced. This can be concluded because the measured threshold-cycle for HCV RT-PCR in both setting is close to each other. In such experiments, one way to express the antiviral effectiveness of a compound is to subtract the threshold RT-PCR cycle of the test compound with the average threshold RT-PCR cycle of the negative control. This value is called DeltaCt (ΔCt or DCt). A ΔCt of 3.3 equals a 1-log reduction (equals $EC_{90}$) in replicon production. Compounds that result in a reduction of HCV replicon RNA levels of greater than 2 ΔCt values (75% reduction of replicon RNA) are candidate compounds for antiviral therapy. Such candidate compounds are belonging to structures with general formula (I) Table 24 gives the average ΔCt values (N=times tested) that can be obtained if the target compounds are incubated in the described way for 96 hours. As a positive control, recombinant interferon alfa-2a (Roferon-A, Hoffmann-Roche, New Jersey, USA) is taken alongside as positive control.

However, this HCV ΔCt value does not include any specificity parameter for the replicon encoded viral RNA-dependent RNA polymerase. In a typical setting, a compound might reduce both the host RNA polymerase activity and the replicon-encoded polymerase activity. Therefore, quantification of rRNA (or any other host RNA polymerase I product) or beta-actin mRNA (or any other host RNA polymerase II) and comparison with RNA levels of the no-drug control is a relative measurement of the effect of the test compound on host RNA polymerases. Table 24 also illustrates the ΔCt values for rRNA of the test compounds.

With the availability of both the HCV ΔCt data and the rRNA ΔCt, a specificity parameter can be introduced. This parameter is obtained by subtracting both ΔCt values from each other. This results in Delta-DeltaCT values (ΔΔCt or DDCt); a value above 0 means that there is more inhibitory effect on the replicon encoded polymerase, a ΔΔCt value below 0 means that the host rRNA levels are more affected than the replicon levels. The antiviral activity of tested compounds, expressed as ΔΔCt values, is given in Table 24. As a general rule, ΔΔCt values above 2 are considered as significantly different from the no-drug treatment control, and hence, exhibits appreciable antiviral activity. However, compounds with a ΔΔCt value of less than 2, but showing limited molecular cytotoxicity data (rRNA ΔCT between 0 and 2) are also possible active compounds.

In another typical setting, a compound might reduce the host RNA polymerase activity, but not the host DNA polymerase activity. Therefore, quantification of rDNA or beta-actin DNA (or any other host DNA fragment) and comparison with DNA levels of the no-drug control is a relative measurement of the inhibitory effect of the test compound on cellular DNA polymerases. Table 25 illustrates the ΔCt values for rDNA of the test compounds.

With the availability of both the HCV ΔCt data and the rDNA ΔCt, a specificity parameter can be introduced. This parameter is obtained by subtracting both ΔCt values from each other. This results in ΔΔCt values; a value above 0 means that there is more inhibitory effect on the replicon encoded polymerase, a ΔΔCt value below 0 means that the host rDNA levels are more affected than the replicon levels. The antiviral activity of tested compounds, expressed as ΔΔCt values, is given in Table 25. As a general rule, ΔΔCt values above 2 are considered as significantly different from the no-drug treatment control, and hence, is an interested compound for further evaluation. However, compounds with a ΔΔCt value of less than 2, but with limited molecular cytotoxicity (rDNA ΔCT between 0 and 2) may be desired.

Compounds that result in the specific reduction of HCV replicon RNA levels, but with limited reductions in cellular RNA and/or DNA levels are candidate compounds for antiviral therapy. Candidate compounds belonging to general formula group (I)-(XXIII) were evaluated for their specific capacity of reducing Flaviviridae RNA (including BVDV and HCV), and potent compounds were detected (Tables 21, 24 and 25).

TABLE 24

| ID | n | Ave. HCV RNA ΔCt | Ave. rRNA ΔCt | Ave. ΔΔCt |
|---|---|---|---|---|
| β-D-AA | 3 | 3.83 | 2.41 | 1.42 |
| β-D-AI | 3 | 2.93 | 2.43 | 0.48 |
| β-D-AJ | 22 | 2.92 | 1.74 | 1.18 |
| β-D-AK | 4 | 3.73 | 2.48 | 1.25 |
| β-D-AL | 2 | 3.08 | 2.72 | 0.36 |
| β-D-AN | 6 | 3.33 | 2.11 | 1.22 |
| β-D-AO | 1 | 4.10 | 2.13 | 1.97 |
| β-D-AP | 2 | 3.27 | 3.23 | 0.05 |
| β-D-AQ | 7 | 4.45 | 3.22 | 1.22 |
| β-D-AT | 2 | 3.71 | 3.07 | 0.64 |
| β-D-BE | 2 | 4.44 | 2.80 | 1.64 |
| β-D-BF | 2 | 4.37 | 2.69 | 1.68 |
| β-D-BH | 1 | 3.06 | 0.91 | 2.15 |
| β-D-BJ | 2 | 5.06 | 3.62 | 1.44 |
| β-D-BL | 1 | 2.28 | 1.93 | 0.35 |
| β-D-BO | 1 | 4.52 | 2.95 | 1.57 |
| β-D-BS | 40 | 4.89 | 1.05 | 3.83 |
| β-D-BT | 5 | 4.83 | 3.59 | 1.24 |
| β-D-BU | 4 | 3.46 | 2.18 | 1.06 |
| β-D-BV | 3 | 1.88 | 0.65 | 1.22 |
| β-D-CC | 6 | 5.04 | 4.82 | 0.21 |
| β-D-DD | 1 | 6.60 | 4.99 | 1.61 |
| β-D-DH | 3 | 4.13 | 2.91 | 1.21 |
| β-D-DJ | 5 | 3.51 | 3.62 | −0.11 |
| β-D-EB | 1 | 3.33 | 1.42 | 1.90 |
| β-D-FA | 2 | 3.80 | 3.58 | 1.44 |
| β-D-GA | 4 | 6.04 | 2.10 | 3.93 |
| β-D-HA | 2 | 5.52 | 3.85 | 1.68 |
| β-D-HB | 5 | 2.94 | 1.65 | 1.30 |
| β-D-KB | 2 | 3.61 | 2.52 | 1.10 |
| β-D-LA | 3 | 3.85 | 4.10 | 0.89 |
| β-D-MD | 3 | 3.57 | 1.95 | 1.62 |
| β-D-ME | 1 | 2.89 | 1.25 | 1.64 |
| β-D-MF | 2 | 3.79 | 2.69 | 1.10 |
| β-D-OE | 1 | 4.51 | 4.20 | 0.31 |
| β-D-QA | 3 | 2.91 | 3.81 | −0.89 |

TABLE 24-continued

| ID | n | Ave. HCV RNA ΔCt | Ave. rRNA ΔCt | Ave. ΔΔCt |
|---|---|---|---|---|
| β-D-RB | 2 | 4.30 | 3.18 | 1.12 |
| β-D-TA | 1 | 4.00 | 3.31 | 0.69 |
| β-D-UA | 1 | 2.91 | 1.61 | 1.3 |
| β-D-VA | 1 | 5.56 | 4.17 | 1.39 |
| β-L-FC | 3 | 5.55 | 5.13 | 0.42 |
| β-L-JB | 1 | 3.65 | 4.55 | −0.90 |
| β-L-KA | 1 | 4.10 | 4.84 | −0.74 |
| β-L-KC | 2 | 1.19 | 1.35 | −0.16 |
| IFN | 4 | 5.21 | 0.69 | 4.52 |
| ribavirin | 2 | 3.13 | 2.35 | 0.78 |

TABLE 25

| ID | N | Ave. HCV RNA ΔCt | Ave. rDNA ΔCt | average ΔΔCt |
|---|---|---|---|---|
| β-D-AA | 3 | 3.83 | 2.53 | 1.88 |
| β-D-AI | 1 | 3.76 | −0.96 | 4.55 |
| β-D-AJ | 16 | 2.75 | 0.43 | 2.33 |
| β-D-AK | 1 | 3.51 | 2.69 | 0.79 |
| β-D-AL | 1 | 3.18 | 2.56 | 0.61 |
| β-D-AN | 2 | 3.86 | 2.53 | 1.88 |
| β-D-AO | 1 | 4.10 | 1.84 | 2.26 |
| β-D-AP | 2 | 3.27 | 2.26 | 1.02 |
| β-D-AQ | 3 | 4.75 | 1.78 | 2.73 |
| β-D-AT | 1 | 3.81 | 2.43 | 1.43 |
| β-D-BE | 1 | 4.99 | 2.06 | 2.98 |
| β-D-BF | 1 | 5.27 | 2.04 | 3.28 |
| β-D-BH | 1 | 3.06 | 1.42 | 1.64 |
| β-D-BJ | 1 | 4.34 | 0.81 | 3.53 |
| β-D-BL | 1 | 2.28 | 1.62 | 0.65 |
| β-D-BS | 14 | 4.81 | 0.38 | 4.45 |
| β-D-BT | 2 | 4.44 | 1.17 | 3.39 |
| β-D-BU | 4 | 3.46 | 1.10 | 1.16 |
| β-D-BV | 3 | 1.88 | 0.31 | 1.65 |
| β-D-CC | 3 | 5.84 | 2.17 | 3.66 |
| β-D-DD | 1 | 6.60 | 3.30 | 3.30 |
| β-D-DH | 1 | 4.14 | 0.89 | 3.25 |
| β-D-DJ | 1 | 4.84 | 2.70 | 2.14 |
| β-D-EB | 1 | 3.33 | 0.96 | 2.37 |
| β-D-FA | 2 | 3.80 | 1.92 | 0.78 |
| β-L-FC | 1 | 4.41 | 1.00 | 3.41 |
| β-D-HA | 1 | 5.12 | 2.04 | 3.16 |
| β-D-HB | 1 | 1.90 | 1.19 | 0.40 |
| β-D-KB | 1 | 3.81 | 0.00 | 3.81 |
| β-L-JB | 1 | 3.65 | 1.20 | 2.45 |
| β-L-KA | 1 | 4.10 | 0.42 | 3.69 |
| β-L-KC | 1 | 2.73 | −0.81 | 3.54 |
| β-D-LA | 1 | 3.54 | 1.56 | 1.98 |
| β-D-MD | 2 | 3.50 | 1.58 | 1.46 |
| β-D-ME | 1 | 2.89 | 1.53 | 1.36 |
| β-D-MF | 2 | 3.79 | 2.17 | 1.65 |
| β-D-OE | 1 | 4.51 | −0.04 | 4.60 |
| β-D-QA | 1 | 4.85 | 2.30 | 2.55 |
| β-D-RB | 1 | 4.00 | 1.27 | 2.74 |
| β-D-TA | 1 | 4.00 | 3.07 | 0.93 |
| β-D-UA | 1 | 2.91 | 0.50 | 2.41 |

Example 60

Toxicity Profile of β-D-GA

Cytotoxicity testing as performed here are standard techniques. Briefly, cells are seeded in 96-well plates at various concentrations (dependent on cell type, duration of assay), typically at $5 \times 10^3$ cells per well, in the presence of increasing concentrations of the test compound (0, 1, 3, 10, 33, and 100 μM). Depending on the cell-type incubation with test compound can vary in time, but is usually within the range of 3 to 5 days. Cell viability and mitochondrial activity are measured by adding the MTT-dye (Promega), followed by eight hours of incubation. Afterwards the plates containing the dye are fixed by adding a stop-solution followed by another eight hour incubation. Finally, absorbance is read at 570 nm. Such methodologies are well described and available from the manufacturer (Promega).

While the tested compounds are generally not cytotoxic, surprisingly enough β-D-GA showed a selective cytotoxic effect on CEM cells (Table 21). In order to explore the complete potential of this compound, a set of human malignant T and B cells and various tumor cell lines were incubated with D-D-GA at varying concentrations, and after the absorbance was read, an $IC_{50}$ value was calculated. As a control, Ara-C, 5FU, and cyclo-heximide was taken alongside (Table 26).

β-D-GA has potent toxicity in human malignant T and B cells, but not in human PBM cells and non-T or B neoplastic cells. Compared to Ara-C and 5-FU, the anticancer activity of β-D-GA is highly selective for T and B cells.

TABLE 26

Toxicity profile of β-D-GA against various tumor cell lines ($IC_{50}$, μM)*

| | β-D-GA | Ara-C | 5-FU | Cyclo-heximide |
|---|---|---|---|---|
| PBM | >100 | 7 | 13.7 | 2.6 |
| Vero | >100 | 0.8 | 65 | 2.1 |
| CEM | 2.9 | 0.6 | 90.5 | 0.1 |
| SUDHL-1 | 0.7 | 3.7 | ° | 0.3 |
| SupT1 | 0.3 | ° | 53.6 | 0.6 |
| H9 | 1.4 | ° | 14.2 | 1 |
| JY | 3 | ° | 7.5 | 0.8 |
| BL41 | <1.0 | ° | 24.1 | 0.3 |
| LNCaP | 45.7 | ° | 22.1 | 2.4 |
| SK-MES-1 | >100 | ° | 13.1 | 3.4 |
| SK-MEL-28 | >100 | ° | 11.2 | 1 |
| HEPG2 | >100 | ° | 40.6 | 3.6 |
| MCF-7 | >100 | ° | 43.7 | 1.5 |

*MTT assay (incubation time of 3-5 days)
PBM: Human peripheral blood mononuclear cells
Vero: African green monkey kidney cell line
CEM: Human T-cell lymphoma cell line
SUDHL-1: Human anaplastic large T-cell lymphoma cell line
SupT1: Human T-cell lymphoblast cell line
H9: Human T-cell lymphoblast cell line
JY: Human B-cell lymphoma cell line (transformed with EBV)
BL41: Human B-cell lymphoma cell line
LNCap: Human prostate adenocarcinoma cell line
SK-MES-1: Human lung squamous carcinoma cell line
SK-MEL-28: Human melanoma cell line
HEPG2: Human liver carcinoma cell line
MCF-7: Human breast carcinoma cell line The prevention of β-D-GA-related cytotoxicity in CEM cells (human T-cell lymphoma) and in the SUDHL-1 cells (human anaplastic large T-cell lymphoma cell line) was studied by adding natural nucleosides. This experiment was initiated by adding 50 μM of natural nucleosides into the media, together with increasing concentration of β-D-GA. CEM cells were seeded at 2500 cells per well and incubated for 4 days (=fast growing cell line with a doubling time of 1.3 days). SUDHL-1 cells were seeded at 10,000 cells/well, and incubated for 3 days (=slow growing cell line, doubling time 3 days). The result of this experiment is plotted in FIG. 4. This figure illustrates that cytidine and uridine markedly prevent β-D-GA toxicity in SUDHL-1 cells and also in CEM cells (similar plot, not shown). 2'-Deoxycytidine has modest preventive activity effect. These data allow to conclude that β-D-GA is equally effective against slower growing SUDHL-1 cells and fast growing CEM cells and that Cytidine and uridine prevent the compound related toxicity in both cell lines. The action of β-D-GA may be related to synthesis and functions of host RNA molecules, but not DNA.

The invention has been described with reference to various specific and preferred embodiments and techniques. However, it should be understood that many variations and modifications will be obvious to those skilled in the art from the foregoing detailed description of the invention and may be made while remaining within the spirit and scope of the invention.

We claim:

1. A method of treating a viral infection or abnormal cellular proliferation in a human exhibiting the viral infection or abnormal cellular proliferation, wherein the viral infection is not caused by Human Immunodeficiency Virus, comprising administering to the human an effective amount of a compound of the general formula (I-b)

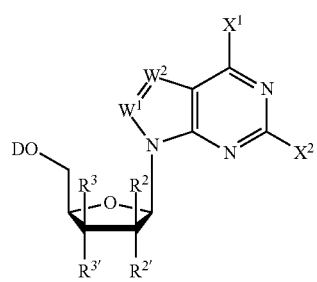

(I-b)

or its β-L enantiomer or its pharmaceutically acceptable salt thereof, wherein:

D is hydrogen;

$W^2$ is N; and wherein the compound of formula (I-b) is selected from one of the following:

| $X^1$ | $X^2$ | $W^1$ | $R^2$ | $R^{2'}$ | $R^3$ | $R^{3'}$ |
|---|---|---|---|---|---|---|
| OH | $NH_2$ | N | H | OH | H | OH |
| OH | $NH_2$ | CH | F | H | H | OH |
| NH-cyclohexyl | H | CH | H | H | H | H |
| $NH_2$ | $NH_2$ | N | H | OH | H | OH |
| $NH_2$ | $NH_2$ | CH | H | OH | H | OH |
| Cl | H | CH | F | H | H | H |
| Cl | I | CH | H | O—Ac | H | O—Ac |
| Cl | H | CH | H | OH | H | OH |
| Cl | H | CH | H | OH | H | H |
| $NH_2$ | H | CH | H | OH | H | F. |

2. The method of claim 1 wherein the viral infection is Flaviviridae.

3. The method of claim 1 wherein the viral infection is Orthomyxoviridae.

4. The method of claim 1 wherein the viral infection is Paramyxoviridae.

5. The method of claim 1 wherein the compound is selected from the group consisting of

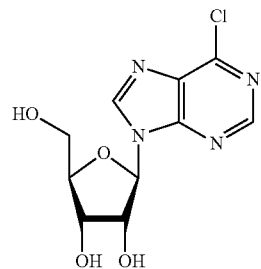

and

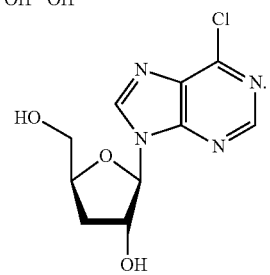

* * * * *

```
                        SEQUENCE LISTING

<160> NUMBER OF SEQ ID NOS: 7

<210> SEQ ID NO 1
<211> LENGTH: 27
<212> TYPE: DNA
<213> ORGANISM: Artificial Sequence
<220> FEATURE:
<223> OTHER INFORMATION: PCR probe
<220> FEATURE:
<221> NAME/KEY: misc_feature
<222> LOCATION: (1)..(1)
<223> OTHER INFORMATION: 6-fam
<220> FEATURE:
<221> NAME/KEY: misc_feature
<222> LOCATION: (27)..(27)
<223> OTHER INFORMATION: tamara

<400> SEQUENCE: 1
aaatcctcct aacaagcggg ttccagg                                          27

<210> SEQ ID NO 2
<211> LENGTH: 23
<212> TYPE: DNA
<213> ORGANISM: Artificial Sequence
<220> FEATURE:
<223> OTHER INFORMATION: PCR primer

<400> SEQUENCE: 2
agccttcagt ttcttgctga tgt                                              23

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
tgttgcgaaa gcaccaacag                                                  20

<210> SEQ ID NO 4
<211> LENGTH: 20
<212> TYPE: DNA
<213> ORGANISM: Artificial Sequence
<220> FEATURE:
<223> OTHER INFORMATION: PCR probe
<220> FEATURE:
<221> NAME/KEY: misc_feature
<222> LOCATION: (1)..(1)
<223> OTHER INFORMATION: 6-fam
<220> FEATURE:
<221> NAME/KEY: misc_feature
<222> LOCATION: (20)..(20)
<223> OTHER INFORMATION: tamara

<400> SEQUENCE: 4
cctccaggac cccccctccc                                                  20

<210> SEQ ID NO 5
<211> LENGTH: 23
<212> TYPE: DNA
<213> ORGANISM: Artificial Sequence
<220> FEATURE:
```

```
<223> OTHER INFORMATION: PCR primer

<400> SEQUENCE: 5
agccatggcg ttagtaygag tgt                                              23

<210> SEQ ID NO 6
<211> LENGTH: 18
<212> TYPE: DNA
<213> ORGANISM: Artificial Sequence
<220> FEATURE:
<223> OTHER INFORMATION: PCR primer

<400> SEQUENCE: 6
ttccgcagac cactatgg                                                    18

<210> SEQ ID NO 7
<211> LENGTH: 23
<212> TYPE: DNA
<213> ORGANISM: Artificial Sequence
<220> FEATURE:
<223> OTHER INFORMATION: PCR primer

<400> SEQUENCE: 7
agccatggcg ttagtatgag tgt                                              23
```